United States Patent
Cho et al.

(10) Patent No.: US 10,816,550 B2
(45) Date of Patent: Oct. 27, 2020

(54) SYSTEMS, APPARATUS, AND METHODS FOR SORTING PARTICLES

(71) Applicants: NANOCELLECT BIOMEDICAL, INC., San Diego, CA (US); The Regents of the University of California, Oakland, CA (US)

(72) Inventors: Sung Hwan Cho, San Diego, CA (US); Jose Morachis, San Diego, CA (US); Yuhwa Lo, San Diego, CA (US); Tsung-Feng Wu, San Diego, CA (US); Ian Quigley, San Diego, CA (US); Kendall Chuang, San Diego, CA (US); Phillip Poonka, San Diego, CA (US); William Alaynick, San Diego, CA (US)

(73) Assignees: NANOCELLECT BIOMEDICAL, INC., San Diego, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 148 days.

(21) Appl. No.: 14/435,710

(22) PCT Filed: Oct. 15, 2013

(86) PCT No.: PCT/US2013/065111
§ 371 (c)(1),
(2) Date: Apr. 14, 2015

(87) PCT Pub. No.: WO2014/062719
PCT Pub. Date: Apr. 24, 2014

(65) Prior Publication Data
US 2015/0268244 A1  Sep. 24, 2015

Related U.S. Application Data

(60) Provisional application No. 61/794,015, filed on Mar. 15, 2013, provisional application No. 61/714,091, filed on Oct. 15, 2012.

(51) Int. Cl.
*G01N 33/574* (2006.01)
*G01N 15/14* (2006.01)
(Continued)

(52) U.S. Cl.
CPC .. *G01N 33/57492* (2013.01); *B01L 3/502761* (2013.01); *G01N 15/1429* (2013.01);
(Continued)

(58) Field of Classification Search
CPC .......... G01N 33/57492; G01N 33/582; G01N 15/1429; G01N 15/1434; G01N 15/1459;
(Continued)

(56) References Cited

U.S. PATENT DOCUMENTS 3,289,687 A    12/1966  Dunaway et al.
3,370,538 A    2/1968   Hines et al.
(Continued)

FOREIGN PATENT DOCUMENTS

CN    101653768 A    2/2010
CN    105283753 A    2/2010
(Continued)

OTHER PUBLICATIONS

Gawad, Shady, Laurent Schild, and Ph Renaud. "Micromachined impedance spectroscopy flow cytometer for cell analysis and particle sizing." Lab on a Chip 1.1 (2001): 76-82.*
(Continued)

*Primary Examiner* — Robert J Eom
(74) *Attorney, Agent, or Firm* — Wilson Sonsini Goodrich & Rosati

(57) ABSTRACT

Provided here are cell detection systems, fluidic devices, structures and techniques related to particle and cell sorting and detection in fluid, for example sorting specific subpopulations of cell types. A method for verification of sorting of particles includes receiving a first detection signal that is
(Continued)

associated with optical characteristics of a particle in a first channel. A sorting channel of a plurality of second channels is determined based on the first detection signal, thereby determining the sorting of the particle into the sorting channel based on the optical characteristics of the particle. A sorting signal for sorting the particle from the first channel into the sorting channel is transmitted. A second detection signal is received that is associated with the presence of the particle in the sorting channel. The sorting of the particle from the first channel into the sorting channel is verified based on the second detection signal.

15 Claims, 83 Drawing Sheets

(51) Int. Cl.
    *G01N 33/58*      (2006.01)
    *B01L 3/00*      (2006.01)
    *G01N 21/64*      (2006.01)
    *G01N 15/10*      (2006.01)

(52) U.S. Cl.
    CPC ..... *G01N 15/1434* (2013.01); *G01N 15/1459* (2013.01); *G01N 15/1463* (2013.01); *G01N 15/1484* (2013.01); *G01N 21/6486* (2013.01); *G01N 33/582* (2013.01); *B01L 2200/0652* (2013.01); *B01L 2300/0636* (2013.01); *B01L 2300/087* (2013.01); *B01L 2300/088* (2013.01); *B01L 2300/0883* (2013.01); *G01N 2015/1006* (2013.01); *G01N 2015/1075* (2013.01); *G01N 2015/1081* (2013.01); *G01N 2015/149* (2013.01); *G01N 2015/1486* (2013.01); *G01N 2201/06113* (2013.01); *G01N 2333/70596* (2013.01)

(58) Field of Classification Search
    CPC ........... G01N 15/1463; G01N 15/1484; G01N 21/6486; G01N 2015/1006; G01N 2015/1075; G01N 2015/1081; G01N 2015/1486; G01N 2015/149; G01N 2201/06113; G01N 2333/70596; B01L 3/502761; B01L 2200/0652; B01L 2300/0636; B01L 2300/087; B01L 2300/088; B01L 2300/0883
    See application file for complete search history.

(56) References Cited

U.S. PATENT DOCUMENTS

| | | |
|---|---|---|
| 3,449,938 A | 6/1969 | Giddings et al. |
| 3,508,654 A | 4/1970 | Glaettli et al. |
| 3,508,655 A | 4/1970 | Kamentsky et al. |
| 3,560,754 A | 2/1971 | Kamentsky |
| 3,675,768 A | 7/1972 | Legorreta-Sanchez et al. |
| 3,790,760 A | 2/1974 | Stiller |
| 3,791,517 A | 2/1974 | Friedman |
| 3,827,555 A | 8/1974 | Kamentsky et al. |
| 3,906,415 A | 9/1975 | Baker |
| 3,984,307 A | 10/1976 | Kamentsky |
| 3,984,621 A | 10/1976 | Propst |
| 4,175,662 A | 11/1979 | Zold |
| 4,279,345 A | 7/1981 | Allred |
| 4,318,483 A | 3/1982 | Lombardo et al. |
| 4,361,400 A | 11/1982 | Gray et al. |
| 4,426,451 A | 1/1984 | Columbus |
| 4,526,276 A | 7/1985 | Shoor et al. |
| 4,572,664 A | 2/1986 | Hanson |
| 4,581,624 A | 4/1986 | O'Connor |
| 4,636,149 A | 1/1987 | Brown |
| 4,676,274 A | 6/1987 | Brown |
| 4,723,129 A | 2/1988 | Endo et al. |
| 4,756,427 A | 7/1988 | Gohde et al. |
| 4,793,705 A | 12/1988 | Shera |
| 4,908,112 A | 3/1990 | Pace |
| 4,936,465 A | 6/1990 | Zold |
| 4,954,715 A | 9/1990 | Zold |
| 4,963,498 A | 10/1990 | Hillman et al. |
| 4,983,038 A | 1/1991 | Ohki et al. |
| 5,030,002 A | 7/1991 | North et al. |
| 5,040,890 A | 8/1991 | North et al. |
| 5,065,978 A | 11/1991 | Albarda et al. |
| 5,092,972 A | 3/1992 | Ghowsi |
| 5,101,978 A | 4/1992 | Marcus |
| 5,126,022 A | 6/1992 | Soane et al. |
| 5,135,306 A | 8/1992 | Kanebako et al. |
| 5,171,132 A | 12/1992 | Miyazaki et al. |
| 5,193,688 A | 3/1993 | Giddings |
| 5,238,223 A | 8/1993 | Mettner et al. |
| 5,265,327 A | 11/1993 | Faris et al. |
| 5,275,787 A | 1/1994 | Yuguchi et al. |
| 5,395,588 A | 3/1995 | North et al. |
| 5,483,469 A | 1/1996 | Van Den Engh et al. |
| 5,486,335 A | 1/1996 | Wilding et al. |
| 5,489,506 A | 2/1996 | Crane |
| 5,541,072 A | 7/1996 | Wang et al. |
| 5,608,519 A | 3/1997 | Gourley et al. |
| 5,699,462 A | 12/1997 | Fouquet et al. |
| 5,777,649 A | 7/1998 | Otsuka et al. |
| 5,789,045 A | 8/1998 | Wapner et al. |
| 5,836,750 A | 11/1998 | Cabuz |
| 5,837,200 A | 11/1998 | Diessel et al. |
| 5,851,488 A | 12/1998 | Saul et al. |
| 5,917,733 A | 6/1999 | Bangham |
| 5,922,591 A | 7/1999 | Anderson et al. |
| 5,976,336 A | 11/1999 | Dubrow et al. |
| 5,988,522 A | 11/1999 | Glezer et al. |
| 5,992,820 A | 11/1999 | Fare et al. |
| 5,998,212 A | 12/1999 | Corio et al. |
| 6,042,709 A | 3/2000 | Parce et al. |
| 6,046,056 A | 4/2000 | Parce et al. |
| 6,049,381 A | 4/2000 | Reinties et al. |
| 6,062,681 A | 5/2000 | Field et al. |
| 6,120,666 A | 9/2000 | Jacobson et al. |
| 6,139,800 A | 10/2000 | Chandler |
| 6,145,247 A | 11/2000 | McKinnis |
| 6,152,181 A | 11/2000 | Wapner et al. |
| 6,184,029 B1 | 2/2001 | Wilding et al. |
| 6,221,654 B1 | 4/2001 | Quake et al. |
| 6,273,553 B1 | 8/2001 | Kim et al. |
| 6,280,590 B1 | 8/2001 | Cheng et al. |
| 6,294,063 B1 | 9/2001 | Becker et al. |
| 6,337,740 B1 | 1/2002 | Parce |
| 6,360,775 B1 | 3/2002 | Barth et al. |
| 6,429,025 B1 | 8/2002 | Parce et al. |
| 6,482,652 B2 | 11/2002 | Furlong et al. |
| 6,488,897 B2 | 12/2002 | Dubrow et al. |
| 6,506,609 B1 | 1/2003 | Wada et al. |
| 6,507,391 B2 | 1/2003 | Riley et al. |
| 6,524,860 B1 | 2/2003 | Seidel et al. |
| 6,532,061 B2 | 3/2003 | Ortyn et al. |
| 6,561,224 B1 | 5/2003 | Cho |
| 6,592,821 B1 | 7/2003 | Wada et al. |
| 6,597,438 B1 | 7/2003 | Cabuz et al. |
| 6,744,038 B2 | 6/2004 | Wang et al. |
| 6,747,285 B2 | 6/2004 | Schueller et al. |
| 6,778,724 B2 | 8/2004 | Wang et al. |
| 6,784,420 B2 | 8/2004 | Wang et al. |
| 6,787,018 B1 | 9/2004 | Miles et al. |
| 6,802,342 B2 | 10/2004 | Fernandes et al. |
| 6,815,664 B2 | 11/2004 | Wang et al. |
| 6,830,936 B2 | 12/2004 | Anderson et al. |
| 6,833,542 B2 | 12/2004 | Wang et al. |
| 6,877,528 B2 | 4/2005 | Gilbert et al. |
| 6,883,957 B2 | 4/2005 | Gilbert et al. |
| 6,909,824 B1 | 6/2005 | Messica et al. |
| 6,936,811 B2 | 8/2005 | Kibar |
| 6,976,590 B2 | 12/2005 | Deshpande et al. |
| 7,068,874 B2 | 6/2006 | Wang et al. |

(56) References Cited

U.S. PATENT DOCUMENTS

| | | |
|---|---|---|
| 7,069,943 B2 | 7/2006 | Gilbert et al. |
| 7,104,405 B2 | 9/2006 | Bohm et al. |
| 7,157,271 B2 | 1/2007 | Ryu et al. |
| 7,157,274 B2 | 1/2007 | Bohm et al. |
| 7,160,687 B1 | 1/2007 | Kapur et al. |
| 7,220,594 B2 | 5/2007 | Foster et al. |
| 7,242,474 B2 | 7/2007 | Cox et al. |
| 7,245,379 B2 | 7/2007 | Schwabe |
| 7,258,774 B2 | 8/2007 | Chou et al. |
| 7,298,478 B2 | 11/2007 | Gilbert et al. |
| 7,303,727 B1 | 12/2007 | Dubrow et al. |
| 7,311,476 B2 | 12/2007 | Gilbert et al. |
| 7,355,696 B2 | 4/2008 | Mueth et al. |
| 7,355,699 B2 | 4/2008 | Gilbert et al. |
| 7,358,476 B2 | 4/2008 | Kiesel et al. |
| 7,389,879 B2 | 6/2008 | Tyvoll et al. |
| 7,402,131 B2 | 7/2008 | Mueth et al. |
| 7,419,784 B2 | 9/2008 | Dubrow et al. |
| 7,452,725 B2 | 11/2008 | Leary et al. |
| 7,476,363 B2 | 1/2009 | Unger et al. |
| 7,479,625 B2 | 1/2009 | Kiesel et al. |
| 7,492,522 B2 | 2/2009 | Gilbert et al. |
| 7,576,861 B2 | 8/2009 | Gilbert et al. |
| 7,595,925 B2 | 9/2009 | Valette et al. |
| 7,611,309 B2 | 11/2009 | Gilbert et al. |
| 7,641,856 B2 | 1/2010 | Padmanabhan et al. |
| 7,658,829 B2 | 2/2010 | Kanagasabapathi et al. |
| 7,701,580 B2 | 4/2010 | Bassler et al. |
| 7,723,116 B2 | 5/2010 | Evans et al. |
| 7,745,221 B2 | 6/2010 | Butler et al. |
| 7,746,466 B2 | 6/2010 | Godin et al. |
| 7,767,444 B2 | 8/2010 | Liu et al. |
| 7,802,686 B2 | 9/2010 | Takagi et al. |
| 7,870,964 B2 | 1/2011 | Gilbert et al. |
| 7,997,831 B2 | 8/2011 | Gilbert et al. |
| 8,026,054 B2 | 9/2011 | Sharma et al. |
| 8,101,137 B2 | 1/2012 | Polwart et al. |
| 8,123,044 B2 | 2/2012 | Johnson et al. |
| 8,198,092 B2 | 6/2012 | Durack et al. |
| 8,263,023 B2 | 9/2012 | Le Vot et al. |
| 8,264,674 B2 | 9/2012 | Takahashi et al. |
| 8,268,177 B2 | 9/2012 | Ying et al. |
| 8,270,781 B2 | 9/2012 | Lo et al. |
| 8,277,764 B2 | 10/2012 | Gilbert et al. |
| 8,290,625 B2 | 10/2012 | Degeal et al. |
| 8,298,399 B2 | 10/2012 | Marchand |
| 8,373,860 B2 | 2/2013 | Kiesel et al. |
| 8,406,498 B2 | 3/2013 | Ortyn et al. |
| 8,409,509 B2 | 4/2013 | Srienc et al. |
| 8,426,209 B2 | 4/2013 | Butler et al. |
| 8,529,161 B2 | 9/2013 | Gilbert et al. |
| 8,567,608 B2 | 10/2013 | Deshpande et al. |
| 8,623,295 B2 | 1/2014 | Gilbert et al. |
| 8,629,981 B2 | 1/2014 | Martini et al. |
| 8,637,803 B2 | 1/2014 | Montes Usategui et al. |
| 8,641,974 B2 | 2/2014 | Bär et al. |
| 8,658,418 B2 | 2/2014 | Daridon |
| 8,679,422 B2 | 3/2014 | Gilbert et al. |
| 8,681,335 B2 | 3/2014 | Sharpe et al. |
| 8,691,164 B2 | 4/2014 | Butler et al. |
| 8,705,031 B2 | 4/2014 | Sedoglavich et al. |
| 8,715,573 B2 | 5/2014 | Ball et al. |
| 8,717,569 B2 | 5/2014 | Lo et al. |
| 8,727,131 B2 | 5/2014 | Deshpande et al. |
| 8,731,860 B2 | 5/2014 | Charles et al. |
| 8,735,853 B2 | 5/2014 | Ayliffe |
| 8,736,837 B2 | 5/2014 | Nolet et al. |
| 8,747,751 B2 | 6/2014 | Duer et al. |
| 8,767,207 B2 | 7/2014 | Benisty |
| 8,798,341 B2 | 8/2014 | Baudry et al. |
| 8,804,105 B2 | 8/2014 | Ayliffe |
| 8,816,234 B2 | 8/2014 | Macdonald et al. |
| 8,822,207 B2 | 9/2014 | Foster et al. |
| 8,824,768 B1 | 9/2014 | Elad et al. |
| 8,828,332 B2 | 9/2014 | Thorslund et al. |
| 8,853,650 B2 | 10/2014 | Duhr et al. |
| 8,863,962 B2 | 10/2014 | Johnson et al. |
| 8,865,455 B2 | 10/2014 | Frayling |
| 8,878,638 B2 | 11/2014 | Bertacco et al. |
| 8,919,383 B2 | 12/2014 | Rodenfels |
| 8,947,662 B1 | 2/2015 | Yufa et al. |
| 8,948,563 B2 | 2/2015 | Hummel et al. |
| 8,961,904 B2 | 2/2015 | Xia et al. |
| 8,962,235 B2 | 2/2015 | Macdonald et al. |
| 8,964,184 B2 | 2/2015 | Gilbert et al. |
| 8,993,311 B2 | 3/2015 | Foster et al. |
| 9,011,797 B2 | 4/2015 | Gilbert et al. |
| 9,018,556 B2 | 4/2015 | Ito |
| 9,039,883 B2 | 5/2015 | Guerrieri et al. |
| 9,050,774 B2 | 6/2015 | Suzuki et al. |
| 9,057,676 B2 | 6/2015 | Sharpe et al. |
| 9,057,730 B2 | 6/2015 | Mir |
| 9,074,978 B2 | 7/2015 | Lo et al. |
| 9,103,975 B2 | 8/2015 | Yu et al. |
| 9,128,016 B2 | 9/2015 | Hulsken et al. |
| 9,134,221 B2 | 9/2015 | Lo et al. |
| 9,176,313 B2 | 11/2015 | Dholakia et al. |
| 9,182,268 B2 | 11/2015 | Blanco-Gomez et al. |
| 9,194,786 B2 | 11/2015 | Foster et al. |
| 9,212,985 B2 | 12/2015 | Vojnovic et al. |
| 9,250,163 B2 | 2/2016 | Gadini et al. |
| 9,255,874 B2 | 2/2016 | Sharpe et al. |
| 9,259,741 B2 | 2/2016 | Glückstad |
| 9,260,693 B2 | 2/2016 | Johnson et al. |
| 9,267,918 B2 | 2/2016 | Joaquim et al. |
| 9,279,802 B2 | 3/2016 | Munaka et al. |
| 9,304,144 B2 | 4/2016 | Humphris et al. |
| 9,335,247 B2 | 5/2016 | Sharpe et al. |
| 9,339,850 B2 | 5/2016 | Deshpande et al. |
| 9,341,562 B2 | 5/2016 | Martini et al. |
| 9,341,620 B2 | 5/2016 | Lowe et al. |
| 9,341,636 B2 | 5/2016 | Poher et al. |
| 9,365,822 B2 | 6/2016 | Seidel et al. |
| 9,376,677 B2 | 6/2016 | Mir |
| 9,389,243 B2 | 7/2016 | Humphris |
| 9,410,894 B2 | 8/2016 | Angelescu et al. |
| 9,421,555 B2 | 8/2016 | Lee et al. |
| 9,446,435 B2 | 9/2016 | Foster et al. |
| 9,446,912 B2 | 9/2016 | Gilbert et al. |
| 9,448,157 B2 | 9/2016 | Ito |
| 9,448,172 B2 | 9/2016 | Griffiths et al. |
| 9,459,211 B2 | 10/2016 | Duhr et al. |
| 9,528,926 B2 | 12/2016 | Ayliffe |
| 9,529,203 B2 | 12/2016 | Perrault, Jr. et al. |
| 9,546,993 B2 | 1/2017 | Vojnovic et al. |
| 9,550,215 B2 | 1/2017 | Deshpande et al. |
| 9,556,429 B2 | 1/2017 | Mir |
| 9,618,442 B2 | 4/2017 | Sharpe et al. |
| 9,638,636 B2 | 5/2017 | Tibbe et al. |
| 9,645,010 B2 | 5/2017 | Lo et al. |
| 9,658,158 B2 | 5/2017 | Renna et al. |
| 9,683,209 B2 | 6/2017 | Dholakia et al. |
| 9,719,934 B2 | 8/2017 | Phelan |
| 9,737,864 B2 | 8/2017 | Leclerc et al. |
| 9,739,798 B2 | 8/2017 | Humphris |
| 9,752,976 B2 | 9/2017 | Gilbert et al. |
| 9,757,726 B2 | 9/2017 | Sharpe et al. |
| 9,778,164 B2 | 10/2017 | Lo et al. |
| 9,778,248 B2 | 10/2017 | West et al. |
| 9,784,735 B2 | 10/2017 | Donolato et al. |
| 9,784,736 B2 | 10/2017 | Donolato et al. |
| 9,816,133 B2 | 11/2017 | Baroud et al. |
| 9,927,345 B2 | 3/2018 | Buchanan et al. |
| 10,029,263 B2 | 7/2018 | Bohm et al. |
| 10,029,283 B2 | 7/2018 | Deshpande et al. |
| 10,065,188 B2 | 9/2018 | Johnson et al. |
| 10,371,622 B2 | 8/2019 | Sharpe et al. |
| 2002/0005354 A1 | 1/2002 | Spence et al. |
| 2002/0011097 A1 | 1/2002 | Kuderer et al. |
| 2002/0037499 A1 | 3/2002 | Quake et al. |
| 2002/0108859 A1 | 8/2002 | Wang et al. |
| 2002/0113204 A1 | 8/2002 | Wang et al. |
| 2002/0115163 A1 | 8/2002 | Wang et al. |
| 2002/0121443 A1 | 9/2002 | O'Connell |

(56) References Cited

U.S. PATENT DOCUMENTS

| | | |
|---|---|---|
| 2002/0122167 A1 | 9/2002 | Riley et al. |
| 2002/0123112 A1 | 9/2002 | Wang et al. |
| 2002/0127736 A1 | 9/2002 | Chou et al. |
| 2002/0137059 A1 | 9/2002 | Wu et al. |
| 2002/0160470 A1 | 10/2002 | Zhang |
| 2002/0166585 A1 | 11/2002 | O'Connor et al. |
| 2003/0119050 A1 | 1/2003 | Shai |
| 2003/0027225 A1 | 2/2003 | Wada et al. |
| 2003/0124516 A1 | 7/2003 | Chung et al. |
| 2003/0137666 A1 | 7/2003 | Johnson |
| 2003/0159999 A1 | 8/2003 | Oakey |
| 2003/0194755 A1 | 10/2003 | Schnabel et al. |
| 2003/0196714 A1 | 10/2003 | Gilbert et al. |
| 2003/0198523 A1 | 10/2003 | Bohm et al. |
| 2003/0211461 A1 | 11/2003 | Kariv et al. |
| 2003/0215791 A1 | 11/2003 | Garini et al. |
| 2004/0009540 A1 | 1/2004 | Soohoo et al. |
| 2004/0011650 A1 | 1/2004 | Zenhausern et al. |
| 2004/0023310 A1 | 2/2004 | Kariv et al. |
| 2004/0033539 A1 | 2/2004 | Schnabel et al. |
| 2004/0037739 A1 | 2/2004 | McNeely et al. |
| 2004/0053209 A1 | 3/2004 | Kariv et al. |
| 2004/0072278 A1 | 4/2004 | Chou et al. |
| 2004/0086872 A1 | 5/2004 | Childers et al. |
| 2004/0161772 A1 | 8/2004 | Bohm |
| 2005/0023137 A1 | 2/2005 | Bhullar et al. |
| 2005/0036139 A1 | 2/2005 | Johnson |
| 2005/0066246 A1 | 3/2005 | Maltseff et al. |
| 2005/0068536 A1 | 3/2005 | Schwabe |
| 2005/0072677 A1 | 4/2005 | Gascoyne et al. |
| 2005/0105077 A1 | 5/2005 | Padnababhan et al. |
| 2005/0112541 A1 | 5/2005 | Durack et al. |
| 2005/0164372 A1 | 7/2005 | Kibar |
| 2005/0258715 A1 | 11/2005 | Schlabach |
| 2006/0060767 A1 | 3/2006 | Wang et al. |
| 2006/0066837 A1 | 3/2006 | Ortyn et al. |
| 2006/0117563 A1 | 6/2006 | Sugahara |
| 2006/0192955 A1 | 8/2006 | Jorgenson et al. |
| 2006/0197033 A1 | 9/2006 | Hairston et al. |
| 2006/0263264 A1 | 11/2006 | Bohm et al. |
| 2006/0282752 A1 | 12/2006 | Kuroda |
| 2007/0086918 A1 | 4/2007 | Hartley et al. |
| 2007/0117086 A1 | 5/2007 | Evans et al. |
| 2007/0128686 A1 | 6/2007 | Jing et al. |
| 2007/0140638 A1 | 6/2007 | Yang et al. |
| 2007/0159627 A1 | 7/2007 | Johnson |
| 2007/0182565 A1 | 8/2007 | Lee et al. |
| 2007/0240495 A1 | 10/2007 | Hirahara |
| 2008/0213821 A1 | 9/2008 | Liu et al. |
| 2008/0233635 A1 | 9/2008 | Evans et al. |
| 2008/0255705 A1 | 10/2008 | Degeal et al. |
| 2008/0261295 A1 | 10/2008 | Butler et al. |
| 2008/0302732 A1 | 12/2008 | Soh |
| 2008/0319680 A1 | 12/2008 | Fox et al. |
| 2009/0027666 A1 | 1/2009 | Godin et al. |
| 2009/0042737 A1 | 2/2009 | Katz et al. |
| 2009/0155832 A1 | 6/2009 | Lo et al. |
| 2009/0190121 A1 | 7/2009 | Hegyi et al. |
| 2009/0194705 A1 | 8/2009 | Kiesel et al. |
| 2009/0195773 A1 | 8/2009 | Bassler et al. |
| 2009/0207576 A1 | 8/2009 | Gardner et al. |
| 2010/0018310 A1 | 1/2010 | Mutharasan et al. |
| 2010/0051828 A1 | 3/2010 | Doemer et al. |
| 2010/0072285 A1 | 3/2010 | Nishijima |
| 2010/0101983 A1 | 4/2010 | Butler et al. |
| 2010/0108577 A1 | 5/2010 | Wang et al. |
| 2010/0117007 A1 | 5/2010 | Kibar |
| 2010/0155572 A1 | 6/2010 | Kiesel et al. |
| 2010/0224493 A1 | 9/2010 | Davalos et al. |
| 2010/0232675 A1 | 9/2010 | Ortyn et al. |
| 2010/0302599 A1 | 12/2010 | Goto et al. |
| 2011/0005978 A1 | 1/2011 | Böhm et al. |
| 2011/0039258 A1 | 2/2011 | McNeeley et al. |
| 2011/0086769 A1 | 4/2011 | Oliphant et al. |
| 2011/0090500 A1 | 4/2011 | Hu et al. |
| 2011/0196637 A1 | 8/2011 | Sharpe et al. |
| 2011/0229872 A1 | 9/2011 | Spence et al. |
| 2012/0009619 A1 | 1/2012 | Gilbert et al. |
| 2012/0011097 A1 | 1/2012 | Matsumura et al. |
| 2012/0012508 A1 | 1/2012 | Deshpande et al. |
| 2012/0015442 A1 | 1/2012 | Gilbert et al. |
| 2012/0045763 A1 | 2/2012 | Sharma et al. |
| 2012/0077191 A1 | 3/2012 | Gunning et al. |
| 2012/0078531 A1 | 3/2012 | Lo et al. |
| 2012/0129716 A1 | 5/2012 | Chee et al. |
| 2012/0138513 A1 | 6/2012 | Johnson et al. |
| 2012/0190105 A1 | 7/2012 | Foster et al. |
| 2012/0202237 A1 | 8/2012 | Sedoglavich et al. |
| 2012/0214224 A1 | 8/2012 | Chan |
| 2012/0255373 A1 | 10/2012 | Foster et al. |
| 2012/0261013 A1 | 10/2012 | Gilbert et al. |
| 2012/0277902 A1 | 11/2012 | Sharpe et al. |
| 2012/0307244 A1 | 12/2012 | Sharpe et al. |
| 2013/0004987 A1 | 1/2013 | Lo et al. |
| 2013/0016335 A1 | 1/2013 | Lo et al. |
| 2013/0083315 A1 | 4/2013 | Lo et al. |
| 2013/0118904 A1 | 5/2013 | Dickerson et al. |
| 2013/0171683 A1 | 7/2013 | Durack et al. |
| 2013/0171685 A1 | 7/2013 | Schutze et al. |
| 2013/0196347 A1 | 8/2013 | Turkcan et al. |
| 2013/0313170 A1 | 11/2013 | Bohm et al. |
| 2013/0316333 A1 | 11/2013 | Roupioz et al. |
| 2013/0334407 A1 | 12/2013 | Perrault, Jr. et al. |
| 2014/0011698 A1 | 1/2014 | Enzelberger et al. |
| 2014/0017709 A1 | 1/2014 | Lowe et al. |
| 2014/0021049 A1 | 1/2014 | Joaquim et al. |
| 2014/0021105 A1 | 1/2014 | Lee et al. |
| 2014/0034555 A1 | 2/2014 | Foster et al. |
| 2014/0048417 A1 | 2/2014 | Heller et al. |
| 2014/0048423 A1 | 2/2014 | Swiegers et al. |
| 2014/0050540 A1 | 2/2014 | Gilbert et al. |
| 2014/0061049 A1 | 3/2014 | Lo et al. |
| 2014/0065658 A1 | 3/2014 | Bertholle et al. |
| 2014/0073000 A1 | 3/2014 | Sun et al. |
| 2014/0073027 A1 | 3/2014 | Dholakia et al. |
| 2014/0085898 A1 | 3/2014 | Perrault, Jr. et al. |
| 2014/0119628 A1 | 5/2014 | Elad et al. |
| 2014/0146315 A1 | 5/2014 | Schwabe et al. |
| 2014/0170673 A1 | 6/2014 | Gilbert et al. |
| 2014/0170697 A1 | 6/2014 | Sharpe et al. |
| 2014/0175711 A1 | 6/2014 | Lee et al. |
| 2014/0176704 A1 | 6/2014 | Perrault, Jr. et al. |
| 2014/0227733 A1 | 8/2014 | Munaka et al. |
| 2014/0234865 A1 | 8/2014 | Gabriel |
| 2014/0244217 A1 | 8/2014 | Lo et al. |
| 2014/0251879 A1 | 9/2014 | Deshpande et al. |
| 2014/0264082 A1 | 9/2014 | Ayliffe |
| 2014/0293731 A1 | 10/2014 | Baaske et al. |
| 2014/0301898 A1 | 10/2014 | Phelan |
| 2014/0309782 A1 | 10/2014 | Sharpe et al. |
| 2014/0318645 A1 | 10/2014 | Koksal et al. |
| 2014/0339445 A1 | 11/2014 | Sharpe et al. |
| 2014/0343869 A1 | 11/2014 | Sharpe et al. |
| 2014/0367315 A1 | 12/2014 | Glückstad |
| 2014/0370536 A1 | 12/2014 | Sharpe et al. |
| 2014/0377879 A1 | 12/2014 | Sharrock et al. |
| 2015/0001085 A1 | 1/2015 | Frayling |
| 2015/0004692 A1 | 1/2015 | Le Berre et al. |
| 2015/0028235 A1 | 1/2015 | Ichiki et al. |
| 2015/0087008 A1 | 3/2015 | Bibette et al. |
| 2015/0122653 A1 | 5/2015 | Schmid et al. |
| 2015/0123017 A1 | 5/2015 | Yu et al. |
| 2015/0125897 A1 | 5/2015 | Duhr et al. |
| 2015/0129688 A1 | 5/2015 | Buchanan et al. |
| 2015/0140545 A1 | 5/2015 | Johnson et al. |
| 2015/0160135 A1 | 6/2015 | Tibbe et al. |
| 2015/0168405 A1 | 6/2015 | Kojic et al. |
| 2015/0203903 A1 | 7/2015 | Mir et al. |
| 2015/0211979 A1 | 7/2015 | Lo |
| 2015/0219685 A1 | 8/2015 | Humphris |
| 2015/0219686 A1 | 8/2015 | Humphris |
| 2015/0224496 A1 | 8/2015 | Guerrieri et al. |
| 2015/0233813 A1 | 8/2015 | Gilbert et al. |
| 2015/0247866 A1 | 9/2015 | Falcon et al. |

(56) References Cited

U.S. PATENT DOCUMENTS

| | | |
|---|---|---|
| 2015/0276576 A1 | 10/2015 | Sharpe et al. |
| 2015/0285836 A1 | 10/2015 | Humphris et al. |
| 2015/0316480 A1 | 11/2015 | Seidel et al. |
| 2015/0322486 A1 | 11/2015 | Shin et al. |
| 2015/0328637 A1 | 11/2015 | Perrault, Jr. et al. |
| 2015/0330385 A1 | 11/2015 | Lofstrom et al. |
| 2015/0331429 A1 | 11/2015 | Lofstrom et al. |
| 2015/0338324 A1 | 11/2015 | Gigan et al. |
| 2015/0352597 A1 | 12/2015 | Deshpande et al. |
| 2015/0352599 A1 | 12/2015 | Deshpande et al. |
| 2015/0375227 A1 | 12/2015 | Quake et al. |
| 2016/0003729 A1 | 1/2016 | Lo et al. |
| 2016/0082480 A1 | 3/2016 | Foster et al. |
| 2016/0084863 A1 | 3/2016 | Holmes et al. |
| 2016/0103059 A1 | 4/2016 | Ayliffe |
| 2016/0122754 A1 | 5/2016 | Mir |
| 2016/0124009 A1 | 5/2016 | Wasson et al. |
| 2016/0129443 A1 | 5/2016 | Tovar et al. |
| 2016/0146798 A1 | 5/2016 | Donolato et al. |
| 2016/0146800 A1 | 5/2016 | O'driscoll et al. |
| 2016/0153959 A1 | 6/2016 | Vojnovic et al. |
| 2016/0153974 A1 | 6/2016 | Donolato et al. |
| 2016/0158758 A1 | 6/2016 | Johnson et al. |
| 2016/0160272 A1 | 6/2016 | Mir |
| 2016/0178518 A1 | 6/2016 | Schwabe |
| 2016/0199840 A1 | 7/2016 | Tachibana et al. |
| 2016/0202172 A1 | 7/2016 | Guck et al. |
| 2016/0231223 A1 | 8/2016 | Wang et al. |
| 2016/0245736 A1 | 8/2016 | Muraki et al. |
| 2016/0252446 A1 | 9/2016 | Smith et al. |
| 2016/0272941 A1 | 9/2016 | Baruch et al. |
| 2016/0291004 A1 | 10/2016 | Sijbers et al. |
| 2016/0296932 A1 | 10/2016 | Tan |
| 2016/0303564 A1 | 10/2016 | Gilbert et al. |
| 2016/0313231 A1 | 10/2016 | Pruneri et al. |
| 2016/0320374 A1 | 11/2016 | Lowe et al. |
| 2016/0327469 A1 | 11/2016 | Sharpe et al. |
| 2016/0377525 A1 | 12/2016 | Foster et al. |
| 2017/0030921 A1 | 2/2017 | Duhr et al. |
| 2017/0066605 A1 | 3/2017 | Gilbert et al. |
| 2017/0091380 A1 | 3/2017 | Vickers et al. |
| 2017/0095814 A1 | 4/2017 | Boehm et al. |
| 2017/0128938 A9 | 5/2017 | Gilbert et al. |
| 2017/0189907 A1 | 7/2017 | Tibbe et al. |
| 2017/0205332 A1 | 7/2017 | Ayliffe |
| 2017/0227466 A1 | 8/2017 | Lo et al. |
| 2017/0239413 A1 | 8/2017 | Hyde et al. |
| 2017/0241878 A1 | 8/2017 | Broyer et al. |
| 2017/0271846 A1 | 9/2017 | Taylor et al. |
| 2017/0299492 A1 | 10/2017 | Rindorf et al. |
| 2018/0163713 A1 | 6/2018 | Morachis et al. |
| 2018/0202916 A1 | 7/2018 | Lo et al. |
| 2018/0214874 A1 | 8/2018 | Koksal et al. |

FOREIGN PATENT DOCUMENTS

| | | |
|---|---|---|
| EP | 1065378 B1 | 4/2002 |
| EP | 1688732 A2 | 8/2006 |
| EP | 2078958 A1 | 7/2009 |
| EP | 2531832 | 12/2012 |
| EP | 2671065 | 12/2013 |
| EP | 2486388 B1 | 1/2014 |
| EP | 2017602 B1 | 2/2014 |
| EP | 2124039 B1 | 4/2014 |
| EP | 2574885 B1 | 4/2014 |
| EP | 2483701 B1 | 5/2014 |
| EP | 2596351 B1 | 6/2014 |
| EP | 1900433 B1 | 7/2014 |
| EP | 2480886 B1 | 8/2014 |
| EP | 2669678 B1 | 8/2014 |
| EP | 2064708 B1 | 11/2014 |
| EP | 2331941 B1 | 11/2014 |
| EP | 2193400 B1 | 12/2014 |
| EP | 2835674 A1 | 2/2015 |
| EP | 2837866 A1 | 2/2015 |
| EP | 2034291 B1 | 3/2015 |
| EP | 2710346 B1 | 3/2015 |
| EP | 2119503 B1 | 4/2015 |
| EP | 2297600 B1 | 4/2015 |
| EP | 2396642 B1 | 4/2015 |
| EP | 2581452 B1 | 4/2015 |
| EP | 2681545 B1 | 4/2015 |
| EP | 2032977 B1 | 5/2015 |
| EP | 2699339 B1 | 5/2015 |
| EP | 2872887 | 5/2015 |
| EP | 1855802 B1 | 6/2015 |
| EP | 2396118 B1 | 6/2015 |
| EP | 2681544 B1 | 6/2015 |
| EP | 2741083 B1 | 6/2015 |
| EP | 2796854 A2 | 6/2015 |
| EP | 1620862 B1 | 7/2015 |
| EP | 2723859 B1 | 7/2015 |
| EP | 2551845 B1 | 8/2015 |
| EP | 2732265 B1 | 8/2015 |
| EP | 1913433 B1 | 9/2015 |
| EP | 2142914 B1 | 9/2015 |
| EP | 2580574 B1 | 9/2015 |
| EP | 2653556 B1 | 9/2015 |
| EP | 2784500 B1 | 9/2015 |
| EP | 1975594 B1 | 10/2015 |
| EP | 2766727 B1 | 10/2015 |
| EP | 2715357 B1 | 11/2015 |
| EP | 2942103 A1 | 11/2015 |
| EP | 2032262 B3 | 12/2015 |
| EP | 1499453 B1 | 1/2016 |
| EP | 2022843 B1 | 1/2016 |
| EP | 2063988 B1 | 1/2016 |
| EP | 2297573 B1 | 1/2016 |
| EP | 2031376 B1 | 3/2016 |
| EP | 2469269 B1 | 3/2016 |
| EP | 2613882 B1 | 3/2016 |
| EP | 2749866 B1 | 3/2016 |
| EP | 1846162 B1 | 5/2016 |
| EP | 1709420 B1 | 6/2016 |
| EP | 2051061 B1 | 7/2016 |
| EP | 2608885 B1 | 8/2016 |
| EP | 2884261 B1 | 9/2016 |
| EP | 2903738 B1 | 9/2016 |
| EP | 2188618 B1 | 10/2016 |
| EP | 2564207 B1 | 10/2016 |
| EP | 2100127 B1 | 11/2016 |
| EP | 2548023 B1 | 11/2016 |
| EP | 1980322 B1 | 12/2016 |
| EP | 2550147 B1 | 12/2016 |
| EP | 2293068 B1 | 1/2017 |
| EP | 2263084 B1 | 2/2017 |
| EP | 1656566 B1 | 3/2017 |
| EP | 2753917 B1 | 3/2017 |
| EP | 2865037 B1 | 4/2017 |
| EP | 2990787 B1 | 5/2017 |
| EP | 3019589 B1 | 5/2017 |
| EP | 2027452 B1 | 6/2017 |
| EP | 2171432 B1 | 6/2017 |
| EP | 2419219 B1 | 6/2017 |
| EP | 2846916 B1 | 6/2017 |
| EP | 2653556 B1 | 7/2017 |
| EP | 1739402 B1 | 8/2017 |
| EP | 2002895 B1 | 8/2017 |
| EP | 2446248 B1 | 8/2017 |
| EP | 2342721 B1 | 9/2017 |
| JP | 02-093344 | 4/1990 |
| JP | 02-304332 | 12/1990 |
| KR | 20100049974 A | 5/2010 |
| KR | 20100056574 A | 5/2010 |
| WO | WO 1994/005775 A1 | 3/1994 |
| WO | WO-9702357 A1 | 1/1997 |
| WO | WO-9943432 A1 | 9/1999 |
| WO | WO-9961888 A2 | 12/1999 |
| WO | WO-0050172 A1 | 8/2000 |
| WO | WO-0070080 A1 | 11/2000 |
| WO | WO-0126813 A2 | 4/2001 |
| WO | WO-0229106 A2 | 4/2002 |
| WO | WO 2002/059577 A2 | 8/2002 |
| WO | WO 2002/101339 A2 | 12/2002 |

(56) References Cited

FOREIGN PATENT DOCUMENTS

| | | |
|---|---|---|
| WO | WO-2007009983 A1 | 1/2007 |
| WO | WO 2007/051170 A2 | 5/2007 |
| WO | WO-2007130647 A2 | 11/2007 |
| WO | WO 2010/104993 A2 | 9/2010 |
| WO | WO 2011/109762 A1 | 9/2011 |
| WO | WO 2012/083250 A2 | 6/2012 |
| WO | WO 2012/094325 A2 | 7/2012 |
| WO | WO 2012/106645 A1 | 8/2012 |
| WO | WO 2012/154614 A1 | 11/2012 |
| WO | WO 2013/010134 A2 | 1/2013 |
| WO | WO 2013/181453 A2 | 12/2013 |
| WO | WO 2013/192342 A1 | 12/2013 |
| WO | WO 2014/016562 A1 | 1/2014 |
| WO | WO 2014/021923 A1 | 2/2014 |
| WO | WO 2014/031900 A1 | 2/2014 |
| WO | WO 2014/033451 A1 | 3/2014 |
| WO | WO 2014/033452 A1 | 3/2014 |
| WO | WO 2014/047206 A1 | 3/2014 |
| WO | WO 2014/057268 A1 | 4/2014 |
| WO | WO 2014/062719 A2 | 4/2014 |
| WO | WO 2014/064412 A1 | 5/2014 |
| WO | WO 2014/070017 A1 | 5/2014 |
| WO | WO 2014/092653 A1 | 6/2014 |
| WO | WO 2014/111721 A1 | 7/2014 |
| WO | WO 2014/111920 A1 | 7/2014 |
| WO | WO 2014/122491 A1 | 8/2014 |
| WO | WO 2014/152039 A2 | 9/2014 |
| WO | WO 2014/152048 A2 | 9/2014 |
| WO | WO 2014/153107 A1 | 9/2014 |
| WO | WO 2014/173526 A2 | 10/2014 |
| WO | WO 2014/196856 A1 | 12/2014 |
| WO | WO 2014/206420 A1 | 12/2014 |
| WO | WO 2014/206968 A1 | 12/2014 |
| WO | WO 2015/015199 A2 | 2/2015 |
| WO | WO 2015/019120 A2 | 2/2015 |
| WO | WO 2015/024690 A1 | 2/2015 |
| WO | WO 2015/040382 A1 | 3/2015 |
| WO | WO 2015/056431 A1 | 4/2015 |
| WO | WO 2015/075030 A1 | 5/2015 |
| WO | WO 2015/075698 A1 | 5/2015 |
| WO | WO 2015/078998 A1 | 6/2015 |
| WO | WO 2015/084257 A1 | 6/2015 |
| WO | WO 2015/122769 A1 | 8/2015 |
| WO | WO 2015/156738 A1 | 10/2015 |
| WO | WO 2015/177373 A1 | 11/2015 |
| WO | WO 2015/185226 A1 | 12/2015 |
| WO | WO 2015/185600 A1 | 12/2015 |
| WO | WO 2015/185763 A1 | 12/2015 |
| WO | WO 2015/189547 A1 | 12/2015 |
| WO | WO 2015/192855 A1 | 12/2015 |
| WO | WO 2015/193194 A1 | 12/2015 |
| WO | WO 2016/016345 A1 | 2/2016 |
| WO | WO 2016/024095 A1 | 2/2016 |
| WO | WO 2016/024114 A1 | 2/2016 |
| WO | WO 2016/033657 A1 | 3/2016 |
| WO | WO 2016/045954 A1 | 3/2016 |
| WO | WO 2016/050837 A1 | 4/2016 |
| WO | WO 2016/054293 A1 | 4/2016 |
| WO | WO 2016/074041 A1 | 5/2016 |
| WO | WO 2016/092449 A1 | 6/2016 |
| WO | WO 2016/092452 A1 | 6/2016 |
| WO | WO 2016/107851 A1 | 7/2016 |
| WO | WO 2016/144260 A1 | 7/2016 |
| WO | WO 2016/178013 A1 | 11/2016 |
| WO | WO 2016/193758 A1 | 12/2016 |
| WO | WO 2016/198321 A1 | 12/2016 |
| WO | WO 2016/198697 A1 | 12/2016 |
| WO | WO 2016/210077 A1 | 12/2016 |
| WO | WO 2016/210128 A1 | 12/2016 |
| WO | WO 2017/001565 A1 | 1/2017 |
| WO | WO 2017/006093 A1 | 1/2017 |
| WO | WO 2017/012986 A1 | 1/2017 |
| WO | WO 2017/029494 A1 | 2/2017 |
| WO | WO 2017/030505 A1 | 2/2017 |
| WO | WO 2017/050977 A1 | 3/2017 |
| WO | WO 2017/055581 A1 | 4/2017 |
| WO | WO 2017/089540 A1 | 6/2017 |
| WO | WO 2017/089599 A1 | 6/2017 |
| WO | WO 2017/108726 A1 | 6/2017 |
| WO | WO 2017/108733 A1 | 6/2017 |
| WO | WO 2017/109201 A1 | 6/2017 |
| WO | WO 2017/133741 A1 | 8/2017 |
| WO | WO 2017/141048 A1 | 8/2017 |
| WO | WO 2017/175237 A1 | 10/2017 |
| WO | WO 2017/214572 A1 | 12/2017 |

OTHER PUBLICATIONS

Cho, Sung Hwan, et al. "Human mammalian cell sorting using a highly integrated micro-fabricated fluorescence-activated cell sorter (µFACS)." Lab on a Chip 10.12 (2010): 1567-1573.*

Chen, C., et al., "Microfluidic cell sorter with integrated piezoelectric actuator," Biomedical Microdevices, 11 (6): 1223-1231, Aug. 2009.

Cho, S., et al., "Micro-fabricated Fluorescence-Activated Cell Sorter," $31^{st}$ Annual International Conference of the IEEE Engineering in Medicine and Biology Society, pp. 1075-1078, Sep. 2-6, 2009.

Cho, S., et al., "Microfluidic Photonic Integrated Circuits," Optoelectronic Materials and Devices, vol. 7135, pp. 1-18, Jan. 2008.

Cho, S., et al., "Optofluidic Waveguides in Teflon AF-Coated PDMS Microfluidic Channels," IEEE Photonics Technology Letters, 21(15):1057-1059, Aug. 1, 2009.

European Patent Application No. EP 13847513.2, Supplementary European Search Report dated Oct. 7, 2016, 13 pages.

European Patent Application No. EP 13847513.2, Supplementary Partial European Search Report dated Jun. 7, 2016, 8 pages.

Fu, A.Y., et al., "A Microfabricated Fluorescence-Activated Cell Sorter." Nature Biotechnology, vol. 17, pp. 1109-1111, Nov. 1999.

Godin, J., et al., "Microfluidics and photonics for Bio-System-on-a-Chip: A review of advancements in technology towards a microfluidic flow cytometry chip." Journal of Biophotonics, 1(5): 355-376, Oct. 2008.

International Preliminary Report on Patentability dated Apr. 21, 2015, for International Application No. PCT/US2013/065111, 9 pages.

International Search Report and Written Opinion dated Apr. 30, 2014, for International Application No. PCT/US2013/065111, 12 pages.

International Search Report and Written Opinion dated Nov. 1, 2007 for International Application No. PCT/US2006/060313 (8 pages).

International Search Report and Written Opinion dated Oct. 26, 2010 for International Application No. PCT/US2010/026884 (10 pages).

Lee, G.B., et al., "Micro Flow Cytometers with Buried SU-8/SOG Optical Waveguides," Sensors and Actuators A: Physical, 103(1):165-170, Jan. 2003.

Lien, V., et al., "Fluidic Photonic Integrated Circuit for In-Line Detection," Applied Physics Letters, 87(19):194106(1-3), Nov. 2005.

Lien, V., et al., "A Prealigned Process of Integrating Optical Waveguides With Microfluidic Devices," IEEE Photonics Technology Letters, 16(6):1525-1527, Jun. 2004.

Lien, V., et al., "High-Sensitivity Cytometric Detection Using Fluidic-Photonic Integrated Circuits with Array Waveguides," IEEE Journal of Selected Topics in Quantum Electronics, 11 (4):827-834, Jul./Aug. 2005.

Lien, V., et al., "Microfluidic-photonic-dielectrophoretic integrated circuits for biophotonic sensing," The 17th Annual Meeting of the IEEE Lasers and Electro—Optics Society, vol. 2, pp. 533-534, Nov. 2004.

Tung, Y.C., et al., "PDMS—based opto-fluidic micro flow cytometer with two-color, multi-angle fluorescence detection capability using PIN photodiodes," Sensors and Actuators B, 98(2-3):356-367, Mar. 2004.

Zhang, H., et al., "Time-of-Flight Optophoresis Analysis of Live Whole Cells in Microfluidic Channels," Biomedical Microdevices, 6(1):11-21, Mar. 2004.

(56) References Cited

OTHER PUBLICATIONS

Chen, C.H., et al., "High-Throughput Cell Sorter With Piezoelectric Actuation," Micro Total Anal Syst. (2008); 2008: 155-157.
International Preliminary Report on Patentability for International Application No. PCT/US2006/060313, dated Apr. 29, 2008, 6 pages.
International Preliminary Report on Patentability for International Application No. PCT/US2010/026884, dated Sep. 13, 2011, 7 pages.
International Search Report and Written Opinion for International Application No. PCT/US2013/056277, dated Nov. 21, 2013, 14 pages.
International Preliminary Report on Patentability for International Application No. PCT/US2013/056277, dated Feb. 24, 2015, 9 pages.
International Search Report and Written Opinion for International Application No. PCT/US2016/038937, dated Sep. 23, 2016, 10 pages.
International Preliminary Report on Patentability for International Application No. PCT/US2016/038937, dated Dec. 26, 2017, 9 pages.
International Search Report and Written Opinion for International Application No. PCT/US2015/053368, dated Dec. 28, 2015, 10 pages.
International Preliminary Report on Patentability for International Application No. PCT/US2015/053368, dated Apr. 4, 2017, 9 pages.
International Search Report and Written Opinion for International Application No. PCT/US2017/036864, dated Sep. 1, 2017, 9 pages.
Blankenstein et al. Modular Concept of a Laboratory on a Chip for Chemical and Biochemical Analysis. Biosensors and Bioelectronics. 1998;13(3-4):427-438.
Olsson et al. A valve-less planar fluid pump with two pump chambers. Sensors and Actuators A 46-47:549-556 (1995).
PCT/US2011/057399 International Search Report and Written Opinion dated Jun. 28, 2012.
Qiao et al, Wirelessly powered microfluidic dielectrophoresis devices using printable RF circuits. Lab Chip 11(6):1074-1080 (2011).
U.S. Appl. No. 12/091,414 Office Action dated Mar. 9, 2012.
U.S. Appl. No. 12/091,414 Office Action dated Nov. 9, 2011.
U.S. Appl. No. 13/254,851 Office Action dated May 22, 2014.
U.S. Appl. No. 13/254,851 Office Action dated Sep. 5, 2013.
U.S. Appl. No. 13/605,925 Office Action dated Jan. 23, 2013.
U.S. Appl. No. 13/605,925 Office Action dated Jun. 27, 2013.
U.S. Appl. No. 14/270,202 Office Action dated Apr. 27, 2016.
U.S. Appl. No. 14/270,202 Office Action dated Mar. 2, 2017.
U.S. Appl. No. 14/270,202 Office Action dated Sep. 17, 2015.
U.S. Appl. No. 14/270,202 Office Action dated Sep. 9, 2016.
U.S. Appl. No. 14/683,572 Office Action dated Mar. 9, 2016.
U.S. Appl. No. 14/683,572 Office Action dated May 22, 2015.
U.S. Appl. No. 14/853,765 Office Action dated Jan. 11, 2016.
Weigl et al. Design and rapid prototyping of thin-film laminate-based microfluidic devices. Biomed Microdev. 2001; 3: 267-274.

* cited by examiner

FIG. 3
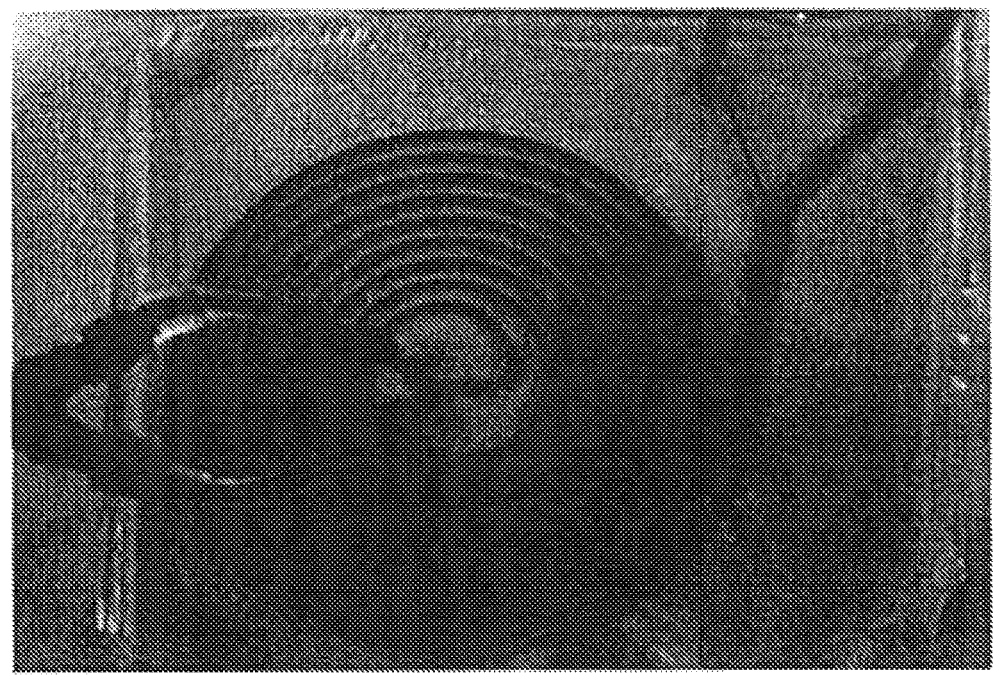
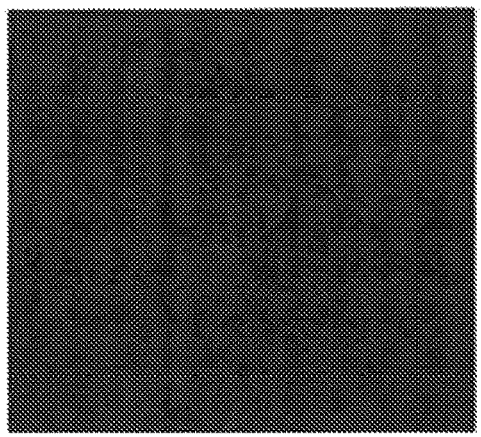
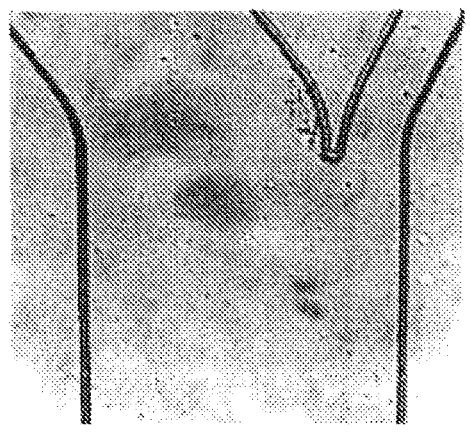
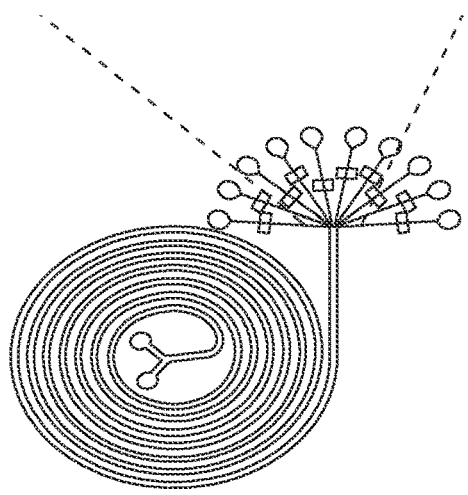
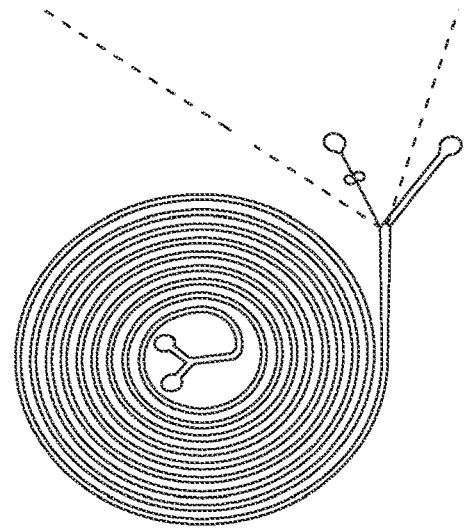
A.
B.
C.

FIG.4
A.
Flow Speed: 400uL/min
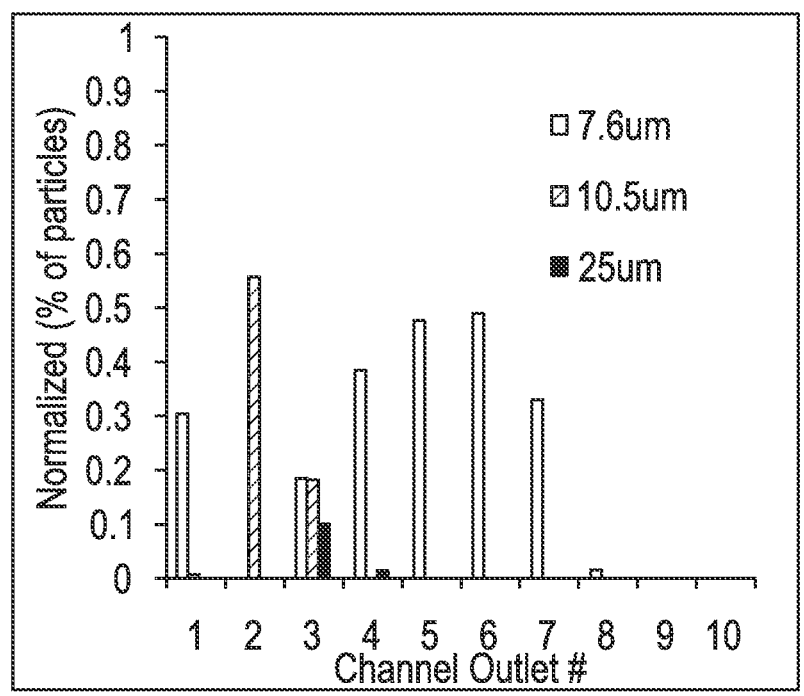
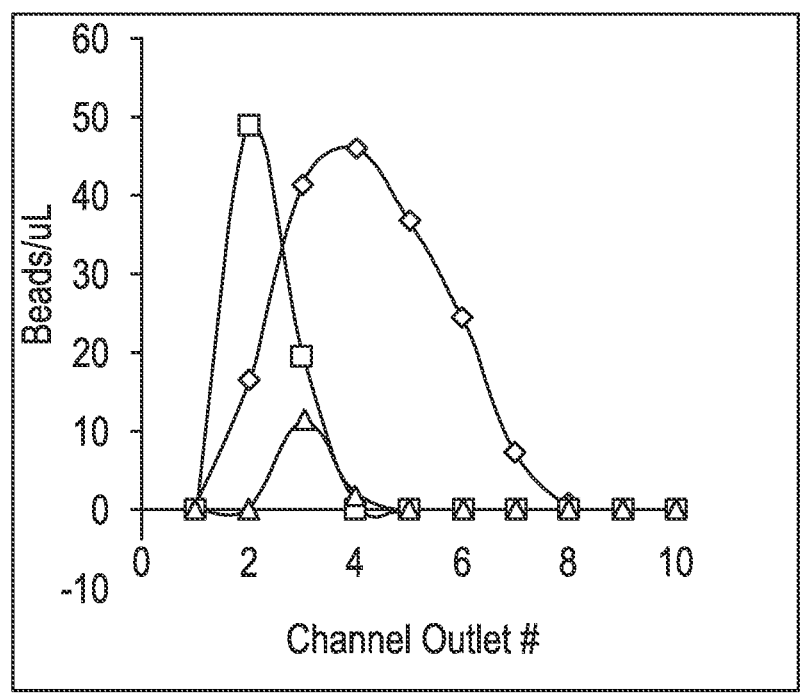

FIG.4
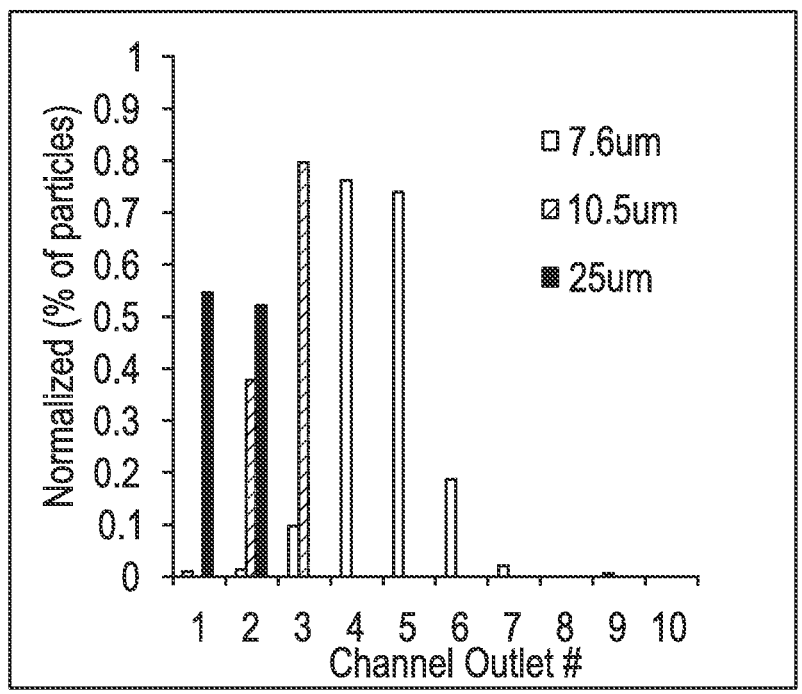
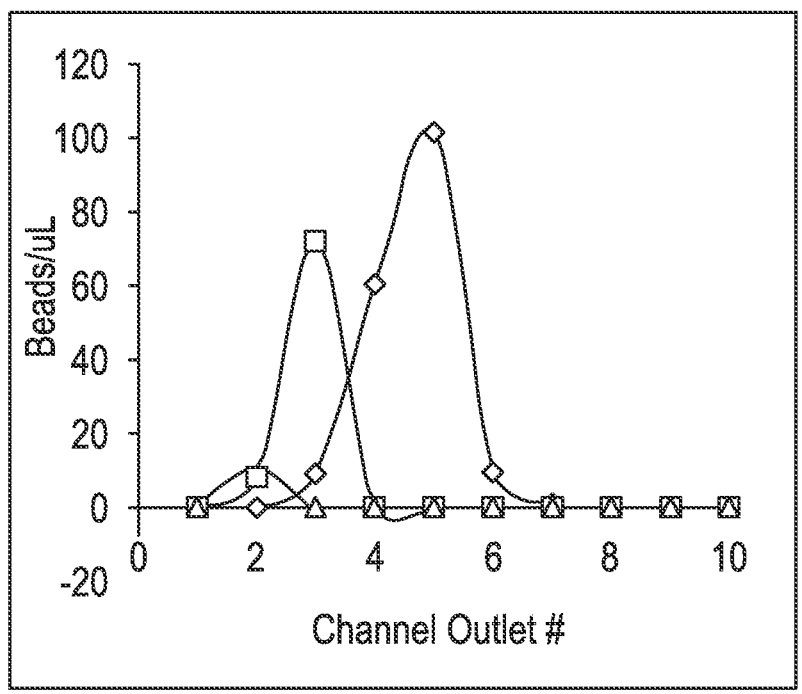

FIG.4
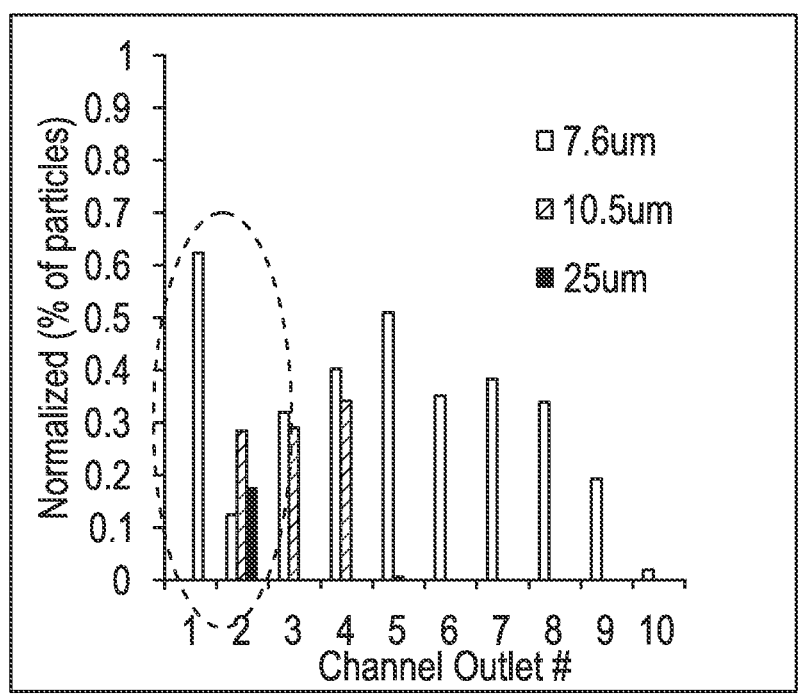
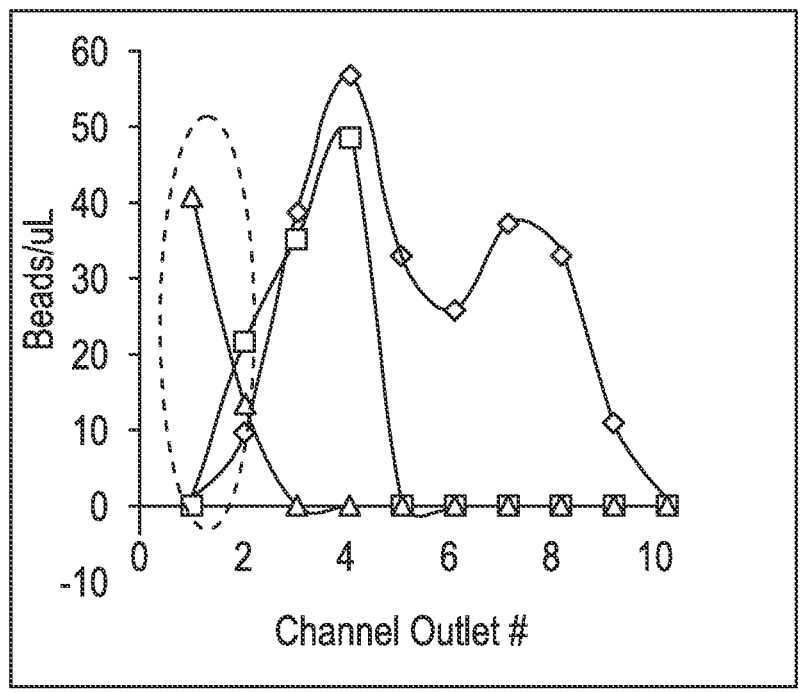

FIG.8
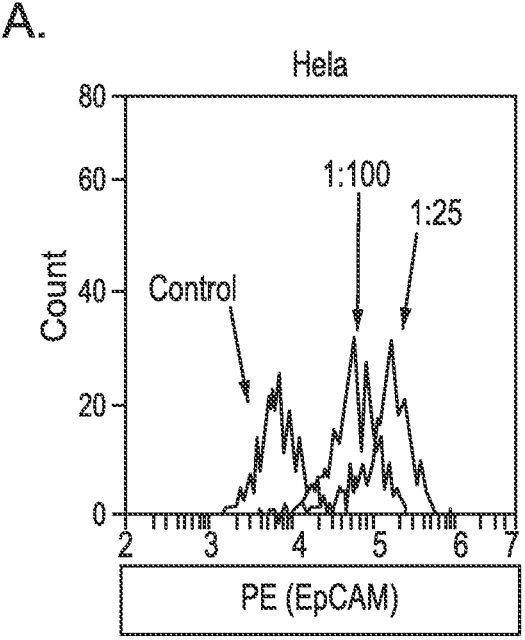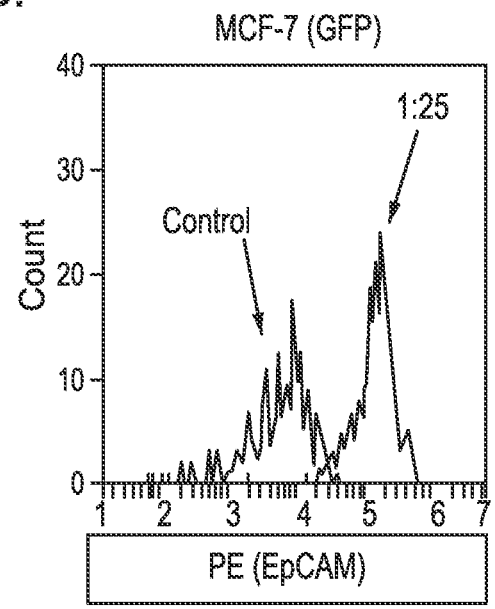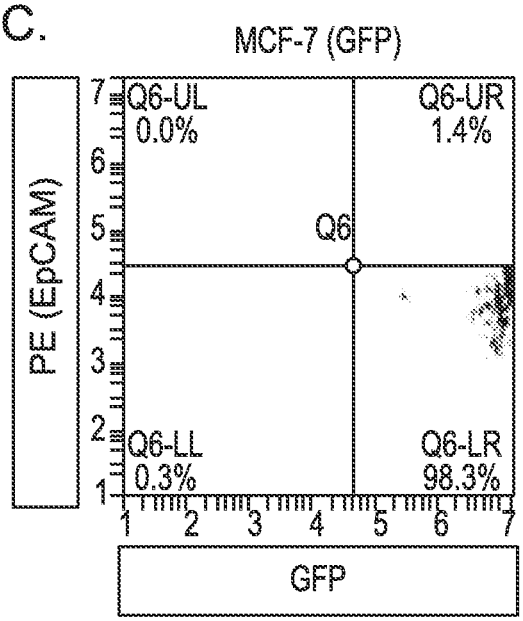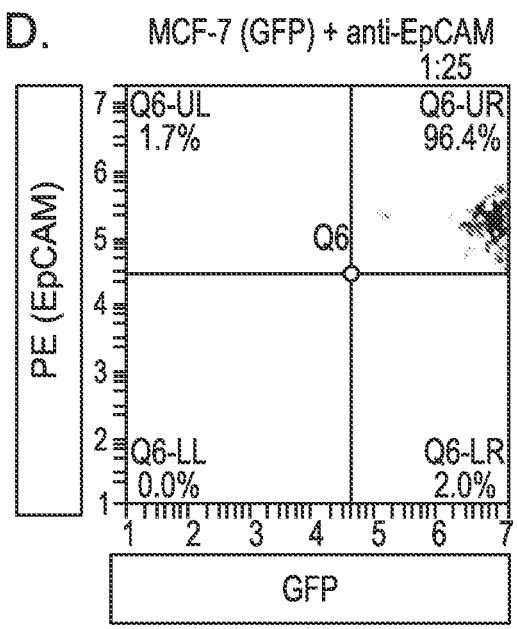

FIG. 11
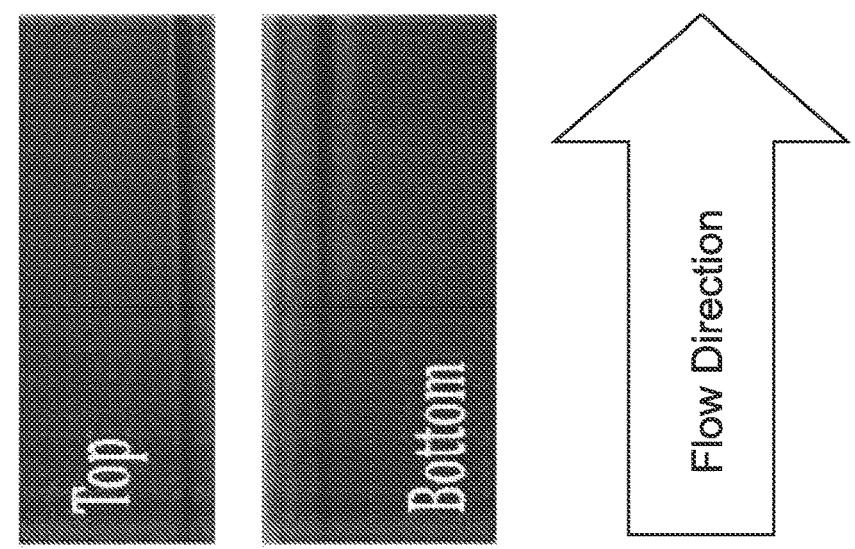
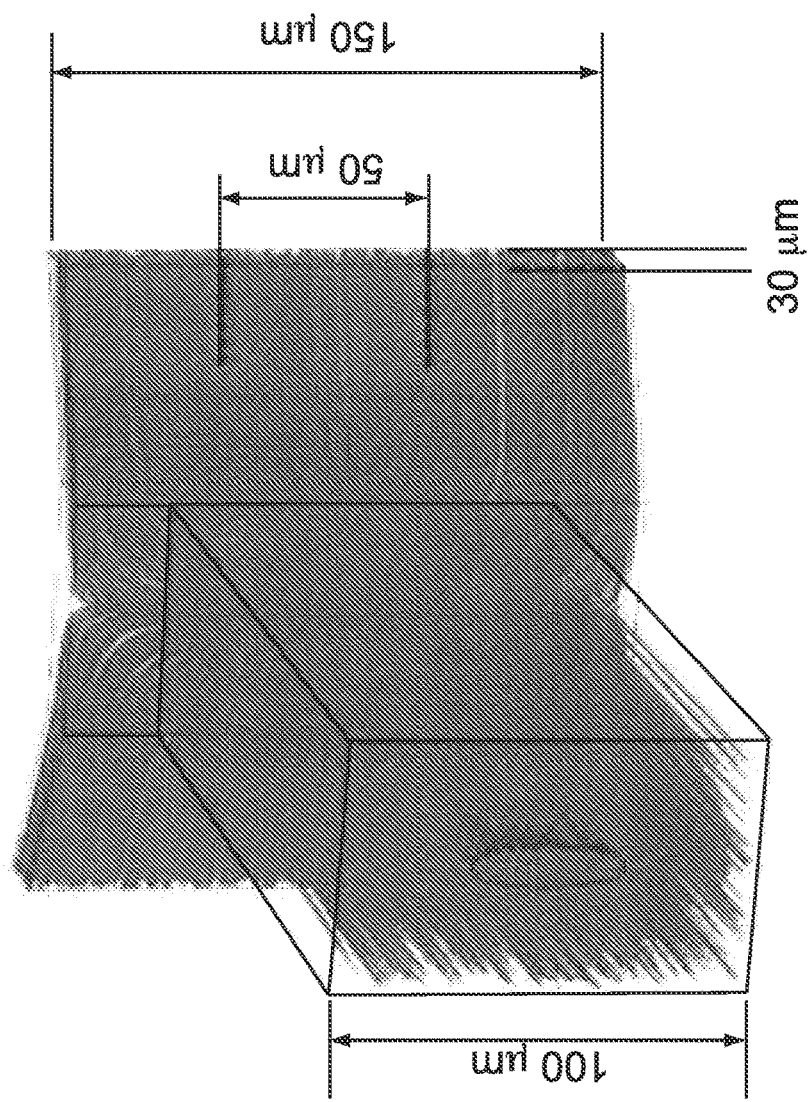

FIG. 12
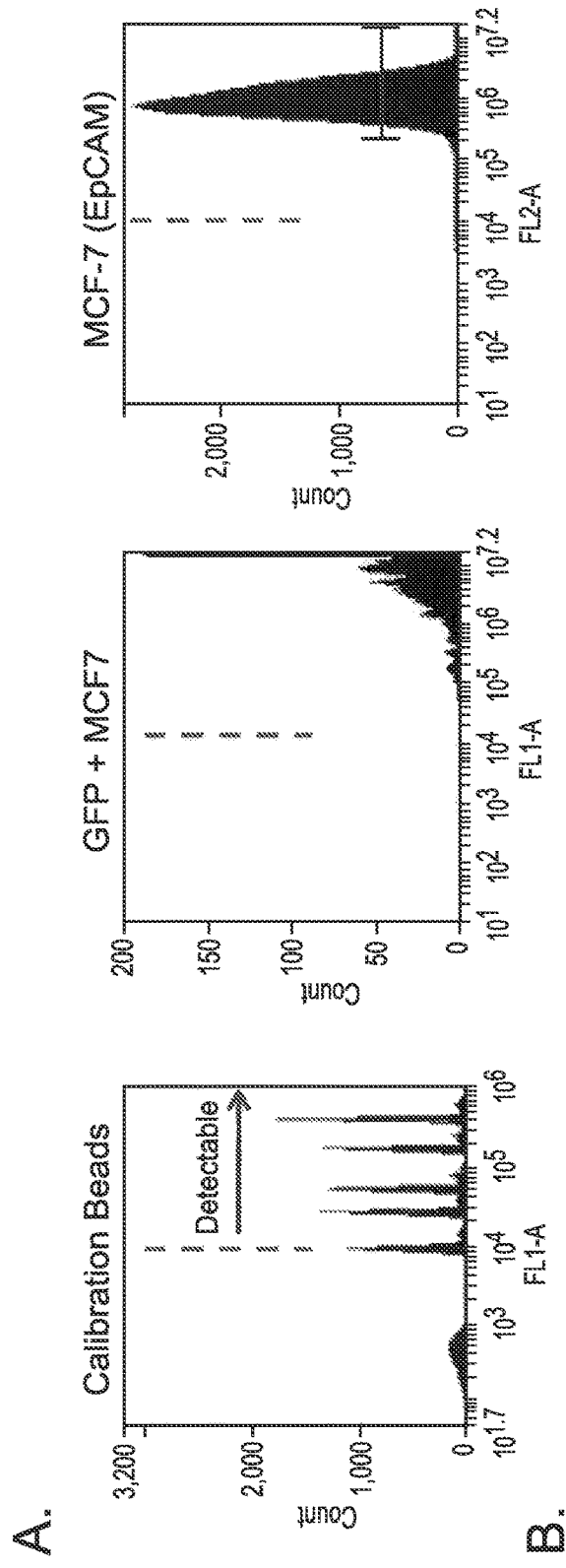
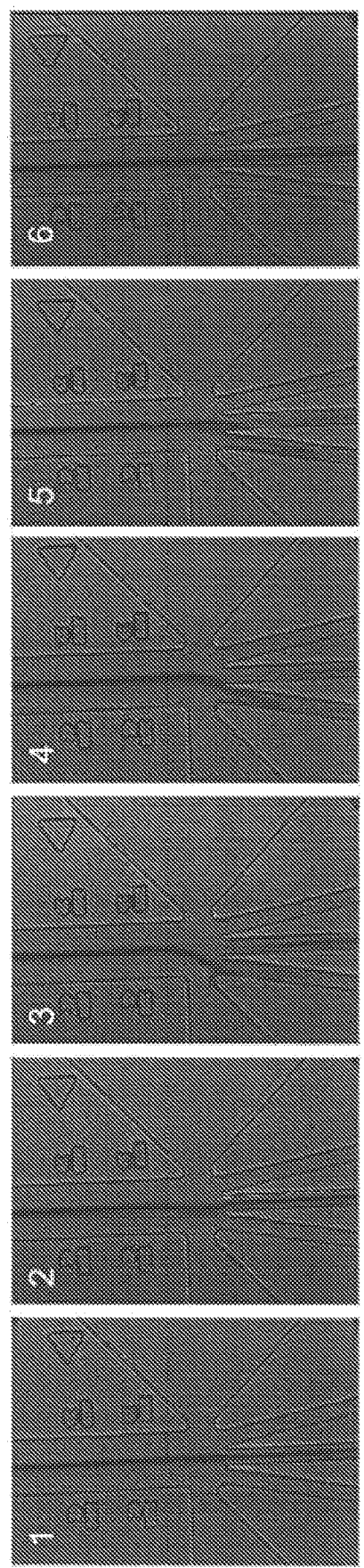

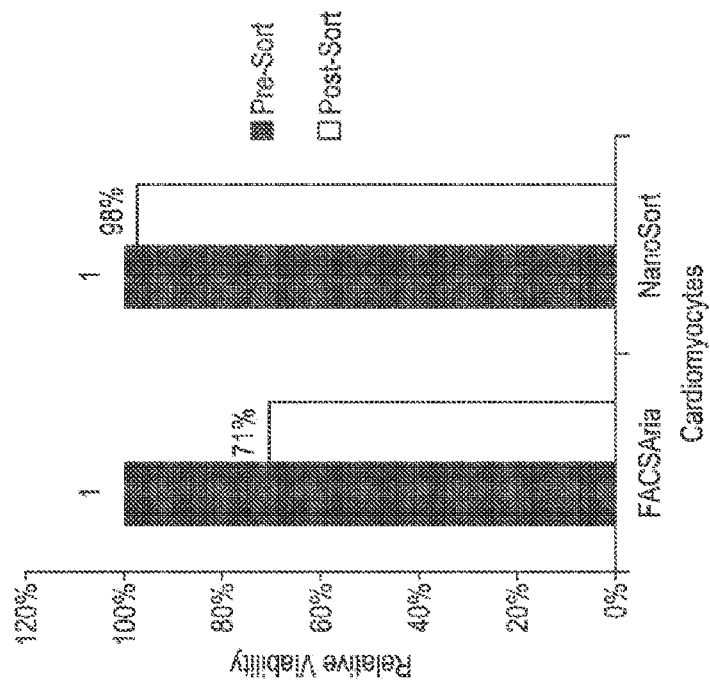
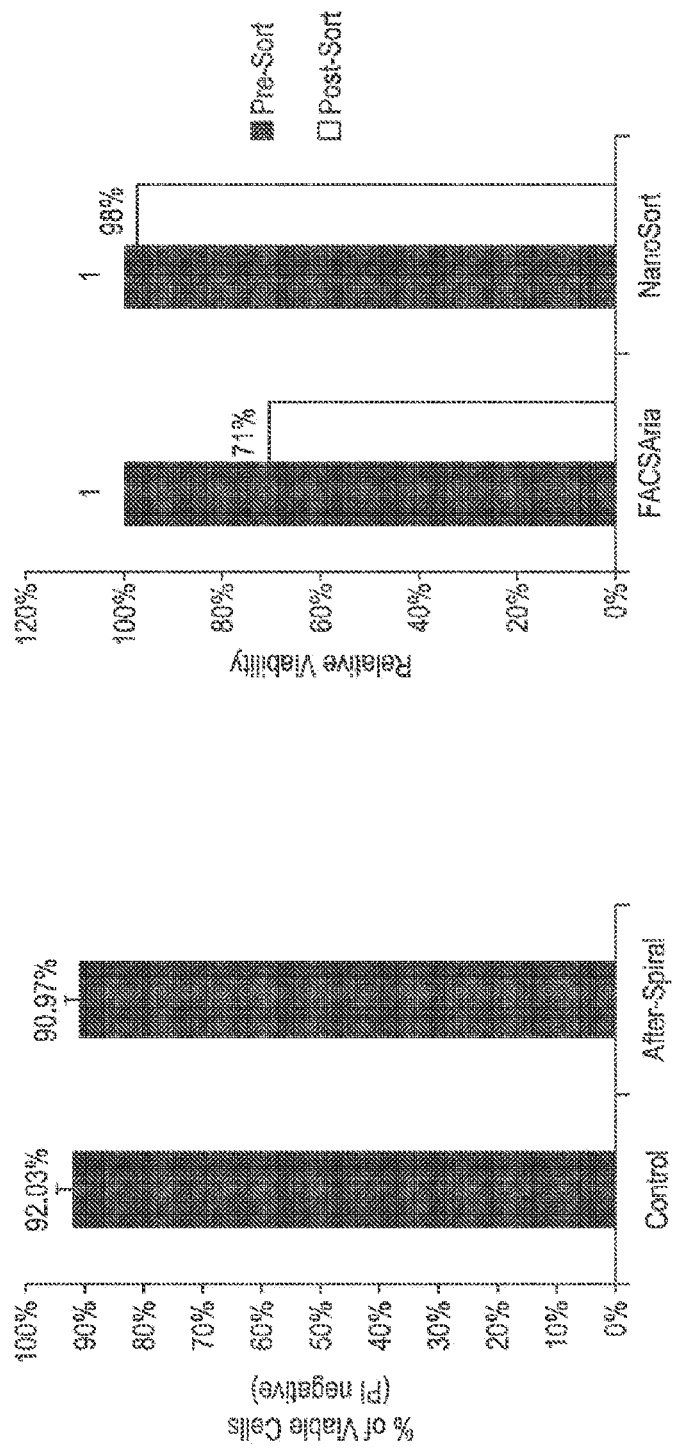
FIG. 13

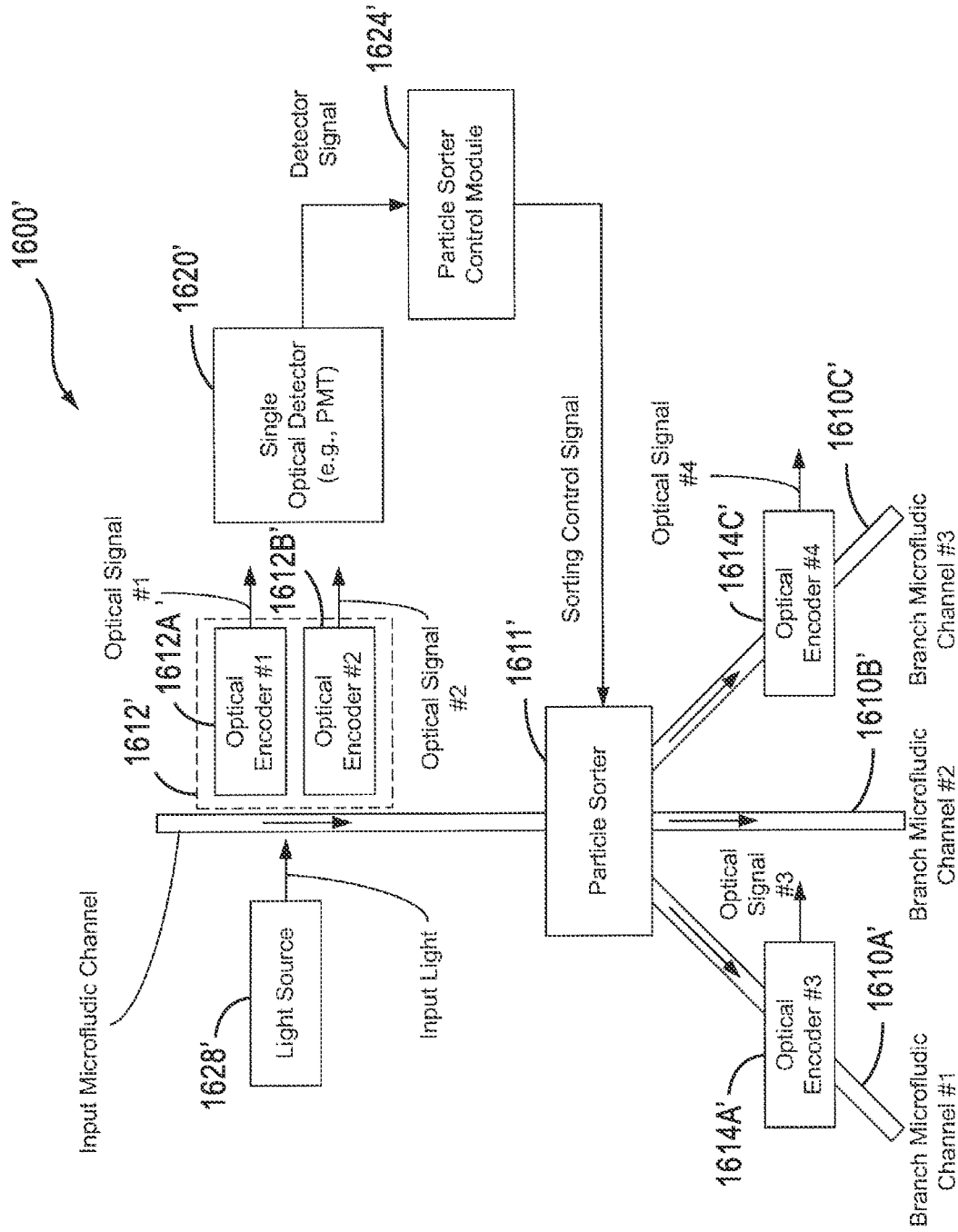

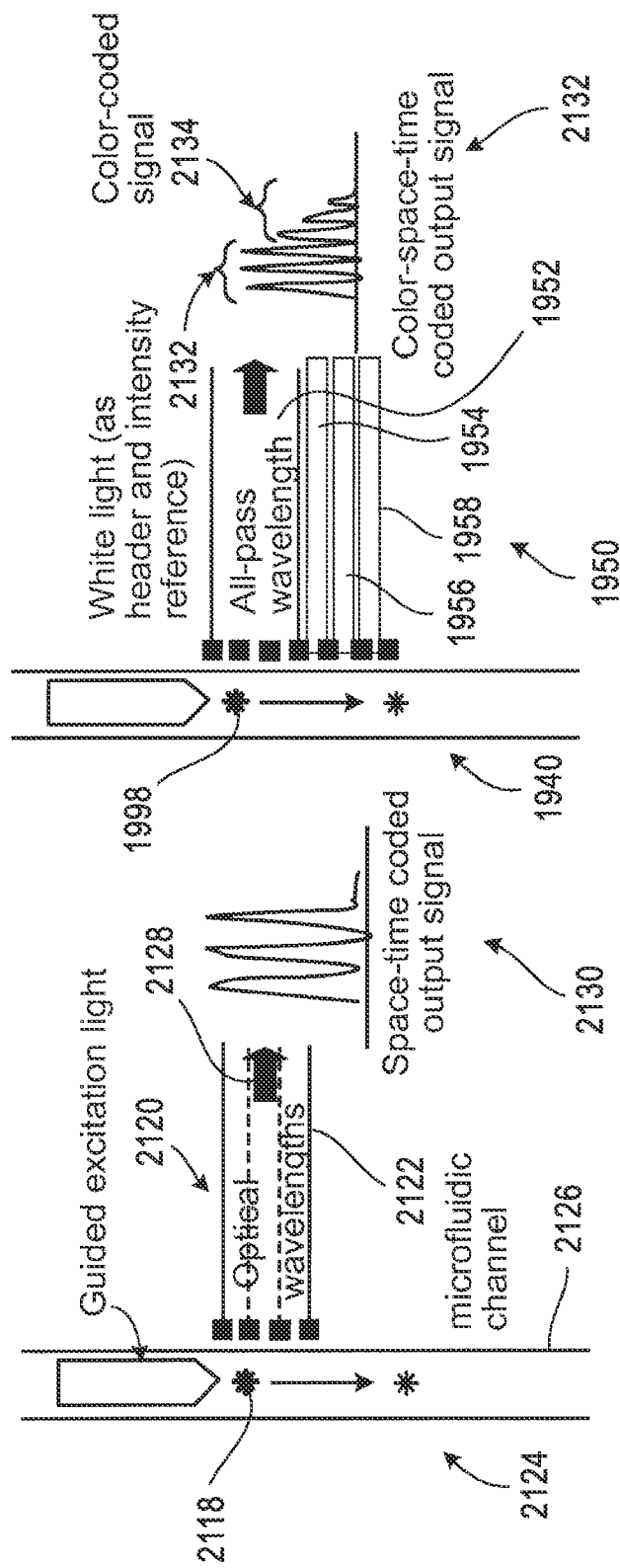

FIG.25
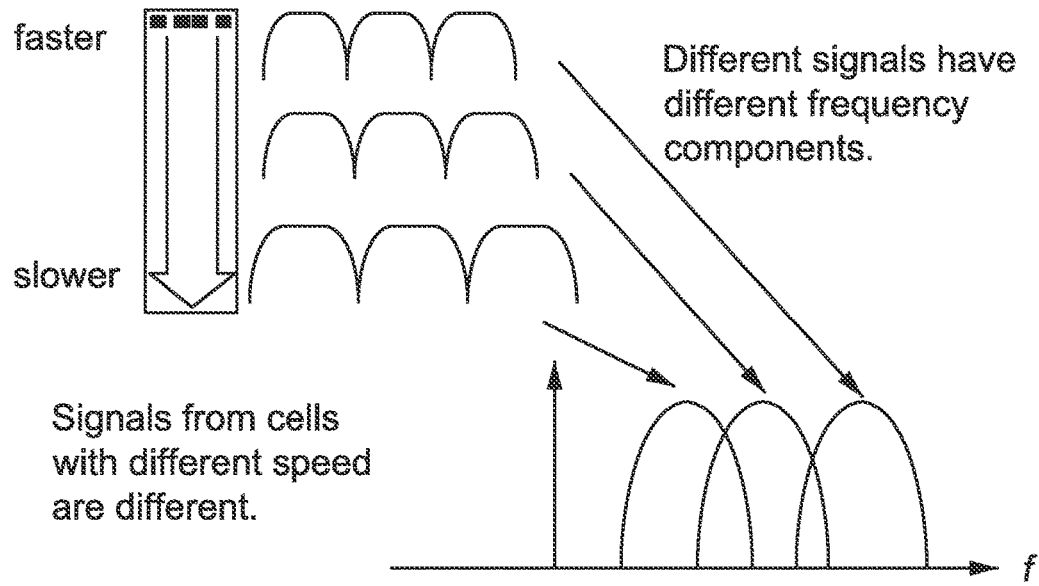
A
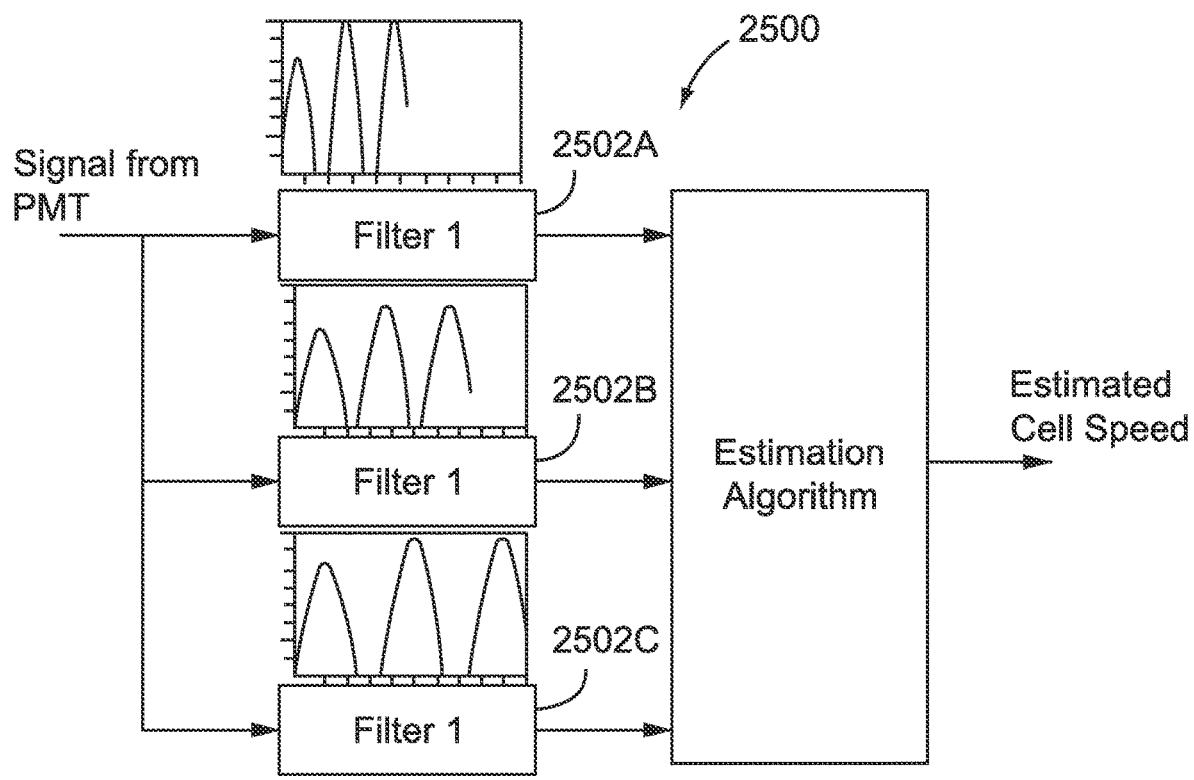
B

C

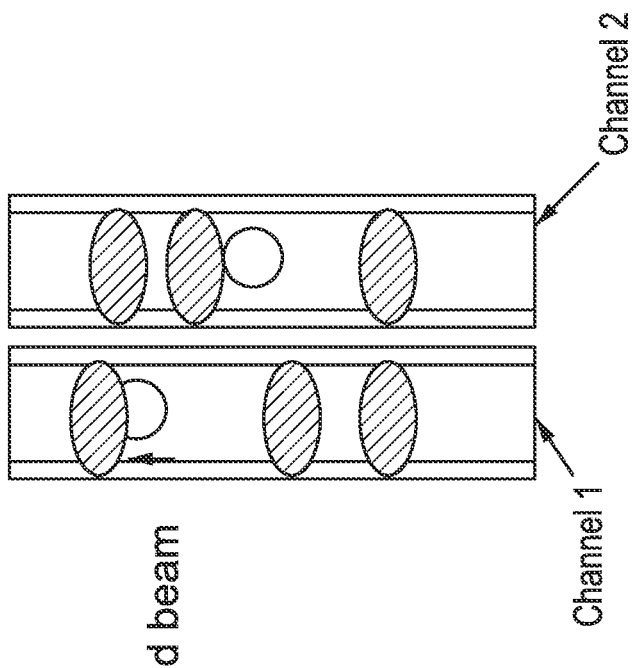
FIG.26A  Top View
Designed beam pattern
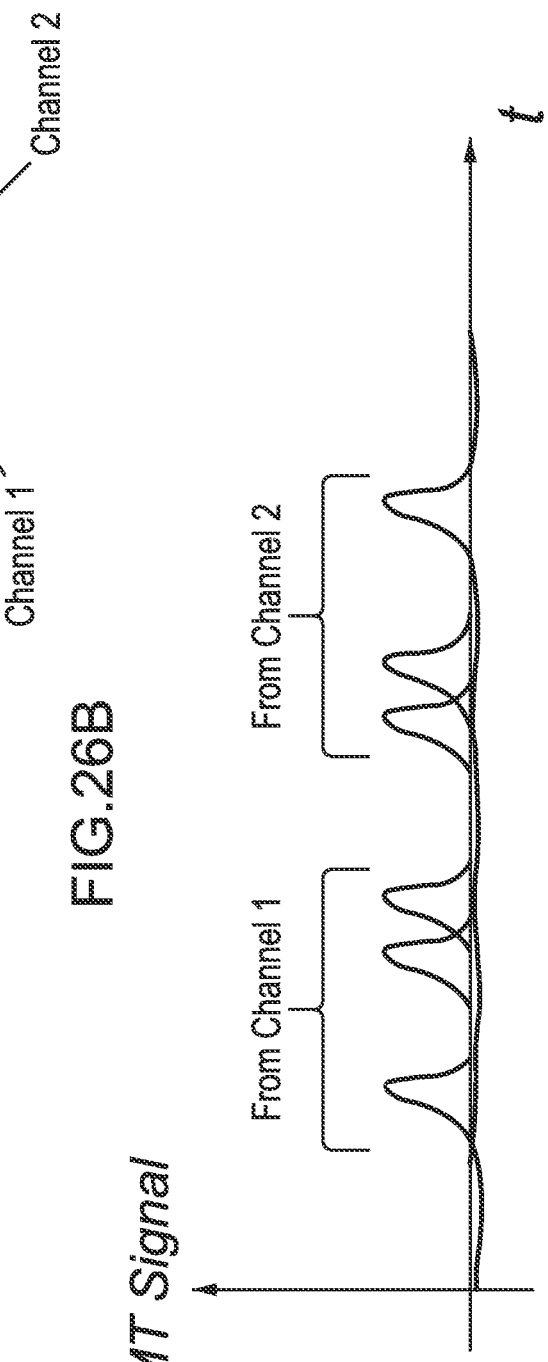
FIG.26B

FIG.39
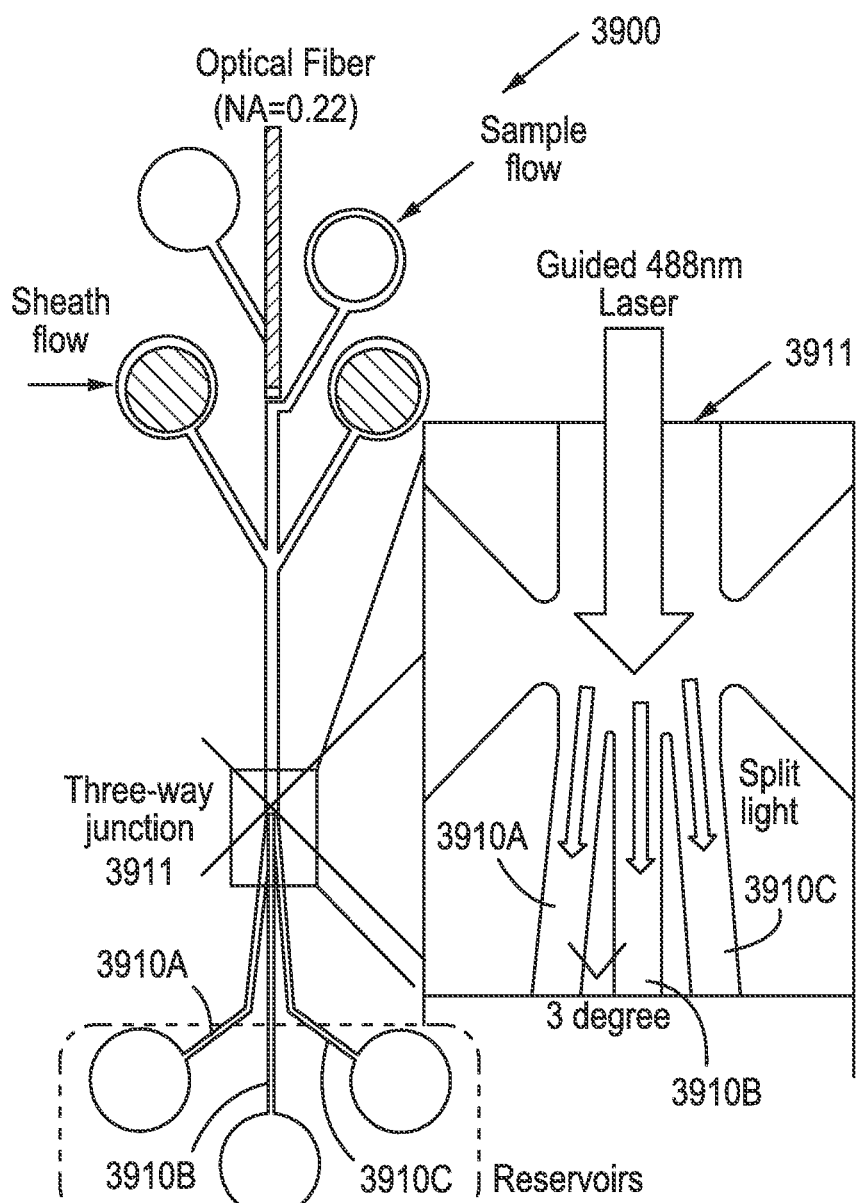

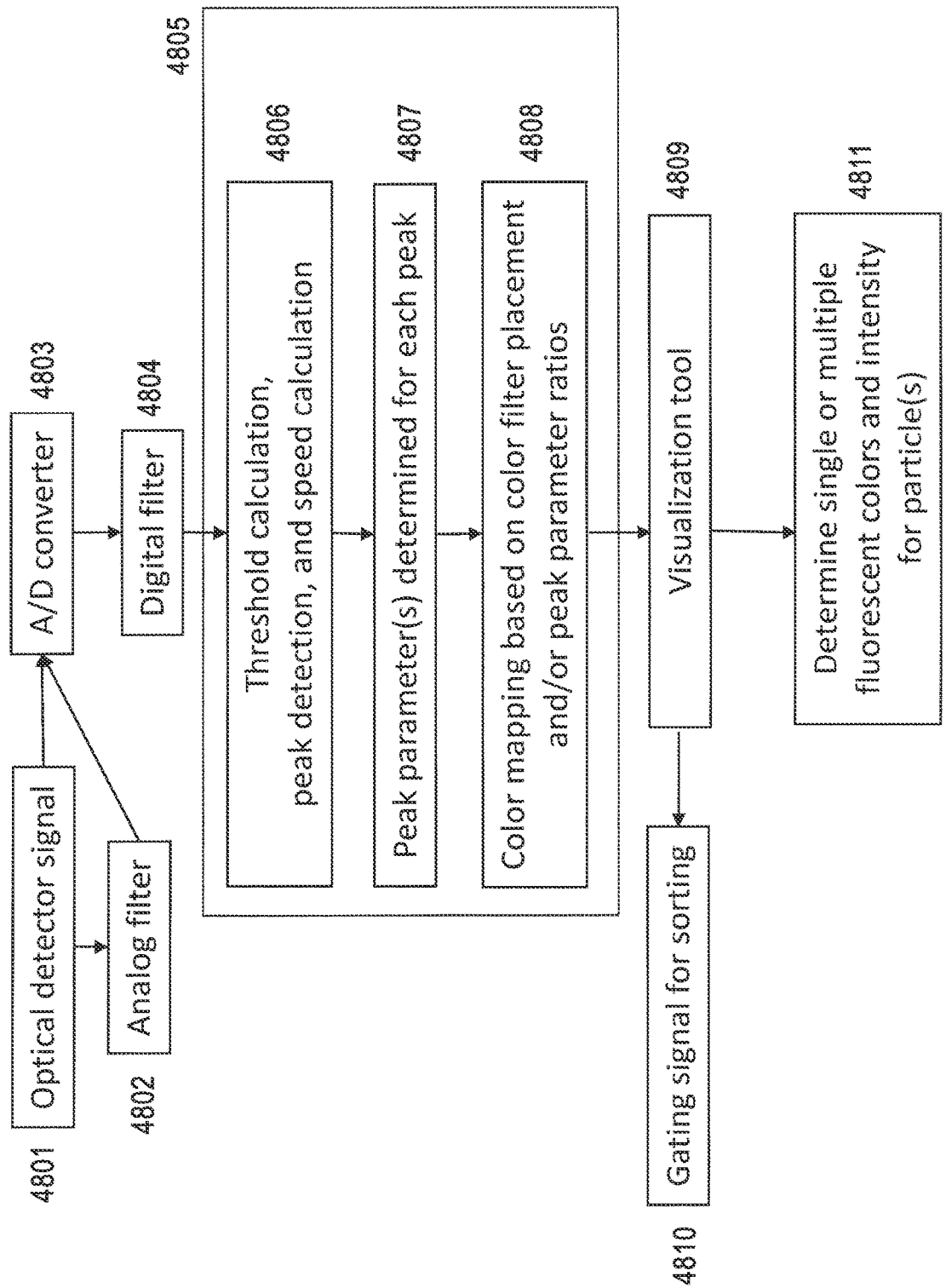

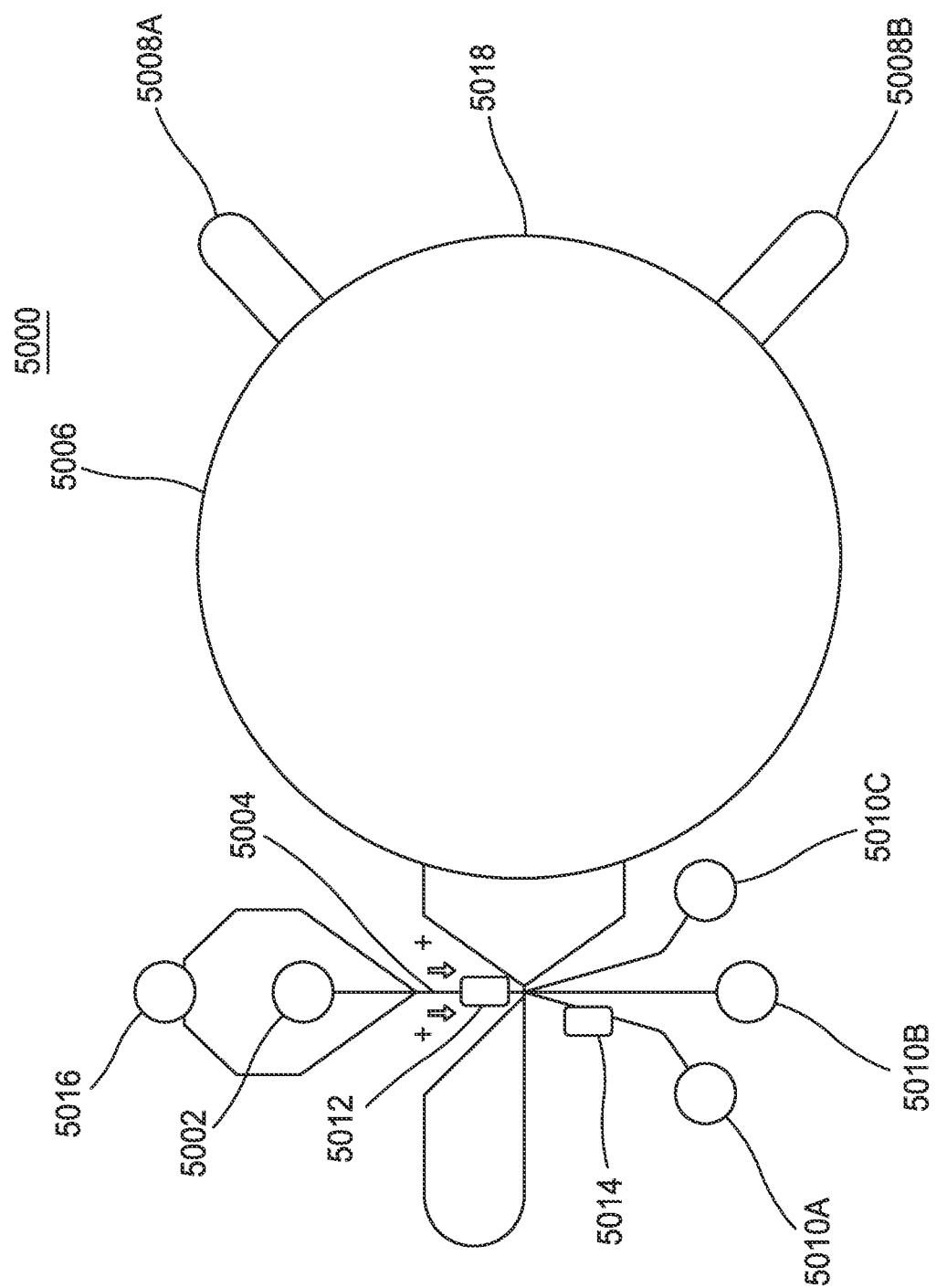

FIG.72
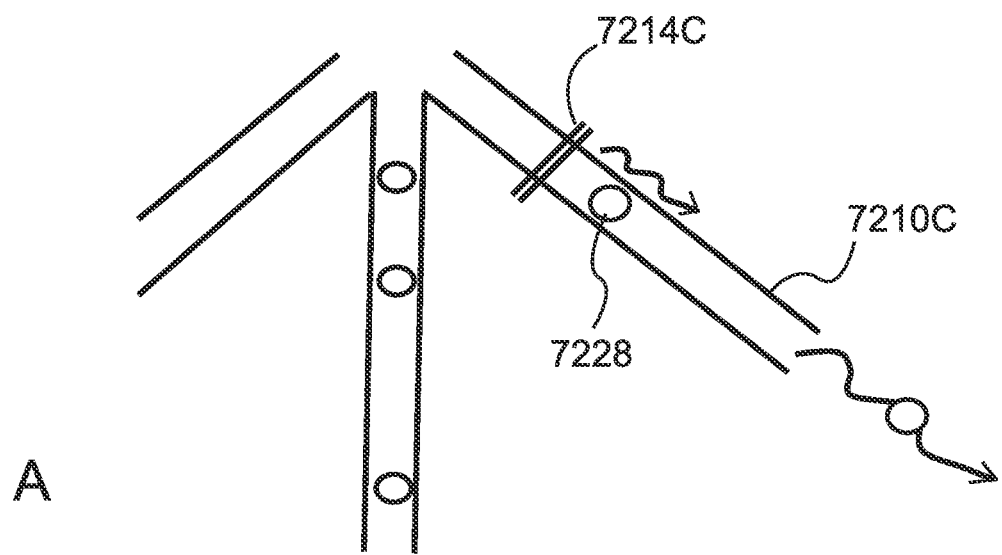
A
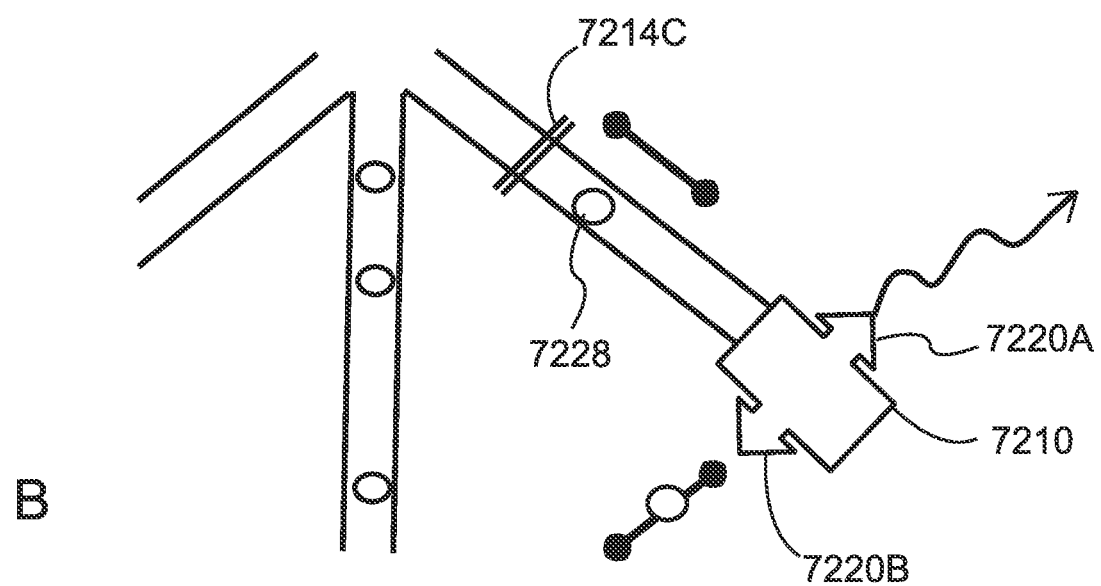
B

SYSTEMS, APPARATUS, AND METHODS FOR SORTING PARTICLES

CROSS-REFERENCE TO RELATED APPLICATIONS

This application is filed pursuant to 35 U.S.C. § 371 as a U.S. National Phase Application of International Application No. PCT/US2013/065111, filed Oct. 15, 2013, which claims priority to U.S. provisional application No. 61/794,015 filed Mar. 15, 2013 and titled "SYSTEMS, APPARATUS, AND METHODS FOR SORTING PARTICLES", and to U.S. provisional application No. 61/714,091 filed Oct. 15, 2012 and titled "CELL DETECTION SYSTEMS AND METHODS", the disclosures of which are incorporated herein by reference in their entirety.

STATEMENT OF GOVERNMENT SUPPORT

This invention was made with government support under grant nos. R44 GM103677, HHSN261201100096C, HHSN261201200072C, and R43 GM103470 awarded by the National Institute of Health. The government has certain rights in the invention.

BACKGROUND

Flow cytometer (FC) devices and systems can be used to characterize and analyze particles in fluid, e.g., physical and biochemical properties of cells, and biochemical molecules or molecule clusters based on their optical responses as they are interrogated by external light sources in a serial manner. Optical signals from such particles can be collected by an optical detector, such as a photomultiplier tube (PMT), and can be analyzed or processed to extract information carried by the optical properties of the particles. The optical signals from the particles can be caused by one or more interactions between the input light and the particles such as forward scattering (FSC), side scattering (SSC), and fluorescence.

Cell sorting can be achieved by various techniques. One example is applying vibrations to jet flow from a nozzle to cause breakage of the jet flow into droplets, and subsequently using electrically charged plates to deflect cell-containing droplets into collection tubes (droplets of no interest flow straight down to a waste tube without deflection).

FC devices and systems can be implemented based on microfluidic technologies for research assays and diagnostics as well as for clinical applications. Microfluidic technologies range from simple microfluidic channels to complex microfluidic devices that can mix fluids, pump fluids, perform digital logic, individually culture cells, and determine optimal reaction conditions, for example. Small-scale fluidic devices have low Reynolds numbers and can be used to achieve controlled laminar flow systems. Microfluidics further offer advantages of small size for miniaturization and parallelization of devices. Additionally, various fabrication processes for microfluidic devices are suitable for mass production which can reduce the cost of such devices. Advances in microfluidic devices can lead to low-cost lab-on-a-chip devices, useful tools to researchers, clinical laboratories, and point-of-care clinicians in remote and/or resource-poor settings.

The field of particle sorting, and cell sorting in particular, has enjoyed a steady growth over the past three decades. Devices such as flow cytometers and cell sorters, and particularly those based on fluorescence activated cell sorting (FACS), have become the gold standard and workhorse for biomedical research and applications. While existing systems attempt to achieve a balance between low cost of operation and advanced cell analysis, few promising commercial developments have been made for flow cytometers with sorting capabilities. As a result, flow cytometers, and particularly those with sorting capabilities, still have a large footprint, are expensive, and technically difficult to manufacture and operate.

In other words, FACS systems have not fundamentally changed since their inception, and as a result, access to FACS is for all practical purposes, limited to shared core facilities at well-funded institutions. Sorting, however, is an important requirement of many applications that can benefit from FACS capabilities, but in a low cost, compact, and easy to operate form. It is against this background that the disclosed systems, apparatus, and methods for sorting particles were developed.

SUMMARY

Provided in certain aspects are methods for detecting the presence, absence or amount of a cell type in a composition. The methods include contacting a composition including cells, which cells include a first cell type and a second cell type, with a detection agent that associates with the second cell type. The methods also include causing the detection agent to emit light, which light from the detection agent is transmitted to a color filter in a detection system, which color filter includes a plurality of zones. The plurality of zones includes color zones, each of which color zones transmits a portion of the light transmitted to the color filter, wherein a first color zone transmits a portion different than the portion transmitted by a second color zone. The plurality of zones also include a zone that transmits light transmitted by two or more of the color zones. Light emitted by the detection agent at different positions in the detection system is effectively transmitted by different zones in the color filter. The methods also include detecting the light transmitted by the zones in the color filter from the detection agent, whereby the presence, absence or amount of the second cell type in the composition is detected.

Also provided, in one embodiment, are flow cytometry systems. In a further embodiment, the flow cytometry systems include a fluidic device including a detection channel, a channel branch downstream of the detection channel, and a piezoelectric membrane in fluid communication with the branch, which piezoelectric membrane is configured to direct a cell that can flow through the branch into one of a plurality of sorting channels downstream of the branch. In further embodiments, the systems also include a lens configured to transmit light from the detection channel to a focal plane on a color filter, which light is emitted by a detection agent associated with a cell when the cell is flowing through the detection channel. In even further embodiments, the systems further include a detector configured to detect light emitted by the color filter and generate a signal associated with the light detected. In even further embodiments, the systems also include a controller configured to process the signal generated by the detector and control actuation of the piezoelectric membrane. The system, in one embodiment, is capable of isolating about 28% or more, or about 40% or more, of a relatively rare cell present in a composition containing a relatively rare cell type and a relatively abundant cell type.

In one embodiment, systems, apparatus, and methods for sorting particles are provided and described herein. In one aspect, a method for verification of sorting particles is provided. In one embodiment, a method for verification of sorting of particles includes receiving a first detection signal that is associated with optical characteristics of a particle in a first channel. In a further embodiment, the method includes determining a sorting channel of a plurality of second channels based on the first detection signal, thereby determining the sorting of the particle into the sorting channel based on the optical characteristics of the particle. In a further embodiment, the method includes transmitting a sorting signal for sorting the particle from the first channel into the sorting channel. In even a further embodiment, the method includes receiving a second detection signal associated with the presence of the particle in the sorting channel. In one embodiment, the method for verification of sorting of particles also includes verifying the sorting of the particle from the first channel into the sorting channel based on the second detection signal. In one embodiment, the particles are beads or cells.

In another aspect of the invention, a method of feedback based counting of particles is provided. In some embodiments, the method of feedback-based counting of particles includes receiving a plurality of first detection signals, each first detection signal associated with optical characteristics of a particle in a first channel. The method, in one embodiment, further includes determining a first number of particles in the first channel based on the plurality of first detection signals. The first number of particles have similar optical characteristics. In a further embodiment, the method includes determining a sorting channel of a plurality of second channels based on the first detection signals, thereby determining the sorting of all the first number of particles into the sorting channel based on the similar optical characteristics of the first number of particles. In one embodiment, the method further includes transmitting a sorting signal for sorting each particle of the first number of particles from the first channel into the sorting channel, and receiving a plurality of second detection signals. Each second detection signal is associated with the presence of a particle in the sorting channel. In one embodiment, the method further includes determining a second number of particles in the sorting channel based on the plurality of second detection signals. In one embodiment, the method further includes receiving a plurality of third detection signals, each third detection signal associated with optical characteristics of an additional particle in the first channel. In one embodiment, the method also includes determining a third number of particles in the first channel based on the plurality of third detection signals, based on the determined first number of particles and based on the determined third number of particles.

In another aspect of the invention, the present invention provides a method of sorting particles. In some embodiments, the method of sorting of particles includes receiving a first detection signal that is associated with first optical characteristics of a particle in a first volume of a first channel. The method also includes, in one embodiment, receiving a second detection signal that is associated with second optical characteristics of the particle in a second volume of the first channel. The method also includes, in one embodiment, determining a sorting channel of a plurality of second channels based on one or more of the first detection signal and the second detection signal, thereby determining the sorting of the particle based on one or more of the first optical characteristics and the second optical characteristics of the particle. The method further includes, in one embodiment, transmitting a sorting signal for sorting the particle from the first channel into the sorting channel.

In yet another aspect, an apparatus for the sorting of particles is provided. In one embodiment, the apparatus includes a first detection module configured to receive a first detection signal associated with one or more optical characteristics of a particle in a first channel. In one embodiment, the apparatus also includes a sorting module configured to determine a sorting channel of a plurality of second channels based on the first detection signal, thereby determining the sorting of the particle based on the one or more optical characteristics of the particle. The sorting module is further configured to transmit a sorting signal for sorting the particle from the first channel into the sorting channel. In a further embodiment, the apparatus includes a second detection module configured to receive a second detection signal that is associated with the presence of the particle in the sorting channel. In a further embodiment, the apparatus includes a verification module configured to verify the sorting of the particle from the first channel into the sorting channel based on the second detection signal. In one embodiment, at least one of the first detection module, the sorting module, the second detection module, and the verification module is implemented in one or more of a memory and a processing device.

BRIEF DESCRIPTION OF THE DRAWINGS

FIGS. 3A-3C illustrate design and fabrication of a hydrodynamic microfluidic device, according to an embodiment. FIG. 3A illustrates a transparency mask of alpha spiral structures of the hydrodynamic microfluidic device, according to an embodiment. FIG. 3B illustrates a transparency mask of beta spiral structures of the hydrodynamic microfluidic device, according to an embodiment. FIG. 3C illustrates a PDMS prototype device loaded with dye to visualize the channels.

FIGS. 4A-4C illustrate testing of a hydrodynamic microfluidic device loaded with three different sized microbeads (7.6 µm, 10.5 µm, and 25 µm diameter). FIG. 4A illustrates normalized particle number and beads/microliter at a flow speed of 400 pl/min. FIG. 4B illustrates normalized particle number and beads/microliter at a flow speed of 1 ml/min. FIG. 4C illustrates normalized particle number and beads/microliter at a flow speed of 1.5 ml/min.

FIG. 8A shows flow cytometry analysis of EpCAM labeling of approximately 10,000 HeLa cells.

FIG. 8B shows flow cytometry analysis of EpCAM labeling of approximately 10,000 MCF-7 cells.

FIGS. 8C, 8D shows flow cytometry analysis of EpCAM labeling of approximately 10,000 MCF-7 GFP cells. FIG. 8C shows GFP positive MCF7 that were not treated with anti-EpCAM antibodies. Cells in FIGS. 8C and 8D were gated to differentiate between GFP positive and GFP/EpCAM positive signals after mixing.

FIG. 9A shows EpCAM-PE antibody added to MCF-7s (10,000/µl) at 1:25 with no agitation or mixing and assayed at 0, 5, 15 and 30 minute time points. FIG. 9B shows EpCAM-PE antibody added to MCF-7s at 1:25 and passed through the on-chip mixing structure.

FIG. 10A illustrates design of a microfluidic detector, according to an embodiment. FIG. 10B shows a manufactured microfluidic detector made of PDMS, and a quarter is placed alongside for size comparison. FIG. 10C shows a chip cartridge for insertion and rapid exchange of a new chip.

FIG. 11 illustrates a fluidic dynamic simulation, according to an embodiment. The left panel shows a 3D COMSOL simulation showing the sheath flow streamline (150 µm wide) and the sample streamline (50 µm wide). The sample flow is centered laterally and vertically. The right panel shows a sample flow visualized from the side showing a focused sample flow horizontally and vertically.

FIGS. 12A, 12B illustrate alpha microfluidic detector sensitivity and sorting, according to an embodiment. In FIG. 12A, using a 488 nm laser with 20 mW power output and off-the-shelf optics, sensitivity to detect GFP-positive MCF-7 cells (middle panel) or cells labeled with PE-conjugated EpCAM antibody (right panel) is achieved. FIG. 12B shows a microfluidic sorting junction as visualized using a high speed CMOS camera and rhodamine dye in the sample. As the PZT actuator surface bends downwards (e.g., pushing the fluid in the chamber), the rhodamine stream is switched to the left channel, as successively illustrated starting with panel 1, to panel 6.

FIGS. 13A, 13B shows the viability of cells after passage through a spiral enrichment structure (FIG. 30A) and a microfluidic detector (FIG. 30B). FIG. 13A shows viability of MCF7 cells after being pumped through a microfluidic spiral enrichment structure (after-Spiral) or kept in buffer (Control). Propidium Iodide was then added and cells viability was analyzed by flow cytometry. FIG. 13B shows viability of rat cardiomyocytes that were sorted using a commercial FACS or a microfluidic detector as disclosed herein. Cells were then stained with trypan blue to measure cell viability.

FIG. 16B illustrates a microfluidic detector, according to an embodiment.

FIG. 21A is a schematic illustration of space-time coding operation of a microfluidic detector, according to an embodiment.

FIG. 21B is a schematic illustration of a Color-Space-Time (COST) coding operation of a microfluidic detector of FIGS. 19A-20C.

FIG. 25A illustrates how particles (e.g., cells with fluorophores or quantum dots) with different speeds generate different signals in time and frequency domains. FIG. 25B illustrates how a Filter-bank architecture can be applied to estimate the speed of each individual particles by matching its signal waveform to different filters in the filter-bank. FIG. 25C illustrates a processing example.

FIGS. 26A and 26B illustrate an exemplary signal encoding structure (FIG. 26B) in fluidic channels (FIG. 26A) for a microfluidic detector.

FIG. 28 illustrates the scenario where no sorting occurs (no membrane movement). FIG. 28 illustrates the scenario where the particle is sorted into channel 116C (upward bending). FIG. 28 illustrates the scenario where the particle is sorted into channel 116A (downward bending).

FIG. 29A illustrates a particle traveling directly from the main/source channel to the waste-collection channel because the piezoelectric membrane does not move. FIG. 29B illustrates a particle being sorted out to the sorting channel on the right when the piezoelectric membrane is deflected upward on receiving a sorting triggering signal. FIG. 29C illustrates a particle being sorted out to the sorting channel on the left when the piezoelectric membrane is deflected downward on receiving a sorting triggering signal.

FIG. 39 illustrates a layout of a device where light can be split and guided at the 3-way junction, and a photograph of the device fabricated in PDMS.

FIG. 48 is a method for deciphering the fluorescent color of a sample from the COST signal, according to an embodiment.

FIG. 49A illustrates an exemplary 4-slit spectral filter. FIG. 49B illustrates an exemplary continuously graded COST filter.

FIG. 50 is an illustration of a particle sorter, according to an embodiment.

FIG. 69A, FIG. 69B illustrate normalized signature waveforms for fluorophore 1 and fluorophore 2, respectively. FIG. 69C illustrates light intensity from fluorophore 1 and fluorophore 2 obtained from (Eq. 5). The COST filter is assumed to consist of two slits of all-pass window followed by a color filter with a continuous transmission spectrum from red to green color.

FIGS. 72A, 72B illustrate the modification of a sorting channel of a particle sorter (FIG. 72A) with a post-sort valve (FIG. 72B), according to an embodiment.

DETAILED DESCRIPTION

As used in this specification, the singular forms "a," "an" and "the" include plural referents unless the context clearly dictates otherwise. Thus, for example, the term "a device" is intended to mean a single device or a combination of devices.

As used in this specification, the term "particle" refers to any entity deemed to have at least one characteristic on the basis of which it can be sorted. Accordingly, the term particle includes, but is not limited to, organic particles, inorganic particles, hybrid particles having organic and inorganic components, and/or the like. The particle is of any suitable size and form, including, but not limited to, beads, nanoparticles, microparticles, and/or the like. The term particle also includes biological entities, such as one or more cells (including mammalian and non-mammalian cells), bacteria, viruses, and/or the like. The term particle can refer to a rare cell type, or an abundant cell type.

As used in this specification, the terms "particle sorter", "cell sorter", "particle detector", "cell detector", "particle analyzer", "cell analyzer", "microfluidic sorter", microfluidic detector", and variants thereof, can be used interchangeably, and can encompass the others. For example, a particle sorter can include particle detector, and a cell detector can include a cell sorter.

As used in this specification, the terms "rare cell", "relatively rare cell", "relatively rare cell type", and variants thereof, when used to describe a cell subpopulation in a composition having two or more cell types, indicates that there is at least one other cell type that is present in greater number in the composition than the relatively rare cell type. As used in this specification, the term "abundant cell", "relatively abundant cell", "relatively abundant cell type", and variants thereof, when used to describe a cell subpopulation in a composition having two or more cell types, indicates that there is at least one other cell type that is present in smaller/lesser number in the composition than the relatively abundant cell type.

When a composition of cells is described as having both a "relatively rare cell type" and a "relatively abundant cell type", it is indicated that the composition contains the relatively abundant cell type in greater number than the relatively rare cell type. In other words, the composition can still still contain other cell type(s) that are present in greater number than the relatively abundant cell type and/or other cell type(s) that are present in smaller/lesser number than the relatively rare cell type.

Figure 1:
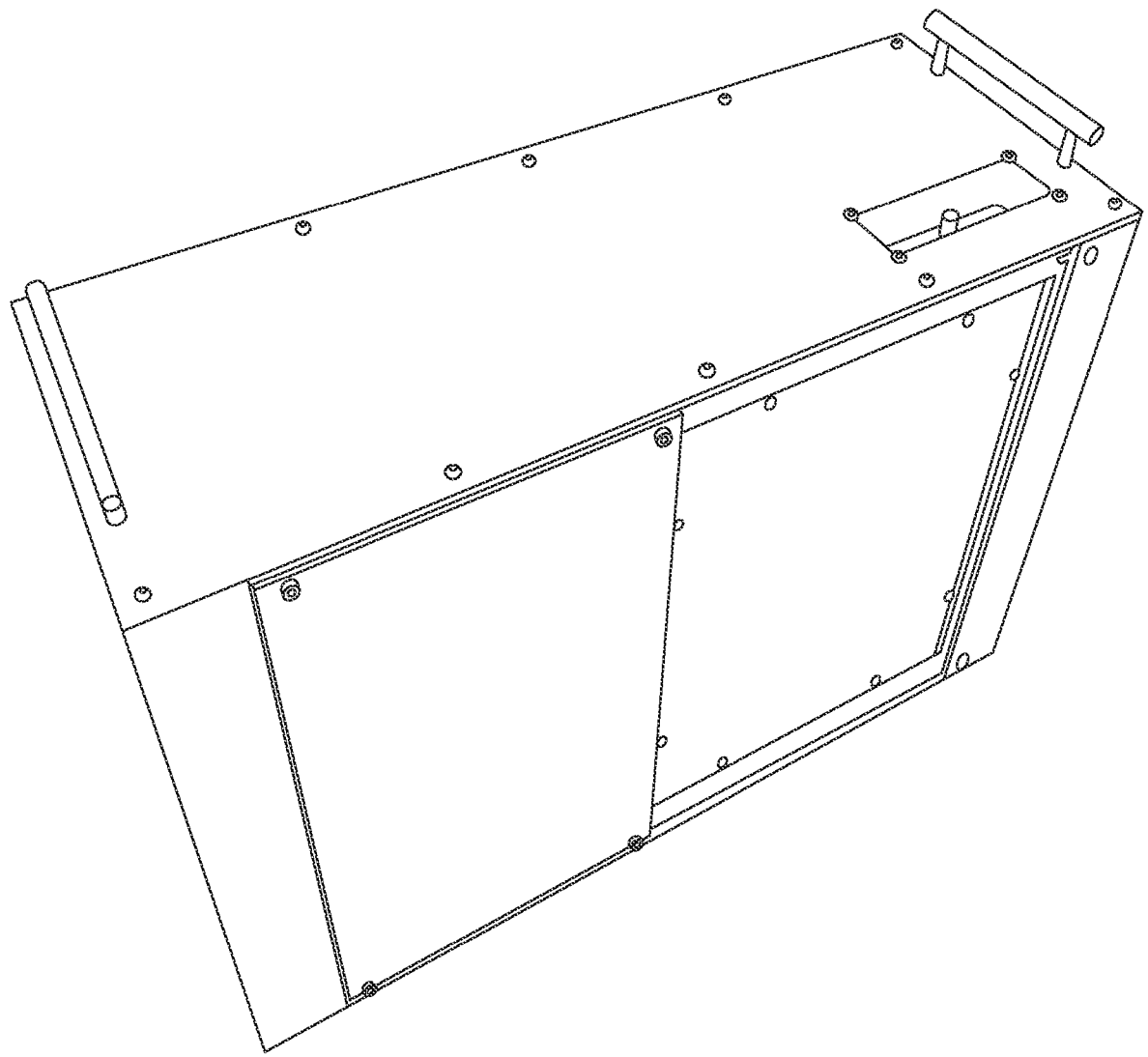
FIG. 1 is an illustrative design of a cell analyzer and sorter.

Some embodiments disclosed herein are operable for interrogation of single particles to determine particle characteristics, where particles with particular characteristics need to be isolated, for follow-up analyses, for example. Advantageously, embodiments disclosed herein are operable to perform this function while reducing the size, cost, and complexity of manufacture and/or operation associated with prior art systems. FIG. 1 illustrates an exemplary embodiment of the modular nature of a particle analyzer and sorter of the invention. With particular reference to cell sorting, embodiments disclosed herein can serve the growing needs for isolation of selected cell subpopulations based on the optical detection of cell properties and/or biological markers.

Current techniques to evaluate multiple biological markers are impractical for rapid results, highly expense, complex, and usually have poor sensitivity. The gold standard assay for detection of low abundant proteins is the enzyme-linked immunosorbent assay (ELISA). ELISA is able to detect proteins in the low ng/mL range and high sample throughput but lacks the ability to be able to detect multiple analytes per sample. Other technology platforms, such as those based on mass spectrometry, have shown some initial success in multiplexing (detecting many proteins per sample) but have moderate sample throughput and detection limits.

Additionally, mass spectrometry approaches are only suitable for proteins/peptides. One known optical approach in the art include a flow cytometry platform that uses a "two-color code" with fluorescent microparticles linked to antibodies combined with a different fluorophore attached to another antibody per analyte. However, such a dual-color code approach requires multiple lasers and optical detectors that make the system bulky and expensive. This is a major drawback that results in a large footprint and high cost of instrumentation.

Additionally, embodiments disclosed herein provide complete systems for particle processing and can encompass, on a microfluidic scale, sample enrichment (e.g., via spiral enrichment structures, described later), sample mixing (e.g., via serpentine mixing structures, described later), sample/particle sorting (e.g., via optical-based particle sorters and piezoelectric actuation), verification of sorting (e.g., via impedance-based sensors), feedback-based optical sorting (e.g., via hybrid optical/impedance based systems). Embodiments described herein can further provide integrated reagent supplies and mixing with samples (e.g., on-chip reagents for pre-sort/post-sort mixing). Embodiments described herein can further provide for optimizing sorted particle collection volumes (e.g. the use of post-sort valves).

Embodiments described herein further provide optical systems and improved methods for particle detection (e.g., the COST method). Exemplary embodiments described herein further provide for improved systems for particle detection that can include color compensation (e.g., when a particle fluoresces at two or more wavelengths) as well as approaches for improving dynamic range in single detector systems.

As a non-limiting example, a sample enrichment structure can receive a sample (e.g. blood), and provide an enriched sample as input to a mixing structure for adding reagents to the enriched sample (e.g., fluorescent markers), from (in some embodiments) an on-chip reagent supply, for example. The mixing structure can provide the sample mixture containing particles to be sorted to the input port of a source channel. An optical detection mechanism (e.g., the COST setup/method as disclosed herein) can detect the particles, and a sorting mechanism can sort the particles based on the optical detection mechanism. A verification mechanism can ensure the particle was properly sorted, and can be used to provide feedback to the sorting mechanism.

In some embodiments, the optical detection mechanism can account for color compensation, and/or can be configured for increasing the dynamic range of a single detector associated therewith. In some embodiments, a post-sort mechanism (e.g. a valve) can be formed in each destination channel to control the volume associated with the sorted particle, based on timing information received from the verification mechanism.

Systems, apparatus, and methods for sorting particles are described herein. In some embodiments, a particle is sorted from a first channel into one of several second channels based on optical characteristics of the particle, as measured by a first detection signal. In some embodiments, the sorting of the particle into the second channel is verified by a second detection signal associated with the presence and/or volume of the particle in the second channel. Aspects of this disclosure hence enable verifying that the optical characteristics of the particle were correctly identified, that the number of particles sorted into each sorting channel was correct, that the particle was correctly sorted, and/or the like. Aspects of this disclosure are further operable to use the verification information for further analysis, such as for feedback control of the sorting, for characterizing the sorted particles, and/or the like.

Circulating tumor cells (CTCs) that can invade, colonize and proliferate in distant sites can be considered as markers for the metastatic malignancy of a given tumor. CTCs collected from peripheral blood or bone marrow hold the promise as "liquid biopsy" to biologically characterize the patient's cancer at the DNA, mRNA, and/or protein level. In conjunction with enumeration of CTCs, such analysis at the molecular level can reveal important information about the nature of metastatic disease, diagnosis and prognosis of a neoplasm, progression of treatment, and development of the most effective, personalized cancer therapy (e.g., chemotherapy).

Flow cytometry (or FACS) can allow for rapid, highly specific, quantitative cell-by-cell analysis by multiple parameters, as well as the ability to sort CTCs for further molecular characterization. Additionally, flow cytometry is a mature, well-recognized, and commercially-viable technology. However, several obstacles make current flow cytometers impractical for point-of-care analysis of CTCs due to their complexity, size, and high costs. Provided here, in some embodiments, is a microfluidic technology that allows for the detection and/or capture of specific cell types/subpopulations (e.g., CTCs) in a composition of a plurality of cell types using, in some embodiments, a closed disposable chip ideal for clinical applications because of reduced risk of contamination and/or carryover.

In some embodiments, a micro cell detection system is described herein including a lab-on-a-chip microfluidic detector that can provide on-chip antibody labeling, enumeration, and sorting of cell populations (e.g., CTCs) suitable for downstream molecular analysis. In some embodiments, a micro cell detection system including a lab-on-a-chip microfluidic detector can provide sorting, detection and/or collection of live (e.g., viable) cell populations, and/or cell subpopulations (e.g., relatively abundant cell types, relatively rare cell types, specific cell types such as CTCs, and/or the like). In some embodiments, a micro cell detection system can include (i) an enrichment structure, (ii) a mixing structure, and (iii) a microfluidic detector. In some embodiments, a cell detection system includes (i) a first-stage cell separation/cell enricher, (ii) a fluid-dynamic assisted mixer and (iii) a bench-top micro-FACS (e.g., a microfluidic detector) for cell isolation.

In some embodiments, a detector system described herein can be a cost-effective, easy-to-use, rapid, and reliable technology and methodology to (1) enumerate (e.g., enrich) and (2) isolate cell subpopulations (e.g., relatively rare cell types/rare cell populations, e.g., CTCs) from whole blood. Detector systems described herein have advantages over conventional FACS systems that are 5-10 times more expensive, complicated to use, and are very large. In some embodiments, a detector system can provide for (1) enrichment of a cell population (e.g., specific cell types, CTCs) by about 100-fold or more (e.g., about 400-fold) utilizing an enrichment structure, (2) labeling of an enriched cell type or enriched cell population with a binding agent (e.g., an antibody) in less than 2 minutes using a mixing structure, and (3) detecting and/or isolating a labeled cell with a recovery rate of about 28% or greater, or about 30% or greater, or about 40% or greater, or from about 28% to about 90%, or from about 28% to about 80%, or from about 28% to about 70%, or from about 28% to about 60%.

Enrichment Structure

In some embodiments, an enrichment structure is provided that can sort, separate and/or collect a first cell type (e.g., CTCs) from a population of cells (e.g., white blood cells). Cell enrichment can refer to sorting, separating and/or collecting a specific cell type (e.g., a relatively rare cell type, or a relatively abundant cell types) from a population of cells that are different than the specific cell type, such as a composition that includes the first cell type and a second cell type. A specific cell type can be a rare cell type, in some embodiments. A specific cell type can be differentiated from other cell types by a physical or biological property (e.g., phenotype, genotype) of a cell. For example, a specific cell type can be differentiated by size, mass, granularity, deformability, polarizability, one or more cell surface markers (e.g., presence or absence of a cell surface molecule), one or more intra-cellular markers (e.g., presence or absence of an intra-cellular molecule, DNA, RNA, protein, a protein modification) and/or function (e.g., a cellular metabolic function, enzymatic function), the like or combinations thereof. In some embodiments, enrichment of cells is provided by an enrichment structure. A suitable cell enrichment structure known in the art can be used in a micro cell detection system.

Non-limiting examples of a technology or device that can be used as a cell enrichment structure include: membrane microfiltration, pinched flow fractionation, deterministic lateral displacement, hydrophoresis, dielectrophoresis (DEP), immunomagnetic-based isolation, asymmetric bifurcation of laminar flow around obstacles (Huang L R, et. al., Science. 2004 May 14; 304(5673):987-90), a massively parallel micro-sieving device (Mohamed H, et. al., IEEE Trans Nanobioscience. 2004 December; 3(4):251-6), biomimetic autoseparation (Shevkoplyas S S, et. al., Anal Chem. 2005 Feb. 1; 77(3):933-7), passively driven microfluidic separation (Cho B S, et. al. Anal Chem. 2003 Apr. 1; 75(7):1671-5), adhesion-based cell separation, microscale laminar vortices, spiral channels, the like or combination thereof. In some embodiments, an enrichment structure can include fluidic channels. In some embodiments an enrichment structure can be embedded on, attached to or embodied on a chip (e.g., a lab-on-a-chip, or the like).

Spiral Enrichment Structure

In some embodiments, a cell enrichment structure is a hydrodynamic microfluidic structure including a spiral channel structure herein termed a spiral enrichment structure for use in separating and enriching cell subpopulations. In some embodiments, a spiral enrichment structure can be embedded on a chip (e.g., a lab-on-a-chip, or the like). In some embodiments, a spiral enrichment structure can be used to separate cells and/or particles based on physical properties such as size, shape, mass and/or density. In some embodiments, a spiral enrichment structure can separate a first cell type having a first size from a second cell type having a second size. In some embodiments, a spiral enrichment structure can be used for separating a relatively rare cell type (e.g., circulating tumor cells) from a solution of other, relatively abundant cell types (e.g., white blood cells, non-informative cells, and/or the like). In some embodiments, a spiral enrichment structure can be used for enriching a rare cell type relative to a more abundant cell type in a composition containing the rare cell type and the abundant cell type. The spiral design can take advantage of the inertial lift and viscous drag forces acting on cells of various sizes to achieve differential migration, and hence separation, of cells. Dominant inertial forces and Dean rotation forces, due to a spiral fluidic channel geometry, can cause larger cells to occupy a single equilibrium position near an inner fluidic channel wall while smaller cells migrate to the outer half of a fluidic channel under the influence of Dean forces resulting in the formation of distinct particle streams which can be collected in separate outlets. In some embodiments, due to large lift forces generated by high aspect ratio channels, complete cell separation or filtration can be achieved in short distances of spiral channels, even at low flow rates. Various embodiments of a spiral enrichment structure are described in more detail herein.

In some embodiments, a spiral enrichment structure can include one or more inner inlets, a fluidic channel arranged in a plurality of circular loops, and two or more outer outlets. Some or all features of an enrichment structure can be fabricated from a suitable micro-fabrication material, non-limiting examples of which include a poly-dimethylsiloxane (PDMS) material, a polymethylmethacrolate (PMMA) material, polycarbonate (PC) material, and/or cyclic olefin copolymer (COC) material, the like, or combinations thereof.

In some embodiments, a first inner inlet can be configured to receive a cell-laden solution that contains cells of various sizes (e.g., CTCs and white blood cells) and a second inner inlet is configured to receive a buffer. In some embodiments, one or more inner inlets can be connected to ports or other coupling devices (e.g., configured to mate with a syringe) to allow a solution to enter a spiral enrichment structure. In some embodiments, one inlet can be provided. In some embodiments, two or more inlets can be provided.

In some embodiments, an inner inlet and an outer inlet can be fluidly coupled to a spiral fluidic channel that is arranged in a plurality of loops. In some embodiments, a fluidic channel can be of a substantially quadrilateral (e.g., rectangular, parallelogram, rhomboid, kite, trapezoid) cross section, having two first walls and two second walls. In some embodiments, the first walls define a width of the fluidic channel, and (n some embodiments) the second walls define a height of the fluidic channel. In some embodiments, a fluidic channel is substantially circular or oval in cross section. In some embodiments, a fluidic channel includes a portion that is substantially rectangular in cross section and a portion that is substantially circular or oval in cross section. In some embodiments, a fluidic channel having a substantially circular or oval cross section is defined, in part, by an internal diameter and/or radius.

In some embodiments, an inner outlet and an outer outlet are located at opposite ends of a spiral fluidic channel. In some embodiments, separated cells are collected, detected, counted or otherwise analyzed at the inner and/or outer outlets. In some embodiments, separated cells are collected, detected and/or counted at or near an outer outlet. In some embodiments, cells of different sizes are collected at or near one or more outer outlets.

Without being limited by theory, fluid flowing through a spiral fluidic channel (e.g., a spiral enrichment structure) experiences centrifugal acceleration directed radially outward leading to the formation of two counter-rotating vortices known as Dean vortices in the top and bottom halves of the channel. The magnitude of these secondary flows can be quantified by a dimensionless Dean number (De) shown in FIG. 2C, where p is the density of fluid medium (kg/m$_3$), U$_f$ is the average fluid velocity (m/s), µ is the fluid viscosity (kg/m-s). R is the radius of curvature (m) of the path of the spiral fluidic channel, and Re is the flow Reynolds number. For a straight fluidic channel, De=0, indicating absence of Dean flows. In curved channels. De increases with higher curvature (smaller R), larger channel size (larger D$_h$), and faster flows (higher Re). Cells flowing in a curvilinear channel experience a drag force due to the transverse Dean flows. Depending on particle size, this drag force, also know as Dean force ($F_D$) shown in FIG. 2C, can cause cells to move along the Dean vortices (i.e., circulate), and thus move towards either the inner or outer channel wall.

In addition to the Dean force $F_D$, cells in a curvilinear channel experience pressure forces and inertial lift forces. The net lift force (FL) acting on a cell is a combination of the shear-induced inertial lift force and the wall-induced inertial lift force. In Poiseuille flow, the parabolic nature of the velocity profile results in a fluidic shear-induced inertial lift force that acts on cells and is directed away from the fluidic channel center. As the cells move towards fluidic channel walls, an asymmetric wake induced around cells generates a wall-induced inertial lift force away from the wall. The magnitude of these opposing lift forces varies across fluidic channel cross-section, with the wall-induced lift forces dominating near the fluidic channel walls (e.g., inner wall and outer wall) and the shear-induced lift forces dominating near the center of the fluidic channel. The cells thus tend to occupy equilibrium positions where the oppositely directed lift forces are equal and form narrow bands.

In some embodiments, the size dependence of the forces that act on cells flowing in a spiral fluidic channel, namely the Dean force and the inertial lift forces, is manipulated to produce a focused stream of cells of a similar size. The cells, in one embodiment, are referred to as first cells of a first size. In some embodiments, cells not of the first size continue to circulate within the Dean vortices. The spiral geometry of the spiral enrichment structure can, in some embodiments, cause bigger cells to occupy a single equilibrium position near the inner fluidic channel wall and smaller cells experience higher viscous drag due to the Dean flows and will continue to re-circulate along the Dean vortices and can be transposed to the outer half of the fluidic channel. Thus, in some embodiments, a spiral enrichment structure can use inertial migration of larger cells and the influence of Dean drag on smaller cells to achieve a complete separation.

In some embodiments, a spiral enrichment structure design includes a spiral geometry. A spiral geometry can be defined as a curve on a plane that winds around a fixed center point at a continuously increasing or decreasing distance from the center point. A spiral can deviate from the plane in a third dimension and can (in some embodiments) resemble a cone shaped spring. In some embodiments, a spiral enrichment structure can include two or more loops. One loop can be defined as about one complete circle (e.g., one complete spiral, about 360 degrees) around the center point of a spiral enrichment structure. In some embodiments, a spiral enrichment structure includes 3 or more loops, 4 or more loops, 5 or more loops, 6 or more loops, 7 or more loops, 8 or more loop, 9 or more loops or 10 or more loops. In some embodiments, a spiral enrichment structure includes between about 2 and about 100 loops, between about 2 and about 75 loops, between about 2 and about 50 loops, between about 2 and about 25 loops, between about 2 and about 20 loops, between about 2 and about 10 loops, or between about 2 and about 5 loops. In some embodiments, a spiral enrichment structure includes about 1, 2, 3, 4, 5, 6, 7, 8, 9, 10, 11, 12, 13, 14, 15, 16, 17, 18, 19 or about 20 loops. In some embodiments, a spiral enrichment structure includes a 5-loop spiral geometry with two or more inlets and two or more outlets (e.g., bifurcating outlets).

The length of a spiral fluidic channel, in one embodiment, is about 2 cm or more, about 4 cm or more, about 6 cm or more, about 8 cm or more, about 10 cm or more, about 12 cm or more, about 14 cm or more, about 16 cm or more, about 18 cm or more, about 20 cm or more or about 22 cm or more. In some embodiments, the length of a fluidic channel is between about 2 cm and about 50 cm, 2 cm and about 40 cm, 2 cm and about 30 cm, 2 cm and about 25 cm, 2 cm and about 20 cm or about 2 cm and about 15 cm. In some embodiments the length of a fluidic channel is about 2, 3, 4, 5, 6, 7, 8, 9, 10, 11, 12, 13, 14, 15, 16, 17, 18, 19, 20, 21, 22, 23, 24, 25, 26, 27, 28, 29 or about 30 cm.

In some embodiments, spacing between two successive loops of a spiral enrichment structure is about 20 μm to about 2000 μm. In some embodiments, the spacing between two successive loops of a spiral enrichment structure is about 250 μm. In some embodiments, the initial radius of curvature R of a spiral is about 1 mm to about 10 mm. In some embodiments, the initial radius of curvature R of a spiral is about 3 mm.

In some embodiments, a spiral enrichment structure includes 2 to about 20 outer outlets. In some embodiments, a spiral enrichment structure includes about 2 to about 10 outer outlets. In some embodiments, a spiral enrichment structure includes 2, 3, 4, 5, 6, 7, 8, 9, or 10 outer outlets.

In some embodiments, an enrichment structure is fluidically coupled to a mixing structure or a microfluidic detector. In some embodiments, one or more outlets (e.g., outer outlets) of an enrichment structure are fluidically coupled to an inlet of a mixing structure or a microfluidic detector.

Mixing Structure

The diminutive scale of flow channels in microfluidic systems increases the surface to volume ratio, and is therefore advantageous for many applications. However, the specific Reynolds number (Re=1 ρv/η) of liquid flows in such fluidic channels is very small. For example, the Reynolds number is of the order of 0.1 in a typical water-based microfluidic system with a channel width of 100 μm, a liquid flow rate of 1 mm/s, a fluid density of 1 g/cm$^3$ and a viscosity of 0.001 Ns/m$^2$. In such low Reynolds number regimes, turbulent mixing does not occur, and hence diffusive species mixing plays an important role, but is an inherently slow process. In some embodiments, a function of a mixing structure can be to enhance the mixing efficiency in a microfluidic channel such that a thorough mixing performance can be achieved. In some embodiments, a function of a mixing structure is to shorten mixing times and reduce the overall time required to label a cell with a binding agent when using a detector system. In some embodiments, a function of a mixing structure is to shorten the length of mixing channels and reduce the overall size of a detector system. In some embodiments, a function of a mixing structure is to maintain cell viability during a mixing process. In some embodiments, an efficient mixing structure is employed for increasing the throughput of a detector system and to enable an effective lab-on-a-chip system. In some embodiments, a mixing structure includes fluidic channels. In some embodiments, a mixing structure is embedded on a chip (e.g., a lab-on-a-chip, and/or the like).

A mixing structure, in one embodiment, is a suitable microfluidic mixer known in the art. In some embodiments, a mixing structure is an active fluidic mixer. Non-limiting examples of an active fluidic mixer include acoustic mixers, ultrasonic mixers, dielectrophoretic mixers, electrokinetic time-pulse mixers, pressure perturbation mixers, magnetic mixers, thermal mixers, electrohydrodynamic force mixers, magneto-hydrodynamic flow mixers and/or electrokinetic instability mixers, the like and/or combinations thereof. In some embodiments, a mixing structure is a passive fluidic mixer. Non-limiting examples of a passive fluidic mixer include lamination mixers (e.g., wedge shaped inlets, 90 degree rotation), zigzag channels (e.g., elliptic-shape barriers), 3D serpentine structures (e.g., folding structure, creeping structure, stacked shim structure, multiple splitting and stretching, recombining flows, unbalanced driving force), embedded barriers (e.g., SMX, multidirectional vortices), twisted channels (e.g., split and recombine), and/or surface chemistry (e.g., obstacle shape, T-/Y-mixers), the like or combinations thereof.

Serpentine Mixing Structure

In some embodiments, a mixing structure is a serpentine structure (e.g., a serpentine mixer) as shown in FIGS. 7A-7C. In some embodiments, the serpentine mixer is a two dimensional serpentine mixer. In some embodiments, the serpentine mixer includes an inlet port, a continuous fluidic channel, two or more turns and an outlet port located on the opposite end of the channel as the inlet port. In some embodiments, an overall channel length of the serpentine mixer is between about 1 mm and about 10,000 mm. In some embodiments, the overall channel length is between about 1 mm and about 1000 mm. In some embodiments, the channel length is between about 1 mm and about 500 mm. In some embodiments, the serpentine mixer includes between about 3 and 30 turns. In some embodiments, the serpentine mixer includes between about 5 (FIG. 7A) and 20 (FIGS. 7B, 7C) turns. In some embodiments, a serpentine mixer includes between about 5, 6, 7, 8, 9, 10, 11, 12, 13, 14, 15, 16, 17, 18, 19 or about 20 turns. In some embodiments, the serpentine mixer includes 20 turns. In some embodiments, each turn in a serpentine mixer is configured for a 180 degree redirection of fluid flow within a channel. In some embodiments, each turn in a serpentine mixer includes an elliptical curve. In some embodiments, each turn in a serpentine mixer includes a circular curve or a horizontal curve. In some embodiments, the inner radius of a curve (e.g., an elliptical, horizontal or circular curve) that describes a turn in a serpentine mixer is about 20 µm to about 10,000 µm, about 20 to about 1000 µm, about 20 to about 500 µm or about 150 to about 350 µm. In some embodiments, the inner radius of a curve (e.g., an elliptical, horizontal or circular curve) that describes a turn in a serpentine mixer is about 150, 160, 170, 180, 190, 200, 210, 220, 230, 240, 250, 260, 270, 280, 290 or about 300 µm. In some embodiments, the length of the channel between two turns is between about 0.5 mm and 1000 mm. In some embodiments, a serpentine mixer is a mixing structure. In some embodiments, a serpentine mixer is embedded on a chip (e.g., a lab-on-a-chip or the like).

Fluidic Channels

In some embodiments a detection system, detector system, flow cytometry device, enrichment structure, mixing structure and/or microfluidic detector includes one or more fluidic channels. In some embodiments, a fluidic channel, in one embodiment, is a microfluidic channel. A lab on a chip can include one or more fluidic channels. In some embodiments, fluidic channels are embedded on a chip. In some embodiments a fluidic channel is configured to contain a static or dynamic fluid (e.g., a moving fluid or solution) including a cell (e.g., a prokaryotic cell, a eukaryotic cell, a human cell). In some embodiments a fluidic channel is configured to contain a static or dynamic fluid (e.g., a moving fluid or solution) including a particle (e.g., a bead, a bead attached to a cell, a cell attached to a binding agent). One of skill in the art will appreciate that a fluidic channel can be made of a suitable material known in the art. Additionally, the cross section of a fluidic channel can be any suitable shape (e.g., rectangular, circular). In some embodiments, a fluidic channel includes a first end and a second end. In some embodiments a fluidic channel includes a first end and the first end includes a valve, a port, a flow regulator, and/or one or more inlets. In some embodiments, a fluidic channel includes a second end and the second end includes a valve, a port, a flow regulator, and/or one or more outlets. In some embodiments, a first end and/or a second end of a fluidic channel is configured to provide a continuous channel between an enrichment structure and a mixing structure and/or a mixing structure and a microfluidic detector. In some embodiments, the inner diameter of a fluidic channel can be about 0.2 µm to about 2000 µm or about 10 µm to about 1000 µm. In some embodiments, the inner diameter of a fluidic channel is about 250 µm.

Microfluidic Detector

In some embodiments, a microfluidic detector is provided. In one embodiment, the microfluidic detector combines photonics and microfluidics to detect and/or sort particles or cells (e.g., relatively rare cells in blood such as CTCsm relatively abundant cells, and/or the like). In some embodiments, a microfluidic detector is configured to provide some or all of the functions of a flow cytometer and/or FACS-based cell sorter. In some embodiments, a microfluidic detector includes a flow cytometer device. In some embodiments, a microfluidic detector is part of detection system (e.g., a micro cell detection system). In some embodiments, a microfluidic detector is embedded on, attached to or embodied on a chip. In some embodiments, a microfluidic detector is utilized to detect and optionally sort particles (e.g., beads, cells, viruses, bacteria, the like or combination thereof) according to light emitted by the particles and/or light that has interacted with the particles (e.g., light diffracted, scattered and/or reflected by particles).

The light detected by the detector can be electromagnetic radiation of any wavelength or frequency. The value for the wavelength or frequency generally is for light propagating through a vacuum. Light can be characterized as visible light, ultraviolet light and/or infrared light in some embodiments. Visible light generally is of a wavelength of about 390 nanometers to about 750 nanometers, and generally is of a frequency of about 400 terahertz (THz) to about 790 THz. Infrared light generally is of a wavelength of about 0.74 micrometers to about 300 micrometers, and generally is of a frequency of about 300 gigahertz (GHz) to about 400 THz (near infrared can be about 120 THz to about 400 THz; mid infrared can be is about 30 THz to about 400 THz; and far infrared can be about 300 GHz to about 30 THz). Ultraviolet light generally is of a wavelength of about 10 nanometers to about 400 nanometers, and generally is of a frequency of about 0.75 petahertz (PHz) to about 30 PHz (near ultraviolet can be about 400 nm to about 300 nm, mid ultraviolet can be about 300 nm to about 200 nm, and far ultraviolet can be about 200 nm to about 122 nm). A photon is a quantum of light and a photon can have a particular photon energy.

In some embodiments, a particle is an agent that emits light (e.g., a fluorophore), and/or can be a complex of molecules that includes an agent that emits light. In some embodiments, a particle can include a one or more biological agents (e.g., cell, protein, nucleic acid, biological membrane (e.g., vesicle, liposome, the like and combinations thereof). A particles, in some embodiments, one or more antibodies in association with one or more biological agents (e.g., bound to a biological agent). In some embodiments, an antibody is linked to an agent that emits light (e.g., a fluorophore). In some embodiments, a combination of different particles is introduced to a flow cell or fluidic channel of a microfluidic detector. In some embodiments, a combination of different particles includes different particles that emit different wavelengths of light.

In some embodiments, a particle refers to a cell, and the cell can be caused to emit, scatter, reflect, deflect or diffract light. In some embodiments, a cell is associated with a detection agent that can emit, scatter, reflect, deflect or diffract the light. In some embodiments, the detection agent is connected to a binding agent that can associate with or bind to a cell (e.g., specifically associate with or specifically bind to a particular cell type or cell component). In some embodiments, a binding agent binds to a cell surface protein.

In some embodiments, a microfluidic detector, or part thereof, is illuminated by a light source. In some embodiments, light introduced by a light source can be transmitted though a fluidic channel wall into the channel interior. The angle of light emitted by a light source can be at an angle with respect to the channel wall suitable for illuminating a particle within the channel. In certain embodiments, a particle in a fluidic channel can interact with light introduced into a channel, and light that has interacted with the particle and can be scattered, reflected or diffracted by the particle can be transmitted from the channel to one or more other components in a microfluidic detector.

In some embodiments, a particle in a fluidic channel emits light of a particular wavelength or in a particular wavelength range, and all or a portion of the wavelength range is transmitted from the channel to one or more other components in a microfluidic detector. In one embodiment, a particle emits light of a particular wavelength or wavelength range, which wavelength or wavelength range is different than the wavelength or wavelength range emitted by a light source (e.g., excitation wavelength(s) emitted by the light source may excite a fluorophore particle or fluorophore attached to a particle and the fluorophore may emit light of different wavelength(s)). In one embodiment, light emitted by a particle, or that has interacted with a particle, is transmitted through a fluidic channel, and transmitted through or conducted by one or more intermediary structures, to a detector. Non-limiting examples of intermediary structures include a mask, color filter, waveguide, mirror, lens, filter, photodiffractive component (e.g., prism, diffraction grating), the like and combinations thereof.

In some embodiments, a microfluidic detector includes an optical filter, a reflector and/or combinations thereof. A microfluidic detector, in one embodiment, includes one or more optical filters. In a further embodiment, the optical filter is an absorptive filter, color filter, dichroic filter, monochromatic filter, infrared filter, ultraviolet filter, neutral density filter, longpass filter, bandpass filter, shortpass filter, guided-mode resonance filter, metal mesh filter, polarizer filter, optical notch filter (e.g., precision optical notch filter) the like or combinations thereof. Non-limiting examples of filters, such as color filters, are described in greater detail herein. In one embodiment, the device includes one or more components that reflect light, non-limiting examples of which include flat mirrors, curved surface mirrors, parabolic surface mirrors and dichroic mirrors. In some embodiments, a mirror substantially reflects light of a particular wavelength range and is substantially transparent to, and does not reflect, light of a different wavelength range. A mirror in some embodiments, substantially reflect light in a wavelength range that excites a fluorophore (e.g., a fluorophore particle or fluorophore linked to or associated with a particle) and is substantially transparent to light in a wavelength range emitted by the excited fluorophore.

Figure 18:
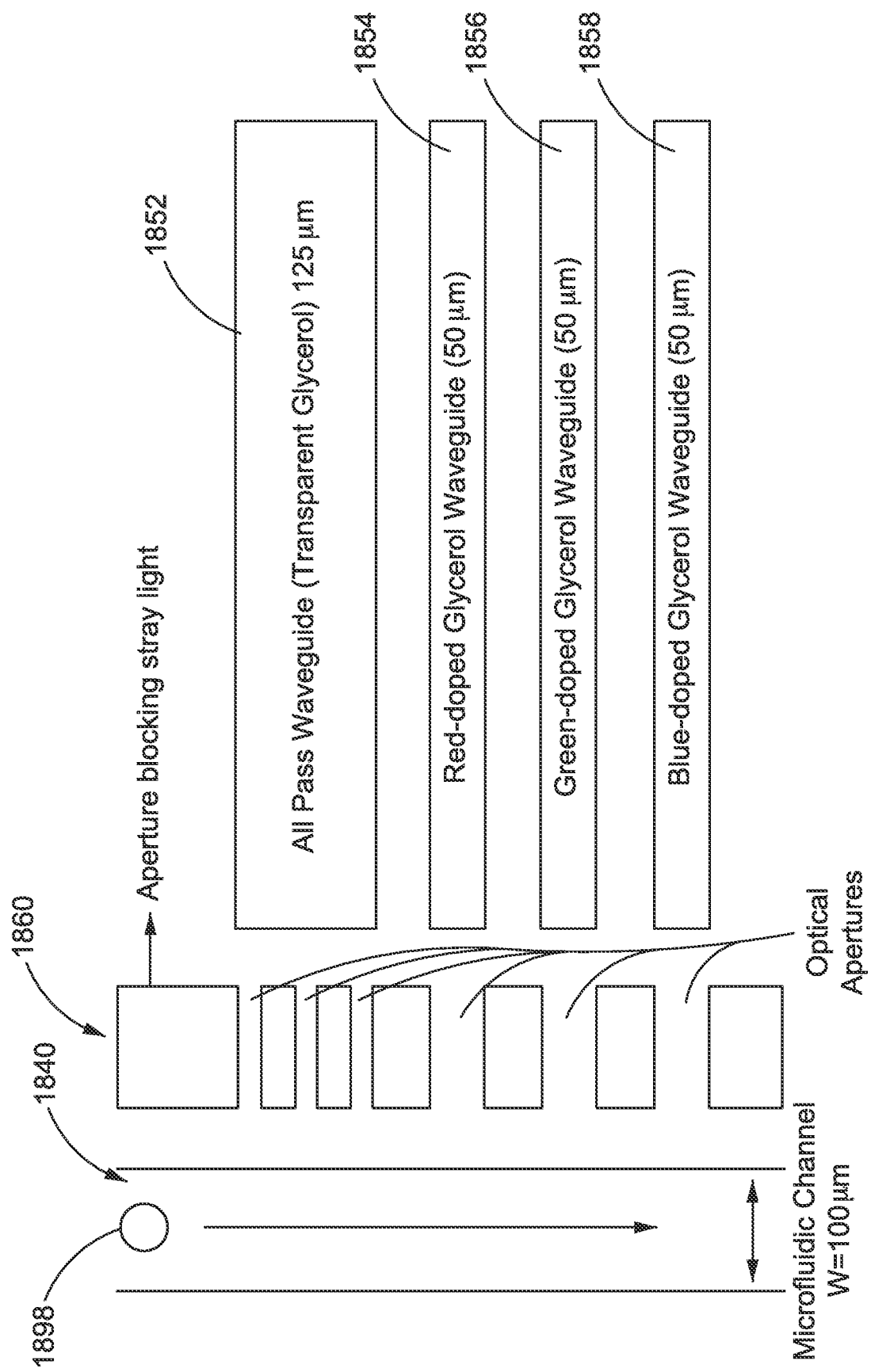
FIG. 18 is a schematic diagram of a microfluidic detector with optical filter waveguides and optical apertures, according to an embodiment.

In some embodiments, light emitted from, or light that has interacted with, a particle in a channel is transmitted from a fluidic channel to a color filter. In some embodiments, a color filter can include two or more zones (e.g., about 2, 3, 4, 5, 6, 7, 8, 9, 10, 15, 20, 25, 30, 35, 40, 45, 50, 60, 70, 80, 90 or 100 or more zones). In some embodiments, a color filter can include a mask including substantially transparent zones and substantially opaque zones (e.g., optical apertures, bands), and waveguides in effective connection with the substantially transparent zones. In some embodiments, some of the waveguides are colored, and transmit a wavelength subrange of the wavelength range transmitted by the mask. In some embodiments, a color filter includes a mask and waveguides, and in some embodiments, is in contact with a fluidic channel in which particles flow, and light from the fluidic channel (in some embodiments) does not transmit through any other component prior to being received by the mask or a waveguide. A non-limiting example of a color filter including a mask 60 and waveguides 52, 54, 56, 58 is shown in FIG. 18.

Figure 49A:
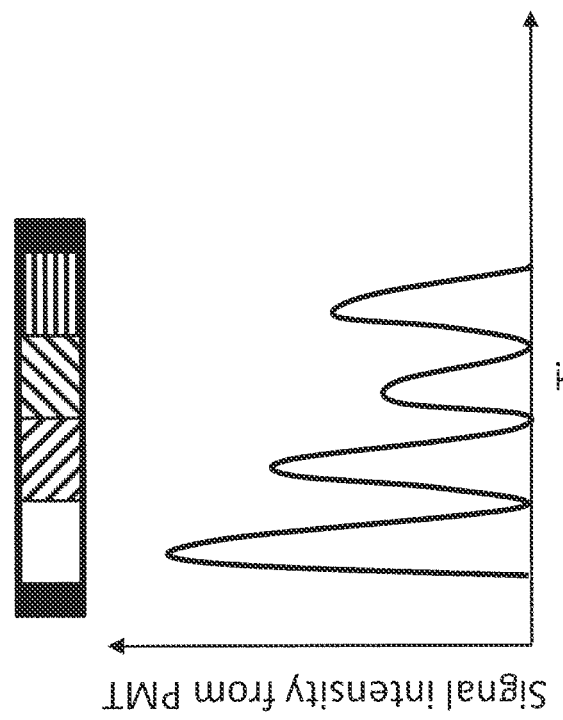
FIG. 49A and FIG. 49B illustrate COST filter designs and the signals detected by the optical detectors in the optical path following corresponding filters, according to embodiments.
Figure 49B:
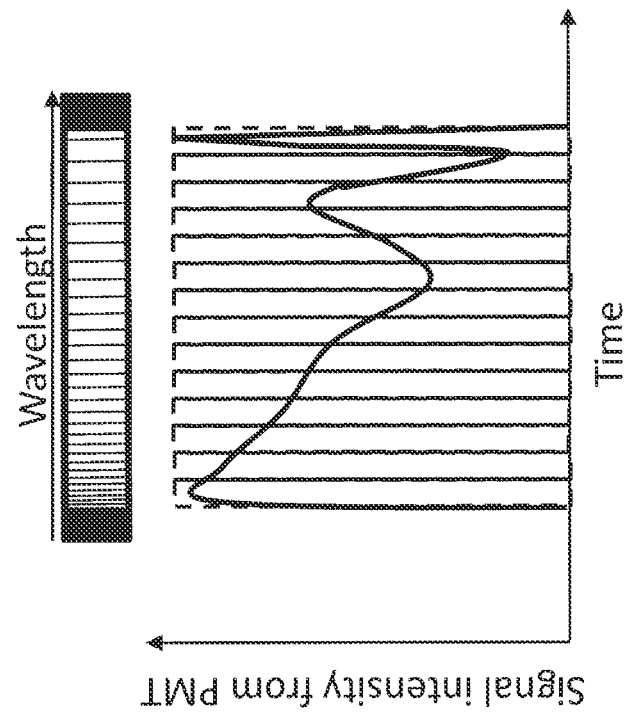

In some embodiments, a color filter is not directly in contact with a fluidic channel in a microfluidic detector. In some embodiments, a color filter is located a certain distance from a fluidic channel in which a particle flows, and in some embodiments a distance of about 1 centimeter (cm) to about 100 cm (e.g., about 5, 10, 15, 20, 25, 30, 40, 50, 60, 70, 80 or 90 cm). In some embodiments, light emitted by a channel can be transmitted through one or more other components (e.g., lens, mirror) before the light, or modified version thereof, contacts a color filter. In some embodiments, zones can be discrete zone segments on a filter, and (in some embodiments) zones are substantially continuous (e.g., continuously graded color zones). A non-limiting example of a color filter that includes substantially discrete zones is illustrated in FIG. 49A, which illustrates signal intensity from discrete (e.g., bandpass) filters. A non-limiting example of a color filter that includes a substantially continuous transition between zones is illustrated in FIG. 49B.

In some embodiments, a color filter can include one or more zones that transmit substantially all of the light that is transmitted to the filter (e.g., all pass filter zone). In some embodiments, a color filter can include two or more zones that transmit a portion of the light transmitted to the filter (i.e., referred to color filter zones), where at least one color zone transmits a different portion of light than another color zone. In some embodiments, color zones in a color filter can perform as broad pass, continuous, band pass filters, the like or combinations thereof. In some embodiments, a different portion of light is a different wavelength subrange of, a different energy subrange of, and/or a different frequency subrange of, the light wavelength range, light energy range and/or light frequency range, respectively, received by the color filter. Thus, a first color zone can transmit a first wavelength subrange, and a second color zone can transmit a second wavelength subrange, which first wavelength subrange and second wavelength subrange are different (e.g., overlapping or not overlapping), and which wavelength subranges are within the wavelength range of the light received by the color filter. The different wavelength subranges transmitted by color zones, in some embodiments, overlaps, and in some embodiments, do not overlap. The lowest wavelength and the highest wavelength in a subrange of light transmitted by a color zone in a color filter (n some embodiments) differ by about 0.1 nm to about 500 nm in some embodiments (e.g., a range of about 1, 5, 10, 15, 20, 25, 30, 35, 40, 45, 50, 55, 60, 65, 70, 75, 80, 85, 90, 100, 150, 200, 250, 300, 350, 400 or 450 nm). In some embodiments, a color filter can include one or more zones that transmit substantially none of the light transmitted to the color filter (e.g., substantially opaque zone). A color filter including multiple zones can, in some embodiments, be referred to as a filter with a "series of optical filters" and an "array of optical filters" herein, where each of the optical filters in the series or the array is a zone.

In some embodiments, a color filter can include three or more zones that transmit different portions of light transmitted to the filter. For example, in one embodiment, a color filter includes a first zone that transmits substantially green light, a second zone that transmits substantially blue light, and a third zone that transmits substantially red light. It should be noted that the latter example is not limiting, and certain color zones within a color filter can transmit any suitable wavelength subrange of the wavelength range of light received by the filter.

In one embodiment, a color filter and zones of a color filter has dimensions suitable for detecting a particle, determining velocity of a particle, determining size of a particle, detecting wavelength(s) of light emitted or that have interacted with a particle, and/or the like. In some embodiments, a color filter is substantially circular and includes suitably shaped zones distributed around the circular structure for transmitting light (e.g., circular, ovoid, rectangular, square, triangular, segment of the circle).

In some embodiments a color filter is substantially rectangular and includes substantially one zone across the shorter rectangular dimension and multiple zones sequentially distributed along the longer rectangular dimension, according to a top view of the color filter. In such embodiments, the width of a discrete zone is the length of the zone parallel to the longer rectangular dimension of the color filter. In such embodiments, the zone widths can be regular or can vary. In color filter embodiments that include varying zone widths, the widths can be distributed in any suitable pattern, non-limiting examples of such patterns including periodic, chirp and pseudo-random patterns. In some embodiments, substantially opaque zones can be distributed in a pattern of varying width, and zones that transmit light (in some embodiments) can be distributed in a pattern of regular widths.

A color filter can be manufactured by any suitable process known in the art. In some embodiments, a color filter includes a structure infused with one or more agents that permit at least one color zone to transmit light having a wavelength range different than the wavelength subrange of light transmitted by another zone. Zones with different transmission properties can include different agents or one agent in different amounts, for example.

A color filter can include multiple layers. In some embodiments, a color filter includes a support structure on which one or more coating layers are deposited. Any suitable structure or support structure can be utilized, and non-limiting examples include glass, polymers and the like. Each zone independently can be of substantially uniform thickness or varying thickness (e.g., stepped thickness, tapered or flared thickness (e.g., substantially uniform taper or flare). Each zone independently, in one embodiment, includes one or more coatings (e.g., same or different materials in each coating) and/or one or more layers (e.g., same or different materials in each layer). A zone including multiple layers can include alternating layers, each layer including different materials. Each coating or layer in a zone can have the same refractive index or may have different refractive indices. Zones of a color filter that transmit different wavelength ranges of light can have the same refractive index or may have different refractive indices. Zones that transmit different wavelengths of light can, in some embodiments, have a different number of layers, different materials, different thicknesses, the like or combination thereof. Where adjacent zones have different thicknesses, the transition from one thickness to another cab be any suitable transition, such as, for example, stepped, tapered or flared.

In some embodiments, a microfluidic detector includes a splitter that effectively receives light emitted by, or light that has interacted with, a particle in a fluidic channel. The light emitted from the fluidic channel can be transmitted through one or more other components in the device (e.g., lens, filter) prior to the splitter receiving such light. A splitter can split received light into two or more split beams. Each of the two or more split beams can, in some embodiments, be directed to a separate color filter. Said another way, a microfluidic detector, in some embodiments, includes two or more color filters, and each of the color filters can (in some embodiments) include color zones that transmit different wavelength subranges of light than color zones in other color filters. Light in one split beam can be of the same wavelength range or different wavelength range as light in another split beam. Non-limiting examples of splitters include those that include two triangular glass prisms, half-silvered mirrors and dichroic mirrored prisms.

In some embodiments, a flow channel, color filter and optical detector (e.g., photodetector, photosensor) in a microfluidic detector can be configured for detecting light from a particle in the channel multiple times as the particle translocates through the channel. As a particle travels from one position to a second position in a particular portion of a channel in a microfluidic detector, light emitted from the particle, or light that has interacted with the particle, at the first position can be transmitted through the channel to a first position on the image plane of the color filter. Light emitted from the particle, or light that has interacted with the particle, at the second position can be transmitted through the channel to a second position on the image plane of the color filter. In some embodiments, where the first position and second position on the color filter are at different color zones, the wavelength range of light transmitted by each color zone to a photodetector differ, and the photodetector detects two different light signals over time for the same particle at the two different positions in the flow channel. In such embodiments, a color filter can transmit multiple, discrete wavelength ranges of light by multiple, discrete zones in the filter for the same particle to a photodetector (e.g., one photodetector). In some embodiments, a device does not transmit different wavelengths of light from one filter to multiple photodetectors in a photodetector array.

In some embodiments, a color filter in a microfluidic detector can include no mirrored surfaces and, in some embodiments, a color filter is not a Fabry-Perot cavity filter or Fabry-Perot etalon. In some embodiments, a color filter in a microfluidic detector is not a Bragg reflector, where a Bragg reflector is defined as having multiple layers and reflecting light having a wavelength about four times the optical thickness of the layers.

In some embodiments, a color filter is not directly in contact with a photodetector component of a device. In some embodiments, a color filter can be located a certain distance from a photodetector component surface, for example a distance of about 0.1 cm to about 20 cm away from a photodetector component surface (e.g., about 0.5, 1, 2, 3, 4, 5, 6, 7, 8, 9, 10, 15, 20 cm, and all values in between). In some embodiments, one color filter can be oriented with one photodetector such that light transmitted by the color filter is transmitted to the one photodetector and no other photodetector. A device includes no photodetector array in some embodiments, and one color filter is in detectable association with one photodetector and no other sensor cells of a photodetector array. In some embodiments, a photodetector component surface is not directly in contact with, and (in some embodiments) not distributed along, a fluidic channel in a microfluidic detector and, in some embodiments, can be located a certain distance from the fluidic channel.

In some embodiments, a microfluidic detector can include one or more lenses. A lens can be a single lens or an array or plurality of lenses (e.g., compound lens; a lens array may include about 2, 3, 4, 5, 6, 7, 8, 9, 10 or more lenses). A lens can be constructed from any suitable material for transmitting light, and (in some embodiments) can be constructed from glass and/or a polymer, for example. A lens can be of a suitable geometry for transmitting light, and non-limiting examples of lenses include biconvex (double convex, convex), equiconvex, biconcave (concave), piano-convex, piano-concave, convex-concave (meniscus). In some embodiments, the lens can focus light. In some embodiments, the lens can focus light on an image plane of a color filter and, in other embodiments, a lens focuses light on an image plane of a photodetector. In some embodiments, the lens can magnify an image, such as an image transmitted from a flow channel. A lens, in some embodiments, can demagnify an image, such as an image transmitted from a color filter to a photodetector. Magnification or demagnification can be at any suitable level, and (in some embodiments) is about 2× to about 1,000× (e.g., about 10×, 50×, 100×, 200×, 300×, 400×, 500×, 600×, 700×, 800×, 900× magnification or demagnification, and any value in between). In some embodiments, a lens can receive light from a channel and focus that light on an image plane of a color filter. In some embodiments, a lens can receive light from a color filter and focus the light on an image plane of a sensor surface.

In some embodiments, a microfluidic detector can include a waveguide and (in other embodiments) include no waveguide (e.g., no waveguide in association with a channel in which particles flow). In some embodiments, a microfluidic detector can include a structure that substantially blocks ambient light from interacting with one or more components of the device. Such a structure (in some embodiments) can be one or more tubes of suitable cross section (e.g., rectangular, square, circular, ovoid) and is a box in some embodiments, for example. A structure that substantially blocks ambient light can (in some embodiments) functions as a support for certain components (e.g., lens).

Any of the detectors illustrated in the embodiments in FIGS. 28 to 32 and 35 to 49B can be coupled with one or more sorting components described herein. In some embodiments, a microfluidic detector can contain fluid, and there is substantially no air-to-fluid interface, or meniscus, located between a piezoelectric actuator and a fluidic channel. In some embodiments, a microfluidic detector can contain fluid and there is substantially no air-to-fluid interface, or meniscus, located between a piezoelectric actuator and a particle to be sorted. In some embodiments, channels in a microfluidic detector can contain fluid and (in some embodiments) there is substantially no air-to-fluid interface or meniscus in the channels of the device. In some embodiments, a microfluidic detector can include no gas-filled reservoir, substantially no gas pocket or component that applies a gas (e.g., air) to a channel.

Figure 14:
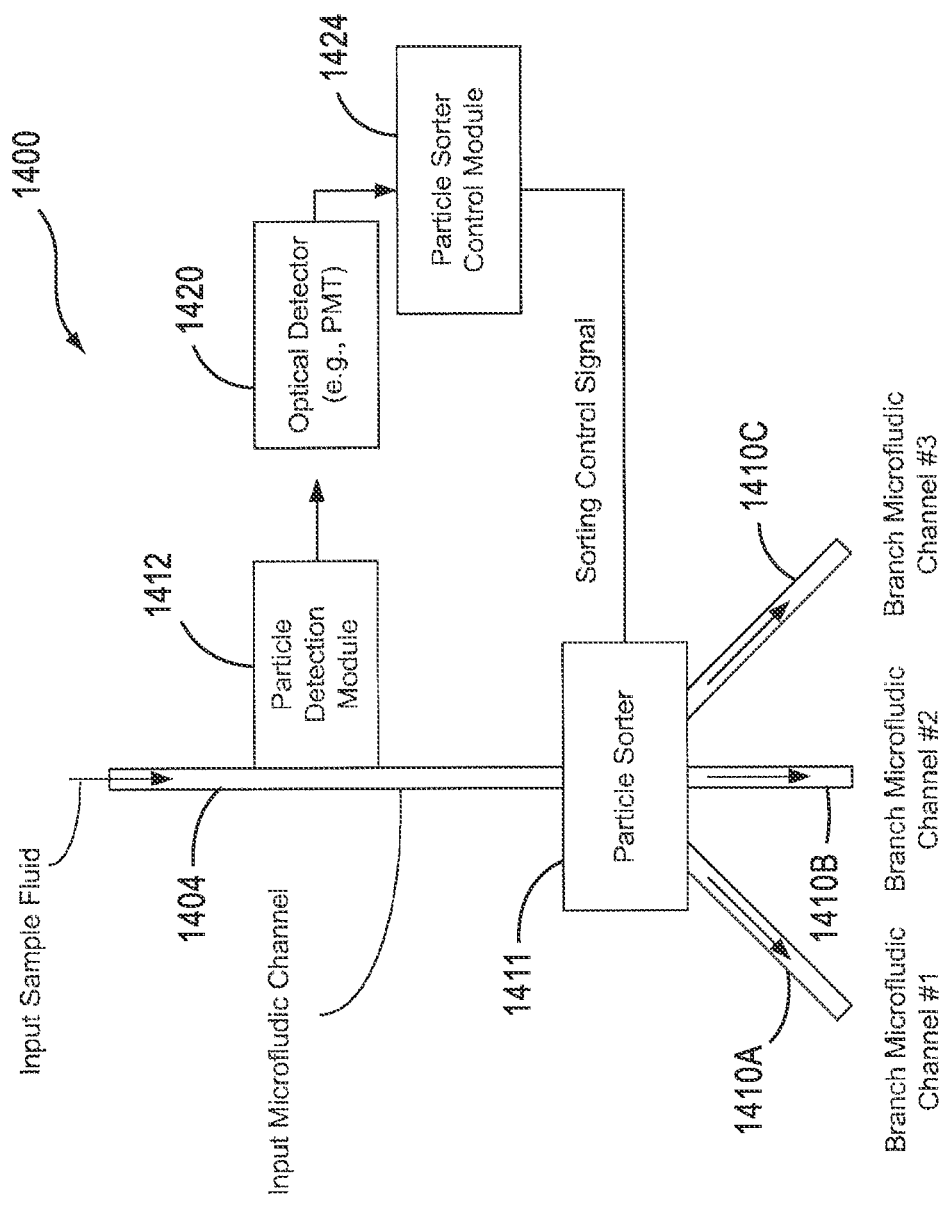
FIG. 14 illustrates a microfluidic detector, according to an embodiment.

The embodiment in FIG. 14 illustrates an example of a microfluidic detector 1400 for flow cytometry in which various features described herein can be implemented. The microfluidic detector 1400 includes an input fluidic channel 1404 including a first port (not shown) for receiving a sample fluid or the input sample fluid, and a second port (not shown) for outputting the received sample fluid. In some embodiments, a particle sorting junction or a particle sorter 1411 can be provided for sorting particles within the sample fluid and can be coupled to the second port of the input fluidic channel. In some embodiments, downstream from the particle sorting junction, two or more branch fluidic channels 1410A-1410C can be coupled to the particle sorting junction as outlets of the sample fluid from the second port of the input fluidic channel. In some embodiments, an actuator can be coupled to the particle sorting junction 1411 to control a direction of the sample fluid in the particle sorting junction in response to a sorting control signal. In some embodiments, the actuator can reside inside the particle sorting junction 1411 or in a fluid containing region that is adjacent to or in fluid communication with the particle sorting junction 1411, so that the movement of the actuator causes movement of the sample fluid at the particle sorting junction to change the flow direction of the sample fluid. In some embodiments, the actuator can be structured to interact with the sample fluid to change the direction of sample fluid to be in different directions corresponding to the branch fluidic channels, respectively, in response to changes in the sorting control signal. In some embodiments the actuator can be operable to direct a target particle in the sample fluid into a selected one of the branch fluidic channels.

The actuator for sorting particles in the embodiment of FIG. 14 can be implemented based on various cell sorting techniques. Non-limiting examples of sorting techniques include electric field-based sorting, dielectrophoretic (DEP) sorting, magnetic sorting, and hydrodynamic sorting. Sorting can be useful for the detection and isolation of stem cells, circulating tumor cells, and *E. coli* cells, among others. In some embodiments, implementation of a hydrodynamic sorter can involve external check values, integrated valves, or external syringe pumps.

In some embodiments, the actuator in FIG. 14 can be implemented to include a piezoelectric actuator that moves in response to a voltage signal as the sorting control signal to cause the sample fluid in the particle sorting junction 1411 to change the flow direction. In some embodiments, a microfluidic detector can be a cell sorter and include one or more integrated piezoelectric actuators. A microfluidic detector including piezoelectric actuators can operate at low voltages, e.g., less than 10 Vp-p. In the experiment of instantaneous flow switching, a piezoelectrical actuator can be operated to change the flow stream at a relatively high frequency (e.g., ~1.7 kHz) and the amount of deflection of cells/particles in the flow can be precisely controlled. In some embodiments, particles of varying size, shape, and density of interest can be individually sorted in a controlled manner by a piezoelectrical actuator. Using *E. coli* deflection as an example, a sinusoidal voltage can deflect cells at a rate of 330 cells/sec and shows a highly repeatable operation in consistent with the theory. In some embodiments, using a specially design spatial filter and a real-time signal processing algorithm implemented in FPGA, a closed-loop sorting system can be built with a low error rate and a sorting efficiency of around 70%. Compared with other microFACS systems, these embodiments of a microfluidic detector (i.e., sorting system) disclosed herein have a number of advantages. For example, the spatial filter design and the real-time signal processing algorithm can enhance the signal-to-noise ratio by 18 dB and allow verification of sorting.

In some embodiments, a PZT-actuated sorting module consumes little power (e.g., 0.1 mW), operates at a low voltage (e.g., <10 Vpp), and has a much faster response (e.g., 0.1-1 ms) than off-chip mechanical actuators such as check-valves and syringe pumps. In some embodiments, an FPGA-based electronics control can enable real-time signal amplification, user-defined delay time, programmable output waveform, and low timing jitter (e.g., <10 μsec). In some embodiments, these features can contribute significantly to a low-cost sorter that can perform high-throughput particle sorting at a single-particle level.

In some embodiments, a detector system can include a particle detection module 1412 that is coupled to an input fluidic channel to receive light from the sample fluid in the input fluidic channel (FIG. 14). The light can be obtained form a light source such as a laser or other light source and the light can be directed to illuminate the sample fluid in the input fluidic channel. This illumination of a particle in the sample fluid can cause light to be generated by the particle. As such, the particle detection module 1412 can produce one or more first optical signals from the received light indicative of at least a speed of a particle in the sample fluid detected by the particle detection module. In some implementations, the particle detection module 1412 can include an encoding structure that produces different optical signals from the received light and encodes the different optical signals with different codes. This encoding can be spaced-based codes or time-based codes and allows for using a single optical detector to detect multiple optical signals in a microfluidic detector, e.g., different optical signals from different locations in a microfluidic detector. In some embodiments an optical detector 1420 such as a PMT and/or avalanche photodiode can be provided to receive the one or more optical signals from the particle detection module 1412 or light from other locations in the microfluidic detector 1400 to produce a detector signal that carries information carried by the received light. In some embodiments, the information in the received light can be extracted out by processing the detector signal from the optical detector 1420 for various purposes, including controlling the actuator and the respective sorting in the particle sorting junction.

In the embodiment of FIG. 14, a particle sorter control module 1424 is provided to be in communication with the particle detection module to receive the detector signal and in communication with the actuator to send the sorting control signal to the actuator. In some embodiments, the particle sorter control module 1424 can include a signal processing mechanism to extract information from the detector signal by processing the detector signal with proper processing techniques, e.g., by using a digital signal processing (DSP) circuitry. When the optical signals are encoded, the signal processing mechanism can process the detector signal based on the different codes in the different optical signals to separate information carried by different optical signals. The particle sorter control module 1424 can also include a control mechanism that produces the sorting control signal based on the extracted information, including timing of a particle detected at the particle detection module for arriving at the particle sorting junction.

In the embodiment of FIG. 14, different branch microfluidic channels 1410A, 1410B, and 1410C are coupled to the particle sorting junction 1411 to receive the sorted particles from the particle sorting junction.

Figure 15:
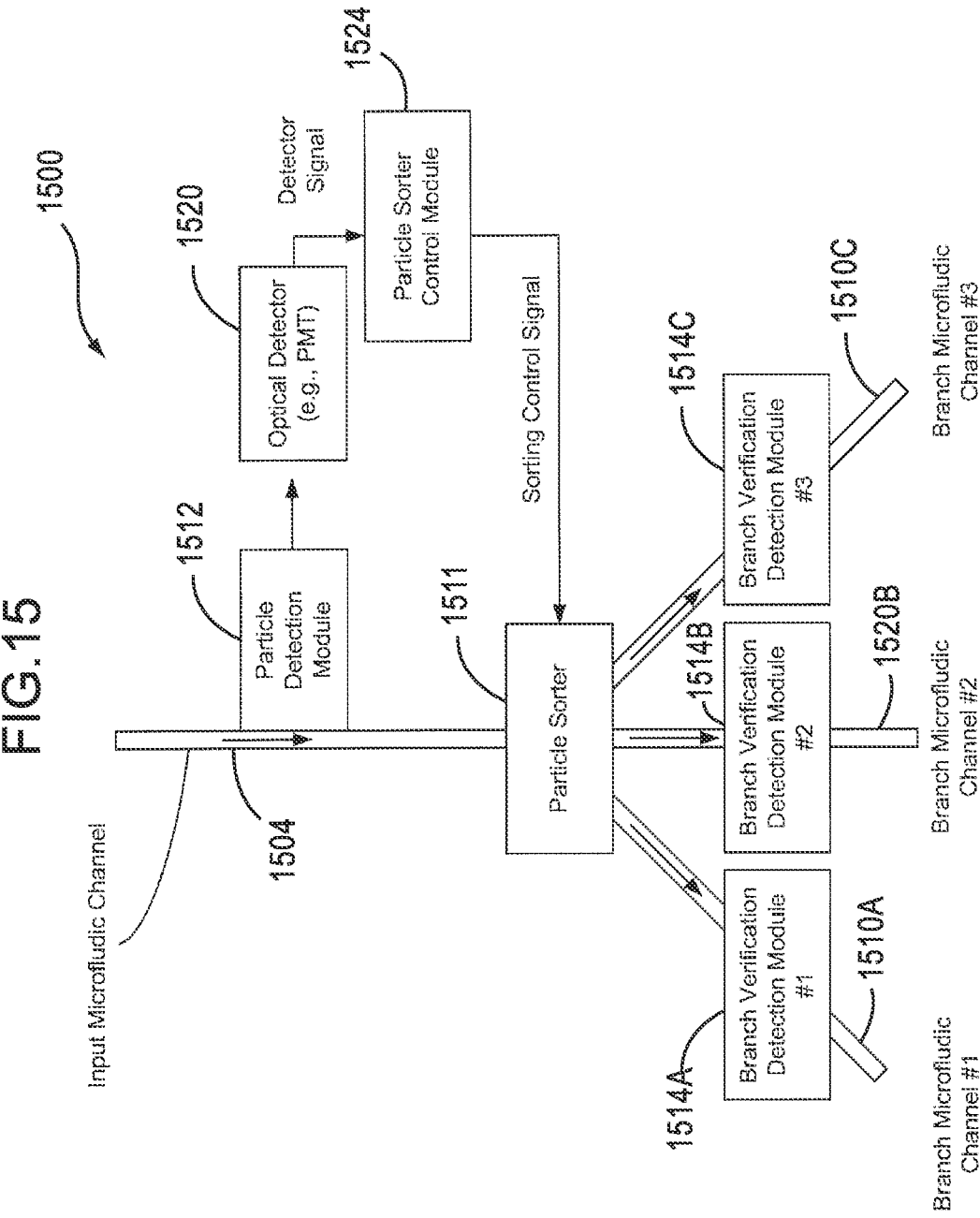
FIG. 15 illustrates a microfluidic detector, according to an embodiment.

In the embodiment of FIG. 15 a microfluidic detector 1500 includes an optical sensing mechanism (e.g., reference characters 1514A-1514C, described in more detail below) in one or more branch fluidic channels 1510A-1510C downstream from the particle sorting junction 1511. In some embodiments, the combination of using the optical sensing at a pre-sorting location and optical sensing at a post-sorting location in a microfluidic detector can be used to provide better controlled operation for more efficient flow cytometry measurements. In the illustrated embodiment, the post-sorting sensing can be used to verify whether a desired particle sorting performed by the actuator in the particle sorting junction 1511 is properly executed. In the illustrated embodiment, the post-sorting sensing can be used as input for operating a post-sort valve (see Examples below).

In some embodiments, the embodiment of FIG. 15 includes a branch verification structure (e.g., 1514A) that is coupled to one of the branch fluidic channels (e.g., the channel 1510A) to receive light from the one branch fluidic channel and to produce a branch verification optical signal that can be used to verify whether a target particle is directed by the actuator into the one branch fluidic channel. Two or more such branch verification structures can be implemented in some embodiments. In the embodiment of FIG. 15, all three branch fluidic channels 1510A-1510C have such verification detection modules 1514A-1514C. In other embodiments, some branches can have such verification structures, when other branches may not.

In the embodiment of FIG. 15, the optical detector 1520 is located to receive light which includes at least the one or more optical signals from the particle detection module 1512 and the branch verification optical signal from the verification detection modules 1514A-1514C. In some embodiments, an optical detector produces a detector signal that carries information contained in the received light. The signal processing mechanism in the particle sorter control module 1524 extracts information of the branch verification optical signal to produce an indicator that verifies whether a target particle is directed by the actuator into the one branch fluidic channel. In some embodiments, this verification can be automatically fed back to the particle sorter control module 1524 which can, in response to a verification of malfunction in the sorting, interrupt the system operation (e.g., stopping the incoming sample flow and the sorting operation by the actuator). In some embodiments, an alert signal (e.g., a visual signal such as a pop-up warning and/or a blinking light, an audio signal such as a beep, and/or the like) can be generated by the particle sorter control module 1524 to alert the operator of a microfluidic detector of the malfunction in the sorting.

A limitation in conventional flow cytometry systems is using multiple PMTs to respectively detect optical signals at different fluorescent wavelengths. Presence of multiple PMTs in such systems complicates a microfluidic detector design, increases the cost, and renders the systems bulky and heavy. In some embodiments, a microfluidic detector as disclosed herein can provide signal encoding in multiple different optical signals so that different optical signals are encoded with unique and mutually different or orthogonal codes. In some embodiments, these optical signals can be multiplexed together for optical detection by a single optical detector and the information carried by the different optical signals can be separated by demultiplexing based on the unique and mutually different or orthogonal codes. The demultiplexing can be performed via digital signal processing.

Figure 16A:
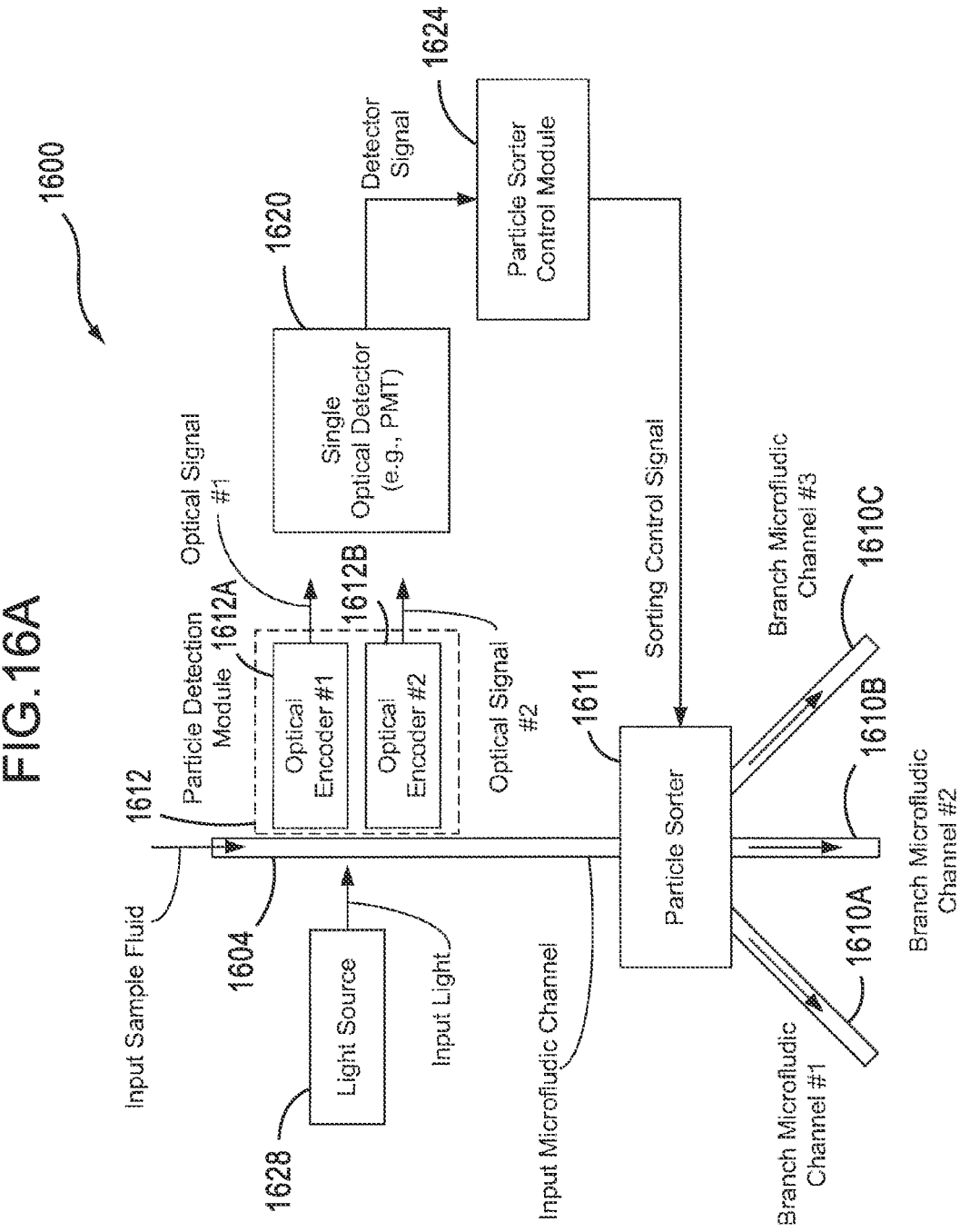
FIG. 16A illustrates a microfluidic detector, according to an embodiment.

Embodiments of FIG. 16A and FIG. 16B illustrate examples of two microfluidic detector that implement such signal encoding.

As illustrated in FIG. 16A, the particle detection module 1612 coupled to the input fluidic channel 1604 is structured to include an encoding structure that produces different optical signals from the received light and encodes the different optical signals with different codes. In some embodiments, as illustrated, optical encoders 1612A, 1612B are shown as examples of such an encoding structure. The optical encoder 1612A produces a first optical signal #1 with a first code and the optical encoder 1612B produces a second optical signal #2 with a second code that is different from the first code. In some embodiments, the optical detector 1620 receives the different optical signals to produce a detector signal that carries information of the different optical signals and the different codes. In some embodiments, the signal processing mechanism, e.g., the DSP, of the particle sorter control module 1624 extracts information of the different optical signals from the detector signal based on the different codes in the different optical signals. In some embodiments, the control mechanism in the particle sorter control module 1624 produces the sorting control signal based on the extracted information, including timing of a particle detected at the particle detection module for arriving at the particle sorting junction.

As illustrated in FIG. 16B, additional optical encoders are provided in a microfluidic detector 1600' to allow for the same optical detector 1612' to detect the encoded optical signals. The additional optical encoders 1614A' and 1614C' are shown as examples of encoding structures in the branch fluidic channels 1610A', 1610C' respectively. In some embodiments, the optical encoder 1614A' produces a third optical signal #3 with a third code different from the first and second codes and the fourth optical encoder 1614C' produces a fourth optical signal #4 with a fourth code that is different from all other three codes. In some embodiments, the optical detector 1620' receives the different optical signals #1-#4 to produce a detector signal that carries information of the different optical signals #1-#4 and the different codes. In FIG. 16B, the third and fourth optical signals can be the branch verification optical signals, when each of the optical encoders 1614A' and 1614C' are implemented as branch verification structures. In some embodiments, the optical detector 1620' receives both the optical signals #1 and #2 and the branch verification optical signals #3 and #4.

Figure 16C:
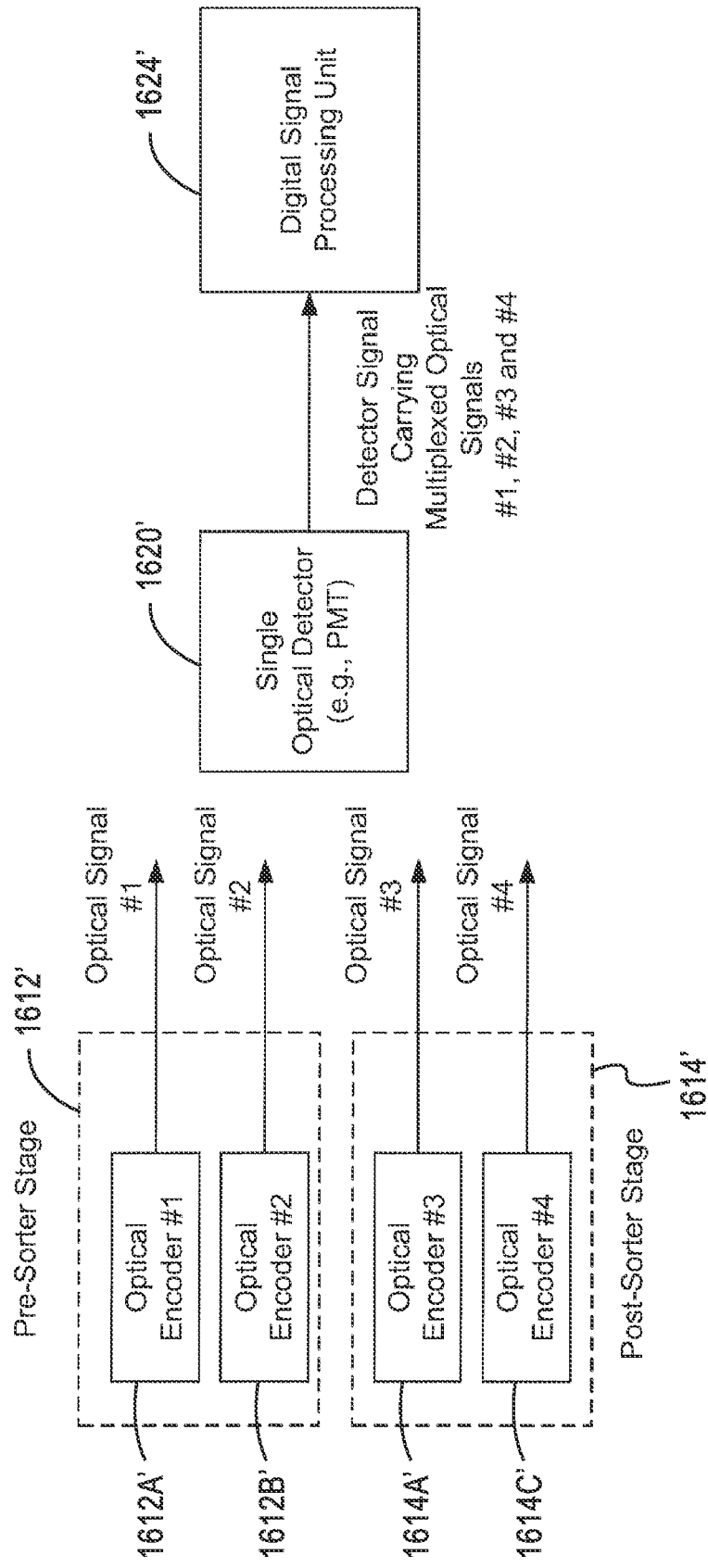
FIG. 16C illustrates optical signal processing by a microfluidic detector, according to an embodiment.

The embodiment of FIG. 16C shows the signal detection and processing in embodiment FIG. 16B. In some embodiments, signal detection is performed by the single optical detector 1620' that receives light of all four optical signals #1-#4 which are multiplexed together as the input light which is converted into the detector signal carrying the multiplexed signals #1-#4. In some embodiments, after an analog to digital conversion, a DSP unit (e.g., such as can be part of the particle sorter control module 1624') is used to process the multiplexed signal and to separate the four different signals based on their unique codes.

In some cases optical encoding and decoding in a microfluidic detector are based on an optical interrogation method with a single optical detector based on signal encoding via optical signal structures, like optical encoders illustrated in FIGS. 16A-16C. In some embodiments, this method can include directing light to one or more of the fluidic channels that are coupled to form a network of fluidic channels to illuminate fluid carried by the fluidic channels and providing optical signal structures that are respectively coupled to at least some of the fluidic channels at different locations to produce optical signals from the light illuminating the fluid. In some embodiments, each optical signal can carry information indicative of a property of a particle carried in the fluid at a location of the respective optical signal structure. In some cases the optical signal structures are structured to produce, respectively, unique codes in the optical signals that are different from one another. In some embodiments, this method can use a single optical detector to collect light from all the optical signals generated at the optical signal structures to produce an electrical detector signal in response to the collected light. In some embodiments, the electrical detector signal can be processed based on the unique codes in the optical signals to separate information carried by the optical signals to extract information carried by each of the optical signals.

In some embodiments, a microfluidic detector can utilize signal encoding and decoding based on a COlor-Space-Time (COST) to support detection of multiple (e.g., 20 or more) fluorescent wavelengths using a single detector and, more particularly in some embodiments, a single photo-multiplier tube (PMT) or single-photon avalanche detector (SPAD) or avalanche photodiode. In some embodiments, a microfluidic detector is implemented using lab-on-a-chip technology and architecture. A simpler version of such architecture (which can be referred to as space-time coding) in some embodiments is also provided to allow for multi-point detection and the consequent generation of "verification signals" to record sorting efficiency and accuracy in real time.

The following embodiments include methods, systems, and/or devices including such, for COST coded detection of multiple fluorescent wavelengths using a single detector within a lab-on-a-chip microfluidic detector. A microfluidic detector can include a lab-on-a-chip fluorescence-activated cell sorter (FACS) or lab-on-a-chip flow cytometer. Such embodiments can be considered an extension of space-time coding, which is modified to include color coding by incorporating color dyes in the waveguides transmitting the fluorescence to the detector. In some embodiments, with the appropriate choice of dyes and calibration of the absorption spectrum, twenty or more fluorescent wavelengths can pass through the color-filter waveguides and be detected using a single detector such as a PMT or SPAD. Although in some embodiments, colored waveguides/filters are integrated on a chip to achieve COST coded detection. In some embodiments, it is also possible to implement the COST concept using one or more external color filters not integrated with the chip. In some embodiments, when the chip is disposed of after a single use or a few uses, the color filter(s) is/are not (or need not be) disposed of.

In some embodiments, a microfluidic detector includes one or more additional components and/or features. In some embodiments, these can include, for example, an array of integrated lenses that focus light and shorten the interrogation zone to enhance detection throughput. In some embodiments, these features can include flow disturbance minimization, 3D flow confinement and/or cascaded sorting strategies to achieve >1M enrichment factor with minimum cell loss. In some cases these features can include system integration architectures with real-time electronic control and signal processing algorithms to coordinate detection and sorting, enhance sensitivity and minimize sorting error. In some embodiments, the COST approach provides an integrated, optofluidic solution to multicolor detection thus enabling the construction of microfluidic detectors that are orders of magnitude smaller, lighter and/or less expensive than existing commercial systems.

In some embodiments, a microfluidic detector includes a microfluidic channel, and a first light conveying structure configured to convey substantially all visible light components, and having a first end proximate the microfluidic channel. A microfluidic detector can also include at least one second light conveying structure having at least one second end proximate the microfluidic channel, and extending substantially alongside the first light conveying structure, where the at least one second light conveying structure is configured to convey at least one subset of the visible light components. In some cases, A microfluidic detector further includes a light sensing device arranged proximate respective additional ends of each of the light conveying structures, the respective additional ends being respectively opposite the respective first and second ends. Respective portions of light emanating from material passing through the microfluidic channel are received by the respective light conveying structures and communicated at least in part thereby to the light sensing device, whereby an indication of the material passing through the microfluidic channel can be determined based upon one or more signals output by the light sensing device.

Additionally, in some embodiments, a method of performing flow cytometry includes injecting first light into a microfluidic channel through which material is passing, and receiving second light from the microfluidic channel into a plurality of waveguides, where a first of the waveguides is conductive of substantially all visible light components, and a second of the waveguides is conductive of a subset of the visible light components. In some embodiments, the method can further include conveying first and second portions of the second light through the first and second waveguides from respective first ends of the waveguides to respective second ends of the waveguides, communicating at least some of each of the conveyed first and second portions of the second light to a photodetector, and outputting a color-space-time signal from the photodetector.

Further, in some embodiments, a method of performing flow cytometry can includes injecting first light into a microfluidic channel through which material is passing, and receiving second light from the microfluidic channel into a plurality of optical filters, where a first of the filters is conductive of substantially all visible light components, and a second of the filters is conductive of a subset of the visible light components. In some embodiments, a method additionally includes communicating at least some of each of the conveyed first and second portions of the second light to a photodetector; and outputting a color-space-time signal from the photodetector.

Figure 17:
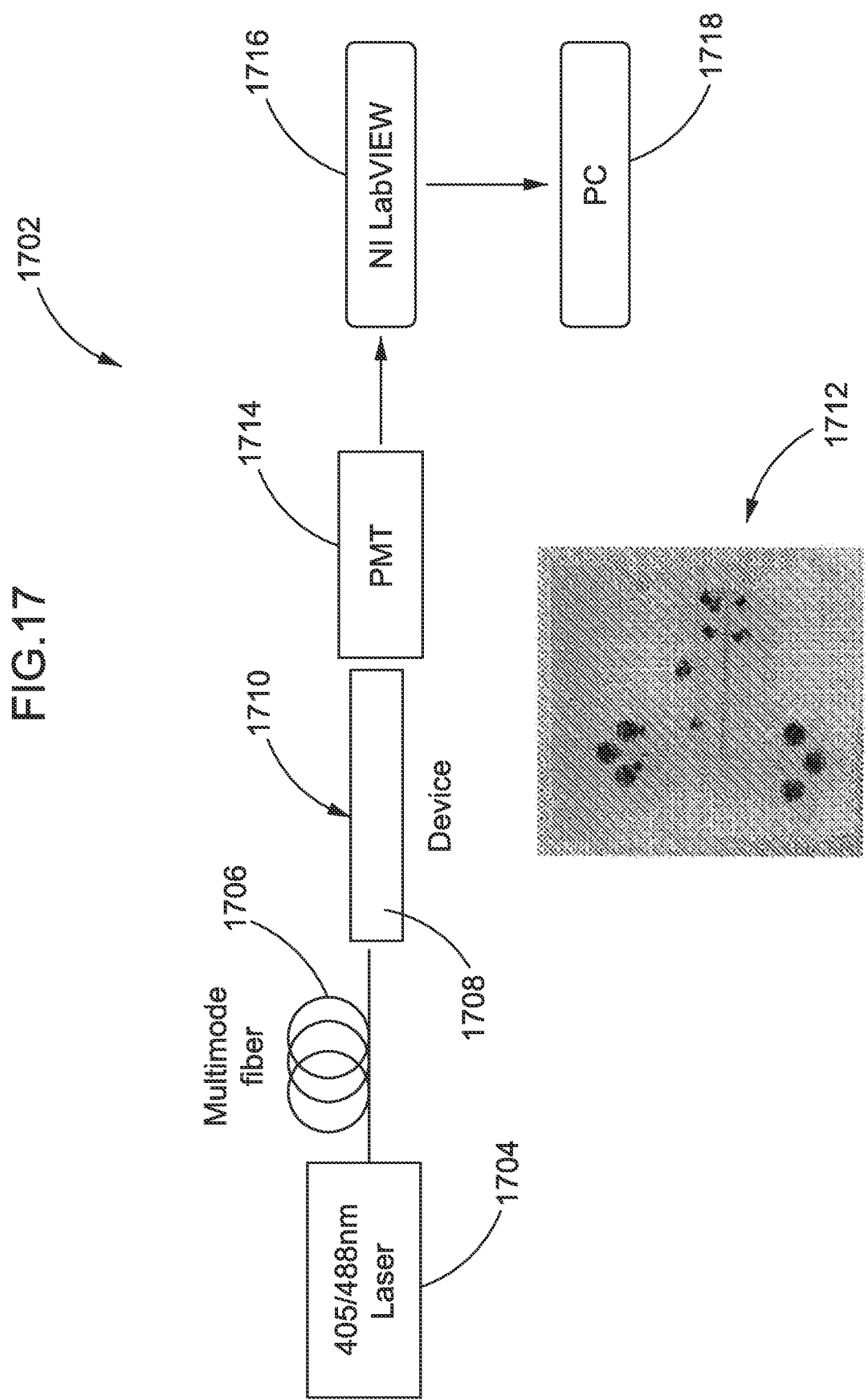
FIG. 17 is a schematic diagram showing components of a microfluidic detector, according to an embodiment.

The embodiment of FIG. 17 illustrates a schematic view of a microfluidic cell detector 1702. In some embodiments, the microfluidic detector 1702 includes a laser 1704 that generates laser light and provides that light into a multimode fiber 1706. In some embodiments, the multimode fiber 1706 in turn directs the light toward a microfluidic channel 1710 represented schematically by a box 1708. In some embodiments, an image 1712 of internal components of the microfluidic channel 1710 is also provided adjacent to the box, and those internal components are described in further detail below. After the light has been provided to the microfluidic channel 1710, the light interacts with the cells or other materials or matter passing through a microfluidic channel (described further below) of that device and, as a result of that interaction, resultant light is provided from the microfluidic channel 1710 to a photo-multiplier tube (PMT) 1714 that senses that light. The PMT 1714 upon sensing of the light in turn output signals indicative of the sensed light to National Instruments LabView-based software 1716 (available from National Instruments Corp. of Austin, Tex.), which in turn provides data to personal computer 1718 (notwithstanding the representation provided in FIG. 14, the software 1716 can be considered implemented on the personal computer).

In the embodiment in FIG. 17 and at least some other embodiments, multiple parameter detection is achieved by applying COlor-Space-Time (COST) coding technology. Multiple parameter detection is of greater interest when it allows for detection of 12 or more different fluorescent wavelengths of light emanating from the microfluidic detector 1710 of any of the embodiments described and illustrated herein. In the embodiment of FIG. 17, it is the microfluidic detector 1710 can support detection of multiple (e.g., 20 or more) fluorescent wavelengths of light emanating from a microfluidic detector using a single detector. The single detector can take different forms depending upon the embodiment and, while FIG. 17 illustrates the PMT 1714 as the single detector, in other embodiments (not shown), the detector can take other forms, for example, a single-photon avalanche detector (SPAD).

In some embodiments, the laser light source 1704 can include a 405/488 nm (or Blu-ray standard) laser. In some embodiments, a variety of other excitation lasers can be used (e.g., lasers at 630-650 nm and/or other lasers manufactured by a variety of companies such as Nichia, Sony, Xerox, Omicron, etc.). In some embodiments (e.g., the embodiment of FIG. 17), a microfluidic cell detector 1702 or at least certain portions thereof (e.g., the microfluidic detector 1710) can be devices employing a lab-on-a-chip technology platform that replaces the bulk optics with integrated optics.

FIG. 18 is an exemplary illustration of the design of the microfluidic detector 1710 where the encoding structure includes optical aperture structure 1860 with multiple optical apertures long the sensing region 1840 of the input fluidic channel, and optical waveguides 1852, 1854, 1856 and 1858 that receive light from the sensing region 1840 via the optical apertures in the structure 1860. A particle 1898 (e.g., a cell) in the sample fluid flowing through the sensing region 1840 emits light that sequentially passes through the optical apertures along the input fluidic channel at different positions at different times. The light received by the waveguides 1852, 1854, 1856 and 1858 can be collected by a optical detector (e.g., a PMT, such as the optical detector 1714). The waveguide 1852 can conduct light of all wavelengths emitted by the particles 1898. Waveguides 1854, 1856 and 1858 are optical filter waveguides with optical transmission bands that are respectively centered at different center transmission frequencies. The waveguides 1854, 1856 and 1858 can produce different filtered optical transmission signals with different optical spectral bands centered at the different center transmission frequencies, e.g., red, green and blue wavelengths and at different times to be received by the optical detector. In some embodiments, the waveguides 1854, 1856 and 1858 are configured to have spectral overlaps in the optical transmission bands respectively centered at different center transmission frequencies. Accordingly, the red waveguide 1854 that transmits at a red center wavelength also transmits some light at green wavelengths and some light at blue wavelengths; the green waveguide 1856 that transmits at the green center wavelength also transmits some light at red wavelengths and some light at blue wavelengths; and the blue waveguide 1858 that transmits at a blue center wavelength also transmits some light at green wavelengths and some light at red wavelengths. In this design, the signal processing may be based on the overlapping spectral information in each of the different filtered optical transmission signals to improve the signal processing fidelity. For example, the imaging processing by the human visual system based on signals from the red, green and blue color receptors or cone cells in the eye with overlapping spectral ranges can be modeled for the signal processing in the above device.

Figure 19A:
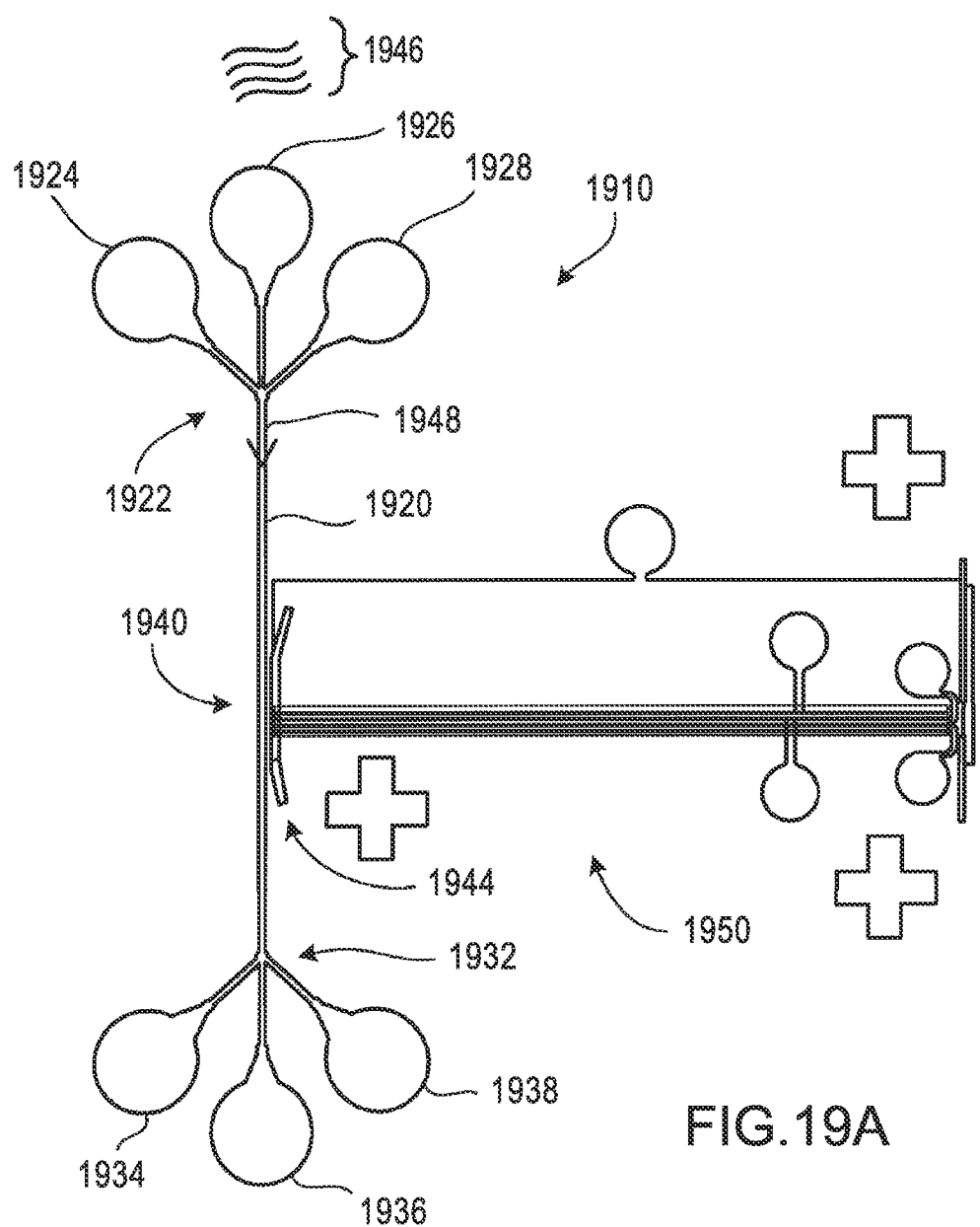
FIG. 19A is a top view showing in more detail components of the microfluidic detector of FIG. 36.

FIG. 19A illustrates the components of a microfluidic detector 1910 in more detail. As shown, a microfluidic detector 1910 in some embodiments can include a microfluidic channel 1920 through which particles, cells or other matter of interest, suspended in fluid, can pass. The microfluidic channel 1920 at a first end 1922 is coupled to first, second and third entry orifices or ports 1924, 1926 and 1928, respectively, and at a second end 1932 is coupled to first, second and third outlets/outlet ports 1934, 1936 and 1938, respectively. At a sampling region 1940 of the microfluidic channel 1920 intermediate its ends 1922, 1932, an additional waveguide structure 1950 is provided. The additional waveguide structure 1950, along with the sampling region 1940 of the microfluidic channel 1920, is shown in more detail in FIG. 19B. A microfluidic detector 1910 can in at least some embodiments be considered disposable because of its low fabrication cost.

Figure 19B:
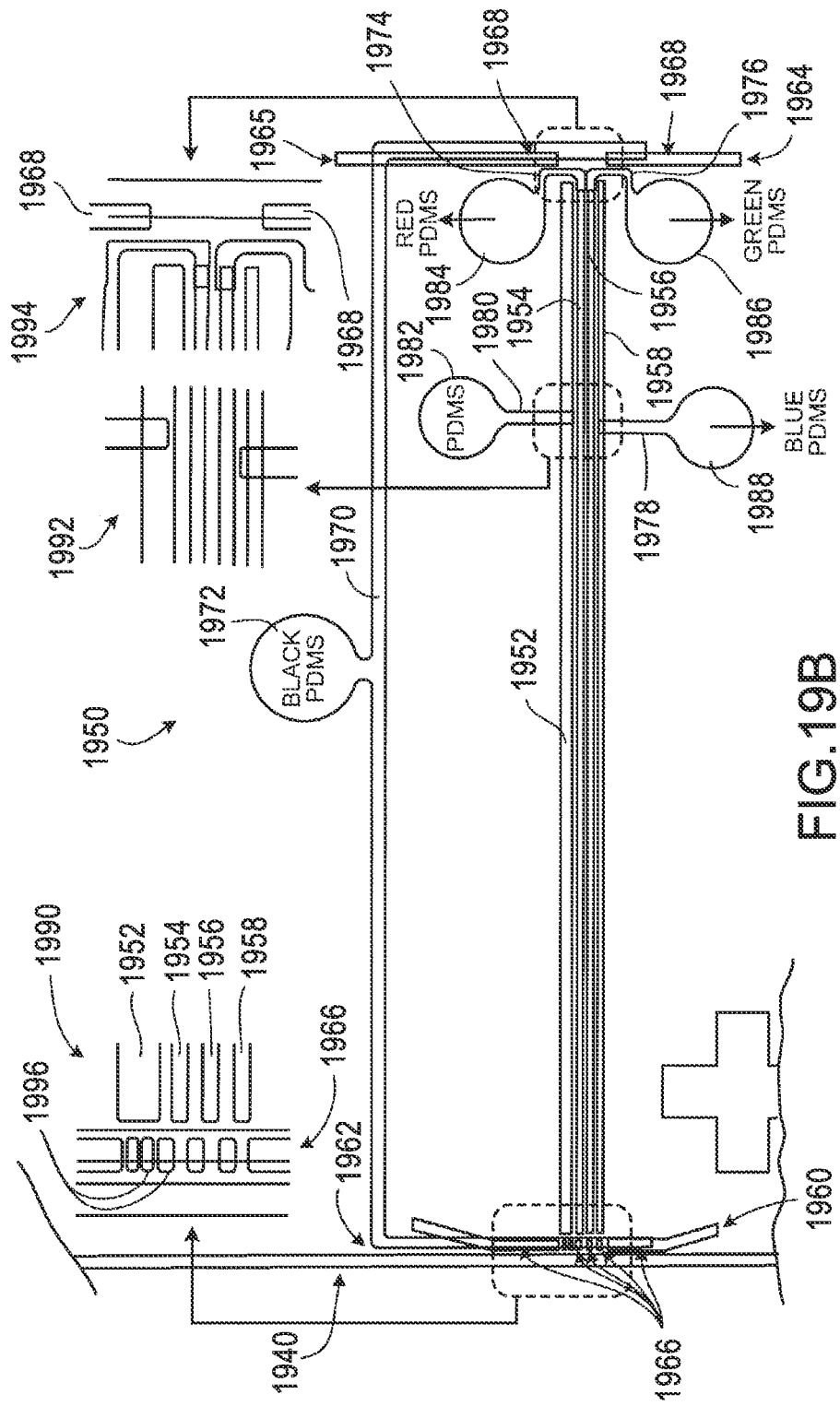
FIG. 19B is an additional view showing portions of the microfluidic detector of FIG. 38 in cut-away in greater detail, further including three inset image portions.

In the embodiment of FIGS. 19A-19B, to improve reliability and reusability of a microfluidic detector 1910 as a lab-on-a-chip device, the microfluidic channel 1920 is (in some embodiments) made of polydimethylsiloxane ("PDMS"), and in some embodiments the PDMS surfaces that are in contact with fluid (e.g., the interior surfaces of the channel) are further coated with a thin, smooth, uniform layer of amorphous Teflon (e.g., with Teflon AF), particularly a Teflon coating having a lower refractive index (e.g., ~1.31) than that of water (~1.33). In some embodiments, use of the Teflon coating alleviates concerns (which can be present with a variety of PDMS-based microfluidic devices) associated with the porosity and permeation properties of PDMS (which can present concerns especially when dealing with small molecules).

In addition to the above benefits, another benefit of employing the Teflon-coated microfluidic channel 1920 can be that it facilitates the operation of the microfluidic channel additionally as a low-loss optical waveguide. That is, through the use of the Teflon-coated microfluidic channel 1920, in the present embodiment light 1946 entering a microfluidic detector 1910 (e.g. from a multimode fiber, such as the multimode fiber 1706) during operation generally is directed into and guided within the microfluidic channel 1920 (as indicated by an arrow 1948) toward and into the sampling region 1940 of the microfluidic channel 1920. Upon reaching the sampling region 1940, the light 1946 impinges the cells or other matter of interest passing through the microfluidic channel and causes fluorescent light to be emitted, some or all of which the enters into the additional waveguide structure 1950 arranged along a side 1944 of the microfluidic channel 1920/sampling region 1940.

The above-described embodiment (of FIGS. 19A-19B) of "lab-on-a-chip technology" allows for multiple detection points along the flow path to enhance sensitivity and suppress noise. In some microfluidic detector architectures, light from a light source (such as an excitation laser source) suffers from power splitting loss. In other words, if a cell (or other subject matter of interest) passes several (e.g., four) different optical interrogation zones, the excitation laser power may be divided at each of those zones (e.g., divided 4 times) in a manner that results in excessive splitting loss (e.g., 6 dB splitting loss). In contrast, using the above-described embodiment employing the Teflon-coated microfluidic channel 20, the channel conducting the cells (or other subject matter of interest) serves also as the excitation light-guiding waveguide, and consequently it is possible to achieve multi-point optical interrogation as discussed further below. At the same time, the optical intensity of the guided light is lower than a tightly focused laser beam spot to avoid the effect of photo bleaching.

Referring additionally to FIG. 19B, the microfluidic detector 1910 achieves multi-point optical interrogation by employing the additional waveguide structure 150 extending away from the sampling region 1940 of the microfluidic channel 1920. As shown, then additional waveguide structure 1950 does not merely include a single waveguide, but rather is shown to include first, second, third and fourth transverse waveguides 1952, 1954, 1956 and 1958, respectively. Each of the waveguides 1952, 1954, 1956 and 1958 of the additional waveguide structure 1950 extends between a first filter structure 1960 positioned at a first end 1962 of the additional waveguide structure, which is between the waveguides 1952, 1954, 1956 and 1958 and the sampling region 1940, and a second filter structure 1964 positioned at a second end 1965 of the additional waveguide structure opposite the first end.

In some embodiments, each of the waveguides 1952, 1954, 1956 and 1958 has a different respective color. More particularly, the first waveguide 1952 can be transparent with no particular color (e.g., clear), while the second waveguide 1954, third waveguide 1956 and fourth waveguide 1958 can be red, green and blue, respectively. Consequently, while the first waveguide 1952 is able to transmit all (or substantially all) components of light within the visible light spectrum (e.g., all light components having wavelengths within the range of about 380 nm to 750 nm, or "white light"), the other waveguides 1954, 1956, and 1958 tend to only transmit red, green and blue light components, respectively, with other colored light components being partially filtered out. Thus, the waveguides 1952, 1954, 1956 and 1958 can also be considered optical filters. The first filter structure 1960 encompasses several block features 1966 that are black or blackened/darkened and that can limit the ability of light to proceed form the sampling region 1940 to the waveguides 1952, 1954, 1956 and 1958. Further, with respect to the second filter structure 1964, this structure also includes block features 1968 that are blackened/darkened and that restrict the ability of light to proceed out of the waveguides 1952, 1954, 1956 and 1958 and out of a microfluidic detector 1910 toward a PMT (e.g. the PMT 1714). The features 1966, 1968 in particular serve to increase the contrast ratio and reduce crosstalk, and further serve as a beam block for optical isolation.

Typically, it is desirable to take care with optimizing and characterizing the various waveguides 1952, 1954, 1956 and 1958 (and particularly waveguides 1954, 1956, 1958) to obtain desired operation. To create the red, green and blue waveguides 1954, 1956, 1958 as well as the filter structures 1960 and 1964, red, green, blue, and black color dyes are respectively injected into the transverse waveguides and the filter structures. In some embodiments, the color dyes can be oil soluble and can be mixed with high-index (e.g., n=1.42 to 1.46) PDMS to form a colored optical waveguide/filter structures. The high index PDMS prepolymers fill the waveguide channels, which are formed using low-index (n=1.41) PDMS. By properly choosing the color dye or a mixture of different dyes and by calibrating the absorption spectrum, the waveguides 1954, 1956, 1958 can each have a respective desired transmission spectrum. In the present embodiment, to cover the maximum number of wavelengths, the center wavelength for the three color filters should occur at around approximately 510 nm, 570 nm, and 640 nm.

In some implementations, each of the red, green and blue (RGB) waveguides (which as mentioned above also can be considered optical filters) 1954, 1956, 1958 can be designed to exhibit a gradual change (rather than rapid cutoff) in its transmission characteristics with wavelength. If a single dye is not able to produce the desired spectral response, mixture of dyes may be used. Further, by appropriately coloring/darkening the features 1966, 1968 of the filter structures 1960, 1964, and appropriately choosing the shapes and arrangements of those features, light can be appropriately directed from the sampling region 1940 to the waveguides 1952, 1954, 1956 and 1958 as well as directed out of the waveguides toward a PMT (e.g. the PMT 1714). After the color filter design is chosen, optical design software such as ZEMAX (as available from Zemax Development Corporation of Belleview, Wash.) can be used to further design a COST coding microfluidic detector (e.g. the microfluidic detector 1702).

Still referring to FIG. 19B, in the present embodiment the colored/black dyes are injected into the waveguides 1954, 1956, 1958 and filter structures 1960, 1964 by way of input orifices and channels leading from those input orifices to the waveguides/filter structures. After fluid injection, all PDMS pre-polymers are thermally cured to arrive at the waveguides/filter structures. To avoid formation of gaps or voids during curing, the curing is performed in vacuum. More particularly as shown, a black channel 1970 leads between a black input orifice 1972 and each of the filter structures 1960, 1964, and thus black dye input at the orifice is able to enter into the filter structures 1960, 1964 and form the features 1966, 1968 thereof. Also as shown, red, green and blue channels 1974, 1976 and 1978 respectively lead from respective red, green and blue input orifices 1984, 1986 and 1988, respectively, to the red, green and blue waveguides 1954, 1956 and 1958, respectively, and thus the respective red, green and blue dyes can be injected into the respective waveguides via the respective orifices and respective associated channels. Likewise, a clear channel 1980 leads between a clear input orifice 1982 and the waveguide 1952, allowing for clear dye to be provided to that waveguide.

Additionally, FIG. 19B also includes first, second and third inset images 1990, 1992 and 1994 of FIG. 19B that further illustrate details of the additional waveguide structure 1950 and the sampling region 1940. More particular, the first inset image 1990 shows with more clarity the particular features 1966 of the first filter structure 1960 as arranged in between the sampling region 1940 and the waveguides 1952, 1954, 1956 and 1958. As will be evident from the inset image 1990, the features 1966 (which again are blackened/darkened to restrict light passage therethrough) are positioned generally in between adjacent ones of the waveguides 1952, 1954, 1956 and 1958, with the exception of two small features 1996 that are positioned between the sampling region 1940 and the waveguide 1952. As for the second inset image 1992, that image shows in particular the coupling of the channels 1980 and 1978, respectively, to the waveguide 1952 and the waveguide 1958, respectively. Further, with respect to the third inset image 1994, that image shows the coupling of the channels 1974 and 1976 respectively to the waveguide 1954 and waveguide 1956, respectively, as well as the coupling of the channel 1970 to the second filter structure 1964.

Figures 20A, 20B, 20C:
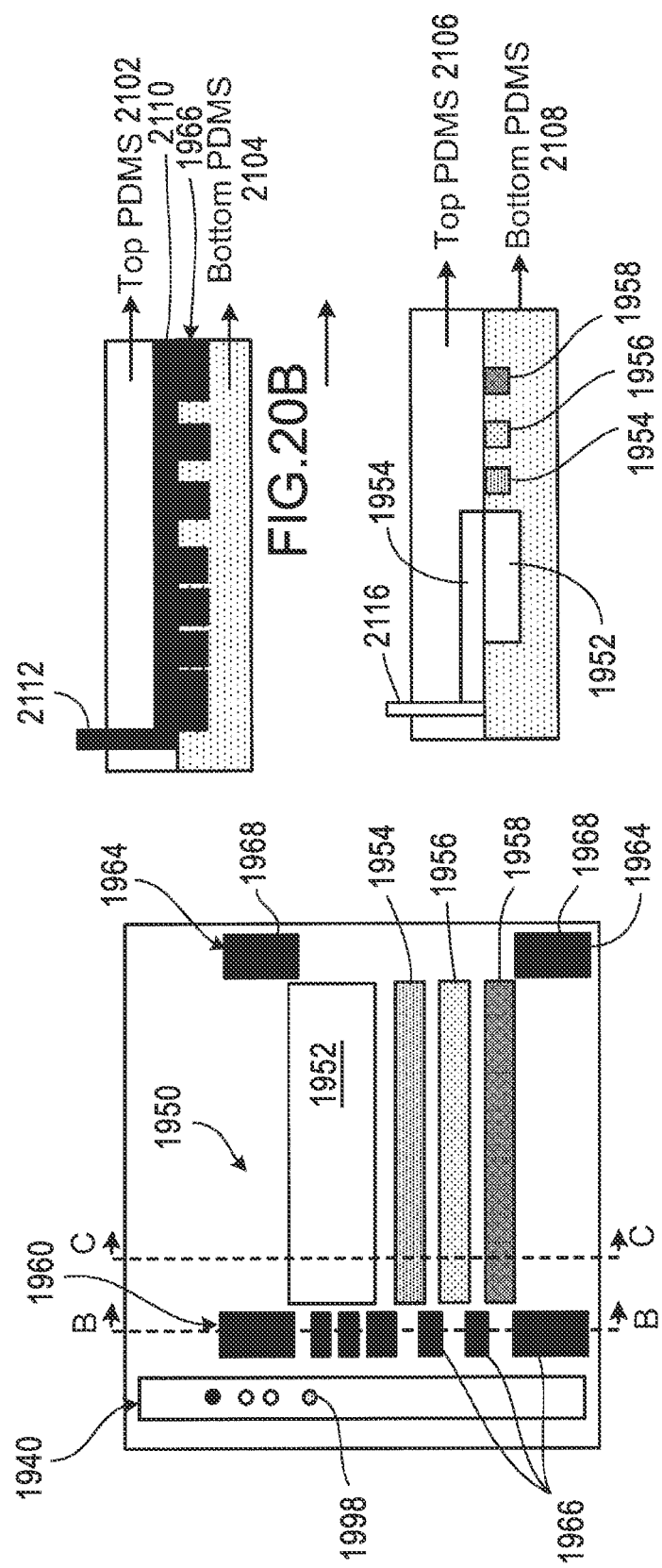
FIG. 20A is an additional view of portions of the microfluidic detector of FIG. 19A, which further shows cells passing through a microfluidic channel of the FAGS device.
FIGS. 20B and 20C are cross-sectional views of the microfluidic detector of FIG. 15-17A, taken along lines B-B and C-C of FIG. 20A, respectively.

Turning to FIG. 20A, a schematic illustration is provided of the sampling region 1940 and portions of the additional waveguide structure 50, namely, the waveguides 1952, 1954, 1956 and 1958 and the first filter structure 1960, including the features 1966 of the first filter structure 1960, and the second filter structure 64 including the features 68 of the second filter structure 1964. FIG. 20A also illustrates the matter of interest, in this example, cells 1998 passing through the sampling region 1940 of the microfluidic channel 1920. As illustrated by different shading of the cells 1998, different ones of the cells have been fluorescently labeled with different dyes, such that when those different cells are impinged by the light 1946 (as shown in FIG. 19A), the different cells give off different colors of light suitable for transmission by the different ones of the waveguides 1952, 1954, 1956 and 1958 (all of the different colors of light are conducted by the waveguide 1952).

It should be understood that, depending upon the embodiment, the additional waveguide structure 1950 can be formed by multiple layers of materials. Referring additionally to FIGS. 20B and 20C, respectively, examples of layers of the additional waveguide structure 1950 taken along lines B-B and C-C of FIG. 17A are shown, respectively. FIGS. 20B and 20C in particular show that, in the present embodiment, the channels 1970, 1974, 1976, 1978 and 1980 by which the colored or black PDMS prepolymers are introduced into the waveguides 1952, 1954, 1956 and 1958 and filter structures 1960, 1964 are at a different layer from the detection plane along which those waveguides/filter structures exist (and along which detected light passes).

More particularly, FIG. 20B shows a cross-sectional view of the additional waveguide structure 1950 particularly at the location of the filter structure 1960. As shown, the filter structure 1960 is formed as a cavity in between a top PDMS layer 2102 and a bottom PDMS layer 104. More particularly, the filter structure 1960 includes both a tunnel region 2110 positioned above the features 1966 that particularly serve as the filtering elements. The tunnel region 2110, which is positioned above the features 1966 (and positioned more within the top PDMS layer 2102 than within the bottom PDMS layer 2104, within which are positioned the features), connects an input orifice 2112 with each of the features so that black dye input at the orifice is able to enter into and form the features 1966. It will be observed that the tunnel region 2110 and input orifice 2112 can be understood to correspond to (and serve the function as) the black channel 1970 and black input orifice 1972 described above with respect to FIG. 19B, albeit the arrangement of these structures is slightly different in FIG. 20B relative to FIG. 19B.

Similarly, FIG. 20C shows a cross-sectional view of the additional waveguide structure 1950 at which are located only the waveguides 1952, 1954, 1956 and 1958 (but not the filter structure 1960). As shown, at the particular location shown (corresponding to line C-C of FIG. 20A), all of the waveguides 1952, 1954, 1956 and 1958 are present, positioned in between a top PDMS layer 2106 and a bottom PDMS layer 2108. Additionally, a tunnel region 2114 is shown positioned above the waveguide 1952 (that is, more within the top PDMS layer 2106 than within the bottom PDMS layer 2108, within which are positioned the waveguides 1952, 1954, 1956 and 1958) that connects that waveguide with an input orifice 2116. It will be observed that the tunnel region 2114 and input orifice 2116 can be understood to correspond to (and serve to function as) the channel 1980 and input orifice 1982 described above with respect to FIG. 19B, albeit the arrangement of these structures is slightly different in FIG. 20C relative to FIG. 19B. It will also be noted that, although corresponding tunnel regions and input orifices can be provided in relation to the waveguides 1952, 1954, 1956 and 1958 (as already discussed with respect to FIG. 19B).

Turning to the embodiment in FIG. 21, operation of a microfluidic detector to perform space-time coding and COST coding is illustrated in greater detail. Referring first to the embodiment in FIG. 21A, a simpler design of a microfluidic detector 2120 is shown that only performs time-space coding. As shown, a microfluidic detector 2120, in contrast to a microfluidic detector discussed above and further below, only has an array of three clear optical waveguides 2122 extending transversely away from the side of the microfluidic channel 2126, and that receive fluorescent light given off by cells 2118 from a sampling region 2124 of a microfluidic channel 2126 as filtered by a filter section 2128. More particularly, one of the fluorescent cells 2118 travels through the channel 2126 at a typical speed of 10 cm/s to 100 cm/s. In the present embodiment, the cell 2118 is optically excited along its way in a light-fluid co-propagation configuration enabled by the Teflon-coating method discussed above.

The three waveguides 2122 of the waveguide array each conduct light away from the microfluidic channel 2126 as indicated by an arrow 2128, and provide their light output to a single PMT detector. Consequently, as one of the cells 2118 travels along the microfluidic channel 2126 successively past the waveguides 2122 of the waveguide array, three serial peaks separated by the time of travel are detected via the PMT, thus converting the space signal (representing the cell positions) into a space-time coded output signal or time-domain signal 2130. Using a digital match filter to match the waveform of the time-domain signal, one can suppress noise and obtain the travel speed of each individual cell, thus establishing the timing for downstream sorting. Further, if one chooses to interrogate a given one of the cells 2118 multiple times along its path (e.g., oversampling to enhance the signal-to-noise ratio or to verify whether the cell is sorted to the right channel), it is possible to alter the coding patterns so that the resulting time-domain signal at each point of detection can be extracted using a corresponding match filter.

Turning to FIG. 21B, COST coding improves upon time-space coding by making use of additional transverse waveguides including colored waveguides such as the waveguides 1954, 1956, 1958 discussed above. As shown, using a microfluidic detector (e.g. the detector 1702), the output signal provided by the additional waveguide structure 1950 to a PMT (e.g. the PMT 1714) in response to fluorescent light coming from the sampling region 40 is now a color-space-time (COST) coded signal 2132. Again, the waveguide 1952 is clear and consequently serves as an "all-pass" waveguide, while the other waveguides 1954, 1956, 1958 only pass light of particular colors corresponding to the coloring of those waveguides. Consequently, the COST coded signal 2132 includes both a white light signal portion 2132 representative of a variety of light components emanating from the waveguide 1952, which can be used to establish a reference for overall fluorescence intensity, and also a color-coded signal portion 2134 representative of the light of specific colors emanating from the waveguides 1954, 1956, 1958. Assuming each fluorescence wavelength has a spectral width of around 30 nm and the three color filter waveguides 1954, 1956, 1958 have their maximum transmission wavelengths at 510 nm, 570 nm, and 640 nm, respectively, it is estimated that more than 20 fluorescent wavelengths can be detected using a single detector (e.g., the PMT 1714).

Although the waveguide 1952 was described above as being a single clear waveguide, as with the array of waveguides 2122 shown in FIG. 21A, the waveguide 1952 can also include more than one waveguides that form an overall waveguide array. Also, since the non-fluorescent dyes in the color filters are not in the path of the excitation laser, the background fluorescence is not a concern.

The above-described COST technology offers significant benefits in system functionality and cost. Further, assuming particular design constraints, the technology also is consistent with satisfactory device throughput. In particular, assuming the entire transverse waveguide area takes 100 um (in width) and the cell travels at 50 cm/s, the time to pass the optical interrogation zone (that is the zone defined by the outermost edges of the outermost waveguides 1952, 1958 of the additional waveguide structure 1950) within the sampling region 1940 is 0.2 ms. This limits the detection throughput to 2,000 to 5,000 cells/s or in the order of 10M cells/hr. Although this can be a satisfactory number for some applications, it still falls short in certain other applications. Therefore, to further increase the throughput, it is further proposed that in certain embodiments in-plane lenses to implement the COST design. In such an integrated lens approach, a lens array creates a series of focal spots that are separated by less than 5 urn from each other, thus reducing the total width of the interrogation zone to be around 25 microns. As a result, the time to travel through the COST region becomes less than 50 µsec. This design can potentially increase the throughput to 20-30K/s or about 100M particles per hour.

Depending upon the embodiment, additional structures can be used to further enhance performance of a microfluidic detector. For example, in at least some embodiments, prisms and other structures can be used as described for example, in U.S. patent application Ser. No. 12/152,665 filed on May 14, 2008 entitled "System and Method for Flow Cytometry", U.S. provisional patent application 61/068,198 filed on Mar. 5, 2008 also entitled "System and Method for Flow Cytometry", and further U.S. provisional patent application 60/917,848 filed on May 14, 2007 and entitled "Light Conveying Device", each of which is hereby incorporated by reference herein.

Figure 22:
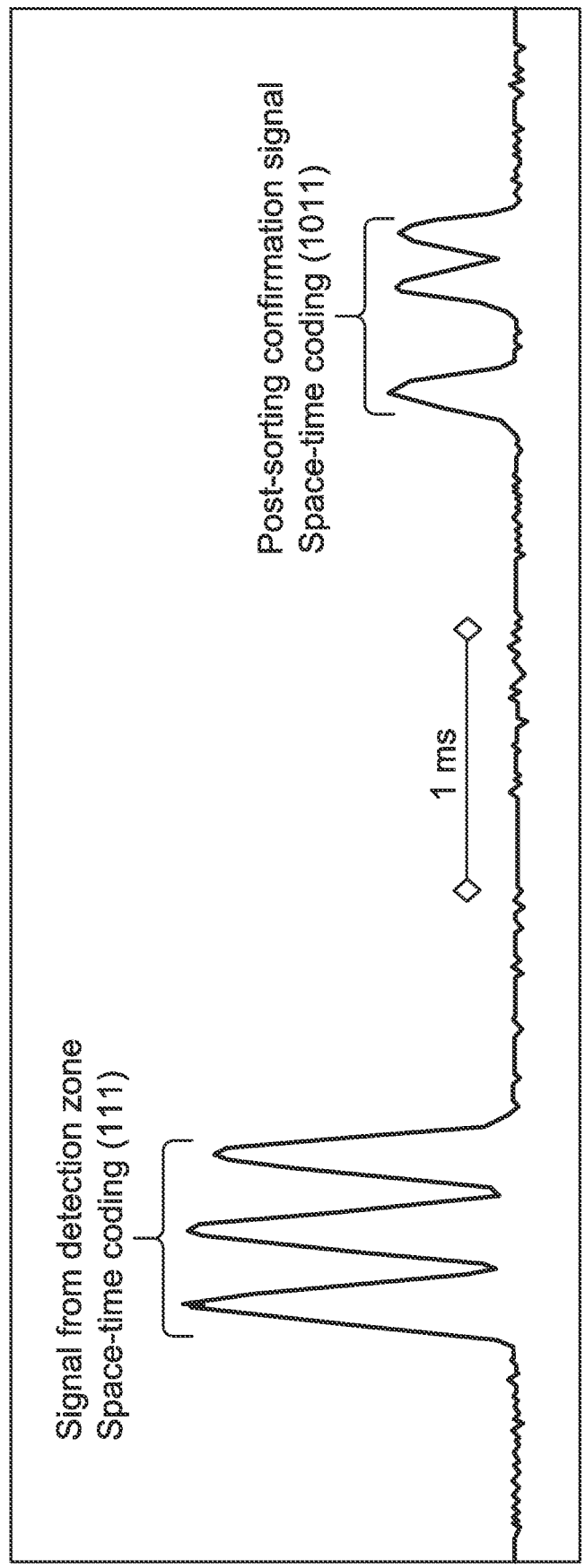
FIG. 22 shows an example of the space-time coding operation of FIG. 21A.

In FIG. 21A, as the fluorescent cell travels through the channel at a typical speed of 10 cm/s to 100 cm/s, the cell is optically excited along its way in a light-fluid co-propagation configuration. Transverse to the fluidic channel is an array of three apertures that feed their optical transmissions to a single PMT detector. As the cell travels across this array of three apertures, three serial peaks separated by the time of travel are detected, thus converting the space signal (i.e., cell positions) into a time-domain signal. Using a digital match filter to match the waveform of the time-domain signal, the noise in the signal can be suppressed to obtain the travel speed of each individual cell, thus establishing the timing for downstream sorting. If the cell is interrogated multiple times along its path (e.g., oversampling to enhance the signal-to-noise ratio or to verify whether the cell is sorted to the right channel), the coding patterns can be altered so that the resulting time-domain signal at each point of detection can be extracted using a corresponding match filter. FIG. 22 shows that the space-time coded signal (111) at the upstream detection area, followed by another space-time coded signal (1011) downstream after sorting, verifying that the sorting was performed successfully. The first signal (111) represents the detected fluorescence when the bead passes the detection zone. After sorting, the second signal (1011) that trails the first signal by about 3.5 ms indicates that the bead has been correctly switched into the sorting channel.

The multi-parameter on-chip detection and the cell sorting need to function in a well coordinated manner controlled by a real-time electronic system. Sensitivity, latency, and timing jitter are three key issues a good electronic control system needs to address. Sensitivity depends on the quality of the device itself and on the effectiveness of the real-time signal processing capability embedded in the electronic system. Latency is the amount of time required for the algorithms to complete computation. Timing jitter is the variation in latency. The control circuit architecture can be implemented in analog circuits, microprocessors, application specific integrated circuits (ASIC), and/or the like. Because of the difficulty in implementing advanced signal processing algorithms in analog circuits and the limited computational power of microprocessors that yields long latency and large timing jitter, the ASIC approach may be implemented for the control circuit. For example, the National Instruments compactRIO system provides a complete embedded system with real-time operating system (RTOS) running on a microprocessor and a field-programmable-gate-array (FPGA), which is basically a highly cost-effective type of ASIC. This system may be used for the control.

The RTOS provides a device driver to access the Ethernet connection chips and the TCP/IP protocol stack for internet communication. This connection is important for data feedback from the compactRIO system and for controlling the real-time hardware. The real-time algorithm can be implemented in the FPGA and the timing jitter is expected to be less than 10 μs. In some embodiments, the electronic control provides at least the following functions: (1) increasing signal-to-noise ratio (SNR) to improve detection efficiency, (2) instant cell speed estimation to improve sorting accuracy, and (3) sorting signal generation through a waveform generator.

Figure 23:
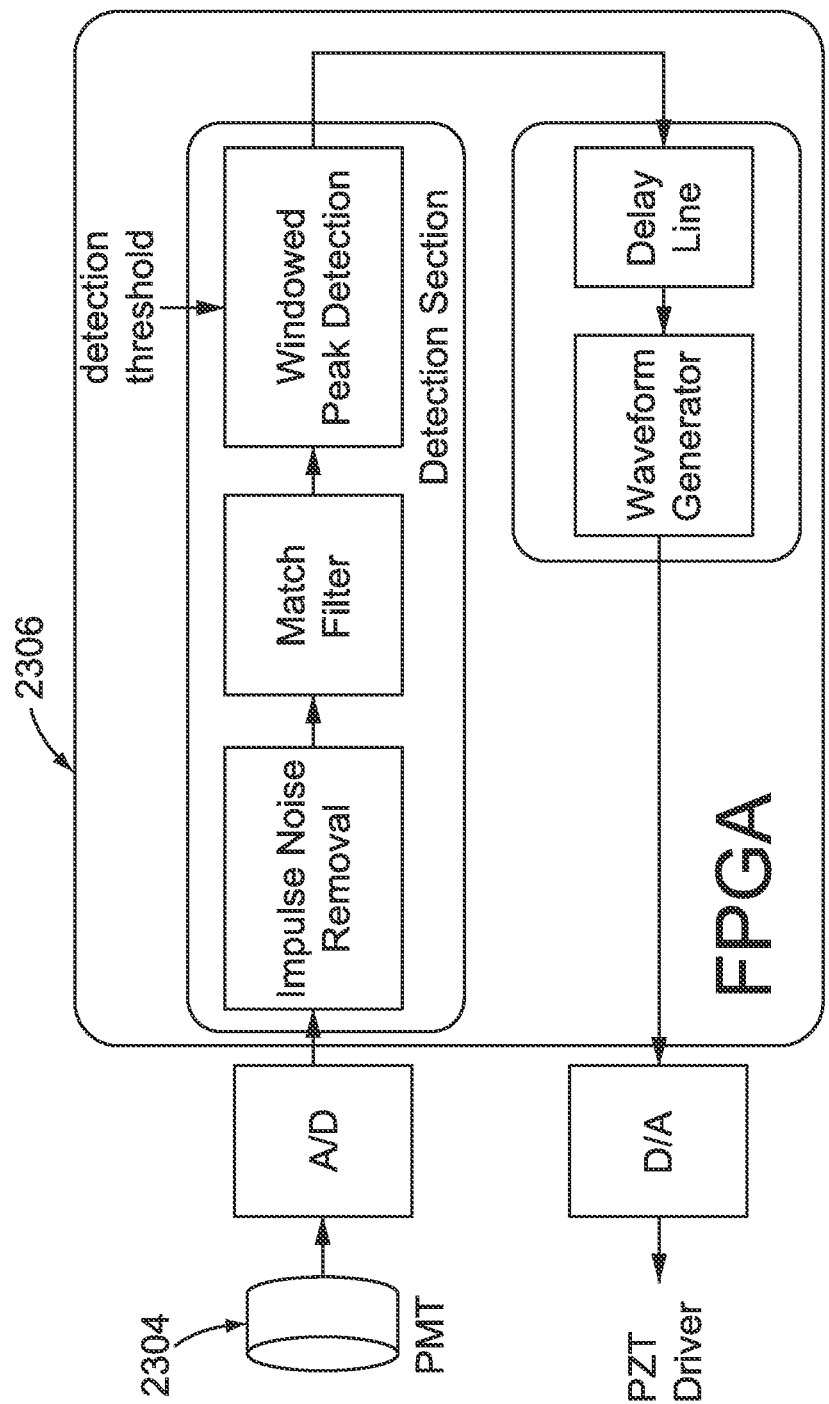
FIG. 23 illustrates an exemplary ASIC architecture of the real-time process control for a microfluidic detector, according to an embodiment.

The real-time processing control unit shown in FIG. 23 includes the detection section 2304 and the control section 2306. The use of the dedicated hardware for cell detection can help achieve low timing jitter and t accurately control the timing between the detection of a cell passing and the firing of the actuator with a synthetic waveform to optimize single-cell sorting.

To increase the accuracy of cell detection, three forms of noise that affect the sensitivity can be considered and addressed in designing the detection circuitry: (1) thermal noise of the detection circuit that is nearly white Gaussian noise (WGN), (2) PMT or SPAD dark count noise, and (3) low frequency noise due to laser power fluctuation and stray light. Understanding the characteristics of the noise spectrum, signals can be generated using the aforementioned space-time and COST design so that the signal frequency band has the least overlap with the noise spectrum. Under the WGN condition, the highest S/N ratio can be achieved with the design of match filter, a filter having a response that is the inverse reciprocal of the waveform of the signal. A finite impulse response (FIR) implementation of the match filters is illustrated in FIGS. 24A-24B.

Figure 24:
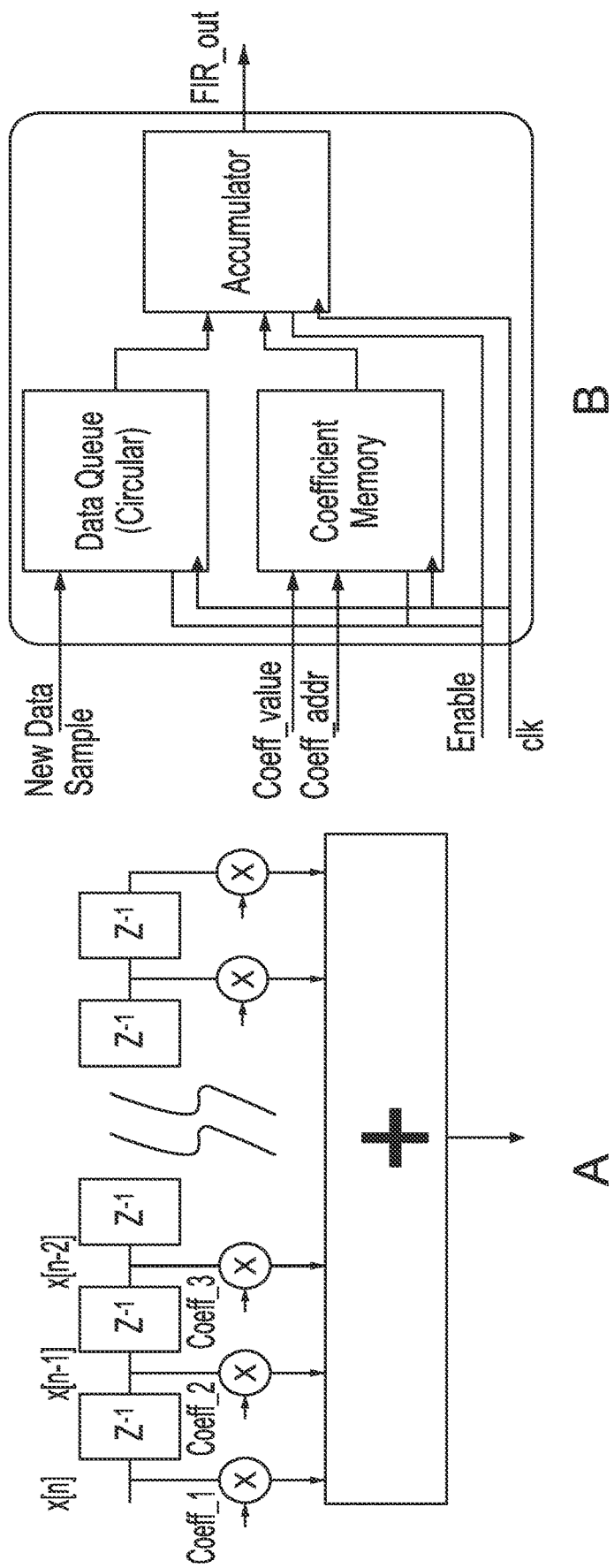
FIG. 24 illustrates an exemplary programmable match filter, according to an embodiment.

FIG. 24A shows the basic structure of an FIR filter. This is used as a programmable match filter. FIG. 24B shows the hardware implementation of the FIR filter. This design utilizes a special hardware component—dual-port random access memory (RAM), which is a RAM module that can read and write at the same time. Dual-port RAM is a built-in module in Xilinx FPGA. By utilizing the dual-port RAM, a very high sampling rate filter can be achieved.

In some implementations, real-time cell speed estimation can be implemented for high accuracy single-cell sorting. As the speed of the flowing cells changes, the signal generated from the passing cell changes as well. If the cell speed in the microfluidic channel increases, the signal duration becomes shorter. If the speed of each cell varies in a random fashion, the variation of cell speed can be treated as an additional source of noise. It affects both the S/N ratio and the timing jitter. A more effective match filter can be designed based on the knowledge of the speed of each cell and the match filter can be programmed accordingly. The acquired information of cell speed can also be used to adjust the timing control for high accuracy single-cell sorting.

Figure 25:
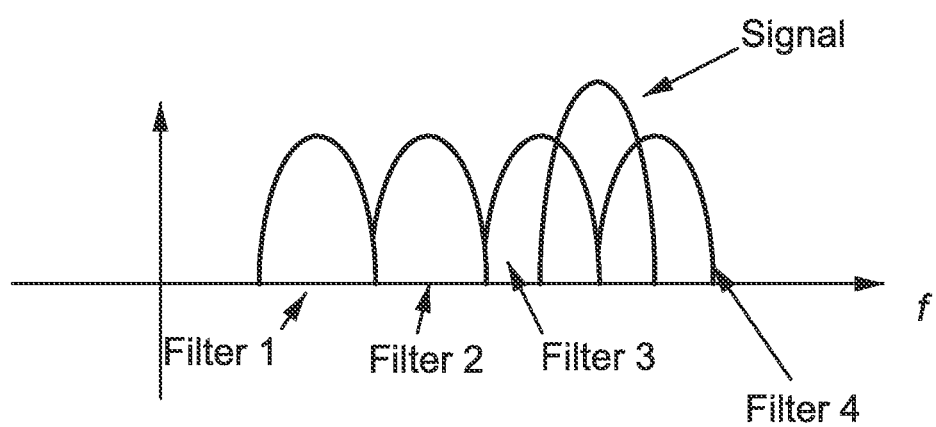
FIGS. 25A-25C show signal processing via a bank of filters at different signal frequencies in determining the cell speed, according to an embodiment.

In the frequency domain analysis, variations in cell speed can be treated as variations of the frequency response of the signal. An increase in cell speed adds more high frequency components to the signal, as illustrated in FIG. 25A. Since the frequency spectra for different cell speeds are different, a filter-bank architecture can be used to estimate the flow speed of each individual cell. An example of such an architecture 2500 including filters 2502A-2502C is shown in FIG. 25B. For example (not shown), a filter bank of 400 FIR filters can be used to measure, in real time, the flow speed from 1 cm/s to 100 cm/s with an accuracy of 0.25 cm/s. FIG. 25C further shows a process for estimating the cell speed based on outputs of the filters in the filter bank, according to some embodiments.

The signal encoding structures used in FIGS. 16A-16C can be in various configurations in addition to the examples shown in FIGS. 18-21B. FIG. 26A, for example, shows another example of a signal encoding structure that uses optical apertures with different inter-aperture spacing to form different beam patterns as the codes. Two fluidic channels with different optical aperture designs are illustrated to provide two signal codes. FIG. 26B shows the PMT signals from the two channels in the time domain.

Referring to optical filter design for COST coding in FIGS. 18, 20A, 20B, and 21B, the wide-band filtering for the waveguides 1854/1954, 1856/1956 and 1858/1958 is a mechanism to reduce the number of samples required to differentiate color, e.g., the three filter waveguides 1954, 1956 and 1958 can be used to differentiate 20 different fluorescent wavelengths without using 20 filter waveguides. This is a drastic reduction in cost. The single PMT can be used in connection with the three filter waveguides 1954, 1956 and 1958 because time-multiplexing is performed on the information from different wavelengths into the PMT. For instance, in the example in FIG. 21B, a PMT receives the red light via the waveguide 1954 first, then green via the waveguide 1956, then blue via the waveguide 1958. This time multiplexing is by utilizing flow and waveguides (or spatial filters). Time multiplexing with wideband filtering allows high-throughput color detection.

Figure 27:
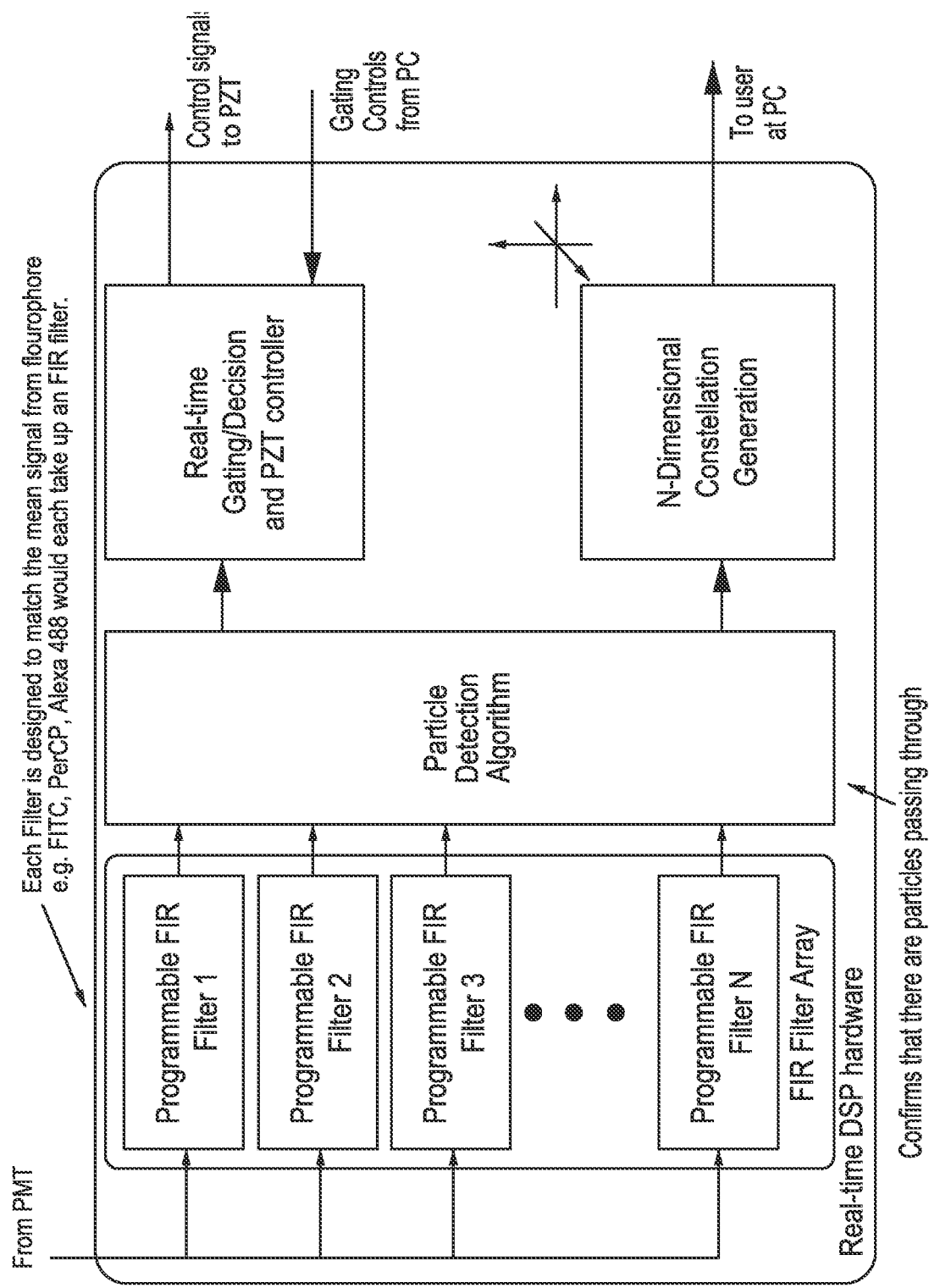
FIG. 27 illustrates an exemplary DSP processing block based on programmable FIR filtering bank.

FIG. 27 shows an exemplary DSP processing block based on programmable FIR filtering bank. The DSP processing block can be a component of, for example, a particle sorter control module (e.g. the control module 1424) as described previously.

The particle sorting mechanism in microfluidic detectors and systems can be implemented in various configurations. The following embodiments disclose a particle sorter based on a piezoelectric actuator which can be configured to operate with low voltage (typically less than 10 Vp-p), having low power requirements (typically less than 0.1 mW), and having a fast response time of approximately 0.1-1 msec with particle flow speeds of approximately 1-10 cm/sec. The particle sorting system is operable in a closed loop manner using a spatial filter and processing techniques for determining the presence of a particle by analyzing a light signal over time, which signal is output by a detector.

Figure 28:
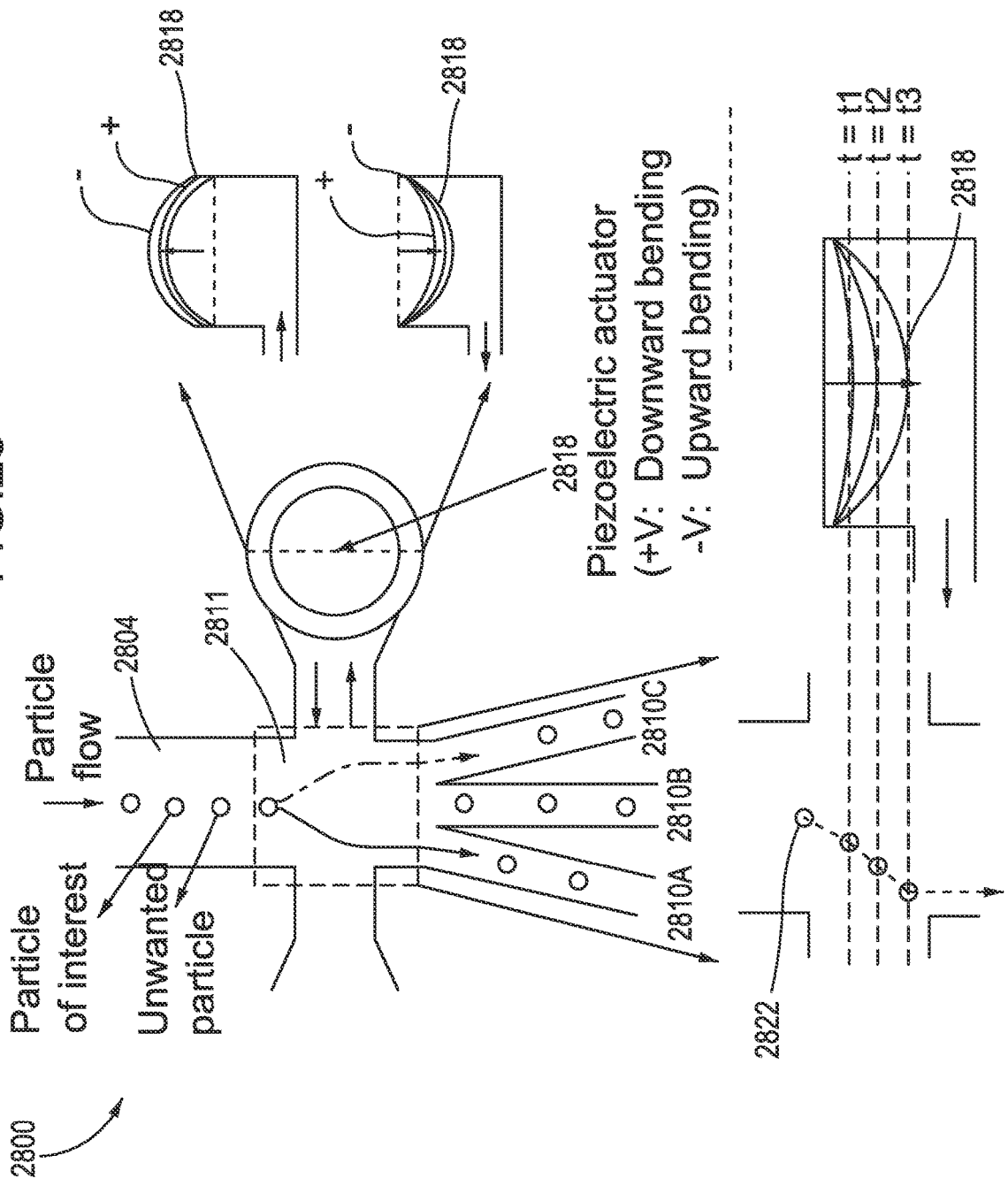
FIGS. 28 illustrates a particle sorter and its operation in accordance with some embodiments.

Referring to FIG. 28, illustrated is a particle sorter 2800 for sorting particles in a fluid. The particle sorter 2800 includes an input channel 2804 connected at an actuation area 2811 to a plurality of output channels 2810A, 2810B, and 2810C. Particles flow through the input channel 2804 to the actuation area 2811, and each particle travels from the actuation area to one of the plurality of output channels 2810A, 2810B, and 2810C.

A piezoelectric actuator 2818 operates to cause a flow disturbance to fluid in the actuation area 2811 in response to a control signal such as a voltage control signal from a controller or driver as illustrated in FIG. 27. For example, as illustrated a positive voltage signal applied to the piezoelectric actuator 2818 causes downward bending, and a negative voltage signal causes upward bending. This bending causes a flow disturbance in the actuation area 2811, specifically by causing a transverse displacement of fluid (on the order of nanoliters). The flow disturbance directs a particle entering the actuation area along a trajectory to one of the output channels 2810A or 2810C, which is different than the output channel 2810B to which the particle would travel without the flow disturbance. For example, as illustrated in the lower portion of FIG. 28, a positive voltage applied results in downward bending of the piezoelectric actuator 2818, causing a flow disturbance in actuation area 2811 causing a particle 2822 to alter its trajectory and travel to the left and to output channel 2810A.

Figure 29A:
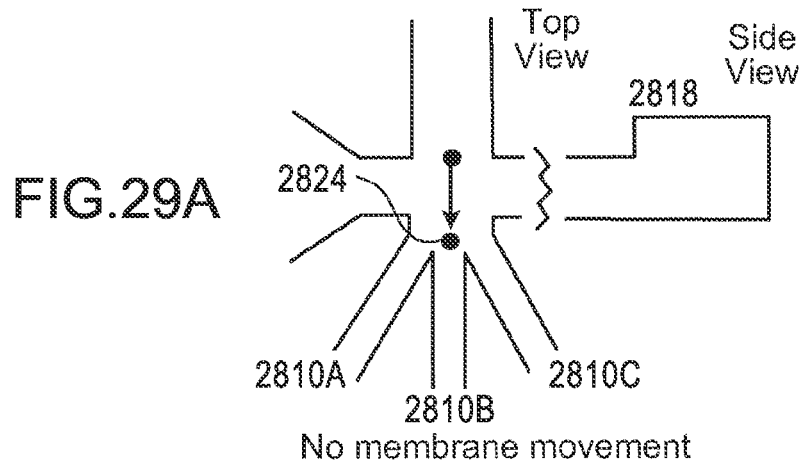
FIGS. 29A-29C further illustrate the operation of the particle sorter of FIG. 14.
Figure 29B:
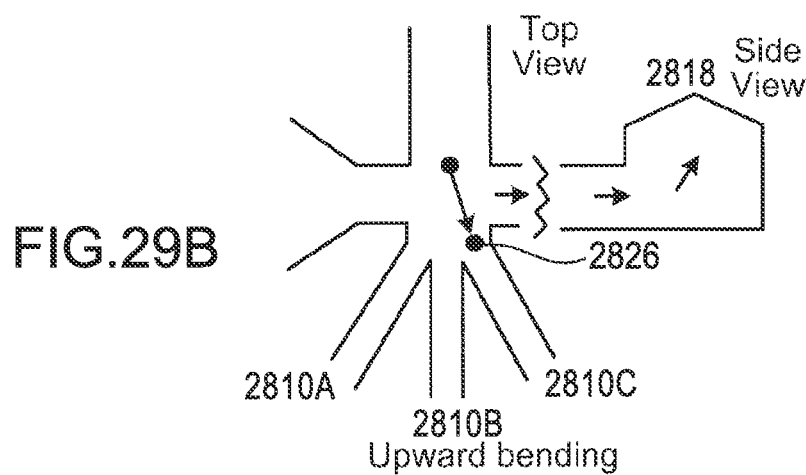
Figure 29C:
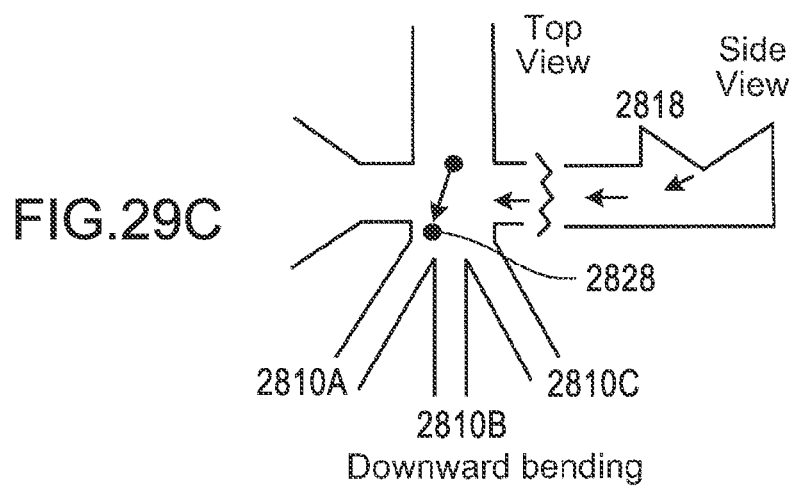

More completely. FIG. 29A illustrates travel of a particle 2824 when there is no control voltage signal applied, showing travel of the particle to output channel 2810B. FIG. 29B shows travel of a particle 2826 to output channel 2810C in response to application of a negative voltage signal. Similarly, FIG. 29C shows travel of a particle 2828 to output channel 2810A in response to application of a positive voltage signal.

Figure 30A:
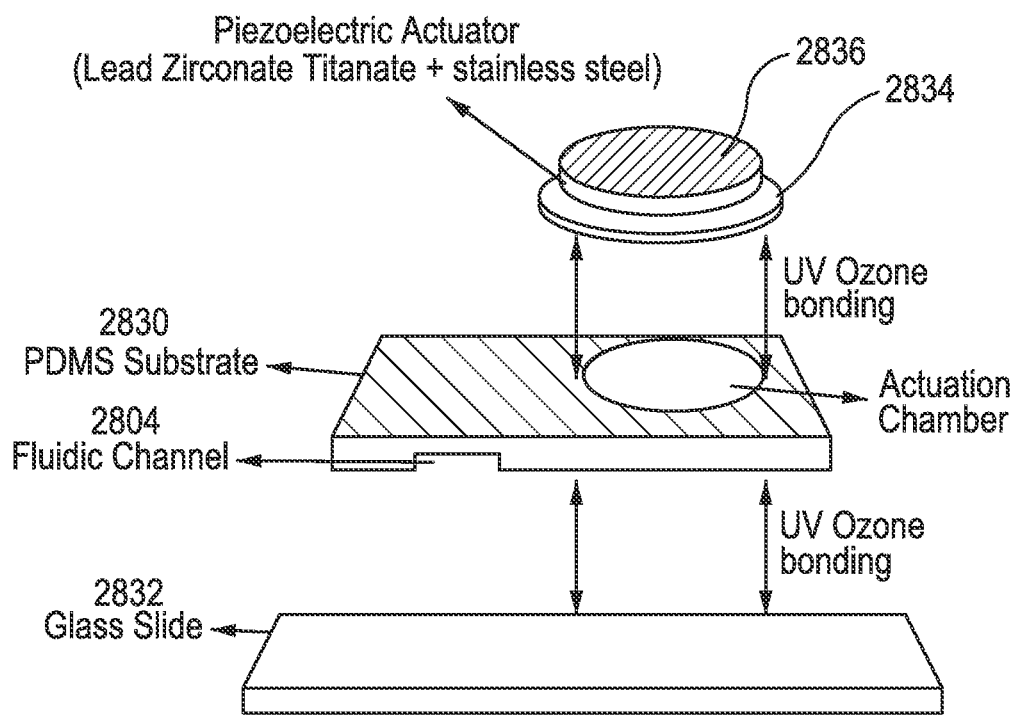
FIG. 30 illustrates the fabrication of the microfluidic detector of FIGS. 28A-28C, according to an embodiment.
Figure 30B:
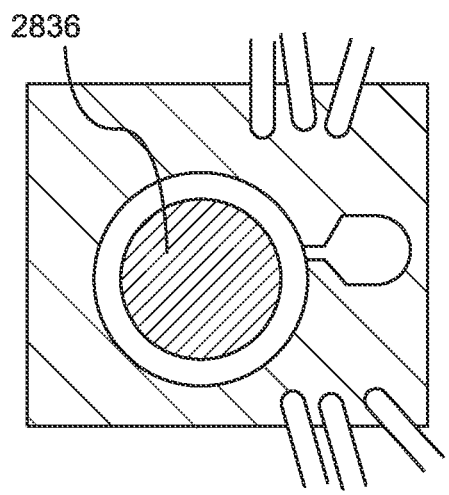
Figure 30C:
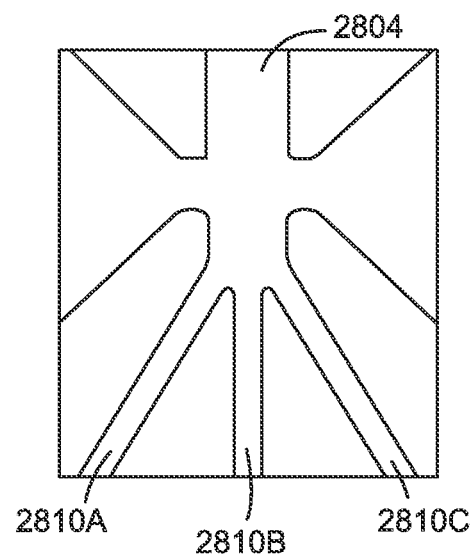

FIGS. 30A-30C illustrates the simple, low cost fabrication of particle sorter 2800, which is accomplished by UV ozone bonding together an etched polydimethylsiloxine (PDMS) substrate 2830 and a glass substrate 2832. The PDMS substrate 2830 has been etched to form the input channel 2804, output channels 2810A-2810C, and actuation area 2811. Specifically, the PDMS substrate and glass substrate are surface treated in a UV ozone chamber with a lamp output of 28 mW at 254 nm, and bonding occurs as the substrates 2830, 2832 physically contact each other.

The piezoelectric actuator is formed using a first layer 2836 such as stainless steel or copper and a second layer 2834 such as lead zirconate titanate. Lead zirconate titanate has a chemical formula of $Pb[Zr_xTi1-x]O3$, where $0<x<1$, and is a ceramic perovskite material that shows a marked piczoelectric effect. It is also known as PZT which is an abbreviation of the chemical formula. Contact pads 2838 are provided for application of the control signal across the two layers.

The piezoelectric actuator 2818 is integrated with the PDMS substrate by first forming a hole in the PDMS substrate, such as by using a 16 mm diameter punch, and then both the PDMS substrate and the piezoelectric actuator 2818 are UV ozone treated for another five minutes. The actuator is then aligned and brought into contract with the PDMS substrate 2830, and the sorter 2800 is then baked at 85 degrees C. for 8 hours.

Figure 31:
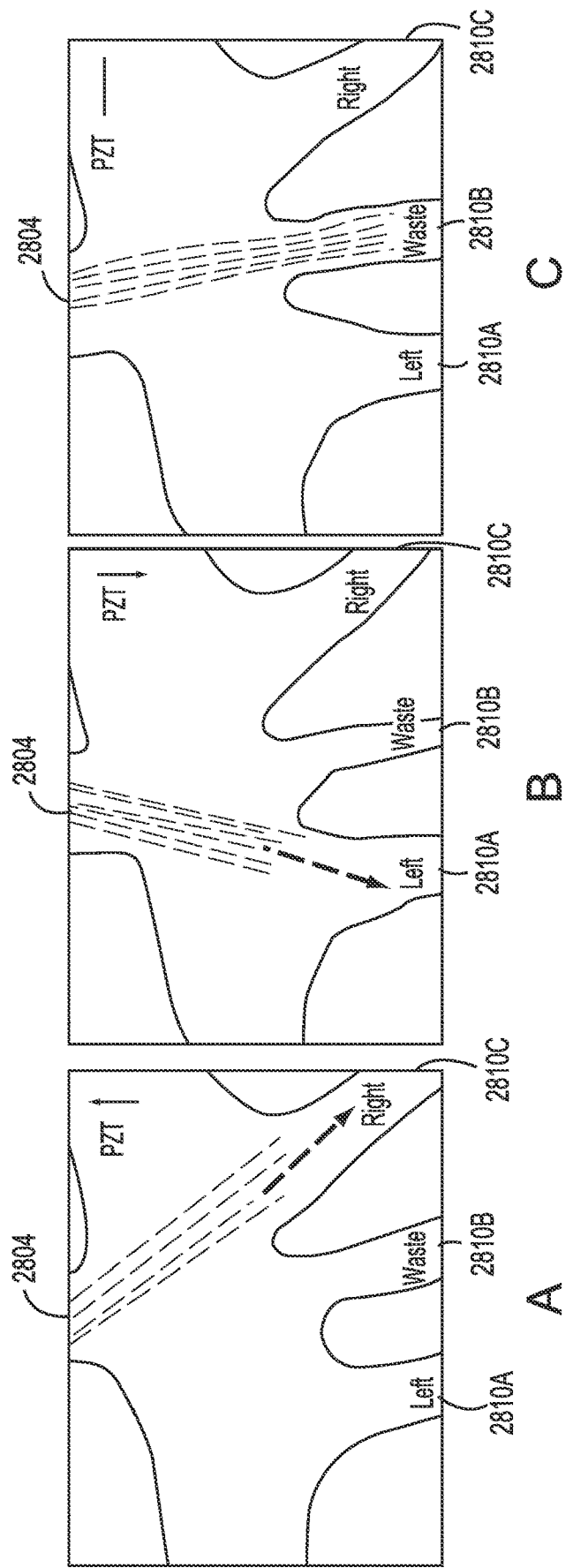
FIGS. 31A-31C show deflection of rhodamine in the microfluidic detector of FIG. 14.
Figure 32:
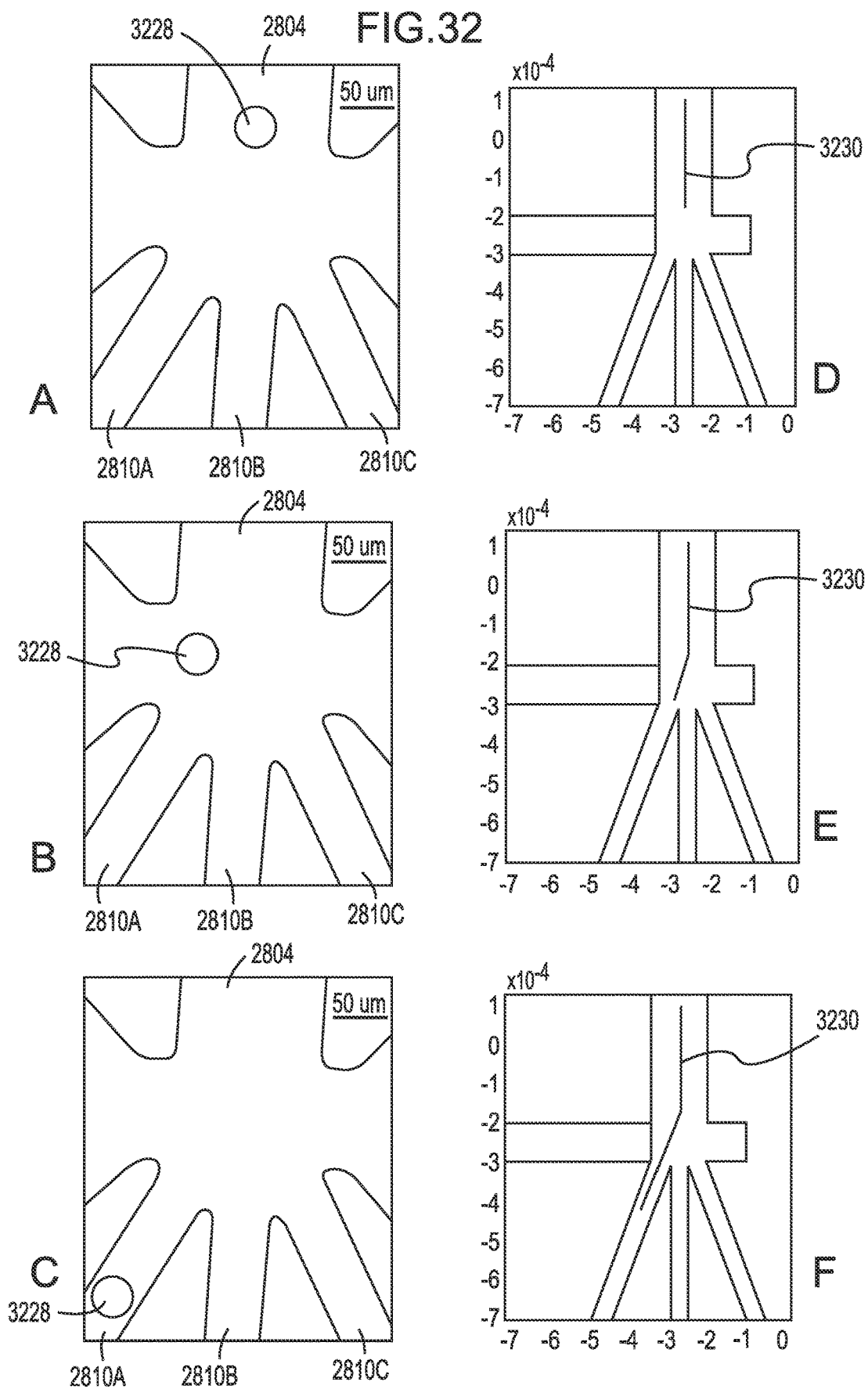
FIGS. 32A-32F show experimental (FIGS. 52A, 52C, 52E) and simulated (FIGS. 52B, 52D, 52F) trajectories of beads.

FIG. 31 illustrates the capability of the particle sorter for sorting particles, and shows the deflection of rhodamine caused by the instantaneous finite fluid displacement in the actuation area. In particular, the sorter 2800 is mounted on a microscope stage with a high-speed video camera attached for visualization, and the control signal to the piezoelectric actuator 2818 is provided by a function generator. Fluid with rhodamine is introduced to the channel, a 250 Hz, 9 V p-p voltage signal provided, and video obtained.

FIGS. 32A-32C illustrate sequential positions of a polystyrene bead 3228 obtained experimentally, and FIGS. 32D-32F illustrate the simulated trajectory 3230 of a bead using the incompressible Navier-Stokes equation shown.

Figure 33:
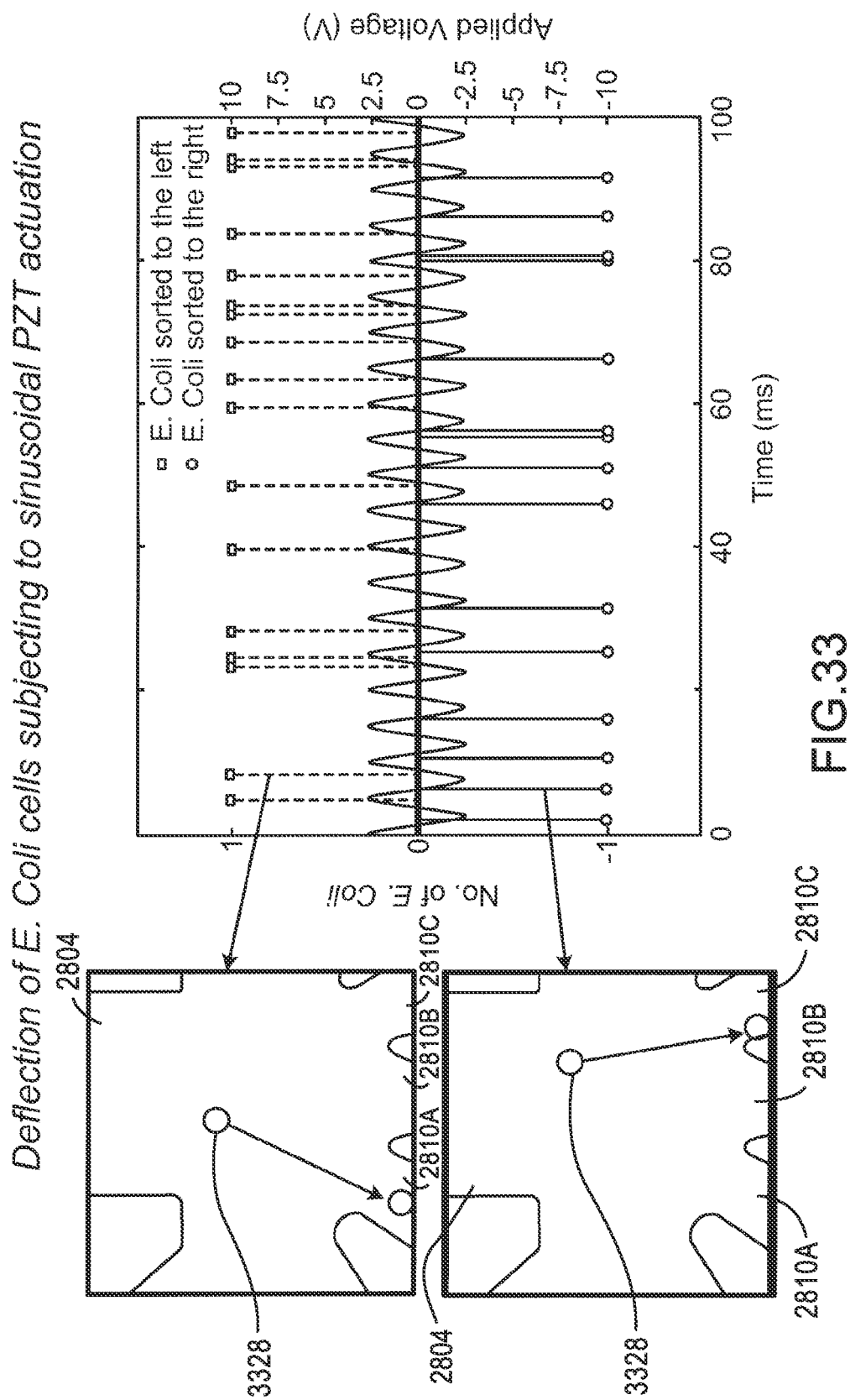
FIG. 33 illustrates the deflection of E. coli cells when subjected to a sinusoidal input voltage as a control signal.

FIG. 33 illustrates the sorting of an *E. coli* cell 3328 subjected to a sinusoidal control voltage signal at 6 Vp-p at 200 Hz.

Figure 34:
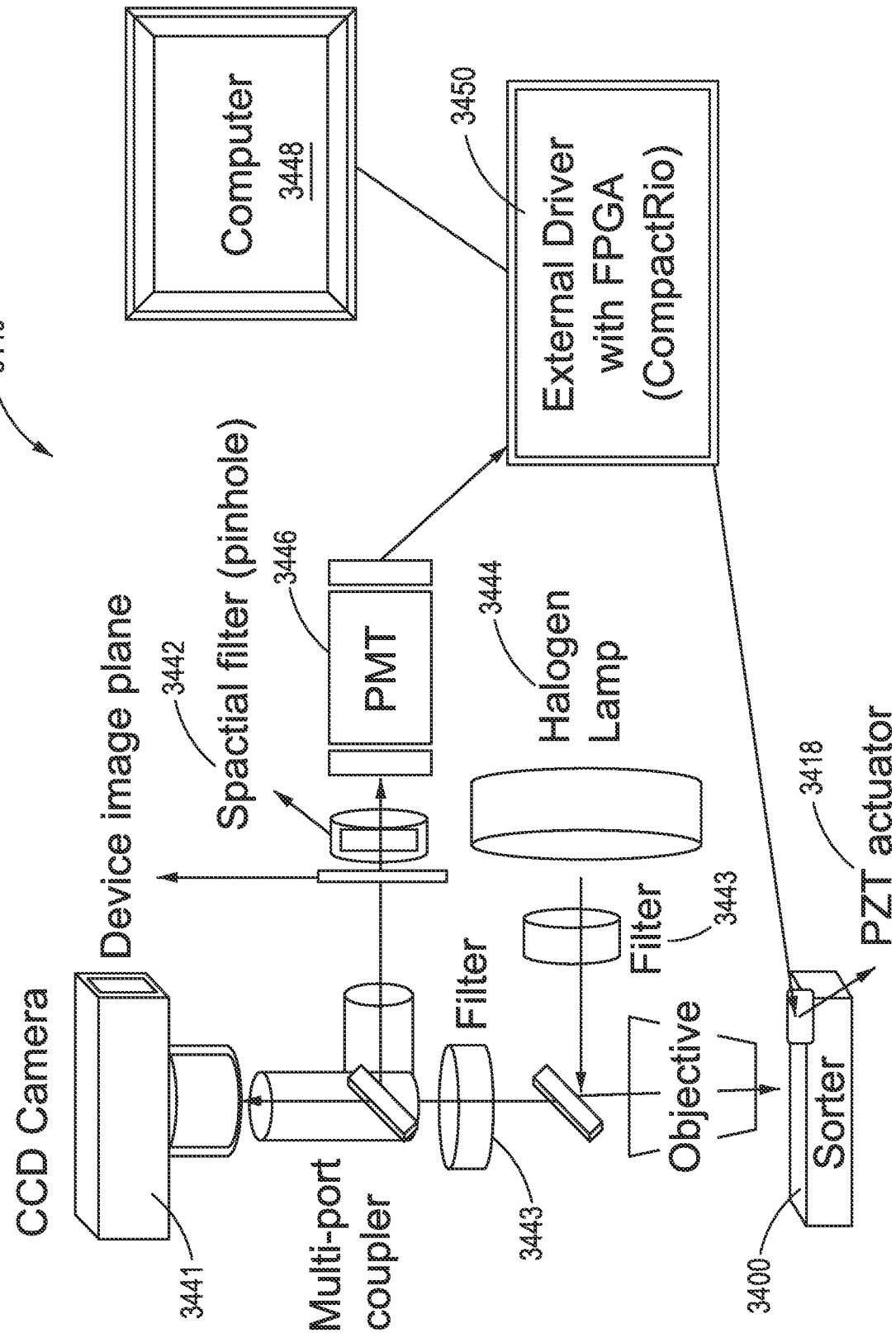
FIG. 34 illustrates a microfluidic detector having a closed loop control, according to an embodiment.

FIG. 34 illustrates a closed loop particle sorting system 2440, including particle sorter 3400, which operates in a closed loop manner to sort particles of interest from other particles in a fluid. A camera 3441 for visualization is provided. The particle sorting system also includes a spatial filter 3442 (see FIG. 35) having one or more slots and coupled to the input channel, as well as one or more optical filters 3443. A light source 3444, such as a halogen light, provides input light to the input channel. A detector 3446 detects light emitted or scattered from a particle of interest in the input channel, which light has passed through the one or more slots of the spatial filter 3442, and provides a detection signal over time. A processor and driver 3450, having one or more components implements as a field programmable gate array (FPGA), is in communication with the detector 3446 and operates to analyze the detection signal over time. The processor and driver 3450 can be in communication with a computer 3448 for receiving user input. The processor and driver 3450 also generates a presence signal indicative of the presence of a particle of interest passing a predetermined location in the input channel, and generates the control signal for the piezoelectric actuator 3418 in response to the presence signal. As described above, the piezoelectric actuator 3418 causes a flow disturbance in the actuation area in response to the control signal, wherein the flow disturbance operates to direct a detected particle of interest along a trajectory to one of the plurality of output channels which is different than the output channel to which the particle would travel without the flow disturbance.

Figure 35:
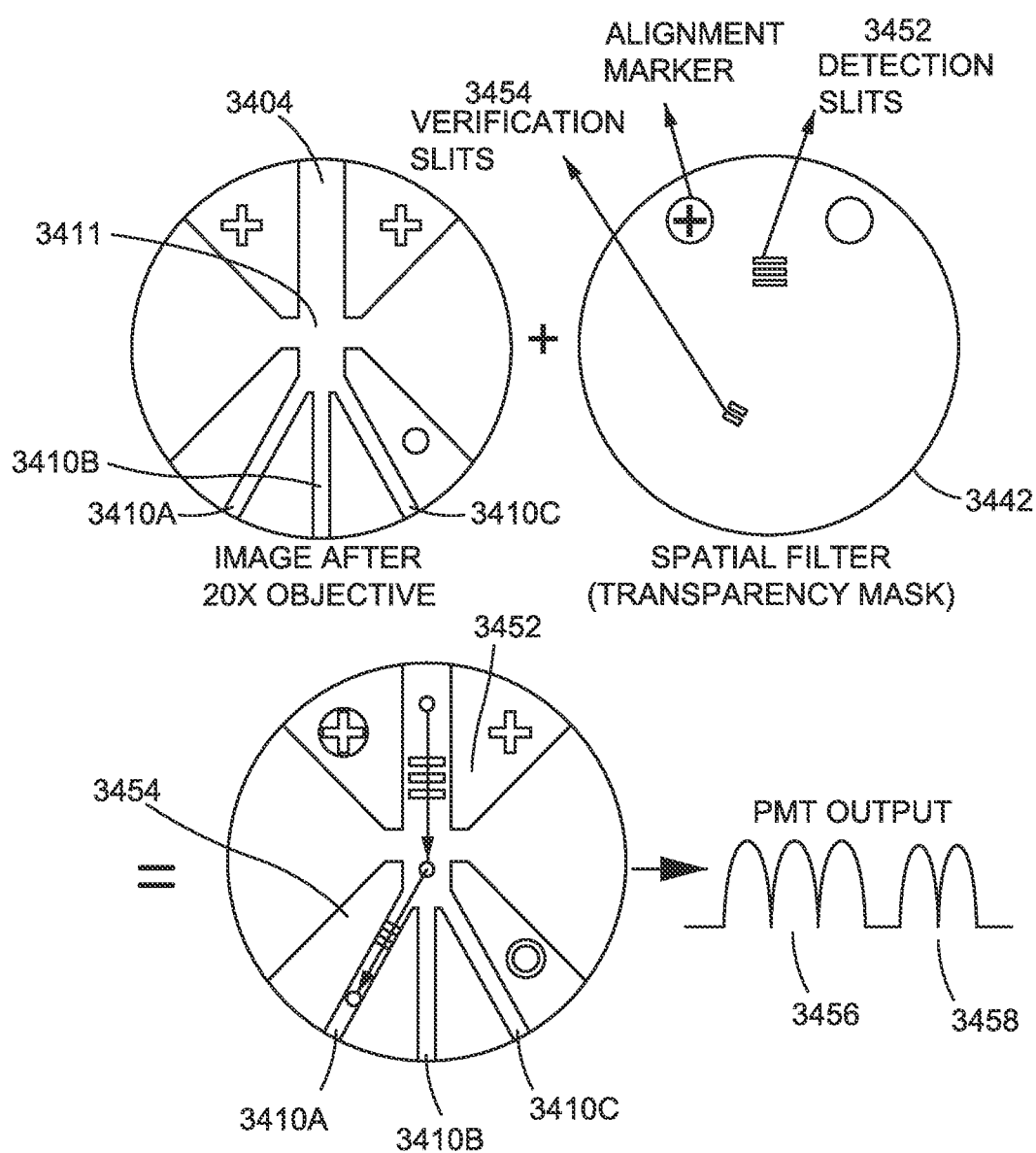
FIG. 35 illustrates a spatial filter for the microfluidic detector of FIG. 34, according to an embodiment.

As shown in FIG. 35, the spatial filter 3442 can include a plurality of detection openings or apertures 3452 which can be aligned with the input channel 3404, and which each allow light from a particle of interest through to the detector 3446. The spatial filter 3442 can also include a plurality of verification openings 3454 aligned with one of the output channels, such as 3410A. When a particle of interest travels past the detection openings 3452, a signal 3456 having an expected pattern (based on flow rate) is produced. This signal can be processed using digital signal processing (DSP) techniques to determine when a particle of interest is present in the input channel. Various DSP techniques can be used, including noise filtering to reduce noise, a finite impulse response filter, or banks of filters. When a particle of interest is present in the input channel, a control signal can be generated, which may need to be delayed so that the flow disturbance occurs when the particle of interest is at an appropriate location in the actuation area 3411. Verification that the particle of interest has actually traveled to the desired output channel 3410A can be obtained by checking that the signal 3458 is obtained following signal 3456.

The above spatial filter in FIG. 35 is an example of an encoding structure. The spatial filter/encoding structure allows only fluorescence from certain areas in the channel to reach the detector, thus cutting down the background and crosstalk. Each of the specially designed patterns 3452 and 3454 spatially encodes a fluorescent signal which is transformed into a temporarily encoded signal as the targeted particle/cell travels at a speed. Photolithographic transparency masks (Cad/art services, Inc.) can be used to create spatial filters. The spatially encoded patterns have triple slits (3452) and double slits (3454). The triple slit pattern (3452) encodes the detection signal and the double slit pattern (3454) the verification signal from the particles/cells sorted into the designated channel. In the sample spatial filter, the width of the slits can be is about 0.25-0.5 mm, translated to 12.5-25 μm on the microfluidic channels before magnified by a 20× microscope objective. The spatial filter can be designed to purposefully coincide with the image plane after magnification. As fluorescent particle passes through detection slits and gets sorted down to the verification slits, the PMT detector is expected to register signals of 3 peaks followed by 2 peaks.

Figure 36:
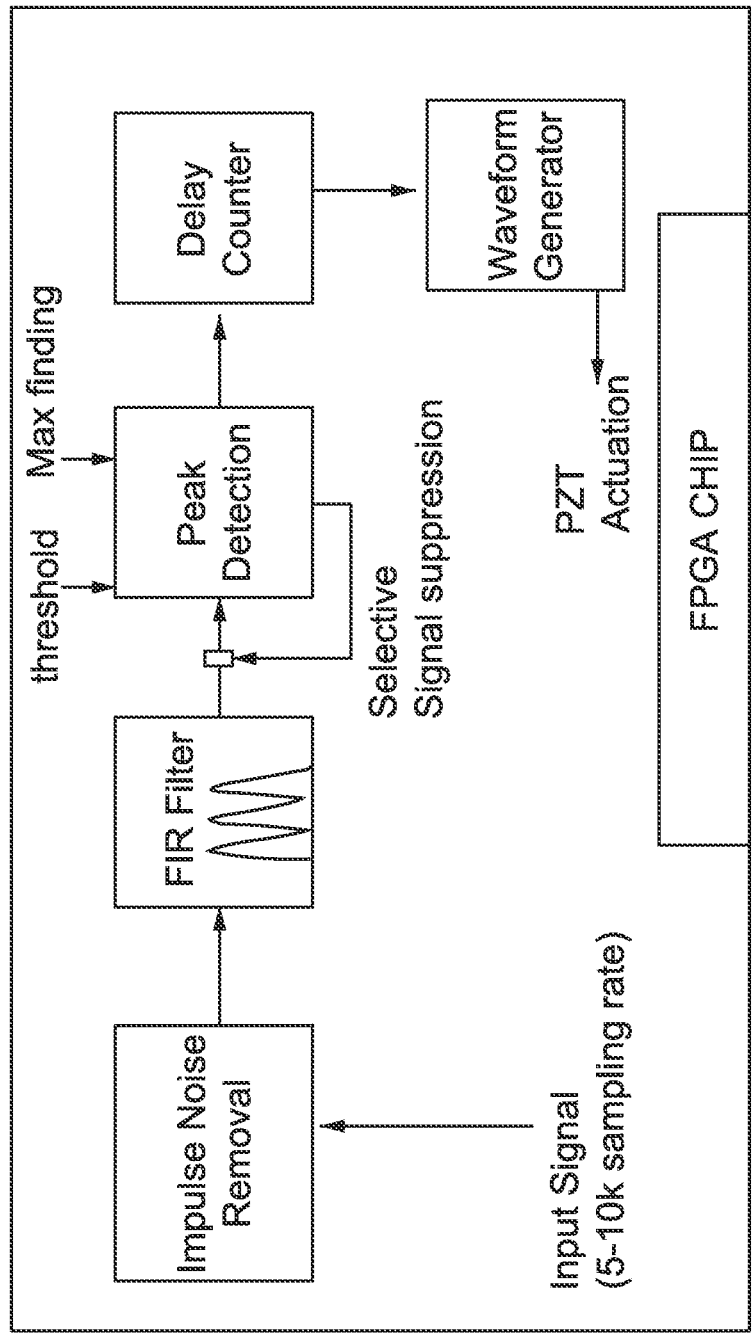
FIG. 36 is a block diagram showing operation of control circuitry for the closed loop system of FIG. 34, according to an embodiment.
Figure 37:
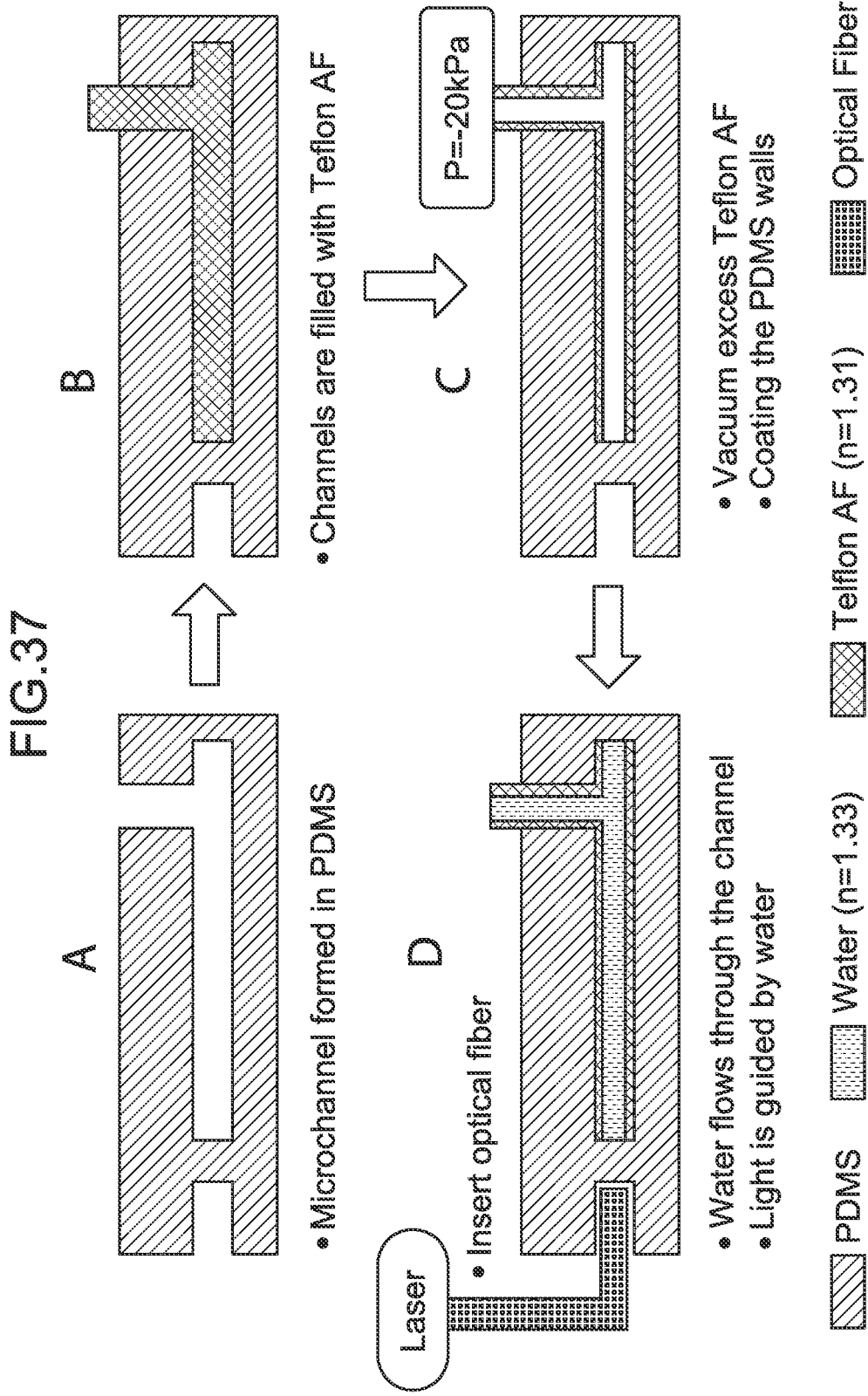
FIGS. 37A-37D illustrate an exemplary fabrication process for Teflon AF coated fluid core waveguides that reduces the elastic mismatch between PDMS and Teflon AF.
Figure 38:
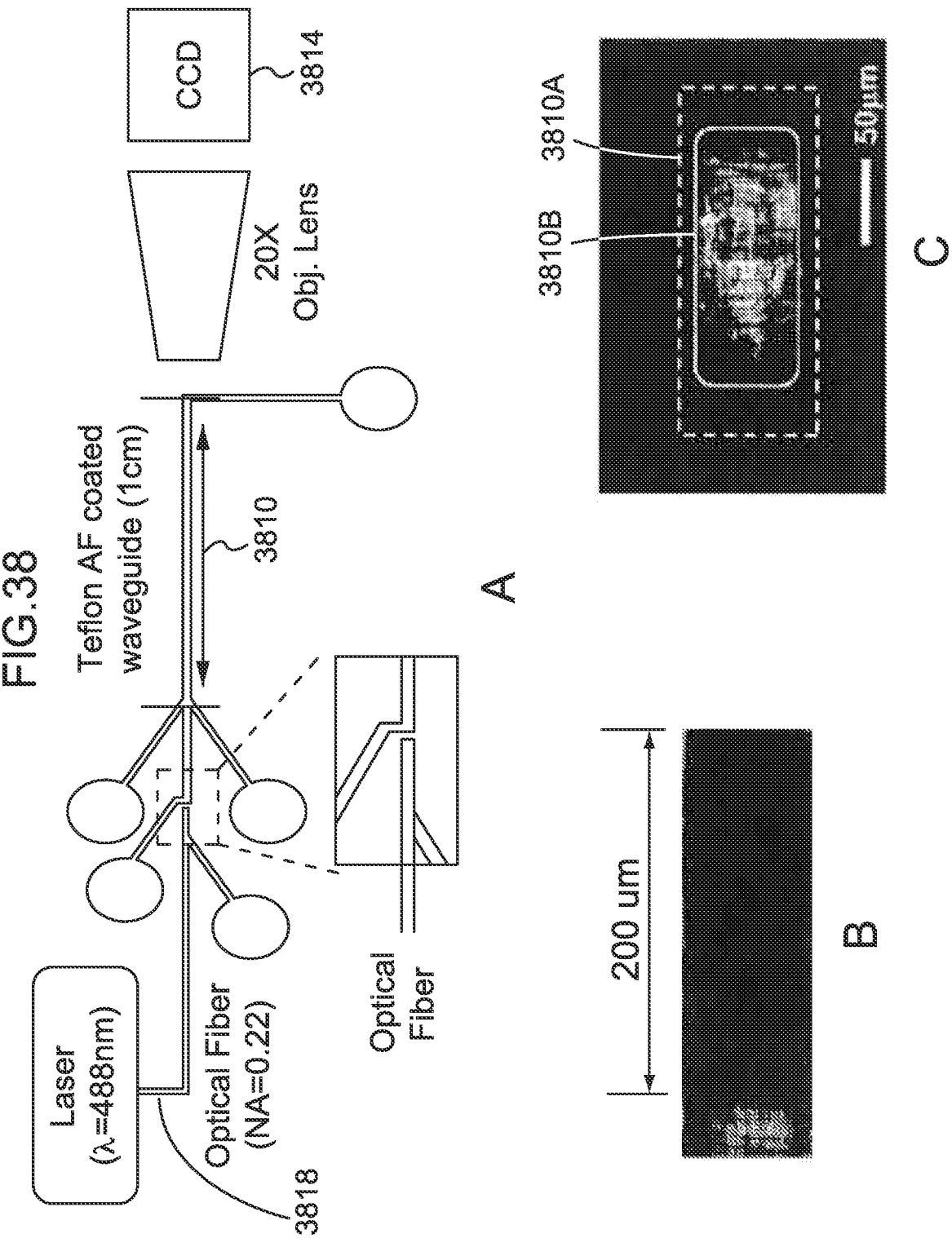
FIG. 38 illustrates an experimental setup for light output measurement, the cross section of the fluid core waveguide, and the light output from a fluid core waveguide with Teflon AF coating, according to an embodiment. The dotted box is the perimeter of the channel, and the solid line is the Teflon AF coated core layer.

FIG. 36 is a block diagram of one embodiment of a processor and driver 3450, showing the process flow of the electronics control algorithm. The algorithm is programmed into the FPGA chip embedded in the external driver. For example, real-time electronic control is programmed using Labview (National Instrument) with a programmable external driver (CompactRio, NI). The external driver has an independent operating system with an embedded field-programmable gate array (FPGA) chip. The measured jitter of a microfluidic detector is less than 10 μsec. The random high pulse noises of PMT (e.g., caused by sporadic discharge of the device) are removed before running the signal amplification algorithm based on finite impulse response (FIR) filtering. With an FIR matched filter, the signal-to-noise (SNR) ratio can be increased by 18 dB. After SNR enhancement, threshold and search of maximum signal criteria are applied to determine the presence of the detected particle. A signal above threshold indicates that a particle/cell to be sorted is found, triggering the following actions: (a) a delay counter delays the firing of the pulse generator, (b) a preprogrammed output voltage signal is fired to drive the PZT actuator, (c) at certain time period a microfluidic detector is ready to detect the "verification" signal from the sorted sample traveling through the "verification zone", and (d) update record of the sorting efficiency and sorting error. The amount of time delay equals the travel time of the particle from the optical detection zone to the sorting junction. Until the sorted particle is verified, the PZT actuator will not be fired again. This avoids the problem of confusing the verification signal with the signal of particles traveling too close to the particle being sorted.

FIGS. 37A-37D illustrate embodiments of a method for fabricating optofluidic waveguide that is compatible with polydimethylsiloxane (PDMS). The light path follows the microfluidic channels, an architecture that can maximize detection efficiency and make the most economic use of chip area in many lab-on-chip applications. The PDMS based microfluidic channels are coated with Teflon amorphous fluoropolymers (Teflon AF) which has a lower refractive index (n=1.31) than water (n=1.33) to form a water/Teflon AF optical waveguide (FIGS. 37A, 37B). Driven by a vacuum pump, the Teflon AF solution was flowed through the channels, leaving a thin (5 to 15 μm) layer of coating on the channel wall as the cladding layer of optical waveguides (FIG. 37C). This coating process resolves the limitations of spin-coating processes by reducing the elasticity mismatch between the Teflon AF cladding layer and the PDMS device body. The resulting optofluidic waveguide confines and guides the laser light through the fluid core channel (FIG. 37D). Furthermore, in some embodiments, the light in such a waveguide can be split when the fluid flow is split. In some embodiments, this approach enables highly integrated biosensors such as a microfluidic detector with on-chip excitation.

Optofluidics is an emerging field that integrates microfluidics and optics on the same device to work synergistically. Devices that contain both microfluidic channels and on-chip photonic circuits, such as integrated biochemical sensors, show enhanced functionality and sensitivity and enable significant cost and size reduction. Flexibility to direct and align the paths of light and fluid is desired and assures that photons and biological samples in the fluid interact most effectively for the highest sensitivity. In some cases, light beams are required to intersect the fluidic channels to localize the interrogation area. In other cases, it is desired that the light wave and the fluid share the same path to maximize their interaction. For the latter case, an effective fabrication method is desired. Due to the fact that most polymers used in lab-on-a-chip devices have a higher index of refraction than water, light traveling in the fluidic channel will not be confined, suffering from high radiation loss. A PDMS-compatible process is provided here for coating microfluidic channels with a layer of low refractive index Teflon AF solution, enabling the water in the fluidic channel to be used as the waveguide's high index core. The Teflon AF coated waveguide works not only for straight fluidic channels but also for split channels. In addition to delivering the light, by Teflon coating the microfluidic channel, a channel is created with low sample adsorption, avoiding a troublesome problem found in many polymer-based microfluidic devices.

Teflon AF is an amorphous fluoropolymer that is chemically stable and optically transparent from UV to IR wavelengths. Unlike other fluoropolymers, Teflon AF has a refractive index (n=1.31) that is lower than the index of water (n=1.33), therefore a Teflon AF coating layer can be used to clad a fluid-core optical waveguide. Light will then be delivered through the same physical path as the fluid flows by total internal reflection (TIR) when the coated channels are filled with water or aqueous solutions. A procedure for coating Teflon AF onto PDMS channel walls is provided here by flowing Teflon AF solution through the micro channel, thereby creating the cladding layer for an optical waveguide along the path of fluid flow. The light introduced to micro channels is confined inside the core of the waveguide (i.e., microfluidic channel) and guided by fluid flowing through the channel.

In some embodiments, microfluidic channels that are 200 μm by 70 μm are fabricated in PDMS. A master mold is lithographically defined on an optically smooth Si wafer using SU-8 50 (MicroChem). Two replicas are created: one replica with microfluidic channels and one replica of an optically smooth blank Si wafer. A solution of 2% 1H,1H, 2H,2H-perfluorodecyltriethoxysilane (Sigma Aldrich Inc.) is spin-coated onto PDMS substrates and heated at 110° C. for 10 minutes to promote adhesion between PDMS and the Teflon AF solution. Both PDMS surfaces are then activated for permanent bonding by UV/Ozone treatment (UVO-CLEANER 42, Jelight Inc.) for 3 minutes and bonded together, thus capping the microfluidic channels. A 6% Teflon AF solution (601-S2, DuPont Corp) is flowed into the microfluidic channels. Once they are filled, vacuum (P=−20 kPa) is applied for 20 minutes to remove excess Teflon AF solution from the channels (e.g., see FIG. 37C). The balance between the vacuum force and the adhesion to the PDMS channel wall determines the thickness of the cladding layer.

The process results in a smooth channel with a hollow core. The Teflon AF-coated PDMS device is heated to 155° C. for 20 minutes to evaporate the fluoroinert solvent, and then heated further to 175° C. (15° C. above the its glass transition temperature) for 20 minutes to form a smooth Teflon AF layer. This relatively low temperature coating is compatible with PDMS process while significantly reducing the consumption of Teflon solution compared to the spin-coating process. Calculations show that a ~5 μm thick Teflon AF film is necessary to confine the light to the fluid core. In some implementations, the cladding thickness is typically 5 to 15 μm, thick enough to confine and guide light waves.

The thickness of the Teflon AF coating layer can be further controlled by adjusting the applied vacuum pressure and concentration of the Teflon AF solution. After slowly cooling the devices to avoid cracking due to thermal mismatch, an optical fiber is inserted into the channel for light coupling. Deionized (DI) water is then introduced into the hollow core to serve as both the sample flow carrier and the core of the optofluidic waveguide.

The flowing DI water transports both the suspended samples and the light in the same channel. FIGS. 38A-38C illustrate the fabrication process of the Teflon AF coated optofluidic waveguide 3810. The numerical aperture, NA= $(n_{core}^2 - n_{cladding}^2)^{1/2}$, of the fluid core waveguide is 0.23, well-matched to the NA of the input multi-mode fiber 3818 (NA=0.22). The cross section of the fluid core waveguide 3810 is imaged by a charged coupled device (CCD) 3814 at the end of the channel as shown in FIG. 38A. FIG. 38B shows the cross section of the fabricated microfluidic channel that is 200 µm by 70 µm. FIG. 38C shows the light output of the optofluidic waveguide 3810 when the laser is on. The dotted box 3810A shows the wall of the PDMS channel, and the solid line 3810B shows the boundary between the Teflon AF cladding layer and the fluid core. It verifies that the light is confined to the fluid core of the optofluidic waveguide by the Teflon AF coating. A waveguide loss of 2.13 dB/cm at 488 nm wavelength is measured. Scattering is the dominant factor compared to light leakage and absorption. With improved smoothness of Teflon AF coating, waveguide loss can be reduced significantly.

FIG. 39A shows the layout of a microfluidic channel/device 3900 which includes a splitting junction 3911, and FIG. 39B is a photograph of the device. Laser light (λ=488 nm) is fiber-coupled into the microfluidic channel, in which water flows. Light is guided by the fluid flow, and at the three-way junction, as shown in the enlarged box in FIG. 39A, the 488 nm light is divided into three paths following the fluid flow towards the channel outlets 3910A-3910C. In order to demonstrate that light can be split and guided through the three channels outlets 3910A-3910C, the device was filled with a diluted Rhodamine 6G solution that emits green fluorescence in all directions after absorption of the guided 488 nm light.

Figure 40:
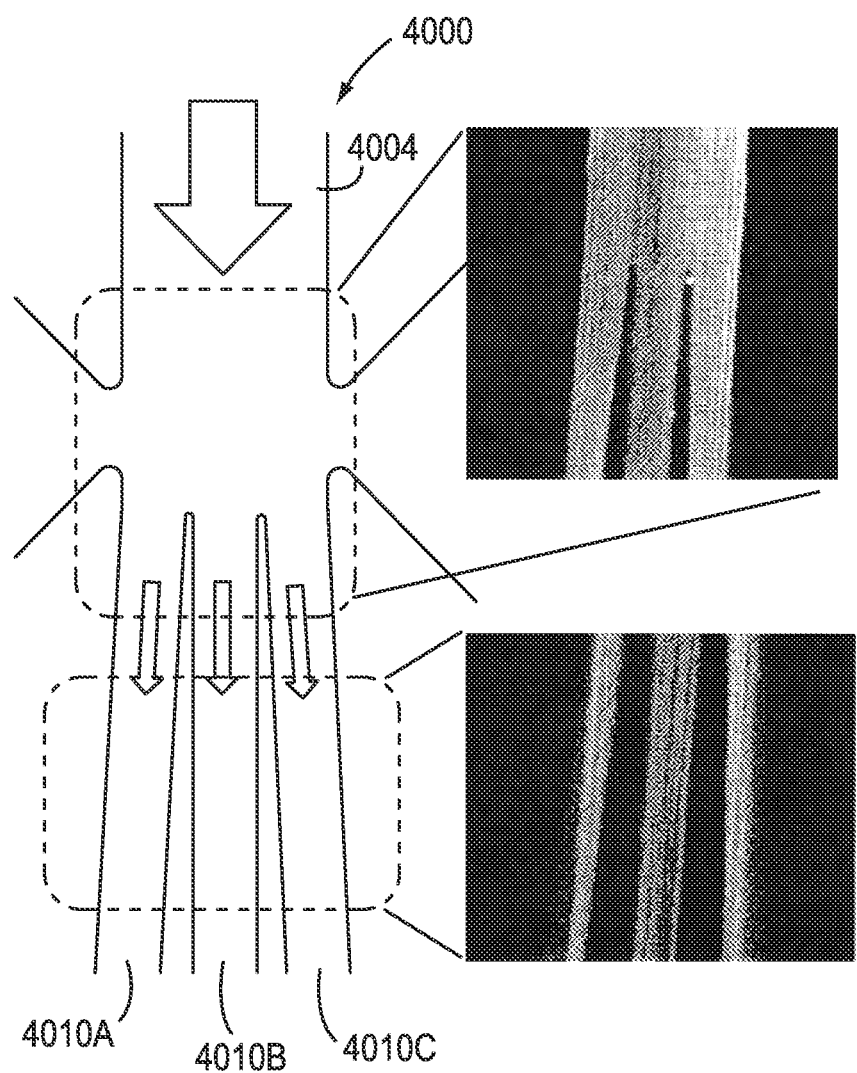
FIG. 40 shows the light emitted by Rhodamine 6G when the fluorescent dye in the fluid is excited by the 488 nm laser light sharing the same paths as the fluid. The 488 nm input light is guided through the entire paths of fluidic channels, even after the three-way split.

As shown in FIG. 40, the light guided from the upstream channel 4004 is divided into three split channels 4010A-4010C separated by, for example, 3-degrees. The result demonstrates that the excitation light is split into the three channels 4010A-4010C and that the split light is still guided through the channels. In some embodiments, since the light always traces the fluid flow in which samples are suspended, excitation is performed at all locations, and thus, in some embodiments, detection can be performed at any position. This unique property can provide a very convenient feature for a microfluidic detector. For example, in some embodiments highly sensitive fluorescence detection is performed at multiple locations using only a single light source, imparting a high degree of design flexibility to a microfluidic detector.

Figure 41:
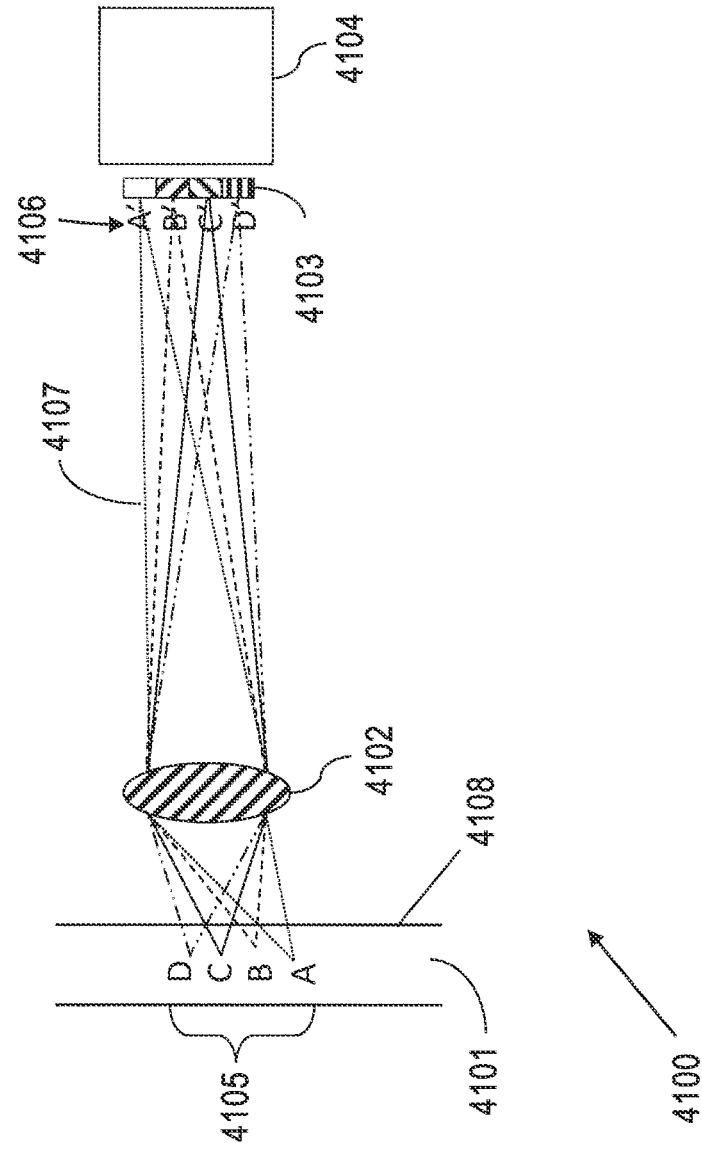
FIG. 41 is a schematic illustration of a specific configuration of a lens of a microfluidic detector used for flow cytometry or fluorescence-activated cell sorting, according to an embodiment.

Shown in FIG. 41 is a schematic illustration of an embodiment of a microfluidic detector 4100 and the use of a COlor-Space-Time (COST) coding operation. The microfluidic detector in FIG. 41 (4100) illustrates an embodiment that includes a fluidic channel (e.g., a microfluidic channel) 4101 where a sample (e.g., a particle or a cell, or including a particle or a cell) flows, channel wall 4108, a lens 4102, a series of optical filters 4103 and an optical detector (e.g., a PMT or photodetector) 4104. A sample (e.g., a particle or a cell) passing through a fluidic channel (e.g., a microfluidic channel) 4101 can emit light (e.g., fluorescent light) originating from positions A, B, C or D. The emitted light can pass through a lens 4102 and arrive at the image plane 4106 and contact one of the optical filters 4103 at the corresponding conjugate points indicated by A', B', C' and D'. Light paths 4107 are indicated by dashed or solid lines. For example light originating from position A will follow the indicated light path to A'. A lens, 4102, can transform light originating from a series of points within the sample path 4105 (located inside the fluidic channel) to the image plane 4106, through an array of optical filters 4103, to an optical detector 4104 (e.g., a PMT or photodetector). An array of optical filters can include a plurality of zones (e.g., color zones), where each zone in the array can transmit a subset of the light. Each optical filter within the array 4103 can have a different transmission spectrum. The energy distribution of light passing through any one of the filters or zones located at points A', B', C' or D' is defined by the spectral properties of the optical filter located at that point.

A light emitting sample (e.g., a particle or a cell) can transiently occupy positions A, B, C and D as it passes through the fluidic channel (e.g., a microfluidic channel) thereby generating multiple signals per sample. The waveform of these signals is determined by the transmission spectra of the optical filters and the characteristics of the sample. The combined optical signals of a sample can be digitally processed to determine the type of the particle and whether to sort the particle into a separate channel in a fluorescence-activated cell sorter system.

A fluidic channel (e.g., a microfluidic channel) can be part of a microfluidic device (e.g., a lab-on-a-chip) using sheath flow to confine the particles to the center of the fluidic channel. The microfluidic device can contain other features such as a sample (e.g., a cell or particle) sorting device. The sample sorting device can be downstream of the optical detection area and separate the sample of interest from the rest of the population. Such a microfluidic device can, in some embodiments, eliminate the generation of aerosols.

Figure 42:
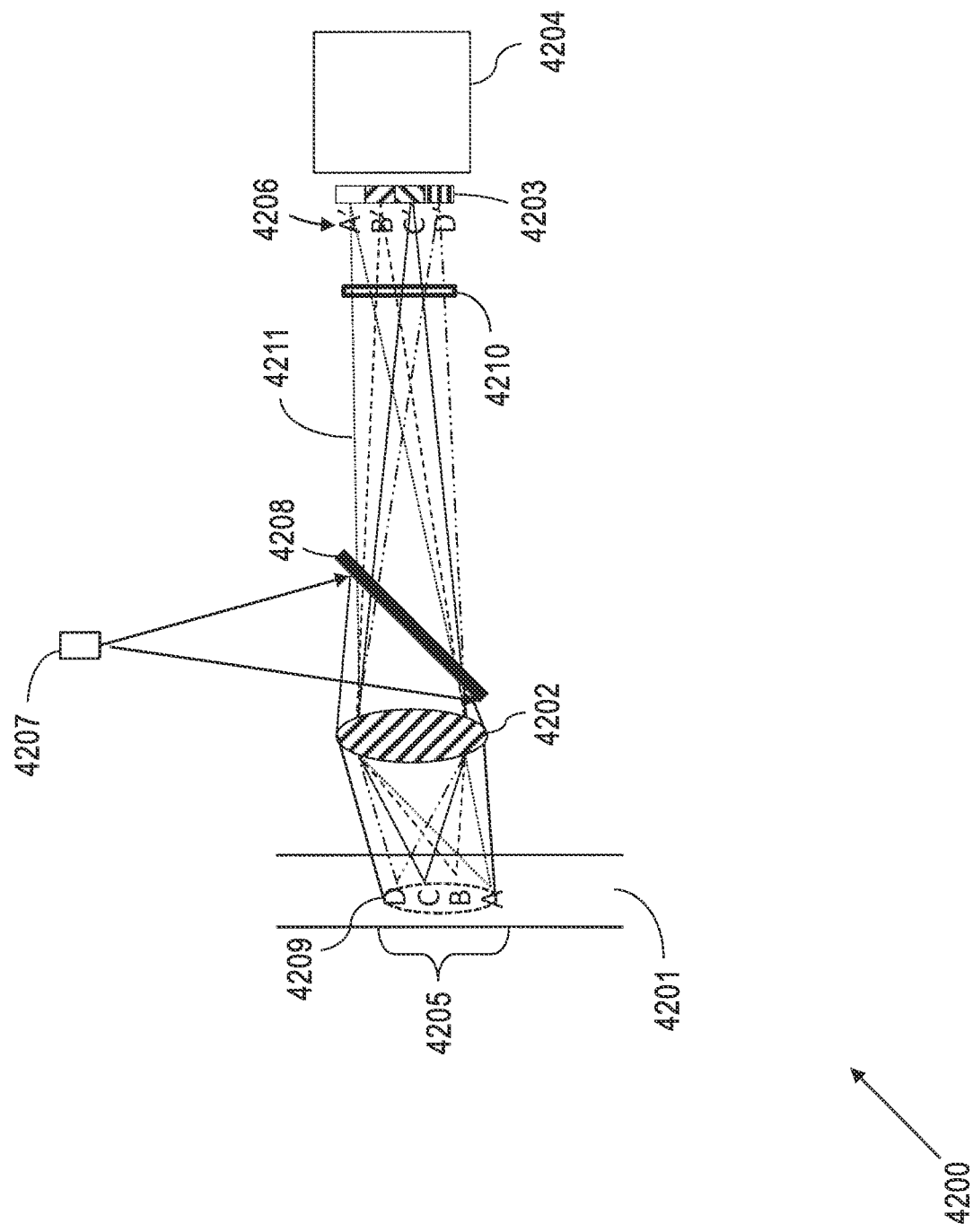
FIG. 42 is a schematic illustration of a specific configuration of an excitation light source for a microfluidic detector used for flow cytometry or fluorescence-activated cell sorting, according to an embodiment.

Shown in FIG. 42 is a schematic illustration showing another embodiment of a microfluidic detector 4200 used for flow cytometry or fluorescence-activated cell sorting (e.g., an example of a COlor-Space-Time (COST) coding operation). This device includes a fluidic channel (e.g., a microfluidic channel) 4201, a lens 4202, a series of optical filters 4203 and an optical detector (e.g., a PMT or photodetector) 4204. Light paths 4211 are indicated by dashed or solid lines. Also shown is an excitation light source (e.g., a laser) 4207 directing light to a mirror 4208 (e.g., a dichroic mirror) which reflects the excitation light to a focal region 4209 within the fluidic channel (e.g., a microfluidic channel). The excitation light may contact a sample (e.g., a particle or a cell) located at any of the positions A, B, C or D within the sample path 4205. The excitation light originating from source 4207 can be focused by a lens 4202 to a desired focal region 4209. Also shown is an optical filter 4210 that can block the transmission of light of an undesired wavelength (e.g., light originating from the excitation light source 4207). Light (e.g., fluorescent light) emitted by a particle at positions A, B, C or D can pass through a lens 4202, a mirror 4208, a filter 4210, and contact one of the optical filters at the corresponding conjugate points on the image plane 4206 indicated by A', B', C' and D'. Light that is transmitted through one of the optical filters or color zones then proceeds on to the optical detector (e.g., a PMT or photodetector) 4204.

In an embodiment, a mirror 4208 (e.g., a dichroic mirror) can be positioned at 45 degrees relative to the sample path 4205 or the image plane 4206. In some embodiments the mirror can be positioned between 30 and 60 degrees relative to the sample path 4205 or the image plane 4206. In some embodiments the mirror can be positioned between 10 and 80 degrees relative to the sample path 4205 or the image plane 4206. In some embodiments the mirror can be positioned at any angle that allows transmission of the excitation light source to a desired focal region 4209. The mirror 4208 can reflect light from an excitation light source (e.g., a laser) while allowing transmission of fluorescent light emitted from a sample. Since the intensity of the excitation laser beam can be many orders of magnitude greater than a fluorescent light signal, an optical filter 4210 can be introduced to block any stray light of the excitation laser from entering the array filter 4203 and optical detector (e.g., a PMT or photodetector) 4204. In some embodiments the optical filter 4210 can be a long pass filter or a precision optical notch filter.

Figure 43:
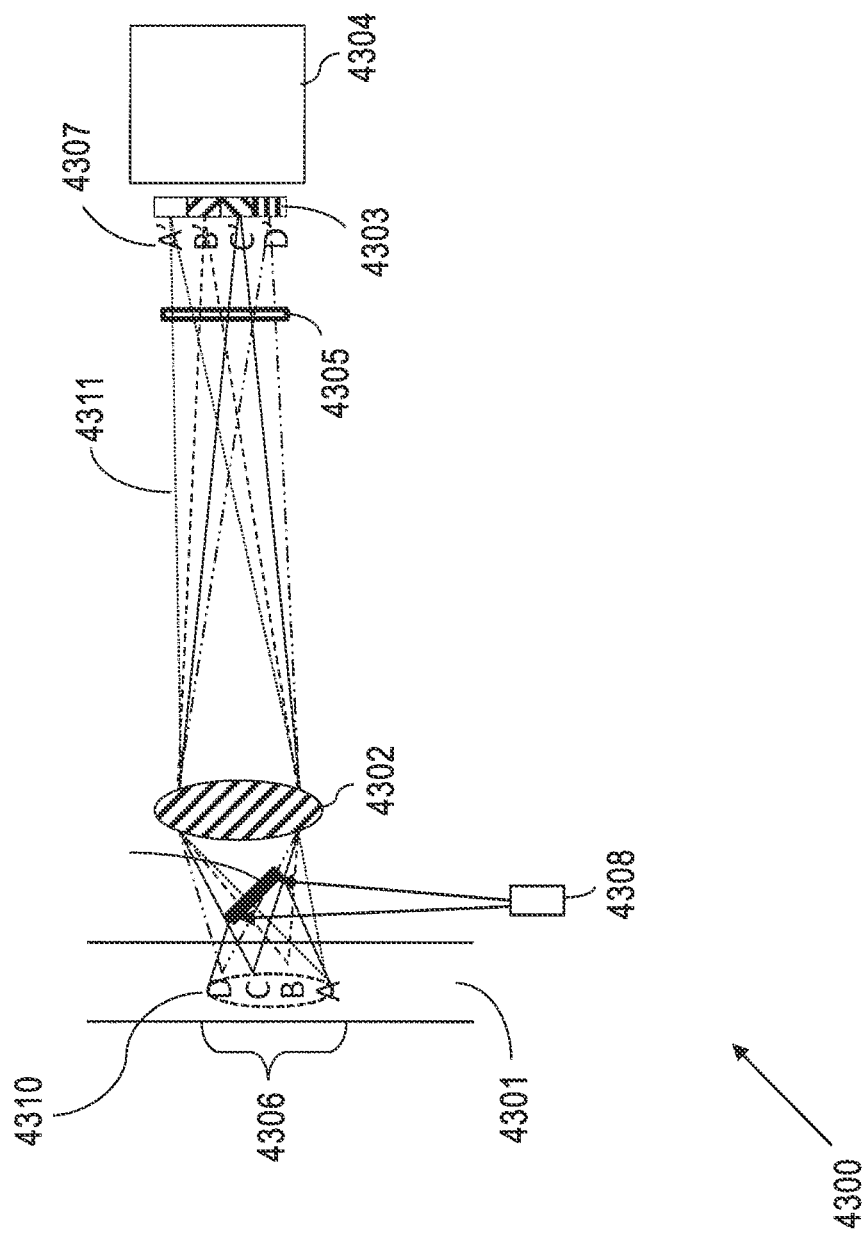
FIG. 43 is a schematic illustration of a specific configuration of an excitation light source (e.g., a laser) of a microfluidic detector used for flow cytometry or fluorescence-activated cell sorting, according to an embodiment.

FIG. 43 illustrates another embodiment of a microfluidic detector 4300 that incorporates an excitation light source (e.g., a laser) 4308 and a mirror 4309. The device illustrated here includes a fluidic channel (e.g., a microfluidic channel) 4301, a focal region 4310, a lens 4302, a filter 4305, a series of optical filters 4303 and an optical detector (e.g., a PMT or photodetector) 4304. The sample path 4306, sample positions A, B, C and D, light path 4311 and contact points A', B', C' and D' at the image plane 4307 are also shown.

The embodiment in FIG. 43 illustrates a mirror (e.g., a dichroic mirror) 4309 angled at about 45 degrees relative to the sample path 4306 or the image plane 4307. An excitation light source (e.g., a laser) 4308 directs light to the mirror 4309 which is reflected to the focal region 4310 located within the fluidic channel (e.g., a microfluidic channel). In this embodiment the mirror 4309 is located between the lens 4302 and the fluidic channel 4301. The mirror 4309 can reflect light from an excitation light source (e.g., a laser) while allowing transmission of fluorescent light emitted from a sample. An optical filter 4305 can be introduced to block any stray light of the excitation light source (e.g., a laser) from entering the array filter 3003 and optical detector (e.g., a PMT or photodetector) 4304.

An advantage of the microfluidic detector illustrated in FIG. 42 or FIG. 43 is a flexible method for introducing multiple excitation lasers for an increasing number of detection parameters. In some embodiments, as illustrated in FIG. 42 or FIG. 43, multiple excitation light sources (e.g., multiple lasers) can be used. In such embodiments, the light source illustrated in FIG. 42 or FIG. 43 can be a combination of several lasers of different wavelengths (e.g., 405 nm, 488 nm, 532 nm, and 630 nm). In some embodiments, light from a light source (e.g., a laser) can emit from a single aperture after being conducted through a beam combiner or a wavelength demultiplexer.

In some embodiments a mirror (e.g., 4208 or 4309) can reflect excitation light of all wavelengths to the focal region. In such an embodiment, the mirror may obstruct or block the transmission of light (e.g., fluorescent light) emitted from a sample. One solution to this potential problem is to position the mirror outside of the emission light path. Therefore in an embodiment a mirror (4208 or 4309) is positioned outside of the emission light path. Another solution is to reduce the size of the mirror so that the amount of emission light blocked (i.e., obstructed light) is reduced to an acceptable level. Therefore in another embodiment a mirror (4208 or 4309) is reduced in size so that the amount of obstructed light is reduced to an acceptable level. An acceptable level of obstructed light (e.g., fluorescent light emitted from the sample) can be between 0% and 50%. In some embodiments an acceptable level of obstructed light (e.g., fluorescent light emitted from the sample) is between 0% and 30%. In certain embodiments an acceptable level of obstructed light (e.g., fluorescent light emitted from the sample) is between 0% and 15%. For example, for a 50× objective lens with an 8 mm diameter aperture, a 1×2 mm mirror may block only about 3% of fluorescent light emitted from a particle.

Figure 44:
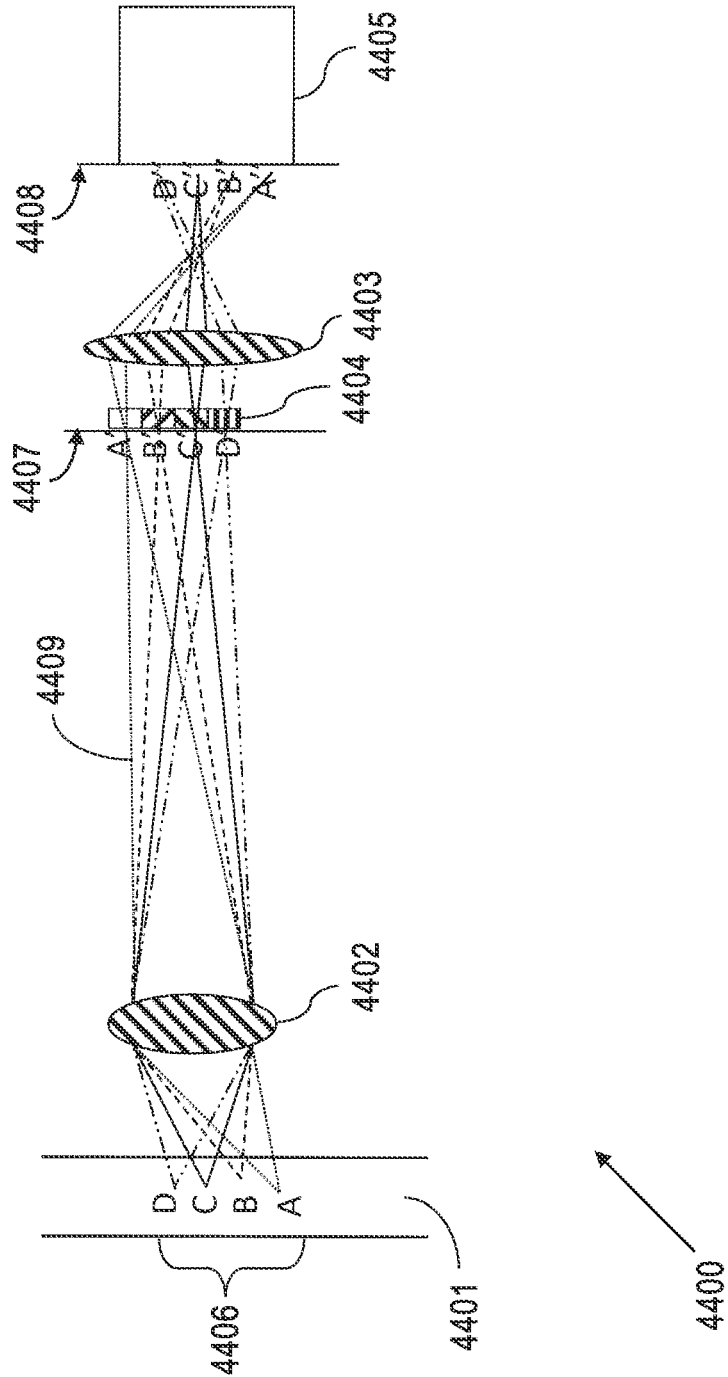
FIG. 44 is a schematic illustration showing a lens located between an array of optical filters and an optical detector (e.g., a PMT or photodetector) in a microfluidic detector used for flow cytometry or fluorescence-activated cell sorting, according to an embodiment.
Figure 45:
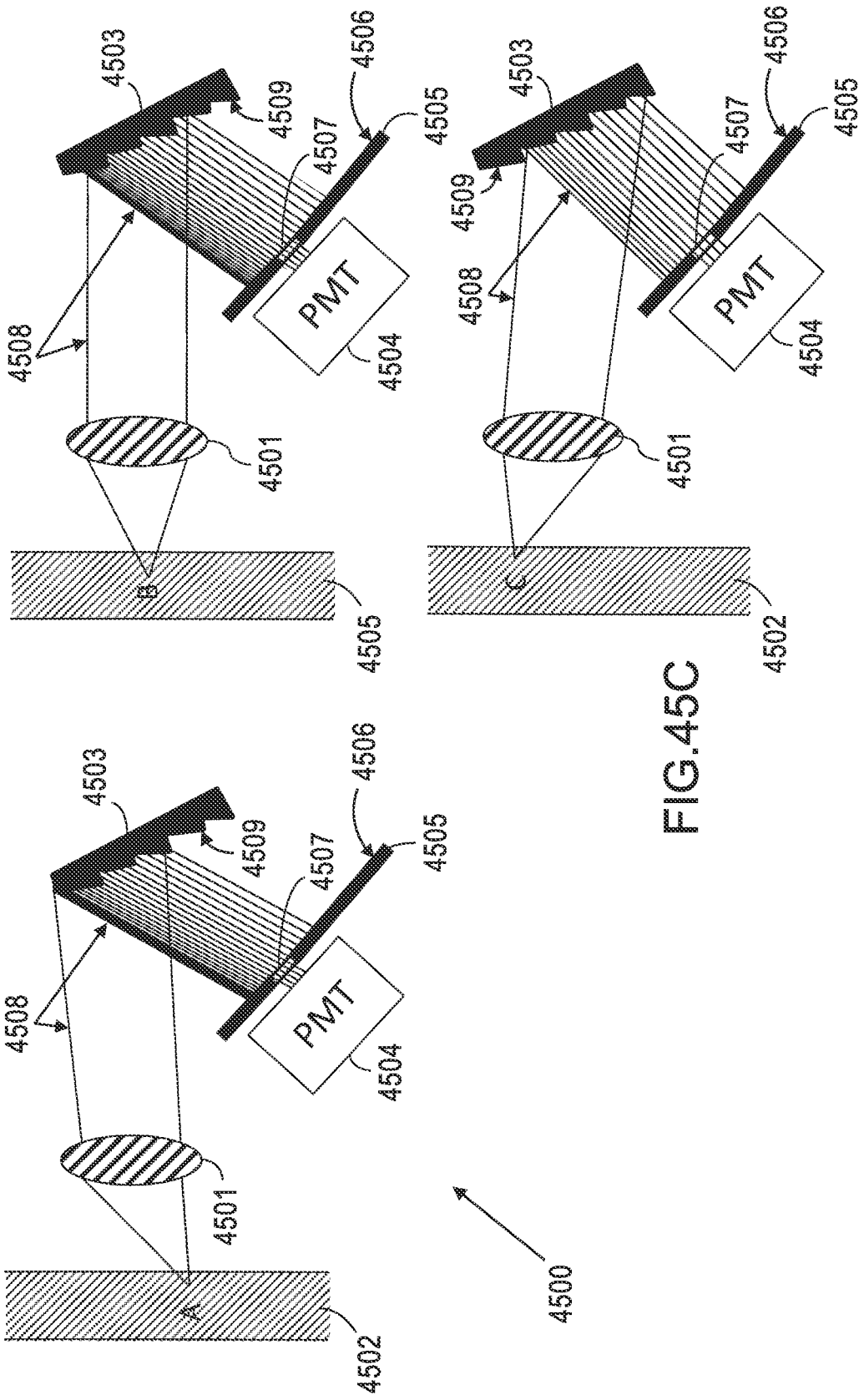
FIGS. 45A-45C illustrate a diffractive grating of a microfluidic detector used for flow cytometry or fluorescence-activated cell sorting, according to an embodiment. When a particles moves from point A (FIG. 45A) to point B (FIG. 45B), and finally to point C (FIG. 45C) in the channel, the PMT registers differently coded spectral information of the cell at points A, B and C, respectively due to the diffraction grating, generating color-space-time coded signals in time domain.

FIG. 44 illustrates another embodiment of a microfluidic detector 4400 that incorporates a lens 4403 positioned between an array of optical filters 4404 and the optical detector 4405 (e.g., a PMT or photodetector). As in the previous embodiment illustrated in FIG. 42, microfluidic detector 4400 includes a fluidic channel (e.g., a microfluidic channel) 4401, a first lens 4402, a series of optical filters 4404 and an optical detector (e.g., a PMT or photodetector) 4405. The sample path 4406, sample positions A, B, C and D, light path 4409 and contact points A', B', C' and D' at the first image plane 4407 are also shown. A second lens 4403 can focus or concentrate light emanating from the first image plane 4407 at points A', B', C' and D' to corresponding points A", B", C" and D" on the second image plane 4408. Therefore light emanating from the sample at positions A, B, C and D can arrive at their corresponding positions A", B", C" and D" at the optical detector. In this embodiment, the number of filters (e.g., color zones) in the optical filter array is not limited by the size or shape of the photo sensitive area of the optical detector (e.g., a PMT or photodetector). In addition, the output waveform of the optical detector (e.g., a PMT or photodetector) is not affected by the non-uniformity of the optical detector (e.g., a PMT or photodetector) itself. Lens 4403 demagnifies images from filter 4404 onto image plane 4408 in some embodiments.

In some instances, as to be discussed herein, the number of fluorescent spectra the COST system can detect is related to the number of filters in an optical filter array. Decoupling the size of the array filter from the photosensitive area of the optical detector (e.g., a PMT or photodetector) can allow for detection of a larger number of parameters.

FIGS. 45A-45C illustrate an embodiment of a microfluidic detector 4500 that includes a diffractive grating 4503 that can be used for the COST technique of sample (e.g., a particle or cell) detection. Microfluidic detector 4500 includes a fluidic channel (e.g., a microfluidic channel) 4502, a lens 4501 (e.g., an objective lens), an optical detector (e.g., a PMT or photodetector) 4504, and a diffractive grating 4503 including a diffractive surface 4509. Diffractive grating 4503 can be any photo diffractive structure, such as a prism for example. Also shown is a plate 4505 including a top surface 4506 and a channel 4507, where channel 4507 includes an aperture at surface 4506. FIG. 45A, FIG. 45B and FIG. 45C differ with respect to the position of a light emitting sample (e.g., a particle or cell), where each sample position is represented by position A, B or C in the illustration. Each position A, B and C is located within the fluidic channel (e.g., a microfluidic channel) and is not part of the device.

A sample (e.g., a single particle or cell) that flows through a fluidic channel (e.g., a microfluidic channel) can transiently occupy positions A, B, or C and emanate light (e.g., fluorescent light). The light path emanating from each position A, B and C is illustrated by solid lines 4508. The position of a sample relative to the diffractive surface of the diffractive grating 4503 defines the wavelength range of light that passes through the aperture defined by channel 4507. For example, FIG. 45A illustrates that the optical detector (e.g., a PMT or photodetector) can detect red fluorescent light when the sample is at position A. FIG. 45B illustrates that the optical detector (e.g., a PMT or photodetector) can detect yellow fluorescent light when the sample is at position B and FIG. 45C illustrates that the optical detector (e.g., a PMT or photodetector) can detect blue fluorescent light when the sample is at position C. Thus, as a particle travels from position A to C, light detected by the photodetector is blue-shifted.

Therefore a sample that emits primarily blue light shows the strongest optical signal at position C, and then the signal diminishes as the particle travels further down the channel. The detected signal of a sample emitting primarily blue light will appear different than the signal from a different sample that emits primarily yellow or green light. Since each specific emission spectrum produces a corresponding output waveform, the output waveform can be treated as the distinguishing characteristics of that sample. Over the past years, due to the rapid development of high resolution, high sensitivity, and high frame-rate CCD and CMOS imagers, image-based cytometry has become a viable alternative to flow cytometry. In image-based cytometry, samples (in some embodiments) can be fixed to a glass slide or a surface and examined. The optical characteristics of a sample can be acquired by a photo detector, such as a CCD or CMOS imager, and then analyzed. Unlike flow cytometry that analyzes samples (e.g., cells or particles) in a serial manner, image-based cytometry (in some embodiments) analyzes samples frame-by-frame in a parallel fashion. Multiple embodiments described herein can be applied to flow-based microfluidic detectors and to image-based microfluidic detectors.

Figure 46:
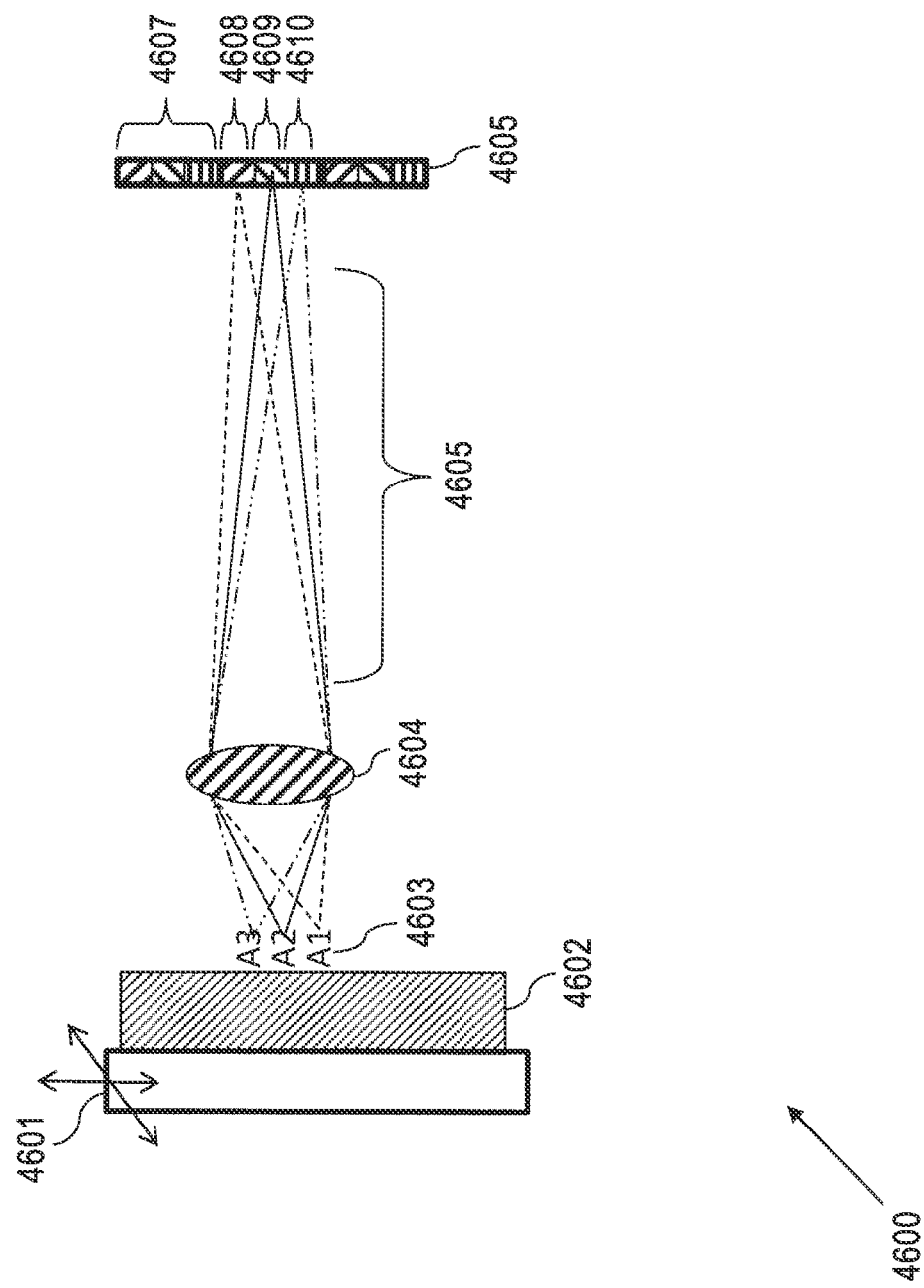
FIG. 46 is a schematic illustration of an image-based microfluidic detector utilizing a Color-Space-Time (COST) coding operation, according to an embodiment.

The embodiment of FIG. 46 is a schematic illustration of an image-based microfluidic detector that can utilize COST techniques. Unlike a flow system where the particle traveling in the fluidic channel (e.g., a microfluidic channel) is detected sequentially by a single, highly sensitive optical detector, an image-based microfluidic detector may use an array of detectors such as those found in CCD or CMOS devices with many (e.g., several million) sensors (pixels) to detect a plurality of particles in parallel. Although the sensitivity of each sensor in a CCD or CMOS device may be lower than an optical detector (e.g., a PMT or photodetector), the detection time for static particles may be longer than for a flowing particle, thus compensating for the sensitivity difference between an imager and an optical detector, such as a optical detector (e.g., a PMT or photodetector). In the embodiment of FIG. 46 the image-based microfluidic detector 4600 includes a moveable stage 4601, a lens 4604, and a CCD or CMOS imager 4606.

The imager may contain millions of pixels, and each of these pixels may be coated with an optical filter to be sensitive to red, green, and blue light, or R, G, B pixels. A set of RGB or RGBG pixels may form a unit 4607. Light emanating from a sample 4602 at position A1 may be projected through a lens 4604 and focused onto a red pixel on 4608. By altering the position of the stage to move the sample to position A2, the light of the same sample is focused onto a green pixel 4609, as indicated by the light path 4605. By altering the position of the stage further to move the sample to position A3, its light is focused onto a blue pixel 4610. By combining the three signals of the RGB pixels, one can determine the fluorescent properties of the sample.

The microfluidic detector in FIG. 46 essentially converts a standard fluorescent microscope into a cytometer system that can produce additional information about a sample. However, because conventional color imagers have 3 colors (R, G, B), the number of detectable colors is limited. The embodiment in FIG. 34 illustrates a schematic of a microfluidic detector that can detect multiple colors.

Figure 47:
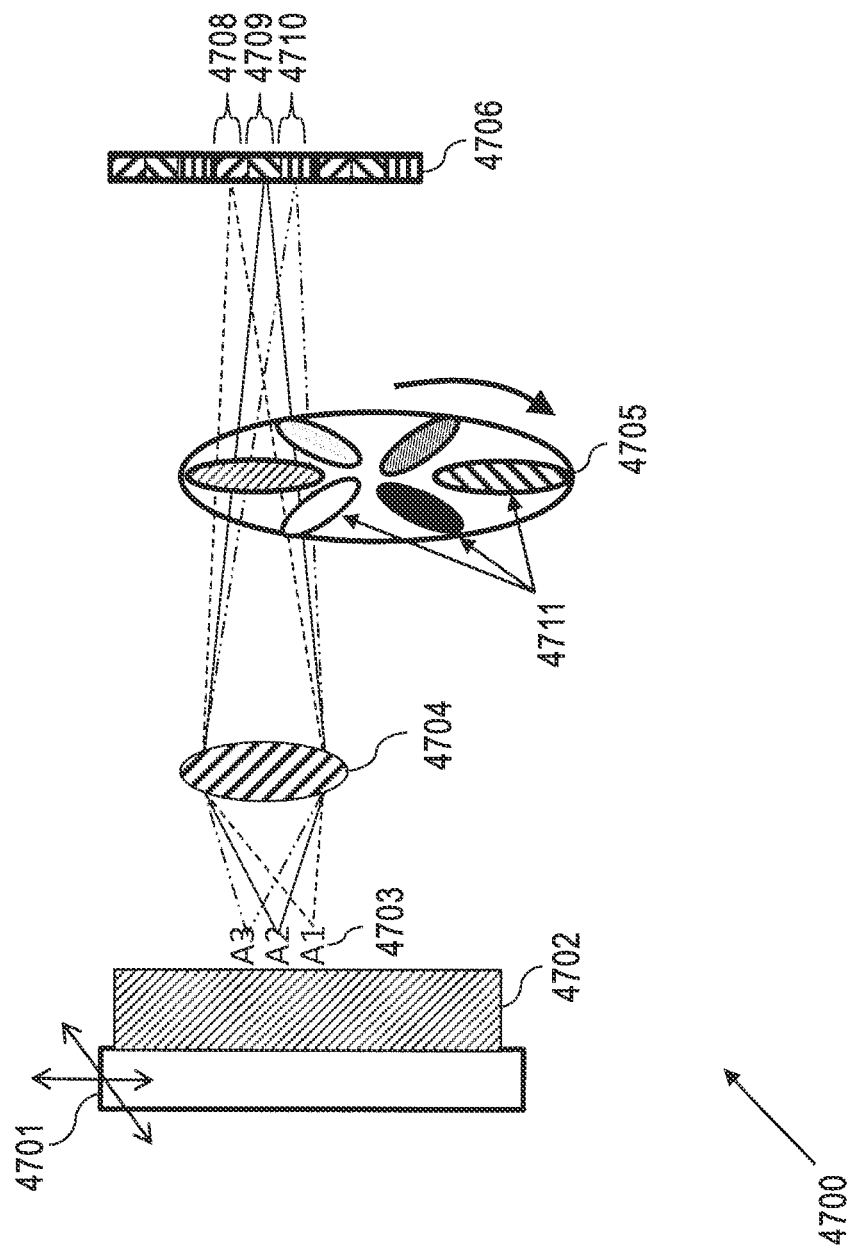
FIG. 47 is a schematic illustration of a rotating wheel with a plurality of spectral filters of an image-based microfluidic detector utilizing a Color-Space-Time (COST) coding operation, according to an embodiment.

Microfluidic detector 4700 of FIG. 47 is similar to microfluidic detector 4600 in that it includes a moveable stage 4701, a lens 4704, and a CCD or CMOS imager 4706. The image-based microfluidic detector 4700 further includes a rotating wheel 4705 with a plurality of spectral filters 4711 located between the lens 4704 and the imager 4706. For each position A1, A2, or A3, light is projected onto the red 4708, green 4709, and blue pixels 4710, respectively, similar to the device in FIG. 46. However, for the device shown in FIG. 47 the light also passes through a series of additional spectral filters 4711 on rotating wheel 4705 before reaching a pixel on the imager. In an embodiment, rotating wheel may contain 8 different spectral filters and therefore allow the detection of 24 different colors.

FIG. 48 illustrates block diagram rendition of a COST coding method that can be utilized for processing an optical detector (e.g., a PMT or photodetector) signal. When a particle passes through a detection zone, emitted light (e.g., fluorescence) can be detected by an optical detector (e.g., a PMT or photodetector). An optical detector (e.g., a PMT or photodetector) signal 4801 optionally can be passed through an analog filter 4802 to enhance the signal to noise ratio, or can be directly passed to an analog to digital converter (A/D converter) 4803. A digital filter 4804 downstream can further enhance the signal to noise ratio. The digital signal then can be processed by a computer processor (e.g., FPGA). Sub-processes 4806, 4807 and 4808 in process 4805 can be carried out by a computer processor. Sub-processes within process 4805 can be carried out as part of Windowed Peak Detection as shown in FIG. 23 in certain embodiments. During signal processing, signals can be processed and waveforms can be analyzed (e.g., all signals and all waveforms can be processed and analyzed). In some embodiments, there can be a threshold calculation phase in which a threshold level is set according to baseline noise (e.g., sub-process 4806). In a second phase, a previously calculated threshold can be used to analyze incoming signals for a waveform/COST signal. The speed of a particle also can be determined based on the location of the peaks (e.g., sub-process 4806). For peak detection, a waveform can be analyzed to identify peaks (e.g., sub-process 4806), and peak parameters (e.g., amplitude, time, area; sub-process 4807).

One or more peak parameters can be adjusted to compensate for an optical irregularity or signal irregularity at a suitable point in process 4805 (e.g., after sub-process 4807 and before sub-process 4808). As part of such adjustment, a calibration can be performed by passing a portion of a sample containing particles through the device configured with an all-pass filter in place of the color filter, where the all-pass filter includes zones that correspond to zones of a color filter. Another portion of the sample then can be passed through the device configured with the color filter, and signals detected from different zones of the color filter can be adjusted based on signals detected from corresponding zones of the all-pass filter.

The color corresponding to each peak can be mapped (e.g., sub-process 4808) based on the filter set used (e.g., color combinations using broad, continuous, or band pass filters among others). For example, a peak parameter can be mapped to a discrete band pass filter (i.e., color zone) in a color filter by placement on the color filter (e.g., sub-process 4808). A peak parameter, in some embodiments, can be mapped to a zone in a color filter including zones of overlapping transparency according to one or more peak parameter ratios, which ratios provide for normalized peak parameters (sub-process 4808). Color mapping based on peak parameter ratios (normalized peak parameters) can be applicable to embodiments in which there is one fluorophore or quantum dot per particle (e.g., cell), and to embodiments in which there are multiple fluorophores or quantum dots per particle (e.g., cell), which are described in greater detail herein. Data can be further analyzed and visualized using a visualization tool 4809, which can reside on a personal computer (PC) to ultimately present and identify the fluorescent color(s) and fluorescent intensity emitted from a particle. A visualization tool can be a user interface that permits a user to analyze detection data and/or select certain parameters and functions of a microfluidic detector. A visualization tool in some embodiments allows a user to analyze detection data and identify particular particles or types of particles flowing through the device (e.g., 4811). In some embodiments, a visualization tool allows a user to select parameters for sorting particular particles (e.g., 4810; select gating signal).

A COST coding process can be applied for detecting a plurality of spectra using a minimum number of optical detectors or imagers. Therefore, the embodiment designs proposed herein have fundamentally changed the scaling rule of flow cytometers which have traditionally required one optical detector for detection of each parameter (spectra).

As stated above, the COST coding process can distinguish a plurality of spectra from various kinds of cells or particles using a single optical detector. For some applications, the COST coding method can be applied in two general scenarios according to optical qualities of a sample (e.g., types of fluorophores effectively linked to cells (e.g., via antibodies)). In certain embodiments, a sample contains a mixture of cells or particles and each cell or particle is labeled by one single type of fluorescent dye or quantum dot. For instance, the sample may include a group of antibody-attached beads targeted to a group of specific antigens and each type of antibody-attached bead is uniquely identified by a specific type of fluorophore(s) or quantum dot(s). By detecting the fluorescence of fluorophore- or quantum dot-conjugated beads using a microfluidic detector to also isolate such beads, one can determine the presence and level of abundance of specific antigens. In such one-spectra-per-particle scenario, one can use a COST filer of four (4) spectra (e.g., white-red-green-blue (W/R/G/B)) to detect more than 20 spectra using the process outlined in FIG. 48. After the analog-to-digital (A/D) converter and removal of spurious optical detector noise and the thermal noise of electronics using digital filters, a peak detection or area detection method is used to identify or signify the signal level corresponding to the amount of light passing the filter of each spectra. Taking the ratio of the signal of each spectra and the signal passing the all-pass (white) filter, the "normalized" R- G- B-signals can be obtained for each sample. Each type of fluorophore or quantum dot possesses its unique ratios for the normalized R-, G-, B-signals. For any two different fluorophores or quantum dots, the amount of signal variation within the same fluorophore or quantum dot is significantly less than the separations among different fluorophores or quantum dots. As a result, one can apply the COST coding process to distinguish a plurality of spectrally distinct samples accurately.

In some embodiments, a single particle is spectrally distinguished by a plurality of fluorophores, and the COST coding process embodiment outlined in FIG. 48, for example, can be used to decipher the COST signal. With the assumption that there are N (e.g., 20) different types of fluorophores each having a specific fluorescence spectrum, according to the following relation in Equation 1, $t_{ij}$ is the transmission coefficient for jth fluorophore through the ith optical filter (e.g., j=1, 2 . . . N and i=1,2,3,4); Cj is the fluorescence intensity of jth fluorophore from the cell; and R, G, B, W represent the detected light intensity through the corresponding filters in the COST coded signal.

$$\begin{bmatrix} t_{11} & t_{12} & & t_{1,N-1} & t_{1N} \\ t_{21} & t_{22} & \cdots & t_{2,N-1} & t_{2N} \\ t_{31} & t_{42} & & t_{4,N-1} & t_{3N} \\ t_{41} & t_{42} & \cdots & t_{4,N-1} & t_{4N} \end{bmatrix} \begin{bmatrix} C_1 \\ C_2 \\ \vdots \\ C_N \end{bmatrix} = \begin{bmatrix} R \\ G \\ B \\ W \end{bmatrix} \quad \text{Equation 1}$$

The transmission coefficient for each of N fluorophores through the spectral filter can be calibrated as the spectral filter is designed. All coefficients tij's therefore are known and can be stored in a data base. The linear system in Equation 1 contains four (4) independent equations, and four (4) fluorophores can be detected in a single particle out of many (e.g., 20) possible spectra. For instance, for a solution for $[C_1, C_2, C_3, C_4, C_5, \ldots, C_{20}]$ in Equation 1 of [0.5, 0.2, 0, 0, 0, . . . 0, 0, 0, 0.7, 1], it can be concluded that the particle contains four (4) types of fluorophores: $C_1, C_2, C_{19}, C_{20}$ with their intensity ratio being 5:2:7:10. In some instances, all C's may have non-zero values due to noise, and a threshold can be chosen to determine the presence of each type of fluorophore in a particle. The number of spectra in the spectral filter can be increased to detect more spectra co-exiting in a single particle. For example, by using an eight (8)-spectra filter, the COST coding process can detect as many as eight (8) fluorophores in one particle.

A continuously color graded spectral filter can be used in certain embodiments. Such a filter can be configured for a transmission spectrum continuously graded from red to blue color without any abrupt boundaries. Such a filter can include an all-pass (white) filter in the beginning and/or at the end of the filter to indicate the beginning and/or ending of the signal. In this manner, a COST signal becomes a continuous waveform (FIG. 49B) instead of a series of discrete peaks (FIG. 49A). One can digitally parse the COST signal into a series of spectral filters according to the transmission spectra at the given positions of the spectral filter. Since the number of filters can be digitally defined, the spectral filter can be divided into a plurality of spectra. A practical constraint of the number of spectra is the noise level that could corrode the signal when each spectral band is too narrow.

Such a dynamically adjusted spectral filter design, as shown by example in FIG. 49B, offers significant flexibility to a detection system. In immunology and cancer diagnosis, users can need to detect a very large number (e.g., 20) of spectra in one particle. One can purposely slow down the flow speed of a sample so that the COST signal covers a wide range in time domain, or in other words, the particle spends a longer time traveling through the detection zone. The longer signal duration allows users to divide the signal into a larger number of spectral divisions with adequate signal-to-noise ratio and enough number of sampling points over each spectral division. In other words, the COST coding technique not only simplifies the microfluidic detector and detector system by replacing multiple optical detectors with a single detector, but also offers the unique capability of trading flow speed (throughput) for the number of spectra a microfluidic detector can detect. Such tradeoffs can be dynamically adjusted by users according to their applications.

When the transmission characteristics of the filter changes continuously, users are given the flexibility of dividing the filter into any chosen number of units (e.g., FIG. 49B). If the particles under test are labeled with a large number of different fluorophores, the user may digitally divide the filter into a large number of units. On the other hand, if the application involves fewer different colors, then dividing the filter into fewer units is desirable for management of signal-to-noise ratio. To determine the speed of the particle, one can repeat a small section of the graded filter or add any "spectral signatures" in the filter (e.g., black out some small areas in the filter). When the signal waveform shows these signature patterns, a microfluidic detector can readily calculate the speed of the particle. This feature can also be used to verify if the actual flow velocity matches the set flow rate by users. This feature is useful since the set flow rate is based on an ideal laminar flow inside the channel. However, not all particles are located at the center of the channel and particle-particle interactions can push particles away from the center. Knowing the speed of each particle, besides the flow rate, helps enhance cell sorting efficiency.

In certain embodiments provided are microfluidic detectors including a microfluidic sensing channel through which sensing channel cells can flow and can be sensed, a branch downstream of the sensing channel, two or more microfluidic branch channels downstream of the branch, and an actuator configured for fluid communication with the branch and configured to drive cells, upon activation of the actuator, to one or more of the branch channels, which device is configured for a cell viability of greater than about 70.8% after cells are flowed through the device. Also provided in some embodiments are flow cytometry methods, including: (a) flowing cells through a microfluidic sensing channel, in which sensing channel cells can be sensed, in a microfluidic detector, which microfluidic detector includes the sensing channel, a branch downstream of the sensing channel, two or more microfluidic branch channels downstream of the branch, and an actuator in fluid communication with the cells, which actuator is capable of driving cells to one of the branch channels upon activation of the actuator, and (b) sorting the cells flowing through the microfluidic channel to one of the branch channels, wherein cells that have passed through the device have a cell viability of greater than about 70.8%. Such microfluidic devices can include a suitable component described herein (e.g., color filter, detector and the like) or known in the art. Cell viability is about 71% or greater, about 75% or greater, about 80% or greater, about 85% or greater or about 90% or greater (e.g., about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater, and all values in between), which cell viability is determined after cells have flowed through the device. In some embodiments, the actuator can be a piezoelectric actuator (e.g., described herein). The actuator in some embodiments is in fluid communication with the branch and/or cells in the device, often with substantially no air between the actuator and the branch and/or the cells. A microfluidic detector (in some embodiments) does not generate droplets and (in some embodiments) does not include an element that electrically charges cells, fluid in the device or droplets.

It has been determined that shear stress to cell membranes follows the following relation: tau ~a (rho) (v) (f) (tan (theta)). Here "a" is the cell radius, "rho" the average density. "v" the flow velocity, "f" the frequency of cell sorting actuator, and "theta" the cell deflection angle by sorting. The product of flow speed and sorter frequency response (vf) determines the throughput, and it is found that the most effective approach of sorter design is to reduce the deflection angle "theta". Under the same transverse force by a piezoelectric actuator, a reduced theta design produces a more uniform transient velocity profile around the cell, thus yielding a significantly lower shear stress for enhanced cell viability. Neonatal rat primary cardiomyocytes sorted on a device including a piezoelectric actuator-driven sorter had a cell viability of 88.7%, compared to conventional sorting with a BD FACSAria system under gentle conditions (refrigerated, 20 psi, 100 µm nozzle) which sorted cells with a cell viability of only 70.8% (25% improved cell viability).

Detection System

Figure 10:
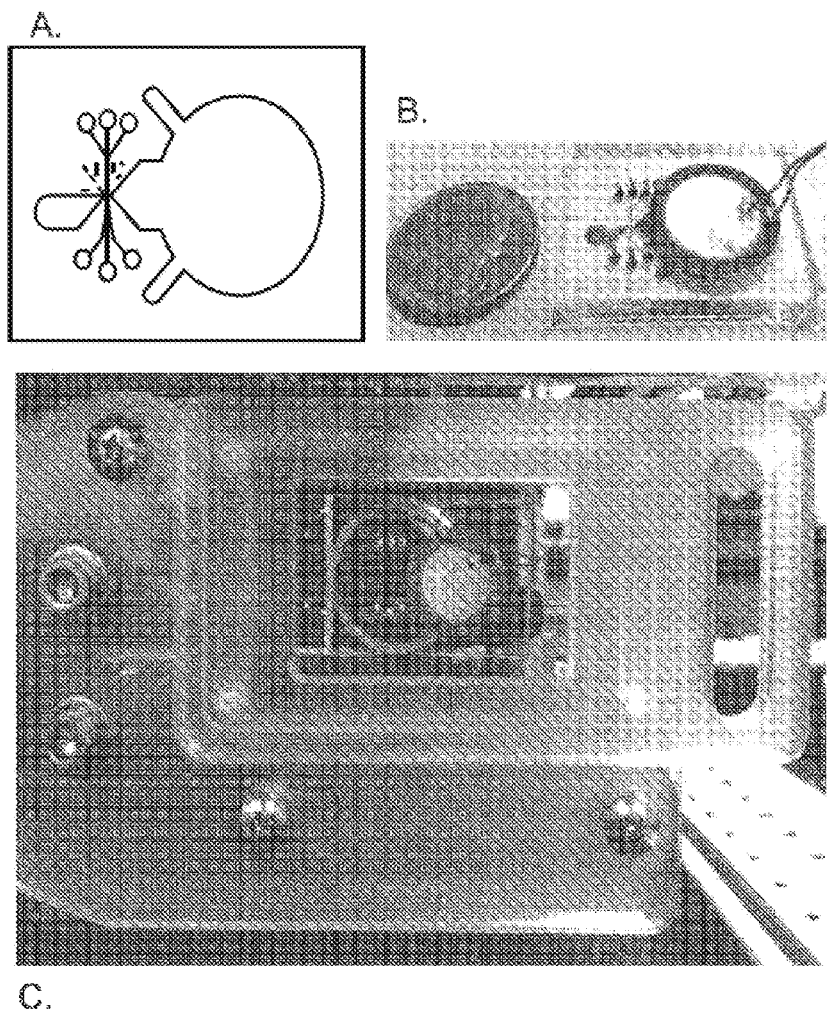
FIGS. 10A-10C illustrates a microfluidic detector design and production, according to an embodiment.

In some embodiments, a detection system is a micro cell detection system. In some embodiments, the detection system includes one or more structures and/or devices described herein or known in the art. In some embodiments a detection system includes a chip (e.g., a lab-on-a-chip). In some embodiments, a lab-on-a-chip (LOC) can be a device that integrates one or several laboratory functions on a single chip of a about a square millimeter to about a few square centimeters in size. A LOC can be removable from a detection system and can be disposable in some embodiments. An LOC is in some embodiments designed in a cartridge format. In some embodiments, an LOC can be assembled in a chip holder (e.g., as shown in FIG. 10C) that in some embodiments allows an LOC to be exchanged after each use. An LOCs can deal with the handling of extremely small fluid volumes down to less than pico liters. An LOC can be fabricated by a method known in the art or described herein and can be manufactured from a suitable material known in the art or described herein. An LOC, in some embodiments includes one or more structures.

In some cases an LOC includes an enrichment structure, a mixing structure, one or more fluidic channels, one or more sample or fluid inlets (e.g., inlet ports or wells) and/or a microfluidic detector or parts thereof. In some embodiments, an LOC includes one or more piezoelectric disk actuators. In some embodiments, an LOC includes an enrichment structure fluidically coupled to a mixing structure. In some embodiments, an LOC includes a mixing structure fluidically coupled to a microfluidic detector, or a part thereof. In some embodiments, an LOC includes an enrichment structure fluidically coupled to a mixing structure and a mixing structure fluidically coupled to a microfluidic detector, or a part thereof.

Binding Agents

The term "binding agent" as used herein refers to a molecular structure that binds specifically to an antigen or to another molecular structure (e.g., protein, lipid, DNA, RNA, carbohydrate, and/or a part or modification thereof). Non-limiting examples of a binding agent include antibodies (e.g., antibodies immunologically or genetically derived from any species (e.g., chicken, human, camel, llama, lamprey, shark, goat, rodent, cow, dog, rabbit, etc.), antibody domains or parts thereof (e.g., Fab, Fab', F(ab')2, Fv, ScFv, VH, VHH, VL, VLRs, the like), diabodies, monoclonal antibodies, serum, polyclonal Abs, mAbdAbs, phage display derived binders, affibodies, heteroconjugate antibodies, bispecific antibodies, evibodies, lipocalins, affibodies, avimers, maxibodies, heat shock proteins such as GroEl and GroES, trans-bodies, DARPins, aptamers, C-type lectin domains (e.g., tetranectins); human γ-crystallin and human ubiquitin derived binders (e.g., affilins), PDZ domain derived binders; scorpion toxin and/or kunitz type domain binders, fibronectin derived binders (e.g., adnectins), receptors, ligands, lectins, streptavidin, biotin, the like, derivatives or combinations thereof.

Detection Agents

In some embodiments a detection agent refers to a binding agent including a fluorescent molecule. In some embodiments, a detection agent can include a bead (e.g., magnetic beads, polystyrene beads, latex beads, glass beads, e.g., luminex beads). In some embodiments, a bead includes a binding agent and/or a fluorescent molecule. A suitable fluorescent molecule known in the art can be used as a detection agent. Non-limiting examples of common fluorescent molecules include fluorescein (FITC), phycoerythrin (PE), R-Phycoerythrin (RPE), Cy2, Cy3, Cy3.5, Cy5PE, Cy5. Cy5.5, Cy7. Cy7PE, Cy7APC, Texas Red (TR), PE-Texas Red, PerCP, PerCP-Cy7, PerCP-Cy5.5, Allophycocyanin (APC), GFP, GFP derivatives or mutations thereof (e.g., EBFP, EBFP2, Azurite, mKalama1, cyan fluorescent protein, ECFP, Cerulean, CyPet, yellow fluorescent protein derivatives, YFP, Citrine. Venus, YPet, and BFP derivatives), Cascade Blue, Pacific Blue, DyLight 405, DyLight 549, DyLight 649, DyLight 680, DyLight 800, aminomethylcoumarin (AMCA), ATTO 425, ATTO 488, ATTO ATTO 550, ATTO 594, ATTO 647N, ATTO 532, ATTO 655, Rhodamine (TRITC), IRDye® 700DX, IRDyc® 800CW, IRDye® 800, AlexaFluor 488, AlexaFluor 647, AlexaFluor 405, the like or combinations thereof.

Rare Cell Types

In some embodiments, rare cell types and/or relatively rare cell types can refer to an uncommon cell type, a cell having an unusual property, a foreign cell type (e.g., a bacteria, a yeast), a diseased cell type (e.g., a cancer cell, a cell harboring a virus), an undifferentiated cell type (e.g., a stem cell or stem cell progenitor), a misplaced cell type (e.g., a cell normally not found in the circulation, e.g., a cardiac myocyte found in the blood after an infarction), a fetus derived cell type, a placenta derived cell type, and combinations thereof. In some cases a rare cell type can be a cell present the blood of an individual that presents a marker (e.g., a label, a dye, e.g., a metabolic dye, a radioactive tracer). Non-limiting examples of diseased cell types include malignant cells, metastatic cells, circulating tumor cells (CTCs) (e.g., cells that have detached from a primary tumor and circulate in the bloodstream, e.g., breast cancer cells). In some embodiments an uncommon cell type can be a pre-cancerous circulating cell (e.g., a cell destined to become cancerous, e.g., a leukemia progenitor cell). Pre-cancerous cells can display specific cell surface markers or intracellular markers (e.g., post translationally modified proteins, e.g., phosphor proteins) or specific combinations of markers known in the art. In some embodiments, a relatively rare cell type is a fetal cell and a relatively abundant cell type is a maternal cell from a sample from a pregnant female (e.g., human female).

Only a few implementations are disclosed. However, variations and enhancements of the described implementations and other implementations can be made based on what is described and illustrated in this document. While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Particle Sorting Systems, Apparatuses, and Methods

FIG. 50 illustrates an exemplary and non-limiting embodiment of a particle sorter 5000 for sorting of particles. The particle sorter 5000 is configurable for sorting a particle injected via a sample inlet 5002 that pass through a source channel 5004 into one of several destination channels 5010A-5010C, each associated with a destination outlet (also referenced using the reference characters 5010A-5010C). The particle sorter 5000 includes a sheath inlet 5016 to provide a sheath flow for the particles injected via the sample inlet 5002, for purposes of hydrodynamic focusing, for example. The source inlet 5002 and the sheath inlet 5016 can be independently and suitably designed for accepting the particles to be analyzed, and the sheath flow, respectively. For example, a cross-sectional shape and area of the source inlet 5002 can be matched to normal pipette tips. In some embodiments, the sheath inlet 116 can be matched to normal pipette tips. Similarly, the destination outlets 5010A-5010C can each independently designed based on application needs, such as including a reservoir for temporary storage of the sorted particles, an interface for withdrawal of the sorted particles, and/or the like.

In one embodiment, the source channel 5004 is formed by the combination of the particles from the source inlet 5002 and the sheath flow from the sheath inlet 5016, such that focusing of the particles is achieved. The source channel 5004 has a length, cross-section profile, and cross-section area as necessary and/or sufficient for generating and/or maintaining sheath flow.

In one embodiment, the particle sorter 5000 further includes a first detection device/component 5012 associated with a first volume of the source channel 5004. In some embodiments, the first detection device 5012 is configured for detection of one or more characteristics of a particle to be sorted as it passes through the first volume, and/or the first volume as the particle passes through it. For example, in one embodiment, the characteristics include optical characteristics such as fluorescence and/or reflectance, and accordingly, the first detection device 5012 can include one or more fluorescence, reflectance detectors, respectively. As another example, in one embodiment, the characteristics include impedance across the first volume that changes when the particle to be sorted passes through the first volume, and the first detection device 5012 includes one or more voltmeters.

It is understood that the first detection device 5012 can not only include detection components, but also additional components as necessary and/or desired for detection of the characteristic(s). For example, if the characteristics include fluorescence as described above, the first detection device 5012 can encompass excitation source(s), coupling (e.g. optical fibers) and other (e.g. filters) optics, control electronics, and/or the like. As another example, if the characteristics include impedance as described above, the first detection device 5012 can encompass a pair of electrodes for generating an electrical signal that measures impedance within the first channel.

In one embodiment, the first detection device 5012 is configured to interact with the first channel in any manner that permits measurement of the characteristic(s) of interest.

For example, in some embodiments, the characteristics include fluorescence, and the first detection device 5012 excites the first volume and detect fluorescence from a region external to the first volume, such as when the particle sorter 5000 is placed on a microscope stage for example. In other embodiments, a more invasive approach such as a fiber optic for excitation delivery/emission collection can be inserted into the first volume. As another example, in some embodiments, the characteristics include impedance, and the first detection device 5012 includes a pair of electrodes in conductive communication with the first volume.

Figure 51A:
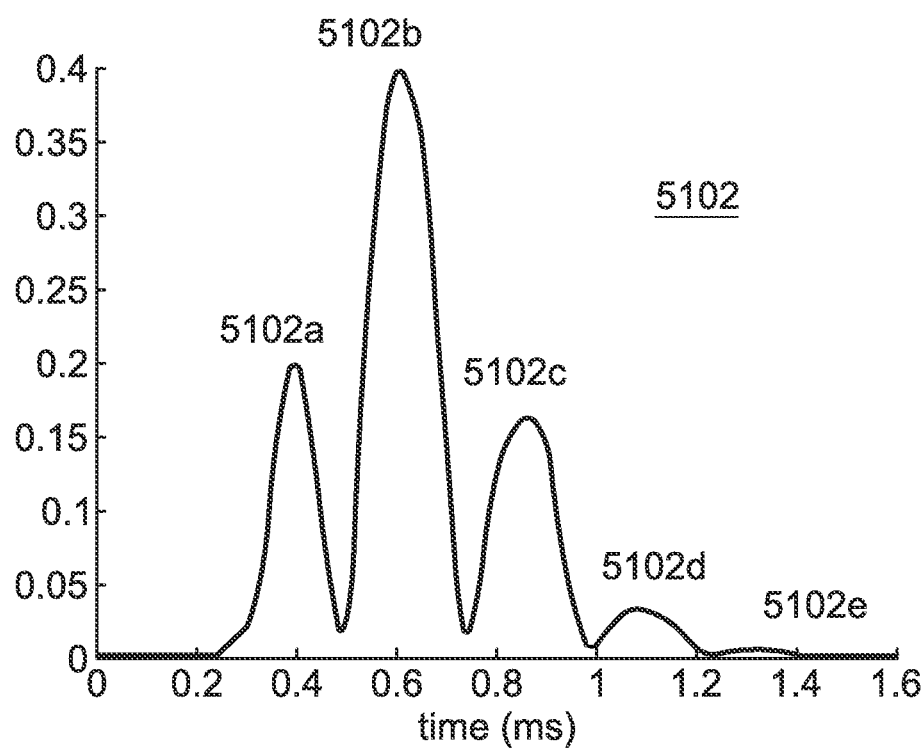
FIG. 51A is exemplary plot of the output of the fluorescence detector of FIG. 50, according to an embodiment.

In some embodiments, the first detection device 5012 detects a first detection signal that is associated with the one or more characteristics. In some embodiments, the first detection signal is associated with optical characteristics of a particle in the source channel 5002. In some embodiments, the characteristic is an optical characteristic. In some embodiments, the optical characteristic is selected from: fluorescence, phosphorescence, chemiluminescence, thermoluminescence, reflectance, scattering (including forward scattering, large angle scattering, side scattering, and/or back scattering), and/or the like. In some embodiments, the optical characteristic includes fluorescence, and the first detection signal includes one or more fluorescence signals as the first from the particles as they pass through the first volume of the source channel 5004. FIG. 51A illustrates an exemplary output of the first detection device 5012 (i.e. an exemplary first detection signal) for a single particle detected in the source channel 5004, according to some embodiments. FIG. 51A, which is be representative of a raw optical signal and/or an analog/digital equivalent thereof, illustrates an optical trace 5102 including five temporally separated peaks 5102a-5102e. In some embodiments, each peak of the peaks 5102a-5102e can be detected at the same detector of the first detection device 5012. In some embodiments, at least one peak is detected at a different detector than one other peak. In some embodiments, at least one of the five peaks 5102a-5102e is a reference intensity signal. In some embodiments, at least one of the five peaks is a fluorescence signal.

Figure 52A:
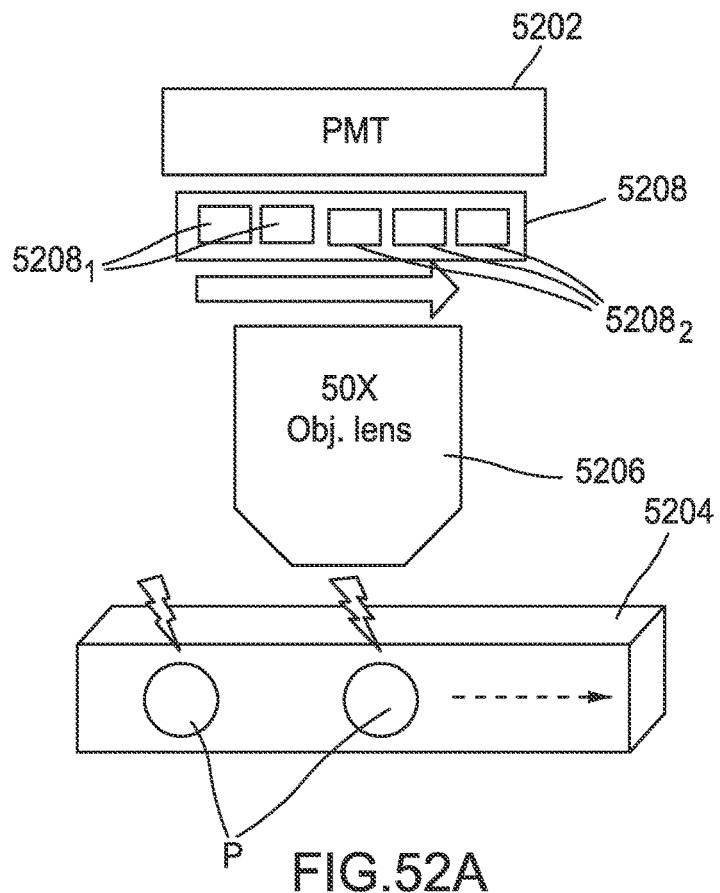
FIG. 52A is an illustration of fluorescence detection, according to an embodiment.

FIG. 52A illustrates an exemplary and non-limiting setup for generating the first detection signal, such as the trace 5102. Fluorescence from a fluorescent particle P in a first volume/source channel 5204 (such as the first volume of the source channel 5004) is obtained via objective lens 5206, such as can be part of an epifluorescence setup of the first detection device 5112, for example. The collected fluorescence is be filtered by a filter array 5208 that includes, as illustrated, reference filters 5208$_1$ and fluorescence filters 5208$_2$. However, any number of reference and/or other filters can be part of the filter array 5208, based on the optical characteristics of the particle P, and/or as necessary for conducting the analysis described herein. Still referring to FIG. 52A, in some embodiments, the reference filters 5208$_1$ are intensity filters that are wavelength-independent, and can include, but are not limited to, all-pass filters. As illustrated in FIG. 52A, in some embodiments, the reference filters 5208$_1$ include at least a pair of reference filters.

Each fluorescence filter 5208$_2$ can be wavelength selective, and can independently be a high-pass filter, a low pass filter, or a band-pass filter for any suitable wavelength(s). As illustrated in FIG. 52A, in some embodiments, the fluorescence filters 5208$_2$ include at least a green filter, a yellow filter, and a red filter. In some embodiments, the green, yellow, and red filters can be narrow band-pass filters, such as those having a bandwidth of 10 nm-30 nm. In some embodiments, at least one of the green, yellow, and red filters can be a wide bandpass filter.

A detector 5202 is configured to collect the filtered fluorescence from the filter array 5208 and generate the first detection signal. In some embodiments, the detector 5202 can include a plurality of detectors. Any suitable detector can be employed such as, but not limited to, photomultiplier tubes (PMTs), photodiodes, charge-coupled devices (CCDs), avalanche photodiodes (APDs), and/or the like. In some embodiments, the detector 5202 includes a PMT as illustrated. The PMT can be similar to the Hamamatsu H9307.

Figure 52B:
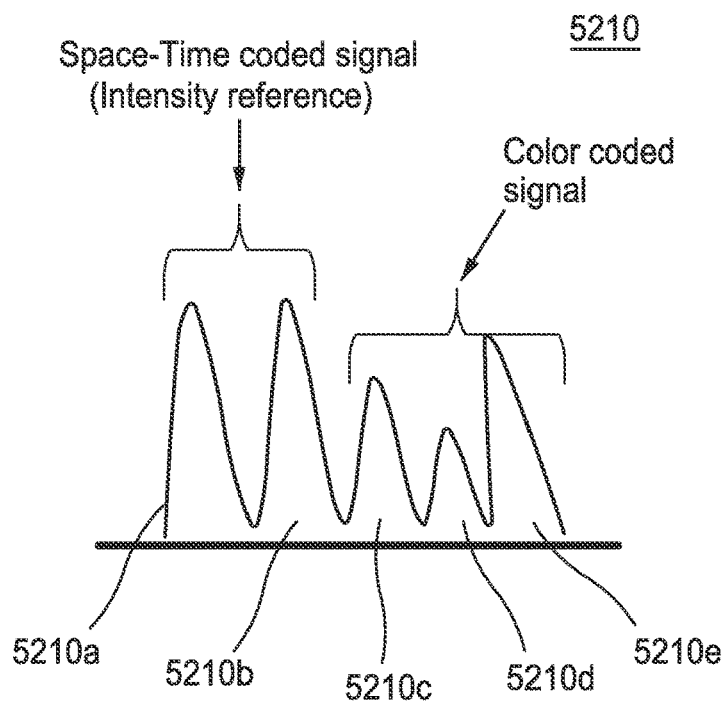
FIG. 52B is an illustrative plot of the output of the PMT of FIG. 52A, according to an embodiment.

The detector 5202, in one embodiment, receives the fluorescence signal of particle P from each filter of the filter array 5208 to generate the exemplary trace 5102, which is more conceptually illustrated in the trace 5210 of FIG. 52B. In other words, in one embodiment, the detector 5202 generates the peaks 5102a-5102e of the trace 5102 as illustrated in FIG. 52B, where peaks 5102a, 5102b correspond to the intensity reference signals 5210a. 5210b from the reference filters 5208$_1$, and peaks 5102c-5102e correspond to the color coded signals 5210c-5210e from the fluorescence filters 5208$_2$. As discussed earlier, the peaks of the traces 5102, 5210 are separated in time, and are detected in the following manner: the movement of the particle P within the first volume causes the fluorescence generated by the particle P to be successively projected onto each filter (by the lens 5206 and/or by any other suitable optics) of the filter array 5208, starting with the first of the reference filters 5208$_1$, and ending with the last of the fluorescence filters 5208$_2$.

Figure 53A:
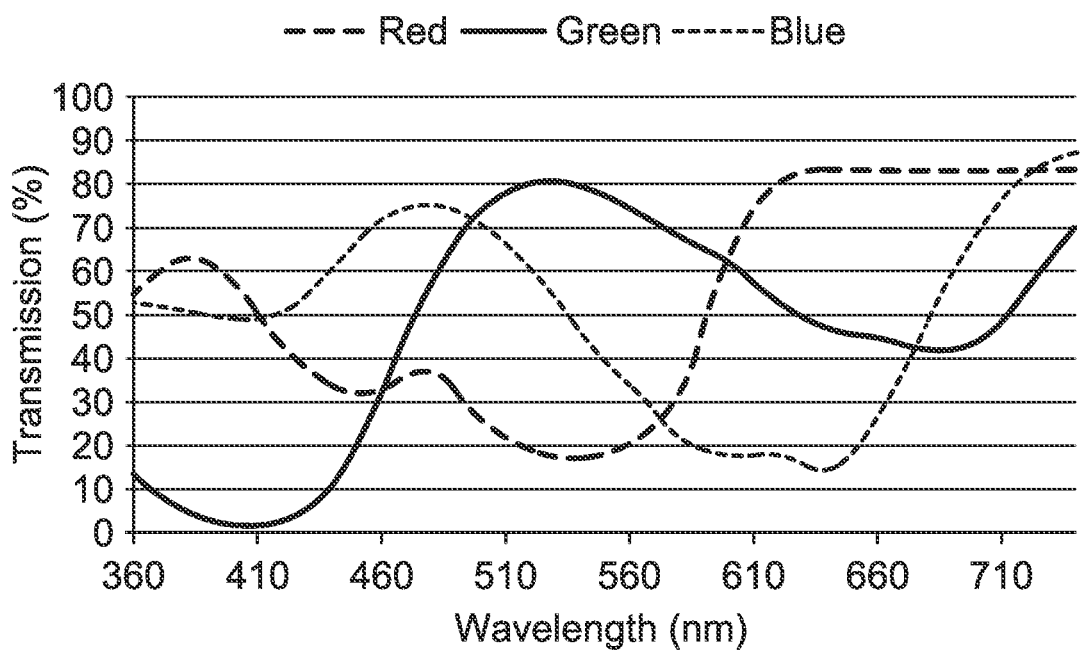
FIG. 53A is an illustration of filter transmission characteristics of the red, green and blue filters of FIG. 52A, according to an embodiment.
Figure 53B:
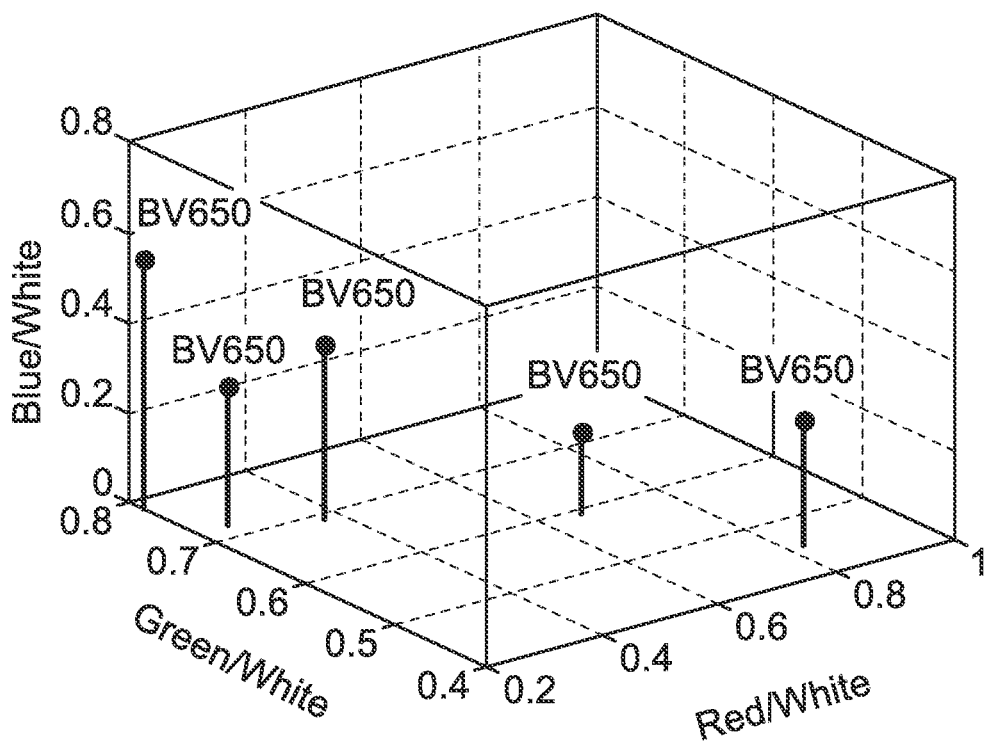
FIG. 53B is a plot illustrating multiple brilliant violet (BV) dyes as sorted by a method and apparatus of the invention.
Figure 53C:
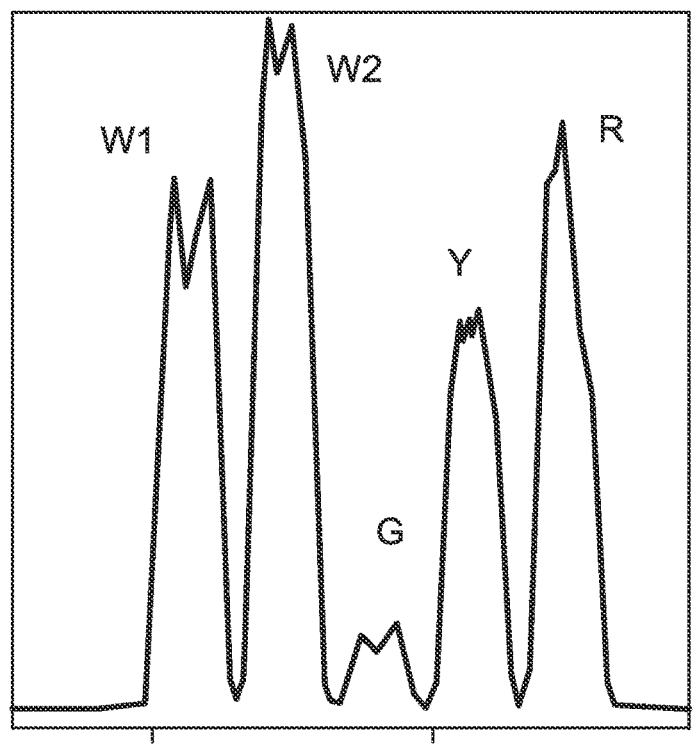
FIG. 53C is an exemplary plot of the output of the PMT of FIG. 52A, according to an embodiment
Figure 53D:
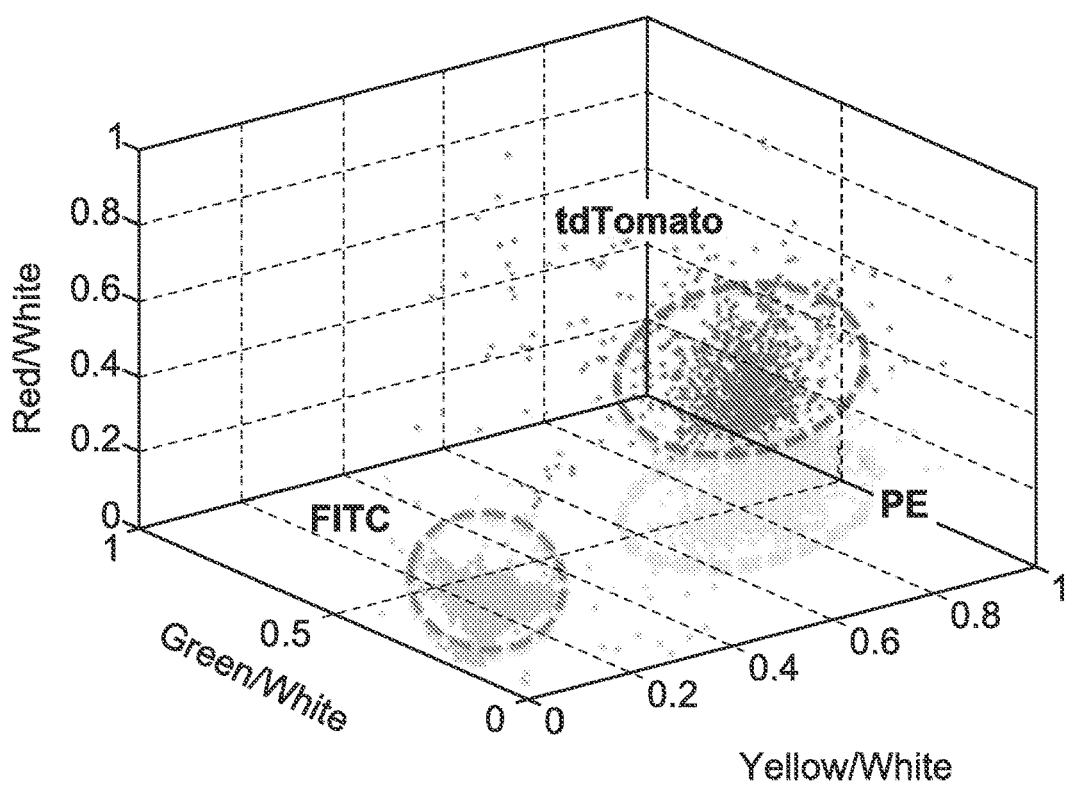
FIG. 53D is a plot illustrating the fluorophores FITC, PE, and tdTomato as sorted by a method and apparatus of the invention.

FIG. 53A illustrates exemplary and non-limiting transmission spectra for some embodiments where the fluorescence filters 5208$_2$ can be red, green, and/or blue filters. In the illustrated embodiment, each color filter has a wide bandwidth with a slowly changing slope, unlike conventional narrow-bandwidth color filters. As illustrated in FIG. 53B, analysis of multiple first detection signals (not shown) associated with a mixture of five types of fluorescent nanoparticles, each having different fluorescence characteristics (e.g. five different Brilliant Violet (BV) dyes) can be used to distinguish the dyes. FIG. 53B illustrates how Red/White, Green/White and Blue/White intensity ratios from the multiple first detection signals (generated using filters with the transmission spectra of FIG. 53B) result in non-overlapping points representing each BV dye indicates the feasibility for color distinction of up to 5 colors using a single PMT. As another example, the filter 5208 can be used to generate an exemplary first detection signal illustrated in FIG. 53C for the fluorophore PE, which, in one embodiment, is then distinguished from other fluorescent agents FITC and tdTomato, analyzed in a similar manner, to generate the plot of FIG. 53D, which indicates the feasibility of color distinction between these fluorophores.

Referring again to FIG. 52B, it thereby follows that the trace 5210 can provide at least the following information about the particle P: (1) speed of the particle P, as determined by the spacing between the peaks 5210a-5210e; the faster the particle is moving, the closer the peaks; (2) Overall intensity of the first detection signal, as determined by any combination of the peaks 5210a. 5210b; and (3) Fluorescence information in the first detection signal based on the fluorescence peaks 5210c-5210e, such as the fluorescence spectrum of the particle P. It is understood that additional inferences can be drawn from the trace 5210 within embodiments. In some embodiments, the peaks 5210a, 5210b are space-time coded signals and establish the reference for the overall fluorescence intensity, so that the fluorescence intensity variations among different particles will not affect its ability to distinguish fluorescent colors. By measuring the time between the first two peaks, the time that the particle P travels from the 1' detection zone 5012 to the sorting junction can be accurately calculated, enabling for high accuracy sorting.

In some embodiments, it follows that information provided by the trace 5210 forms the basis for sorting the particle. Accordingly, in some embodiments, the first detection signal, such as the trace 5210, can be analyzed to determine which destination channel 5010A-5010C should receive the particle to be sorted. Each destination channel 5010A-5010C can be associated, designated and/or otherwise assigned a different set of characteristics of the particle to form a basis for sorting the particle into that channel. For example, the trace 5210 yields particle speed information as described above, and one the destination channels 5210A-5210C can be selected based on the particle speed. Such operations can be useful when, for example, particles of different size, volume and/or stiffness move at different speeds at different equilibrium positions in the channel 5004. In another example, the trace 5210 yields overall fluorescence intensity information as described above, and one of the destination channels 5010A-5010C, in one embodiment is selected based on the overall fluorescence intensity. In some embodiments, at least one of the destination channels 5010A-5010C is designated as a 'waste' channel that receives particles that are deemed undesirable, such as when they do not match any sorting criteria, and/or match undesirable sorting criteria, and/or the like. In this manner, the particle is sorted based on the trace 5210, which in turn is based on the one or more characteristics being detected by the first detection device 5012.

Referring again to FIG. 50 in some embodiments, the sorting is achieved by transmitting a sorting signal, based on the first detection signal, to a sorting element 5006. The sorting element 5006 is configured to cause a displacement of the particle to be sorted in a manner that increases the probability of the particle being sorted into the correct destination channel. The sorting element 5006 can be in communication with a sorting volume of the source channel 5004 that is downstream of the first volume associated with the first detection device 5012.

The sorting signal can be of any specific format that affects the sorting of the particle by the sorting element 5006. For example, the sorting signal, in one embodiment, includes a specification of which of the destination channels 5010A-5010C the particle should be sorted to. In some embodiments, the sorting signal includes an actuating signal of varying intensity, where the intensity is a function of the extent the particle needs to be displaced, and/or the direction of displacement (i.e. towards or away from the sorting element 5006) in order to be sorted to the selected destination channel. In some embodiments, the sorting signal includes timing information for inducing the sorting of the particle. In other words, the sorting element 5006 receives an indication of when the particle will reach the sorting volume. The timing information can be based on the speed of the particle as determined from the first detection signal, based on the distance between the sorting volume and the first volume, and/or the like.

Any suitable technology capable of causing displacement of the particle in a direction lateral to the axial direction of the source channel 5004 can be employed. In some embodiments, the sorting element 5006 includes an electrostatic sorter. In some embodiments, and as illustrated in FIG. 50, the sorting element 5006 includes a piezoelectric actuator. For example, in one embodiment, the sorting element 5006 includes a piezoelectric diaphragm (also referred to with the reference character 5006) that defines a volume 5018 that can be filled and/or emptied via the hole 5008A, 5008B. The diaphragm can be in direct communication with the sorting volume, or with a deformable wall (not shown) of the source channel 5004 adjacent the sorting volume. During operation, the diaphragm 5006 can be rapidly filled/emptied, based on the sorting signal, to create lateral forces in the sorting volume that can push/pull the particle for sorting into a specific one of the destination channels 5010A-5010C.

Once the particle is sorted into a destination channel (e.g. the channel 5010A, which is used here for simplicity of explanation in a non-limiting manner), aspects of this disclosure enable the detection of the particle in the destination channel 5010A to ensure correct sorting of the particle; in other words, to determine that the particle was correctly sorted if the destination channel 5010A was the selected channel for sorting the particle into, and was incorrect sorted if otherwise. Referring again to FIG. 50, a second detection device/component 5014 is associated with a second volume of the destination channel 5010A, although additional detection devices can be associated with the other destination channels 5010B-5010C, and multiple detection devices can be associated with any of the destination channels 5010A-5010C.

Figure 51B:
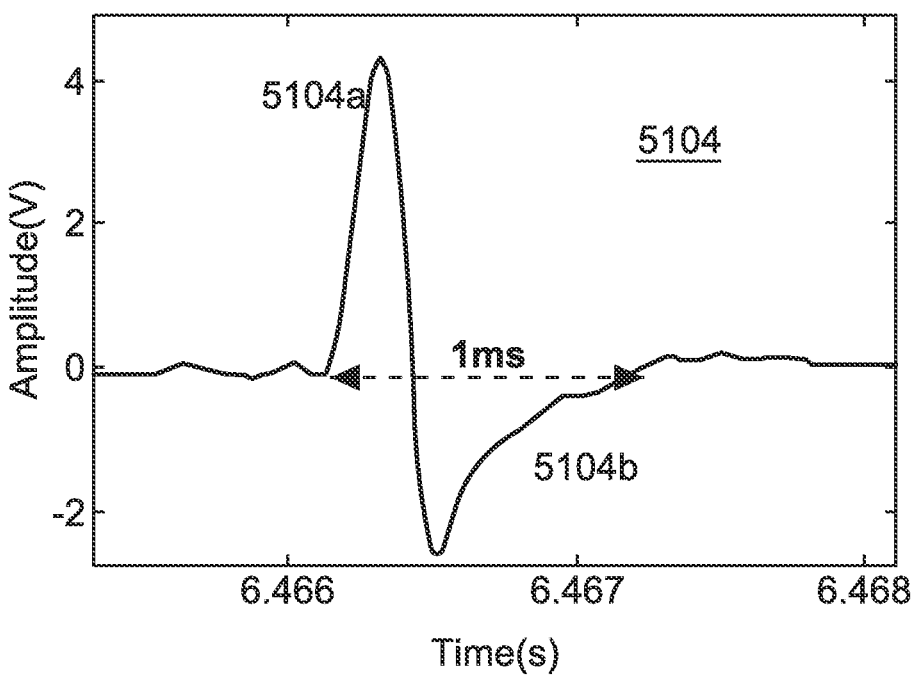
FIG. 51B is exemplary plot of the output of the impedance detector of FIG. 50, according to an embodiment.

The second detection device 5014 can be configured in a manner similar to or different than the first detection device 5012. In some embodiments, the second detection device 5014 is configured to at least detect the presence and/or volume of the particle in the destination channel 5010A, and to generate a second detection signal associated therewith. In other words, while the second detection signal can be of any suitable form (e.g. particle fluorescence, impedance, etc.), in some embodiments, it is primarily analyzed to determine that the particle was sorted into the destination channel 5010A. As an example, in one embodiment, the second detection signal is associated with one or more of fluorescence, reflectance, impedance, and/or the like, as discussed in detail earlier. In some embodiments, the second detection signal permits at least an impedance measurement, and FIG. 51B illustrates an exemplary impedance measurement 5104 of the second volume when the particle passes through it. The measurement can be characterized by the 'width' of the disturbance (1 millisecond in this case), which is a difference between an edge of a first curve 204*a* and an edge of the second curve 5104*b*, and can be characteristic of the particle speed.

Accordingly, in some embodiments, the sorting of the particle from the source channel 5004 to the destination channel 5010A is verified based on the second detection signal. For example, since the speed of the particle can be known (based on the first detection signal, such as the trace 5102), verifying, in one embodiment, includes determining that the second detection signal is received at a time and/or within a time period after the first detection signal. In this manner, when a large number of particles are being singly but rapidly sorted, the possibility of the second detection signal corresponding to another particle can be avoided.

In some embodiments, verifying includes determining that the second detection signal is generated. In this manner, when a sparse number of particles are being sorted, computational overhead associated with the timing particulars of the second detection signal are avoided. Further, simpler detection means can be used that are cheaper, have a smaller footprint, and/or the like.

In some embodiments, the second detection device 5014 is similar to the first detection device 5012. In other words, in on embodiment, for the same particle, the second detection signal and the first detection signal have a set of commonly determined signals. In such embodiments, verifying includes determining that the commonly determined signals are identical, and/or different within threshold limits. For example, in one embodiment, if the second detection signal and the first detection signal both include the setup of FIG. 52A, verifying includes determining that the second detection signal and the first detection signal both include the trace 5102.

In some embodiments, verifying can include providing corrective and/or other feedback signals to modify the operation of the particle sorter and/or parameters of the sorting signal including, but not limited to, intensity, output voltage waveform width, timing, and/or the like.

In some embodiments, verifying can include performing additional tests/operations on the sorted particle to determine it was correctly sorted.

Figure 54:
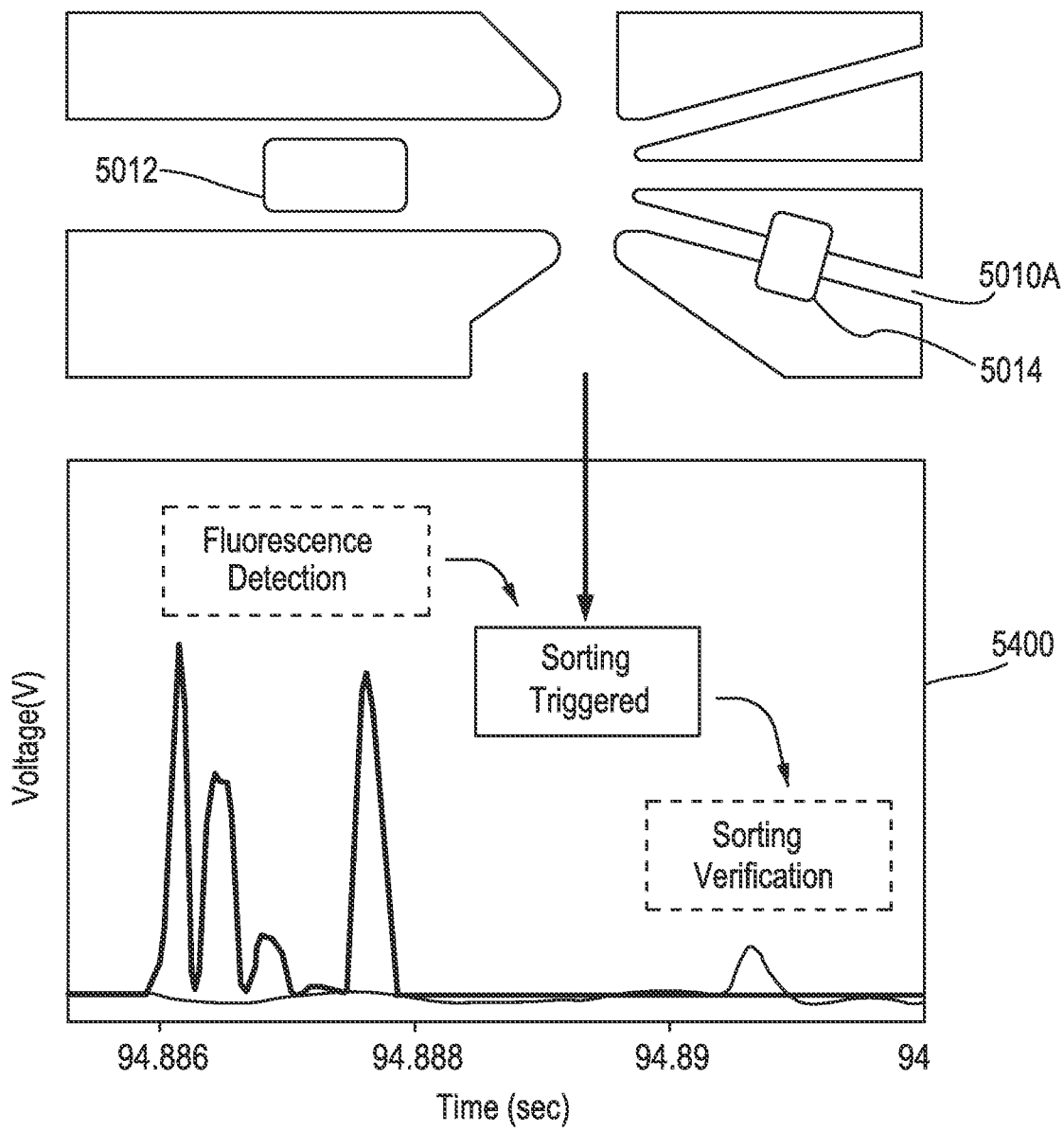
FIG. 54 is an illustrative approach for verification of sorting using the particle sorter of FIG. 1, according to an embodiment.

FIG. 54 illustrates an exemplary output plot 5400 for verification of sorting of a single particle using the particle sorter 5000 that combines the first detection signal and the second detection signal onto a single time-based plot. Fluorescence detection (of a particle to be sorted) at the first detection device 5012 leads to triggering of sorting by the sorting element 5006. The sorted particle is detected by the second detection device 5014 in the destination channel 5010A. A second detection signal is generated by the second detection device 5014, and the sorting of the particle into the destination channel 5010A is verified as discussed above.

Figure 55:
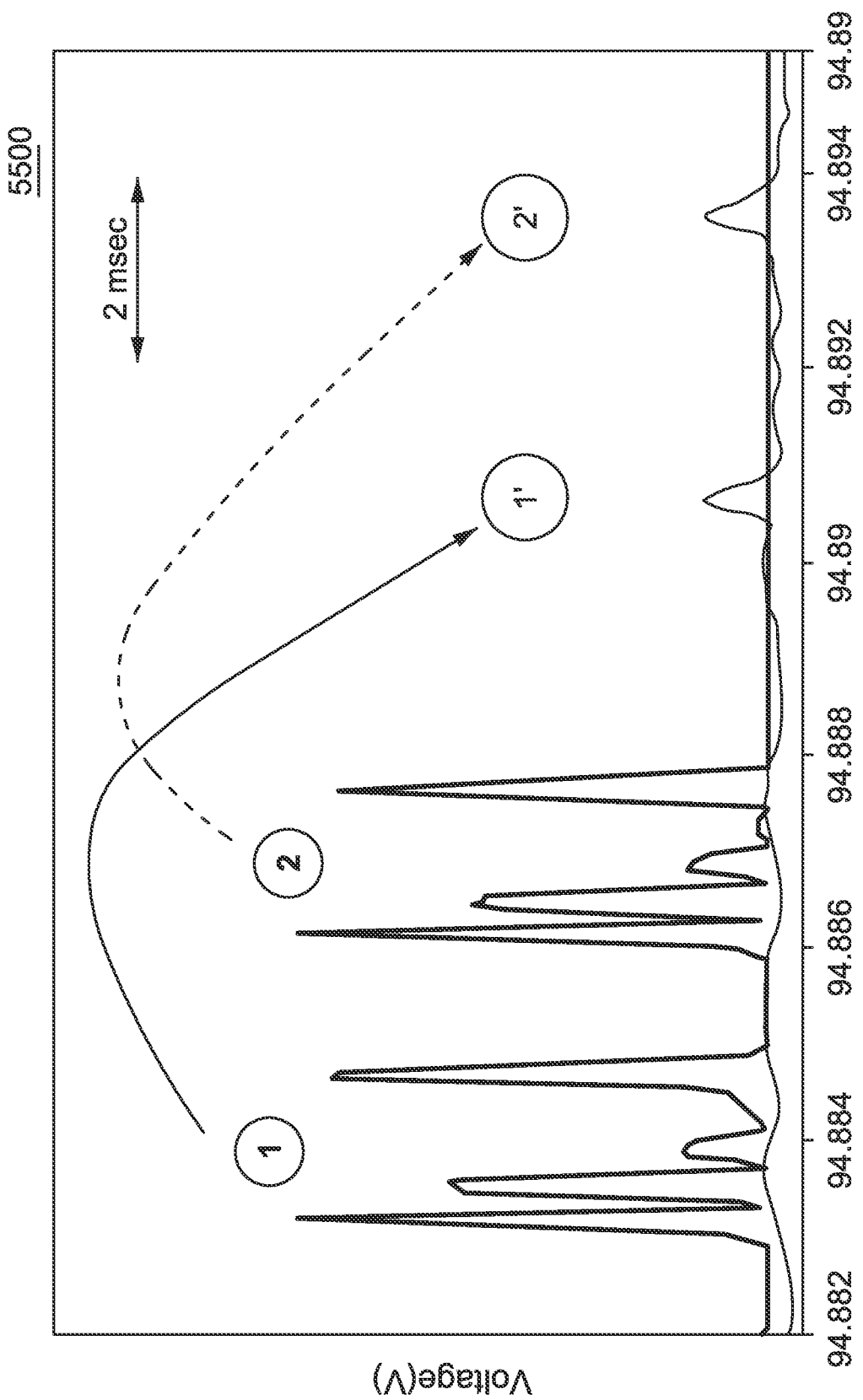
FIG. 55 is an illustrative approach for verification of sorting of two particles, according to an embodiment.

FIG. 55 illustrates an exemplary output plot 5500 for verification of sorting of two particles, where traces 1 and 2 (i.e. first detection signals) are correlated to second detection signals 1' and 2' respectively, thereby determining which first detection signal is associated with which second detection signal, and thereby verifying sorting of the two particles.

Figure 56B:
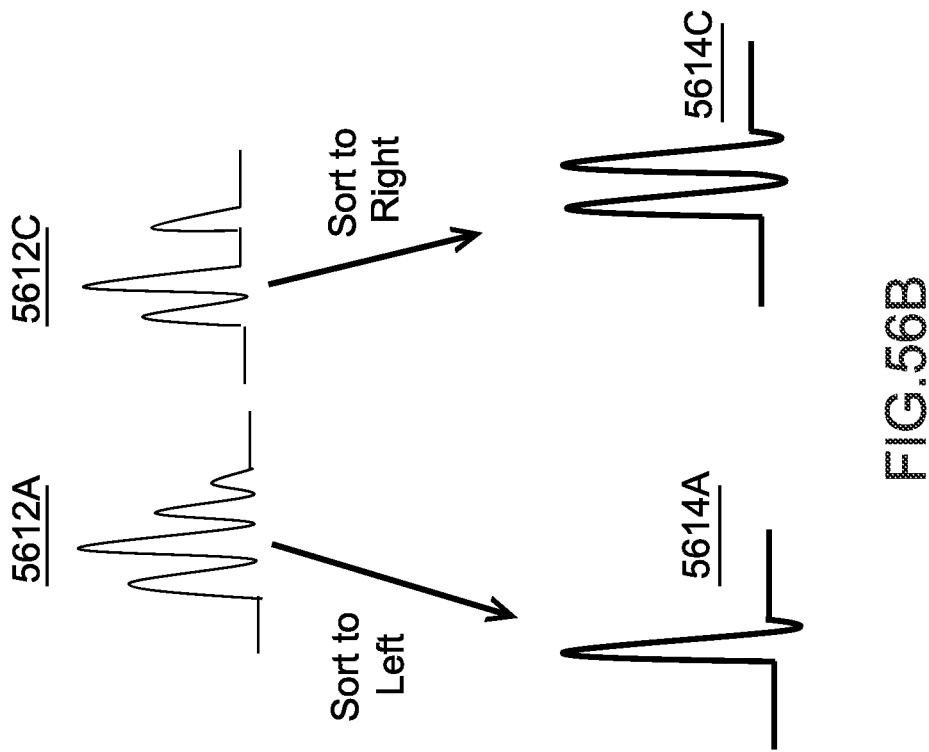
FIGS. 56B-56C are illustrative plots for verification of sorting of particles to multiple channels, according to an embodiment.
Figure 56A:
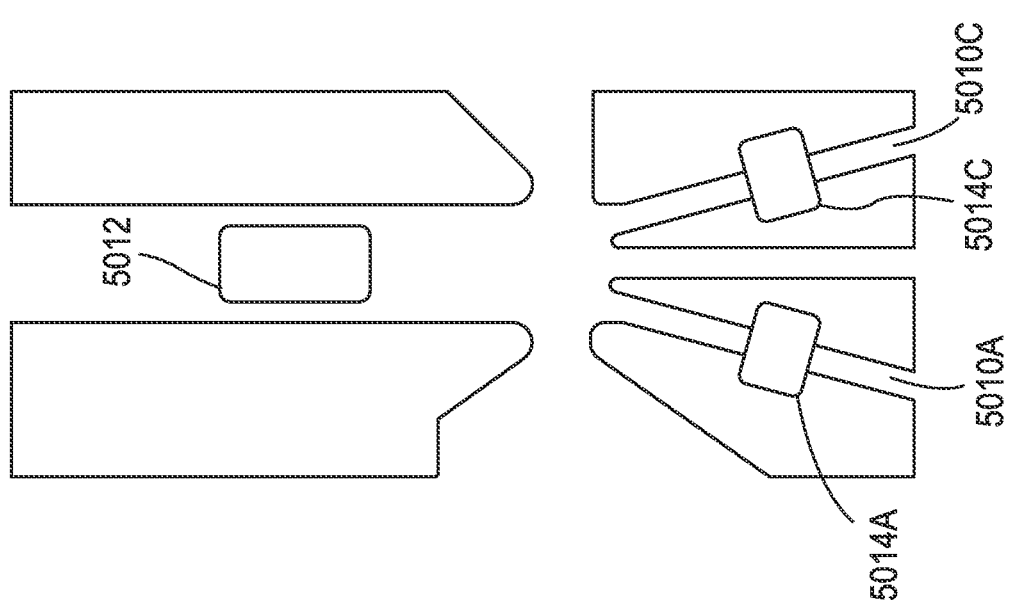
FIG. 56A is an illustration of a particle sorter having multiple impedance detectors, according to an embodiment.
Figure 56C:
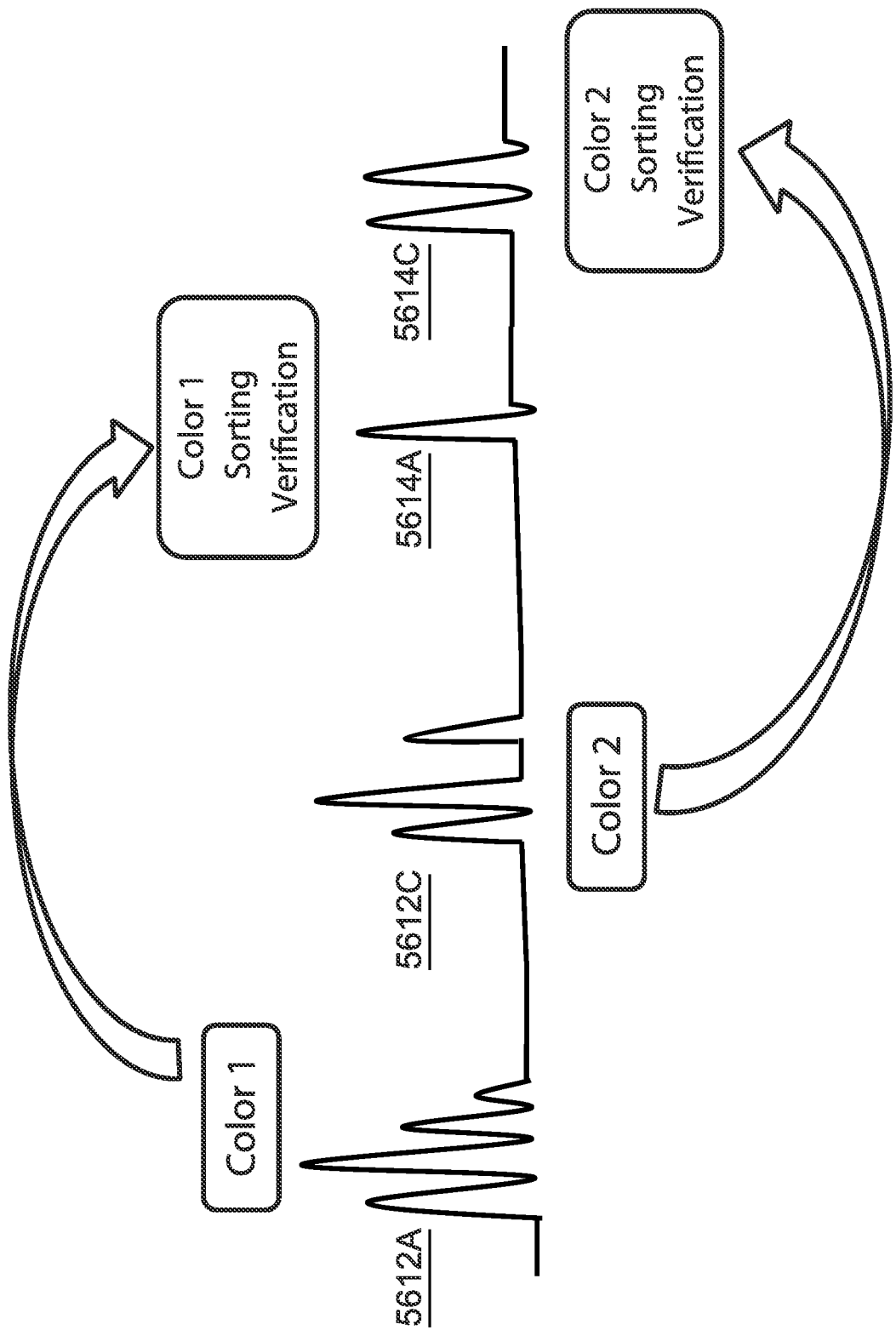

FIGS. 56A-56C illustrate an embodiment where two second detection devices 5014A, 5014C are associated with the destination channels 5010A, 5010C respectively. As seen in FIG. 56B, the destination channel 5010A can be designated to receive a first type of trace 5612A (corresponding to a specific fluorescent agent, for example), while the destination channel 110C can be designated to receive a second type of trace 5612C (corresponding to a different fluorescent agent, for example). The second detection device 5014A can be configured to generate a second detection signal of the form 5614A, and the second detection device 5014C can be configured to generate a second detection signal of the form 5614C. In this manner, when the traces 5612A, 5612C and the second detection signals 5614A, 5614C are plotted together (see FIG. 56C), verification can be more easily performed. While illustrated here for the two second detection devices 5014A, 5014C, it is understood that this approach of each second detection device generating a different second detection signal is easily extended to additional second detection devices in additional destination channel(s).

Figure 57:
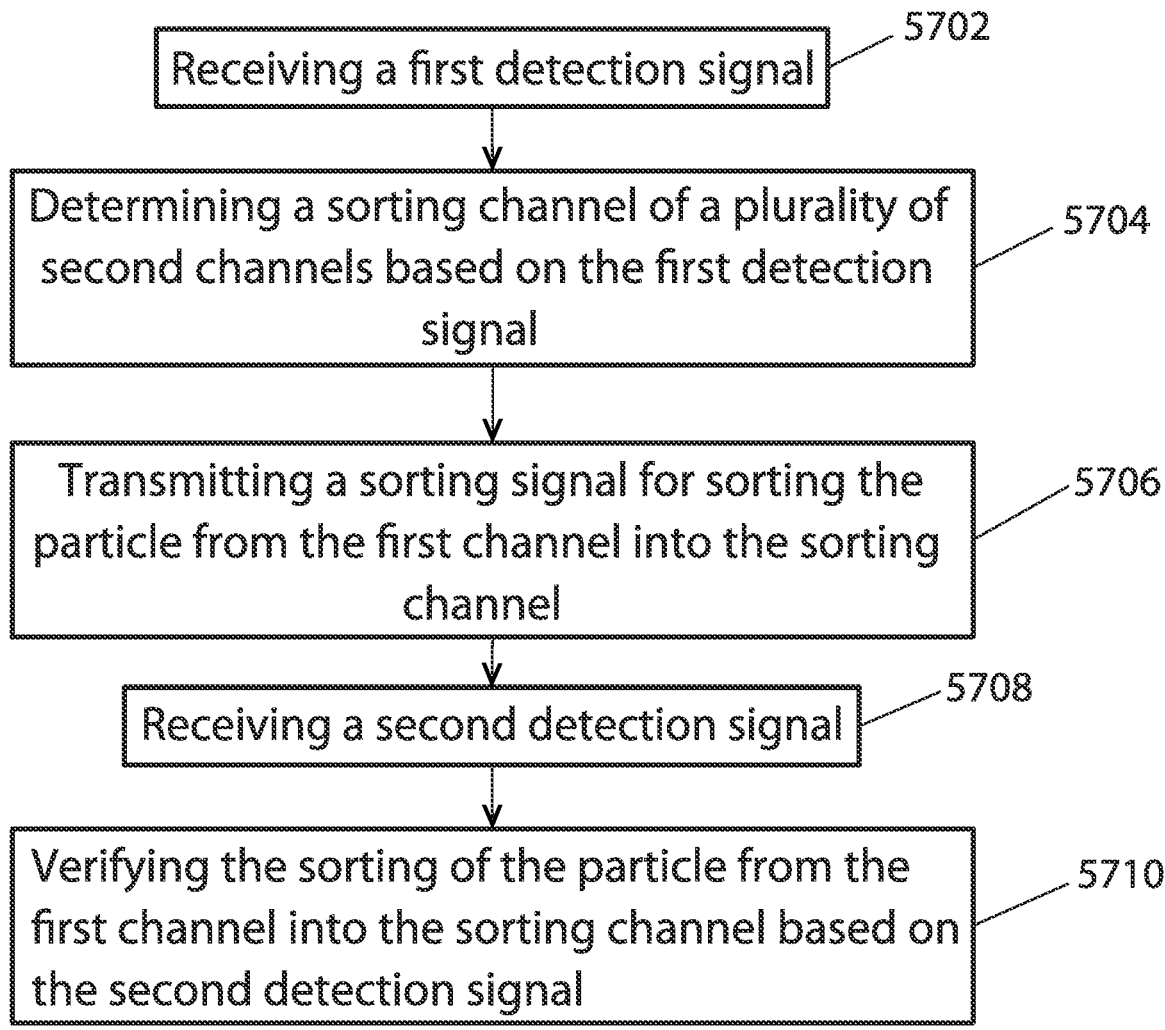
FIG. 57 is a method for verification of sorting of a particle, according to an embodiment.

FIG. 57 illustrates a method 5700 for verification of particle sorting, according to embodiments. In some embodiments, a computer-executable storage media includes computer-executable instructions for executing the method 5700. At 5702, a first detection signal is received. The first detection signal can be associated with optical characteristics (e.g. fluorescence) of a particle in a first channel (e.g. the source channel 5004). In some embodiments, the first detection signal can be associated with a plurality of optical signals. In some embodiments, the plurality of optical signals includes one or more reference signals and one or more fluorescence signals. In some embodiments, the optical characteristics include one or more fluorescence properties of the particle. In some embodiments, the particle is an inorganic particle, an organic particle, a hybrid particle, or one or more cells (eukaryotic or prokaryotic).

At 5704, a sorting channel of a plurality of second channels is determined based on the first detection signal. In this manner, determining the sorting of the particle into the sorting channel is based on the optical characteristics of the particle. In some embodiments, determining the sorting channel is based on the one or more fluorescence properties of the particle.

At 5706, a sorting signal for sorting the particle from the first channel into the sorting channel is transmitted. In some embodiments, transmitting the sorting signal includes transmitting the sorting signal to a sorting element (e.g. the sorting element 5006). In some embodiments, the sorting element includes a piezoelectric actuator, and sorting further includes generating the sorting signal based on a required deformation of the piezoelectric actuator to sort the particle into the sorting channel.

At 5708, a second detection signal is received, where the second detection signal associated with the presence of a detected particle in the sorting channel. In some embodiments, the second detection signal is associated with impedance detection, where the presence of the detected particle in the sorting channel changes the detected impedance in the second detection channel.

At 5710, the sorting of the particle from the first channel into the sorting channel is verified based on the second detection signal.

In some embodiments, the method 5700 further includes receiving an additional first detection signal. The additional first detection signal, in one embodiment, is associated with optical characteristics of a second particle in the first channel. The optical characteristics of the second particle can be the same, or different from the optical characteristics of the first particle. A second sorting channel of the plurality of second channels is determined based on the additional first detection signal. The second sorting channel can be the same or different from the sorting channel. Hence, the sorting of the second particle into the second sorting channel is determined based on the optical characteristics of the second particle. A second sorting signal is transmitted for sorting the second particle from the first channel into the sorting channel. An additional second detection signal can be received that is associated with the presence and/or volume of a second detected particle in the second sorting channel. In some embodiments, the sorting of the particle from the first channel into the sorting channel is verified based on the second detection signal and based on the additional second detection signal. In some embodiments, the sorting of the second particle from the first channel into the second sorting channel is verified based on the second detection signal and based on the additional second detection signal.

As discussed herein, particle speed can be variable, and can be determined based on the spacing between peaks in a first detection signal, such as the trace 5102, for example. Hence, it is possible for two or more particles to be closely spaced, and/or moving at a speed where the trace from one particle can overlap with at least another particle. Aspects of the approaches described herein are operable to distinguish particles with overlapping first detection signals using the second detection signals associated with each particle.

Figure 58:
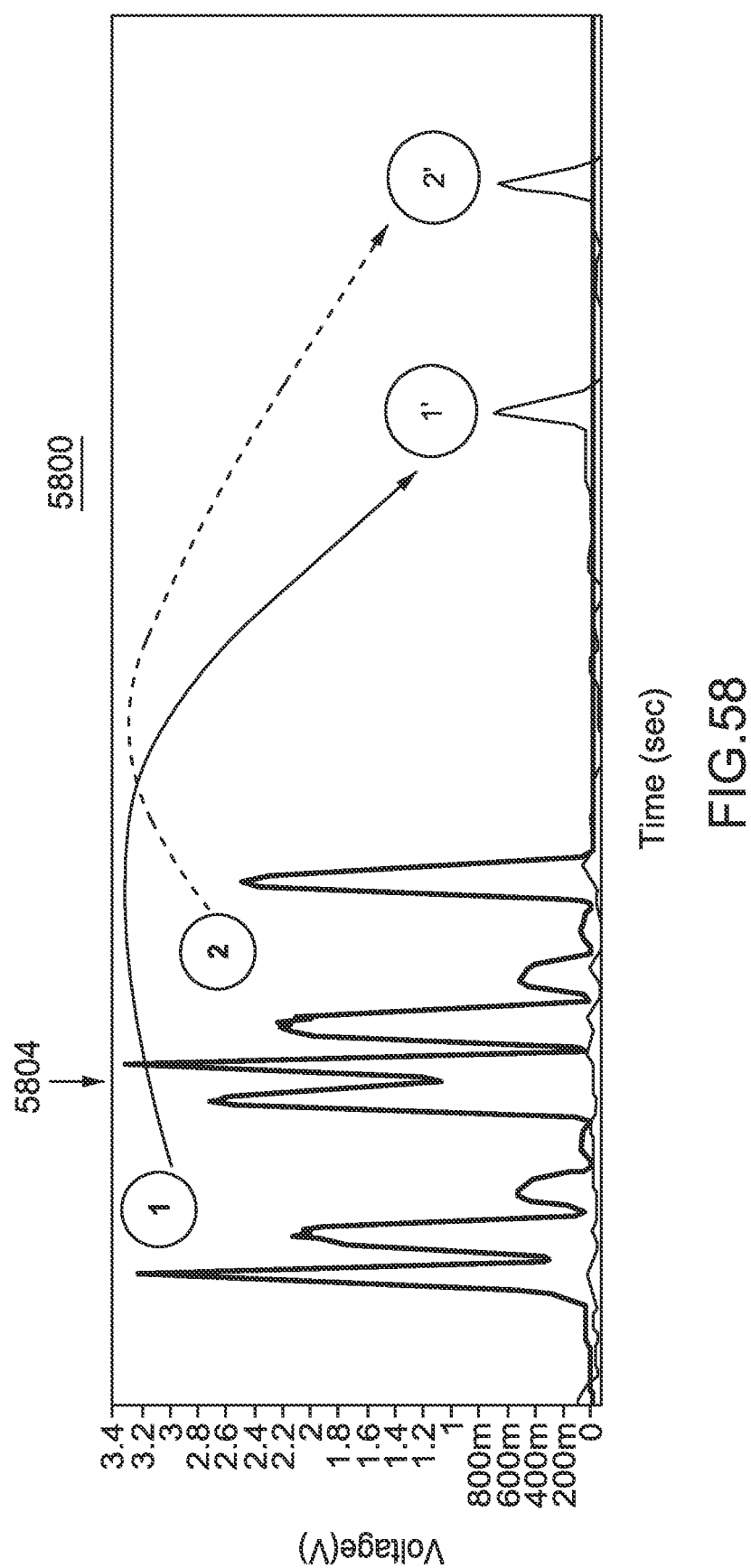
FIG. 58 is an illustrative approach for counting of particles, according to an embodiment.
Figure 59A:
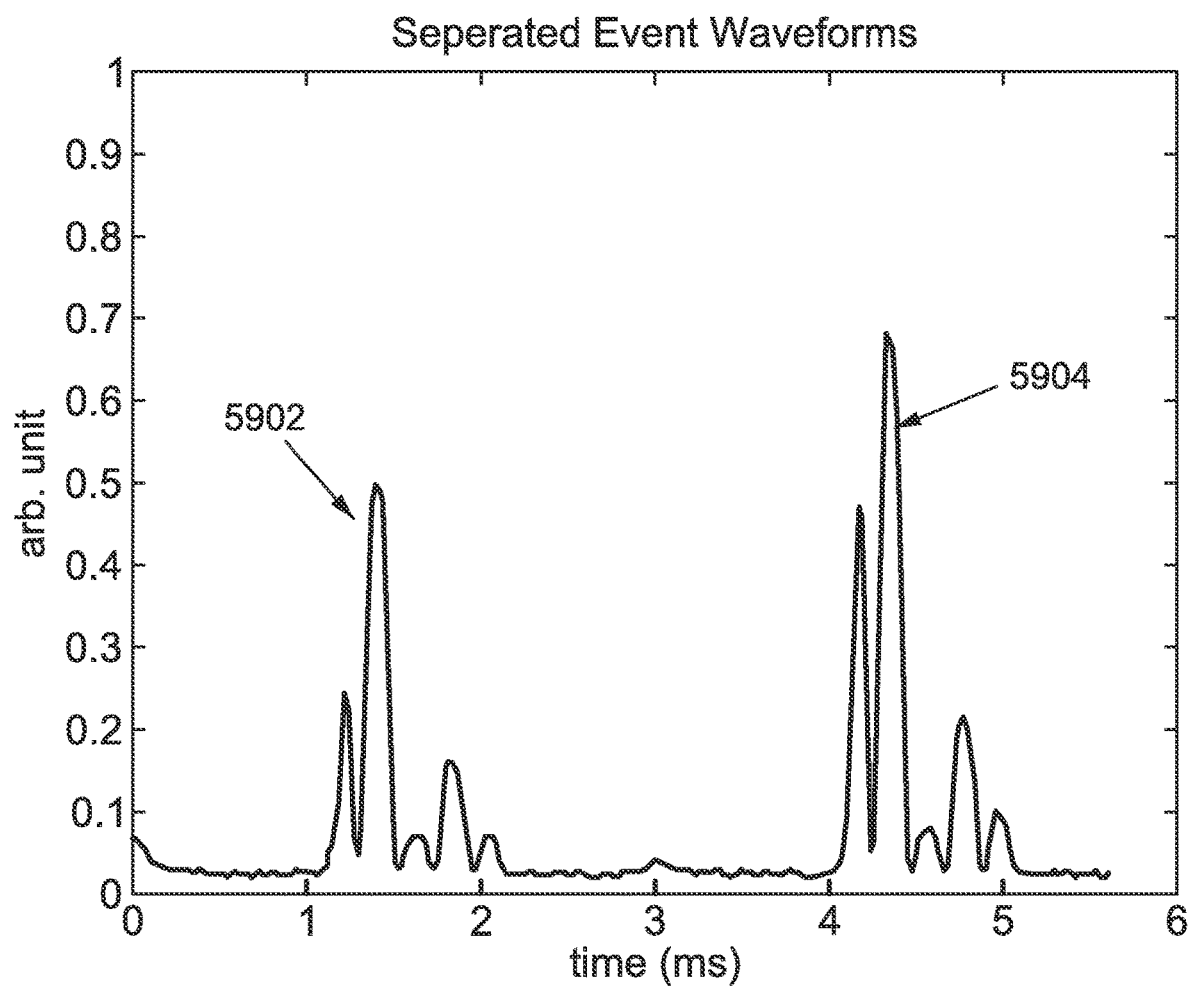
FIGS. 59A-59C are illustrative plots of analysis for counting of particles, according to an embodiment.
Figure 59B:
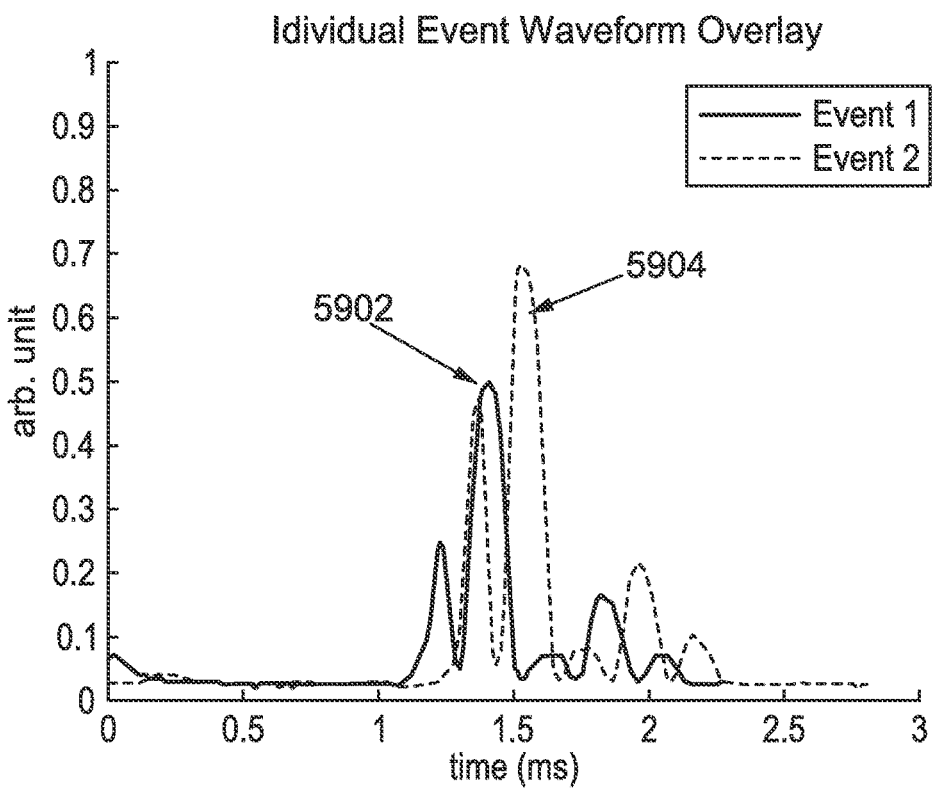
Figure 59C:
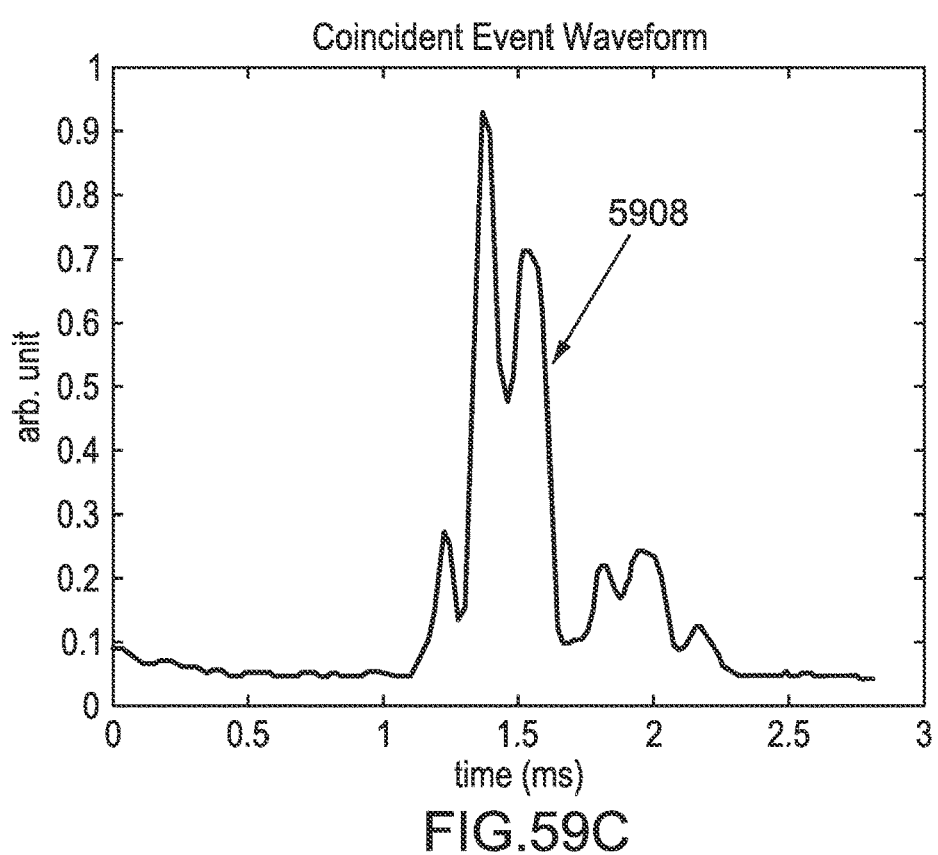

For example, FIG. 58 illustrates an exemplary output plot 5800 of the first and second detection signals (1, 2 and 1', 2' respectively) associated with two serially sorted and detected particles. While an overlap is seen between the traces 1, 2 at 5804, the individual peaks are still distinguishable, and the number of particles can be correctly identified as two based on the second detection signals 1', 2'. FIGS. 59A-59C illustrates the problem discussed here, where the exemplary traces 5902, 5904 from two particles overlap. FIG. 59A illustrates the traces 5902, 5904 separated in time, when they are easily distinguished as individual traces, and accordingly, as individual particles. FIG. 59B illustrates the traces 5902, 5904 as overlapping, such as when the particles are within the first volume (i.e. associated with the first detection device 5012) at the same time. FIG. 59C illustrates the resulting trace 5908, having six discernable peaks, and confounding the particle count determination. Errors in determination of the first detection signal can have significant downstream affects, such as inaccurate particle speed and/or fluorescence spectrum determination, which in turn can lead to not only errors in timing the sorting of the particle (i.e. the sorting signal would have incorrect triggering information for the sorting element 5006), but also in incorrect sorting altogether (i.e. the particle could be deemed to belong to another destination channel).

Figure 60A:
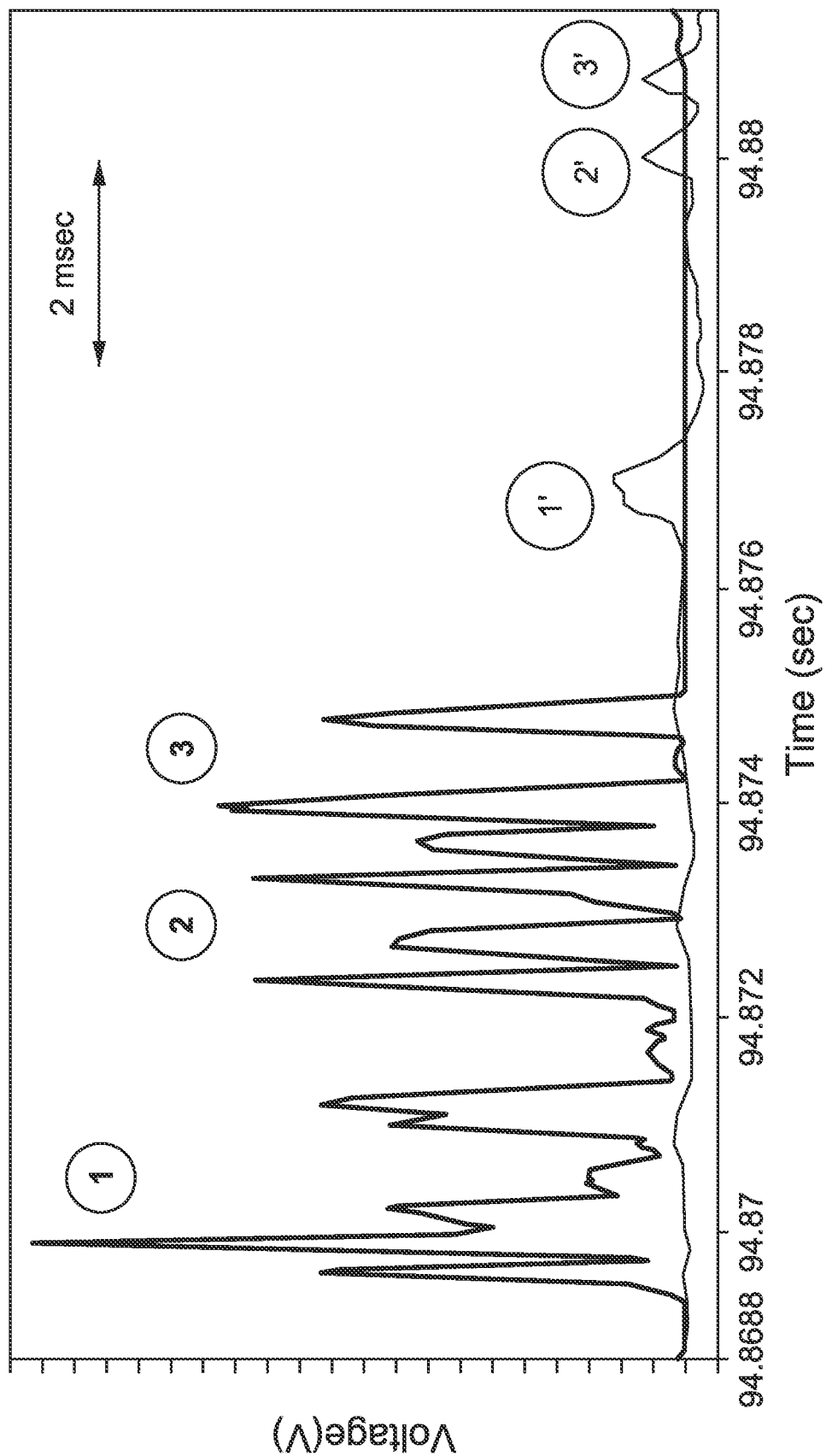
FIGS. 60A-60B are illustrative approaches for determining number of particles, according to an embodiment.
Figure 60B:
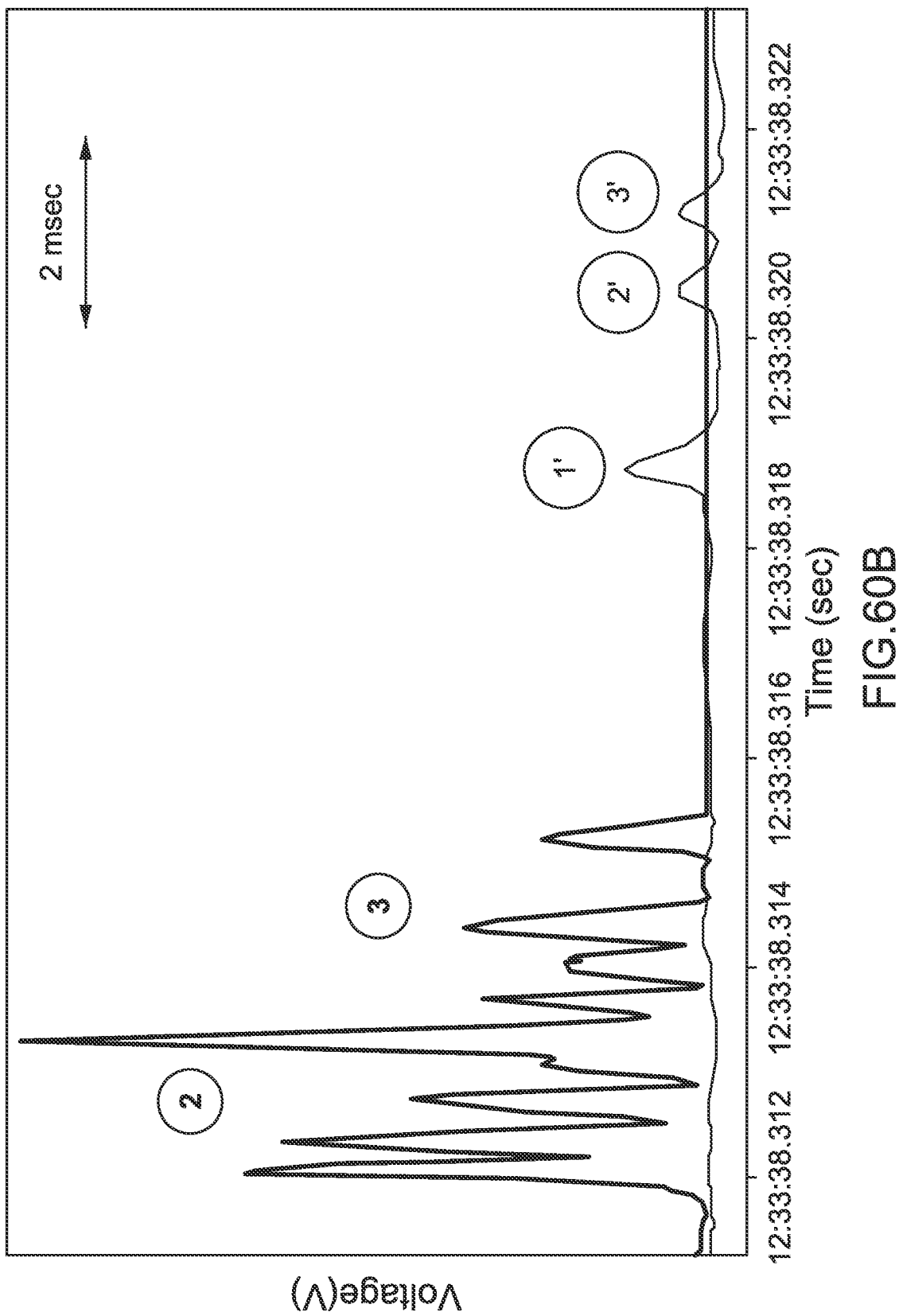

FIGS. 60A-60B illustrate potential errors with particle sorting/counting, where 3 particles are correctly counted based on the second detection signals, even though the first detection signals are overlapping. In particular, the exemplary plot of FIG. 60B illustrates how overlapping first detection signals will not result in the first particle being detected by the first detection device 5012 (where only particles corresponding to traces 2, 3 are detected), but the second detection signals 1', 2', 3' not only indicate that traces 2, 3 are associated with 3 particles, but the temporal separation between the second detection signals 1', 2', 3' provides particle separation information. Namely, the second detection signals 1', 2', 3' indicate that the particles corresponding to the second detection signals 2', 3' are more closely spaced.

Generally, the information gleaned from the second detection signals can hence be used not only for cell counting, but for feedback control of cell sorting, where the approaches described herein can 'learn' from traces associated with past counting errors to analyze future traces. For example, if the traces 2, 3 of FIG. 60B were to arise again, they would likely be more accurately associated with showing three particles. At this point, the three particles will either be sorted accordingly, or if this is not possible (e.g. the sorting element is unable to respond quickly enough), will be accounted for depending on which destination channel they are deemed to end up in (i.e. based on the second detection signals 1', 2', 3').

Further, when the incorrect counting results in incorrect sorting, the approaches described herein can account for the errors in any suitable manner. For example, if the particles being sorted to the destination channel 5010A are to be used to make a vaccine composition, incorrect sorting of undesirable particles into the destination channel 5010A can be accounted for in determining the final vaccine composition and/or purity, where the vaccine composition can be discarded if such composition and/or purity is below required regulatory standards.

Aspects of the approach described herein can hence exploit differences in detection volumes between the first detection device 5012 and the second detection device 5014 to achieve error-compensated cell counting/sorting. In other words, the first detection device 5012 can be associated with a larger detection volume (i.e. the first volume) due to more extensive detection techniques, since the first detection signal can form the basis of sorting the particles. The second detection device 5014, on the other hand, can be configured to simply perform a binary classification (i.e., either the particle is present in the second volume, or it is not), and can employ simpler detection methods using a smaller detection volume, where the chance for multiple particles being present at the same time is greatly reduced. As an example, referring to the exemplary plot of FIG. 55, the trace 1 (first detection signal) has a temporal width of approximately 2 ms, while the corresponding second detection signal 1' has a temporal width of approximately 0.5 ms; for the same particle speed, this can indicate that the first volume is about four times larger than the second volume.

Figure 61:
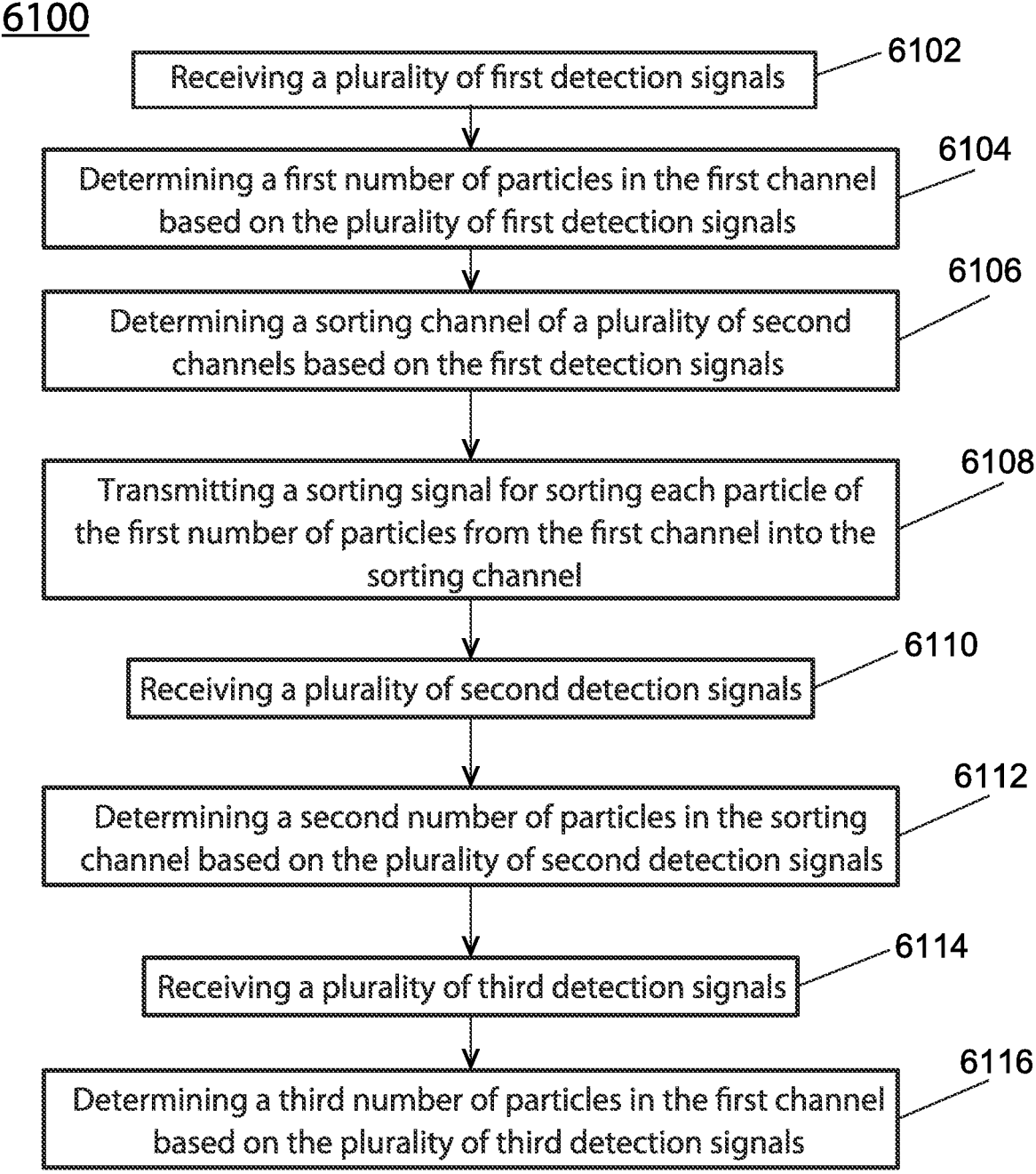
FIG. 61 is a method for feedback-based counting of particles, according to an embodiment.

FIG. 61 illustrates a method 6100 for feedback-based counting of particles, according to embodiments. In some embodiments, a computer-executable storage media includes computer-executable instructions for executing the method 6100. At 6102, a plurality of first detection signals is received, each first detection signal associated with optical characteristics of a particle in a first channel.

At 6104, a first number of particles in the first channel is determined based on the plurality of first detection signals, the first number of particles having similar optical characteristics. In some embodiments, the plurality of first detection signals includes at least an overlapping pair of first detection signals.

At 6106, a sorting channel of a plurality of second channels is determined based on the first detection signals. In this manner, the sorting of all the first number of particles into the sorting channel is determined based on the similar optical characteristics of the first number of particles.

At 6108, one or more sorting signals are transmitted for sorting each particle of the first number of particles from the first channel into the sorting channel. At 6110, a plurality of second detection signals are received, where each second detection signal associated with the presence and/or volume of a particle in the sorting channel. At 6112, a second number of particles in the sorting channel is determined based on the plurality of second detection signals. At 6114, a plurality of third detection signals are received, each third detection signal associated with optical characteristics of an additional particle in the first channel.

At 6116, a third number of particles in the first channel are determined based on the plurality of third detection signals, based on the determined first number of particles and based on the determined second number of particles. In some embodiments, the determined first number of particles is the same as the determined second number of particles, and it is determined that the one or more third detection signals are associated with the determined third number of particles. In some embodiments, the determined first number of particles is less than the determined second number of particles, and it is determined that the one or more third detection signals are associated with a fourth number of particles that is greater than the determined third number of particles.

Figure 62A:
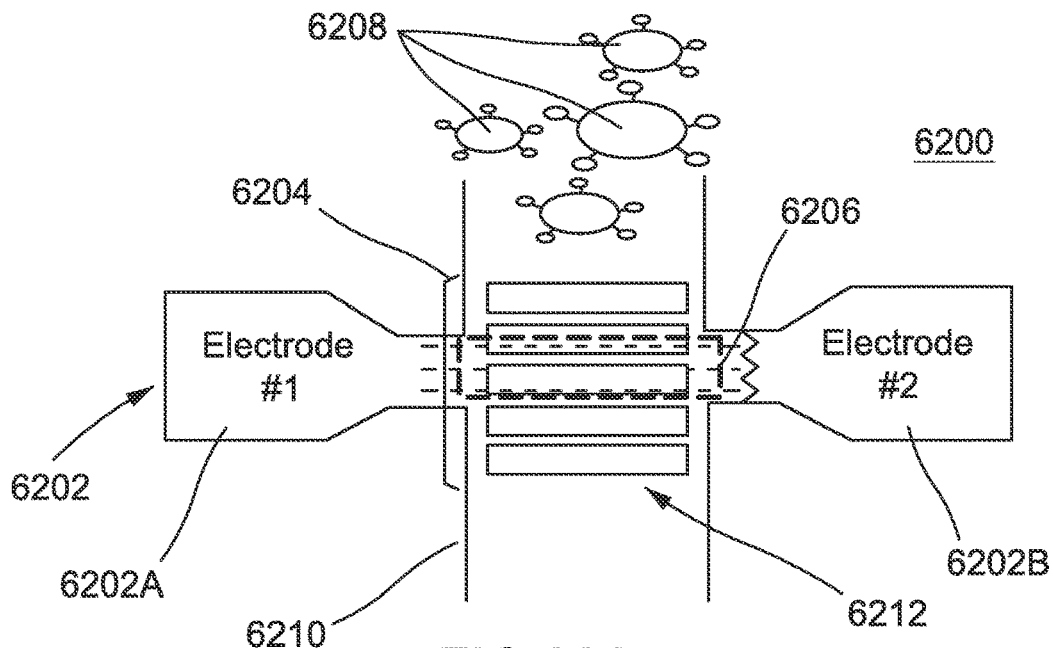
FIG. 62A is a particle sorter having two detection zones in the same channel, according to an embodiment.
Figure 62B:
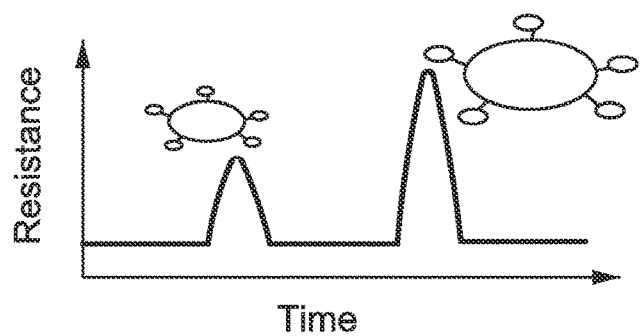
FIG. 62B is an illustrative plot of the output of the impedance detector of FIG. 62A, according to an embodiment.
Figure 62C:
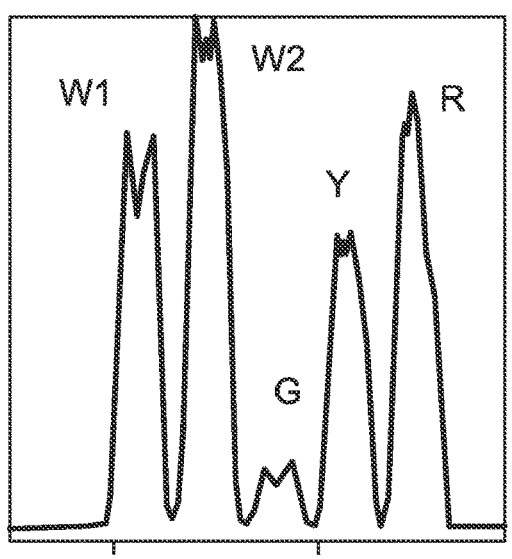
FIG. 62C is an exemplary plot of the output of the fluorescence detector of FIG. 62B, according to an embodiment.

As discussed earlier, the first detection device 5012 and/or the second detection device 5014 can detect multiple characteristics associated with a particle in the detection volume, or with the detection volume itself. FIGS. 62A-62C illustrate an exemplary embodiment showing a portion of a particle sorter 1300 having a channel 1310 containing the particles 1308. While explained herein assuming that the channel 1310 corresponds to the source channel 104, it is understood that these embodiments are just as easily applicable to any of the destination channels 118A-118C.

Referring to FIG. 62A, the sorter 6200 includes, as a first detection device, an intensity reference and fluorescence trace measurement setup 6212 similar to FIG. 52A, wherein the first detection volume 6204 of the channel 6210 is associated with a filter array similar to the filter array 5208. FIG. 62C illustrates an exemplary trace generated by the setup 6212.

The sorter 6200 also includes, as the first detection device, an impedance measuring apparatus 6202 that includes electrodes 6202A, 6202B defining a second detection volume 6206 in the channel 6210. In some embodiments, at least a portion of the first detection volume 6204 overlaps with the second detection volume 6206. For example, FIG. 62A illustrates that the second detection volume 6206 is wholly contained within the first detection volume 6204, although this need not always be the case. For example, the second detection volume 6206 can be formed before or after the first detection volume 6204, in an overlapping or non-overlapping manner. In some embodiments, the second detection volume 6206 is smaller than the first detection volume 6204. FIGS. 62B, 62C illustrates exemplary output plots of the fluorescence setup In some embodiments, the impedance measurement is associated with the presence and/or volume of the particle 6208 in the second detection volume 6206. In some embodiments, the impedance measurement is associated with the size of the particle 6208. FIG. 62B illustrates how the size of the particle can theoretically affect the impedance measurement.

Figure 63A:
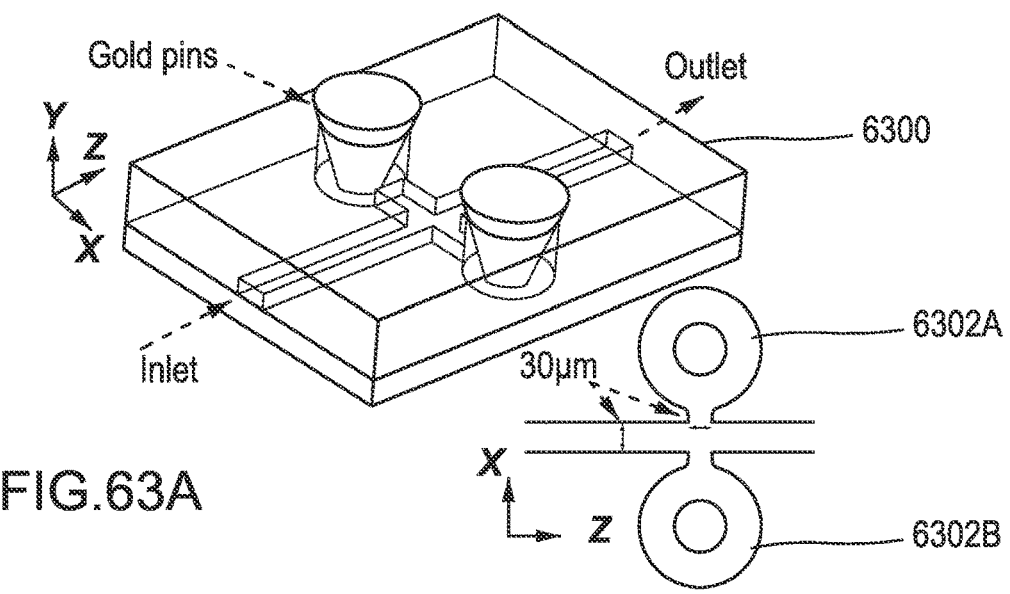
FIG. 63A is a perspective view of an exemplary embodiment of the impedance detector of FIG. 62A, according to an embodiment.
Figure 63B:
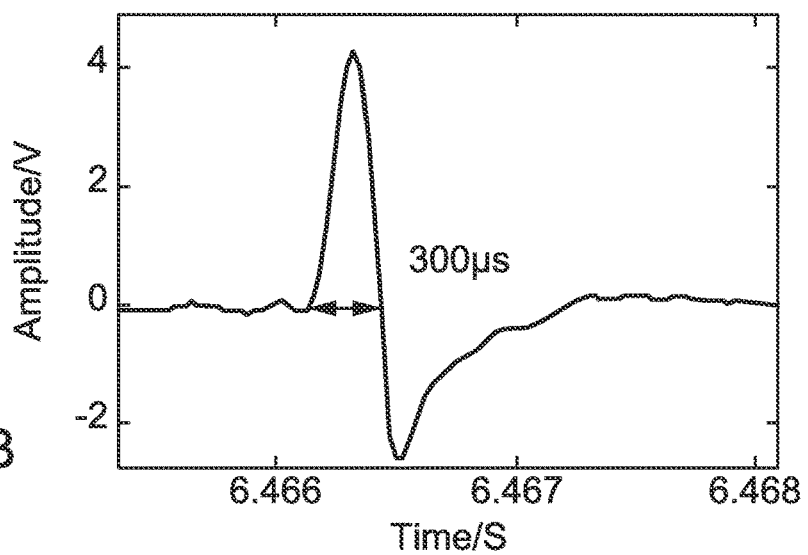
FIG. 63B is an exemplary plot of the output of the impedance detector of FIG. 62A for a single particle, according to an embodiment.
Figure 63C:
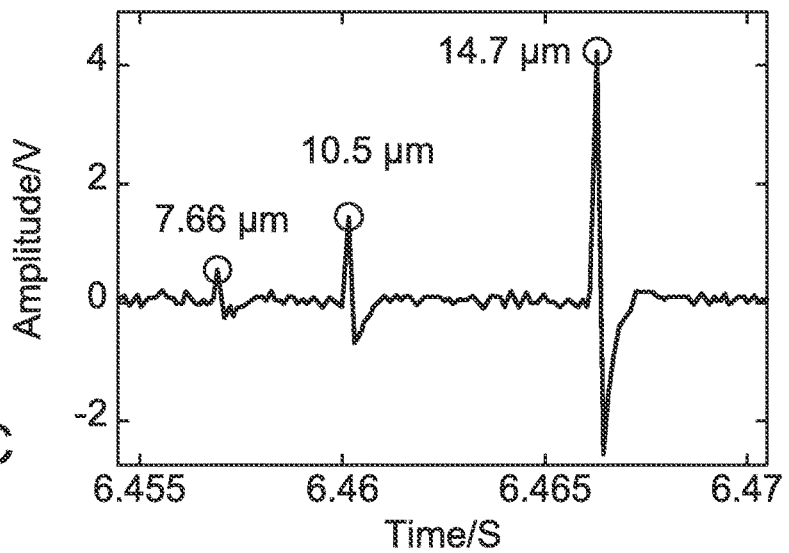
FIG. 63C is an exemplary plot of the output of the impedance detector of FIG. 62A for three particles of different sizes, according to an embodiment.

An exemplary and non-limiting embodiment of the impendence measuring apparatus 6202 is illustrated in FIG. 63A, where the electrodes 6302A, 6302B (which correspond substantially to the electrodes 6202A, 6202B) are formed as gold pins on a substrate of the particle sorter 6300. FIGS. 63B-63C illustrate exemplary impedance measurements made using the particle sorter 6300 on polystyrene beads, where FIG. 63B is a typical measurement, and FIG. 63C is an impedance measurement of three differently sized beads.

In this manner, size and fluorescence information can be acquired at the same location for a particle, and more specific and/or accurate sorting of the particle can be based on both pieces of information. In some embodiments, the size and/or fluorescence information can be used to determine other properties of the particles, such as, but not limited to, biological activity, chemical activity, and/or the like. In this manner, sorting can be based on hypothesis/inferences of relevance associated with the detected signal(s).

Figure 64:
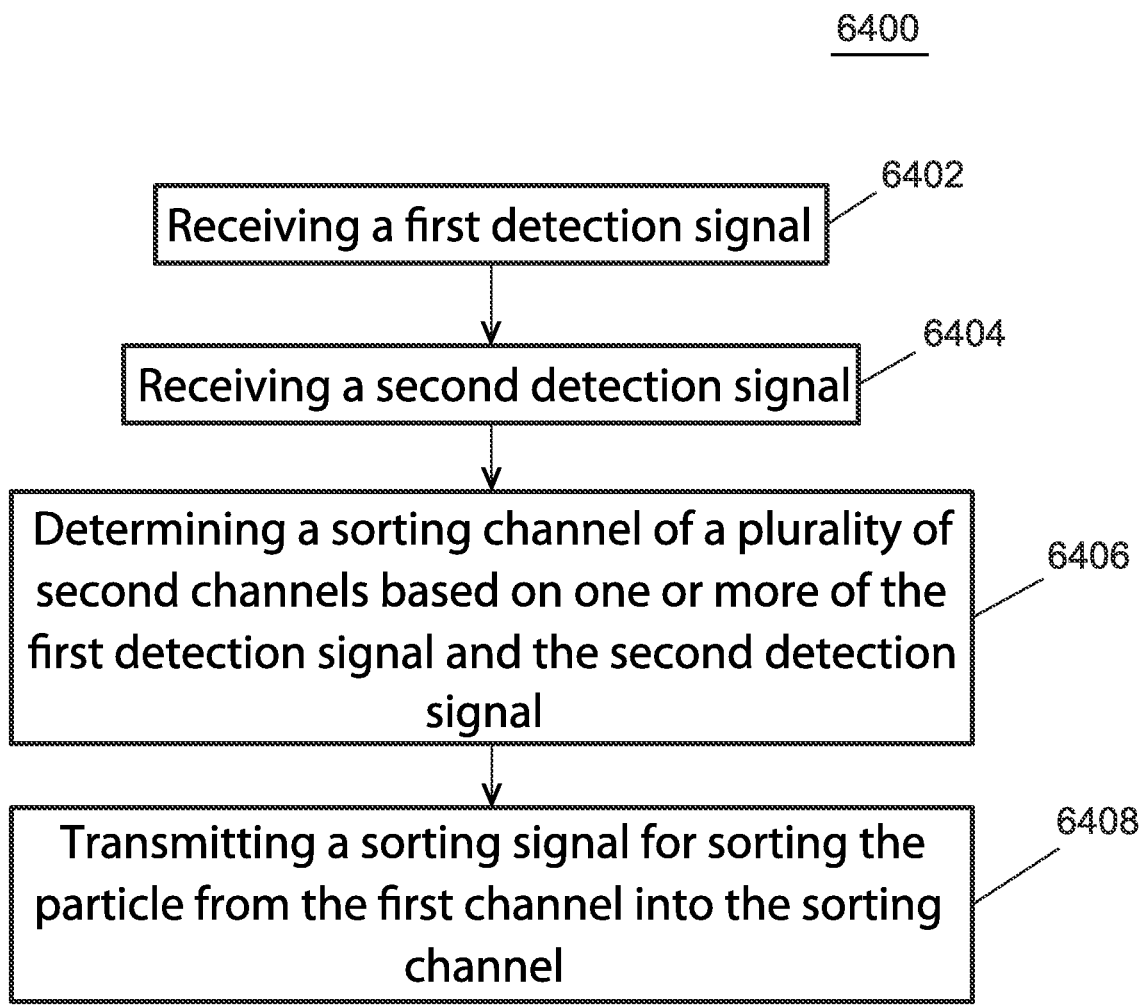
FIG. 64 is a method for sorting of particles, according to an embodiment.

FIG. 64 illustrates a method 6400 for sorting of particles, according to some embodiments. In some embodiments, a computer-executable storage media includes computer-executable instructions for executing the method 6400. At 6402, a first detection signal is received that is associated with first characteristics of a particle in a first volume of a first channel. In some embodiments, the first detection signal is associated with a plurality of optical signals. In some embodiments, the plurality of optical signals include one or more intensity reference signals and one or more color coded signals. In some embodiments, the optical characteristics include one or more fluorescence properties of the particle.

At 6404, a second detection signal is received that is associated with second characteristics of the particle in a second volume of the first channel. In some embodiments, the second detection signal is associated with impedance detection, where the impedance detection is based on the presence and/or volume of the particle in the second volume. In some embodiments, the impedance detection is further based on the size of the particle. In some embodiments, the first volume overlaps with the second volume. In some embodiments, one or more properties of the particle is determined based on one or more of the first detection signal and based on the second detection signal, and the sorting channel is determined based on the one or more properties. In some embodiments, each property is independently selected from one or more of the following: particle size, particle fluorescence, chemical activity, and biological activity.

At 6406, a sorting channel of a plurality of second channels is determined based on one or more of the first detection signal and the second detection signal. In this manner, determining the sorting of the particle is based on one or more of the first optical characteristics and the second optical characteristics of the particle. In some embodiments, determining the sorting channel is based on the one or more fluorescence properties of the particle.

At 6408, a sorting signal is transmitted for sorting the particle from the first channel into the sorting channel.

Figure 65:
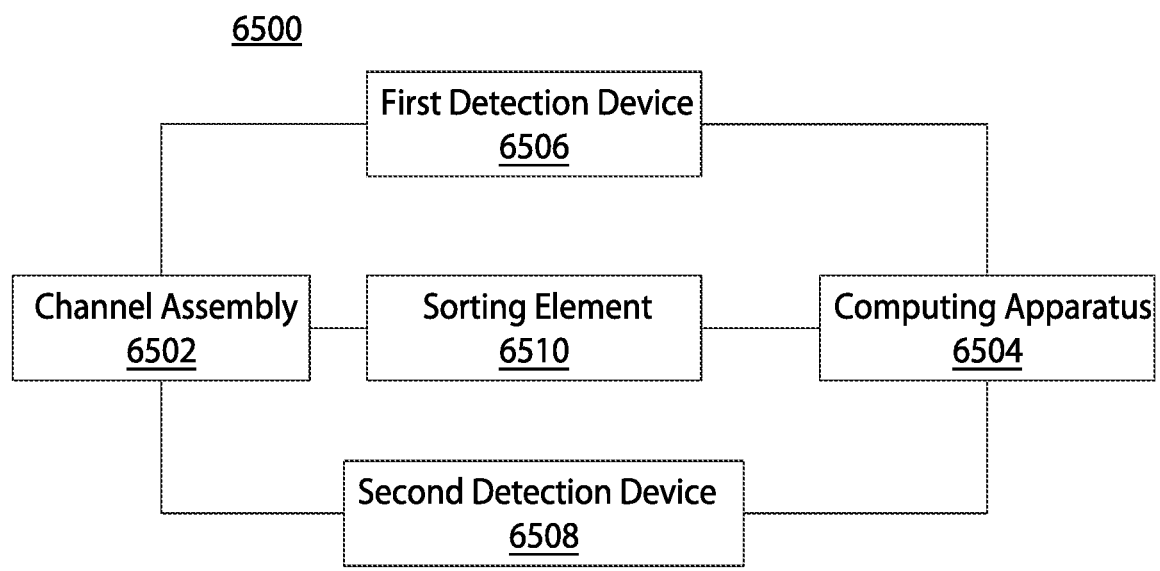
FIG. 65 is a system for sorting of particles, according to an embodiment.

FIG. 65 illustrates a system 6500 for sorting of particles, according to some embodiments. The system 6500 includes a channel assembly 6502, a computing apparatus 6504, a first detection device 6506, a second detection device 6508, and a sorting element 6510. The various components of the system 6500 can be in electrical, optical, wired, and/or wireless communication as indicated by lines in FIG. 65 as appropriate. The computing apparatus 6504 can include a personal computer, a server, a work station, a tablet, a mobile device, a cloud computing environment, an application or a module running on any of these platforms, and/or the like.

The channel assembly 6502 includes at least a source channel and one or more destination channels, as described earlier. Generally, the channel assembly 6502 can be sized to fit onto and/or otherwise interact with an appropriate analysis platform including, but not limited to, a microscope, flow cytometers, biochemical analysis instruments such as PCR, micro-well array-based platforms, and/or the like. Any suitable material can be employed for making the channel assembly 6502, including, but not limited to, silicon, polydimethylsiloxane (PDMS), polycarbonate (PC), poly (methyl methacrylate) (PMMA), cyclic olefin polymer (COP), cyclic olefin co-polymer (COC), and/or the like. In some embodiments, the material of the channel assembly 1602 is biocompatible and/or optically transparent.

The first detection device 6506 is any system suitable for detecting characteristics of the particle and/or the detection volume that can be applied towards cell sorting from the source channel. In some embodiments, the first detection device 6506 is a fluorescence detection system that includes one or more excitation sources, one or more detectors, one or more filter arrays that can include all pass filters and fluorescence filters, and appropriate coupling optics for coupling to the channel assembly 6502.

The second detection device 6508 is any system suitable for detecting characteristics of the particle and/or the detection volume. In some embodiments, the second detection device 6508 is applied towards cell sorting from the source channel. In some embodiments, the second detection device 6508 is applied towards verification of cell sorting in a destination channel. In some embodiments, the second detection device 6506 is an impedance detection system that includes one or more electrodes, and appropriate connecting elements for interfacing the channel assembly 6502.

The sorting element 6510 is any system suitable for affecting lateral displacement of a particle in a source channel to enable and/or otherwise increase the probability of sorting the particle into one of several destination channels. In some embodiments, the sorting element 6510 is a piezoelectric actuator.

Figure 66:
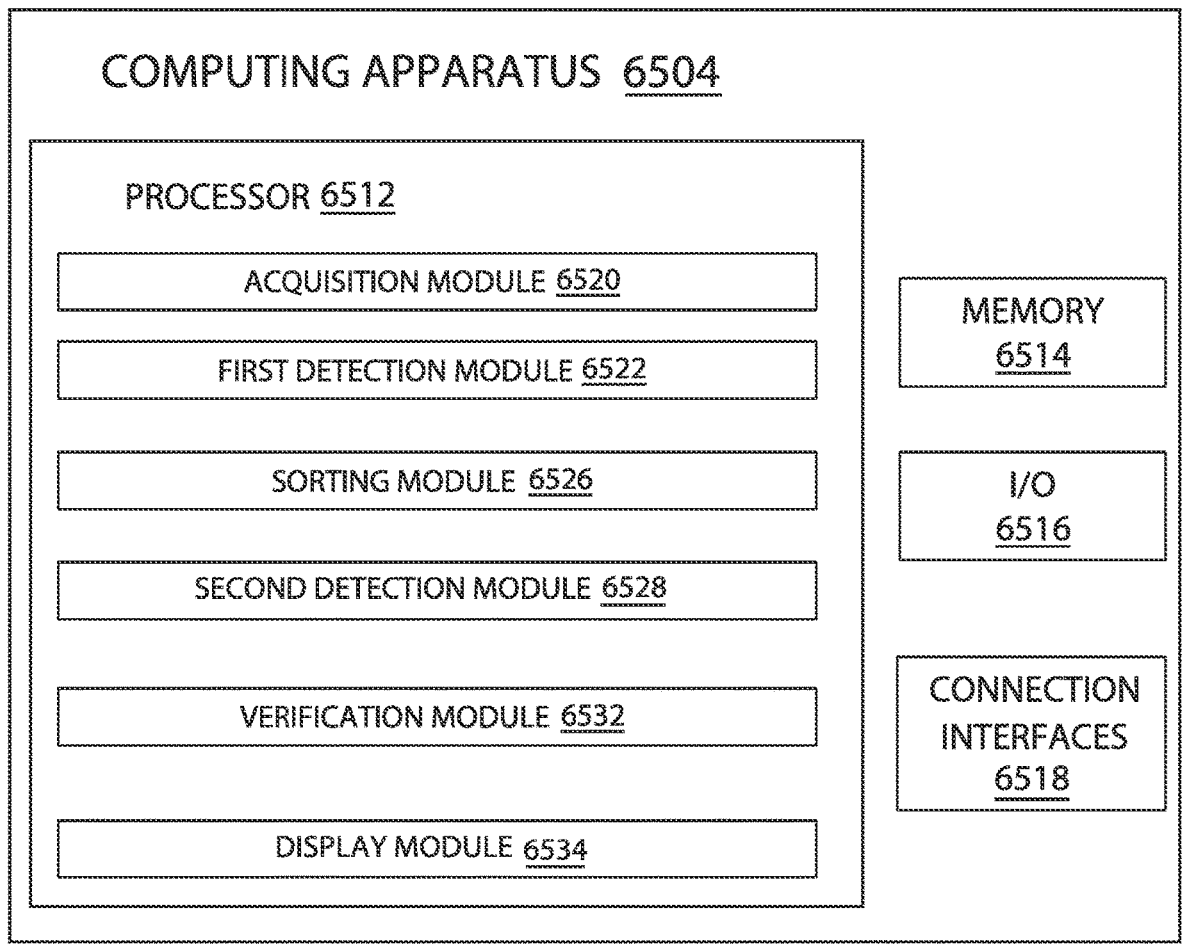
FIG. 66 is an illustration of the computing apparatus of FIG. 65, according to an embodiment.

FIG. 66 illustrates the computing apparatus 6504 according to some embodiments. The computing apparatus 6504 includes at least a processor 6512 and a memory 6514, and further includes I/O interfaces 6516 and connection interfaces 6518. The processor 6504 includes an acquisition module 6520, a first detection module 6522, a sorting module 6526, a second detection module 6528, and a verification module 6532. The processor 6504 also includes a display module 6534 to communicate with and/or control a display device (not shown) associated with the apparatus 6504.

In some embodiments, the apparatus 6504 is configured for sorting of particles as generally described by the method 5700. In some embodiments, the apparatus 1604 is configured for feedback-based counting of particles, as generally described by the method 6100. In some embodiments, the apparatus 6504 can be configured for sorting of particles, as generally described by the method 6400.

In some embodiments, the acquisition module is configured to acquire a plurality of optical signals associated with the first detection signal, the acquisition module further configured to acquire an electrical signal associated with the second detection signal.

In some embodiments, the first detection module 6522 is configured to receive a first detection signal from the first detection device 6506 associated with one or more optical characteristics of a particle in a first channel of the channel assembly 6502.

In some embodiments, the sorting module 6526 is configured to determine a sorting channel of a plurality of second channels based on the first detection signal, thereby determining the sorting of the particle based on the one or more optical characteristics of the particle. The sorting module 6526 can be further configured to transmit a sorting signal to the sorting element 6510 for sorting the particle from the first channel into the sorting channel. In some embodiments, the sorting module 6526 is further configured to determine the sorting channel based on the one or more fluorescence properties of the particle.

In some embodiments, the second detection module 6528 is configured to receive a second detection signal from the second detection device 6508, the second detection signal associated with the presence and/or volume of a detected particle in the sorting channel.

In some embodiments, the verification module 6532 is configured to verify the sorting of the particle from the first channel into the sorting channel based on the second detection signal.

In some embodiments, the first detection module 6522 is further configured to receive an additional first detection signal from the first detection device 6506. The additional first detection signal, in one embodiment, is associated with optical characteristics of a second particle in the first channel, where the optical characteristics of the second particle are different from the optical characteristics of the first particle.

In some embodiments, the sorting module 6526 is further configured to determine a second sorting channel of the plurality of second channels based on the additional first detection signal. The second sorting channel can be different from the sorting channel, thereby determining the sorting of the second particle into the second sorting channel based on the optical characteristics of the second particle. In some embodiments, the sorting module 6526 can be further configured to transmit a second sorting signal for sorting the second particle from the first channel into the sorting channel.

In some embodiments, the second detection module 6528 can be further configured to receive an additional second detection signal from the second detection device 6510, the additional second detection signal associated with the presence and/or volume of a second detected particle in the second sorting channel.

In some embodiments, the verification module 6532 is further configured to verify the sorting of the particle from the first channel into the sorting channel based on the second detection signal and based on the additional second detection signal. In some embodiments, the verification module 6532 is further configured to verify the sorting of the second particle from the first channel into the second sorting channel based on the second detection signal and based on the additional second detection signal.

In some embodiments, a feedback module 6530 is configured to train the sorting module 1626 for sorting additional particles in the first channel into one of the destination channels based on the second detection signal.

In embodiments of the system, apparatus, and methods disclosed herein, patterned slits can be used to (1) code signals from the upstream detection zone, and (2) to temporally encode the signals so the signal-to-noise ratio can be enhanced by digital signal processing. Since the waveform of the signal can be predetermined by the slit patterns placed in front of the photodetector (ex. PMT), digital matched filters can be applied to amplify the signal and suppress the noise. The signal processing algorithm can be implemented with finite-impulse-response (FIR) filters in real time.

In some embodiments, electrodes formed on the bottom substrate across the downstream sorting channels from the sorting junction are designed to produce electrical signals detecting impedance change at the region when a cell, bead, or particle passes by, thus confirming/verifying a successful sorting event. After each cell is deflected to one of the sorting channels, the 'verification' signal should be also detected to confirm the success of the sorting event.

Benefits to the users include: a user can monitor the sorting operation and receive feedback in real time; if no verification signal is observed, the user is required to stop the experiment and tune the sorting parameters such as PZT triggering timing, voltage and/or alignments etc. to make it right until he/she can see the pair of fluorescence-impedance signals; registering fluorescence-impedance signal pairs can be representative of 'sorting accuracy' and 'sorting purity' data in real time. Therefore, the user can know the concentration of the sorted sample, its purity (e.g. how many sample cells and how many non-wanted cells are in the sorted sample) without running the sorted sample through flow cytometer, which, in many cases, lead to cell loss.

Some embodiments are directed to a Lab-On-A-Chip technology that combine optics, acoustics and/or microfluidics on an injection-molded disposable particle sorter. Injection molded chips can be manufactured that can be replaced if it is damaged or fouled. Furthermore, because the chip and fluid path can be made disposable, it is well suited to clinical settings where cross-contamination and sterility must be addressed.

Some embodiments are directed to an on-chip piezoelectric diaphragm to actuate sorting. The rapid and specific deflection of the piezoelectric diaphragm can be exploited by using a defined voltage waveform to drive a small volume of fluid (e.g., 100 pL to 1 nL, or 1 nL to 1 µL) containing a cell or particle towards a specific sorting channel. The piczo diaphragm can be mass-produced and bonded directly to the injection-molded chip. The piezo design can move the fluid with the cell resulting in a very low relative acceleration and shear force between the cell and the fluid (0.1 Pascal).

The following Examples illustrate but do not limit the technology described herein.

Example 1: First-Stage CTC Enrichment Using a Hydrodynamic Microfluidic Device

Figure 2:
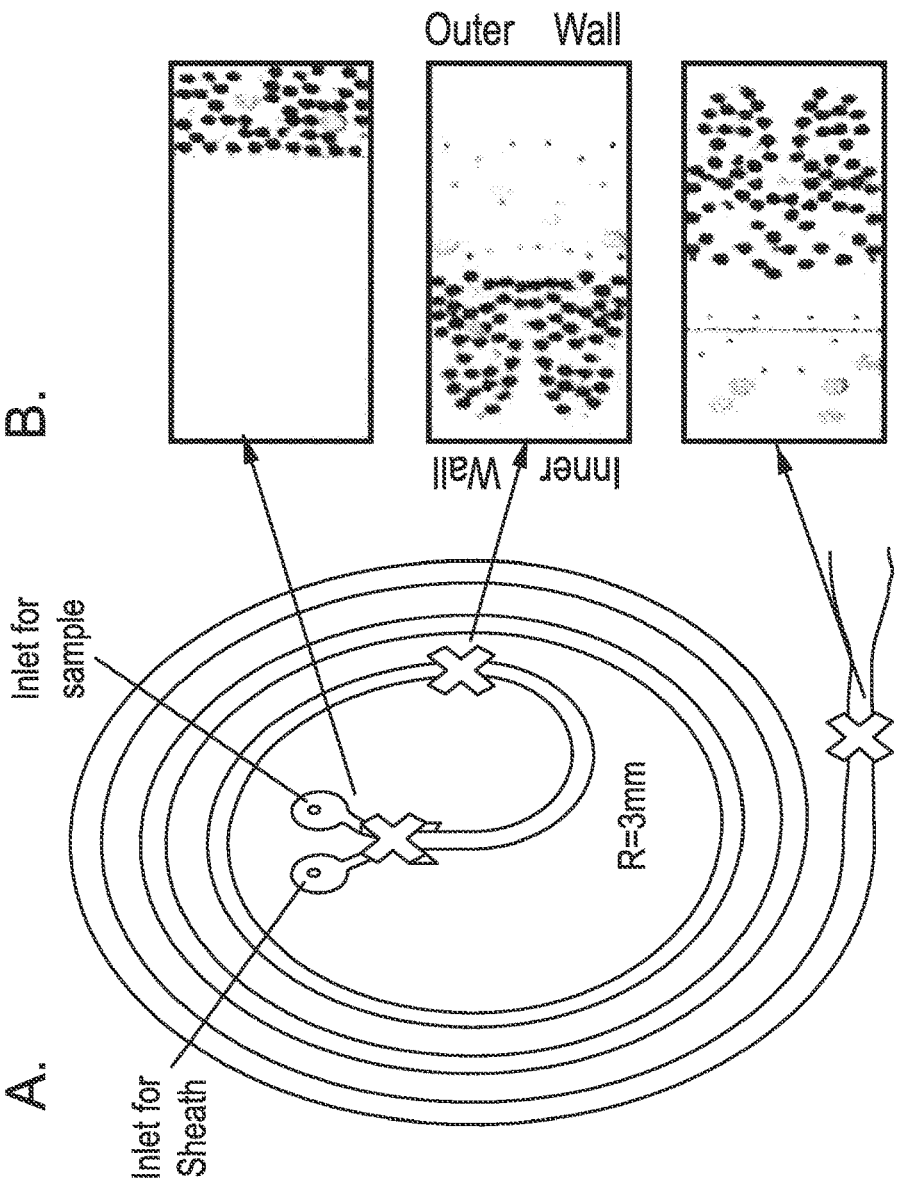
FIG. 2A is a schematic diagram of a spiral enrichment structure, according to an embodiment.
FIG. 2B is a cross-section view of the microfluidic channels of the spiral enrichment structure of FIG. 2A at the beginning (mixed sample), middle section, and final section (separated sample), according to an embodiment.
FIG. 2C lists equations used to calculate Dean force, according to an embodiment.

Hydrodynamic properties can be utilized to obtain 100-fold or better enrichment of CTCs prior to sorting using micro-FACS (see Example 3). In an effort to achieve >100-fold enrichment, several spiral channel devices were designed. Several spiral enrichment structures were designed for the first stage enrichment of CTCs. The spiral device structures take advantage of the physical properties of cells under laminar flow conditions where inertial lift forces and Dean forces allow for the focusing and separation of cells. The balance between inertial lift forces and Dean forces allows for equilibrium position for any kind of sample based on size. This approach resulted in the effective separation of target large cells from a mixture of smaller cells. The general structure and concept is illustrated in FIGS. 2A-2C, with approximate dimensions. In a first step a mixture of different sized cells (e.g., CTCs in blood) and introduce into an inlet channel (center of spiral, FIG. 2A) with buffer solution introduced through the other inlet. After passing through the spiral structure, larger cells are separated from smaller cells due to inertial effect.

A microfluidic device was designed and fabricated using AutoCAD software and was sent for photolithographic mask printing at high resolution (20,000 dpi). Using SU-8 a mold was built. The width of the channel was 250 µn and the height of the channel was 50 µm. At the end of the spiral structure, the main channel can be split into sub channels to collect different cells based on their size (see FIGS. 3A-3C). Multiple varieties of the spiral enrichment structure were designed to improve enrichment, capture efficiency, and manufacturability. Devices with 2 to 10 outflow channels were designed and were used to separate efficiently but provided some difficulty during manufacturing using polydimethylsiloxane (PDMS). A two-channel design was readily manufactured and provided suitable results (shown in FIG. 3C with pink dye to visualize the channels).

Evaluation and Testing

The separation properties of a spiral microfluidic device were evaluated using latex microbeads of different sizes (e.g., 7.6 µm, 10.5 µm, 25.3 µm in diameter) and an exact separation position for each bead size was determined at the end of the collection outlets. To verify the performance (e.g., enrichment) of the device, the initial mixture ratio and the final mixture ratio of the microbeads were measured before and after each run using BD-Accuri C6 at UCSD. The effect of various flow rates during this process at 400 µl/min, 1 ml/min, and 1.5 ml/min was also tested. Beads of 25.3 m in size (similar to most CTCs in size) were separated well from 7.6 µm and 10.5 µm beads through outlet channel 1 and 2 and had the best performance using a 1.5 mL/min flow rate (see FIGS. 4A-4C). The population of 25.3 m beads was enriched by 600 times at this flow condition. Even though the test was performed with microbeads, this enrichment factor clearly validated the design and approach.

Further Modifications and Testing with Spiked CTCs

Figure 5:
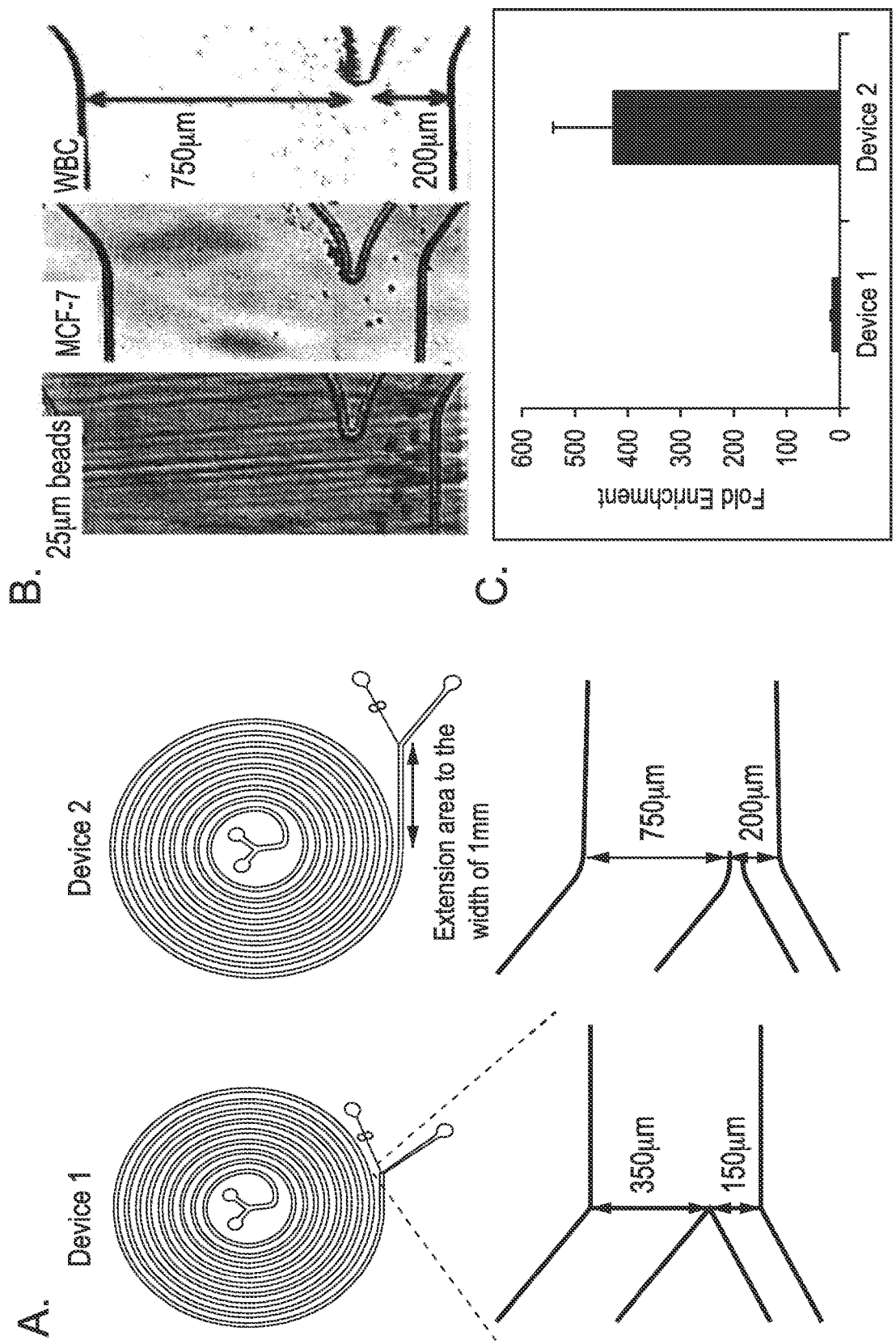
FIG. 5A illustrates two embodiments of an enrichment structure, Device 1 and Device 2, with different outlet structures, according to embodiments.
FIG. 5B shows images of an enrichment structure with 25 µm beads (left panel), MCF-7 cells (middle panel), and white blood cells (left panel) passing through the an enrichment structure outlet.
FIG. 5C is a plot of a comparison of fold enrichment from Device 1 and Device 2 of FIG. 22A using 6 milliliters of blood spiked with about 950 MCF-7 cells (n=6).

After initial evaluations using beads, the microfluidic device was tested using various cancer cell lines (e.g., HeLa, MCF-7, and U2OS cells) and in some cases over 100× enrichment from red blood cell lysed whole blood was observed. In some cases, designs were modified due to manufacturing challenges. One original device had 10 collection channels that were 75 µm wide and 185 µm high. Each outlet channel was separated by only 30 µm, and due to its high aspect ratio (>6) there were challenges in fabricating the device mold using highly viscous SU-8 photoresist. Re-designed devices were tested with 5 and 2 outlets. In some cases designs with fewer outlets than FIG. 3A improved the SU-8 mold fabrication process (see FIG. 5A. Device 1 and Device 2). Re-designed 2-outlet devices were able to clearly separate 25 µm beads, HeLa, and MCF-7 cells into one channel and most white blood cells were exiting through the larger channel (FIG. 5B). Further modifications were made to the two-outlet design to improve purification by changing the size of the channels, making the "Y" junction smoother, and creating an extension area at the end. These modifications resulted in excellent enrichment properties for cancer cells with an average of 429.5-fold enrichment compared to the starting amount.

Figure 6:
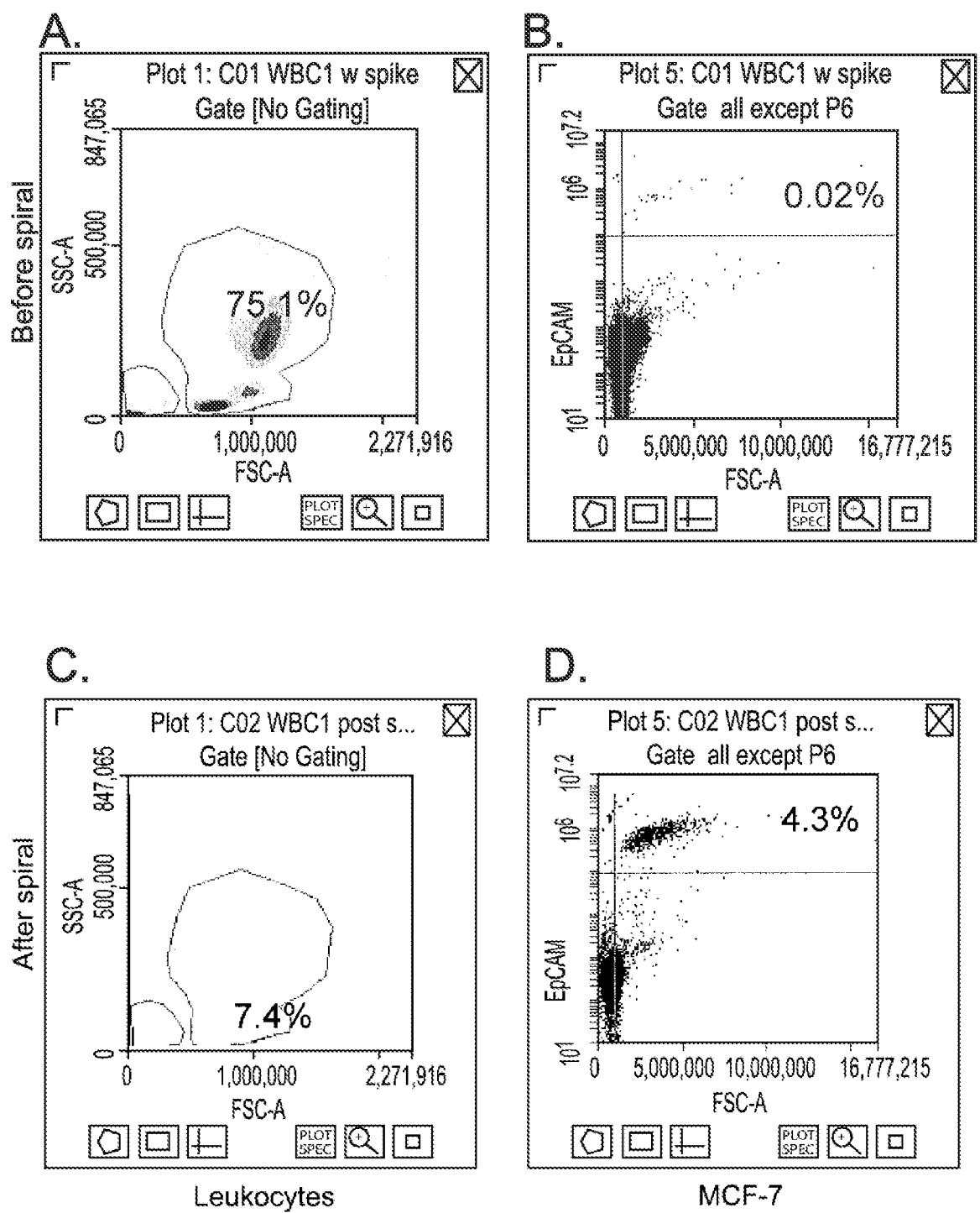
FIGS. 6A-6D illustrate removal of white blood cells (WBCs) and retention of circulating tumor cells (CTCs) by a spiral enrichment structure. 19M white blood cells spiked with ~950 MCF7 cells were assayed before and after a run through the spiral enrichment structure. Robust loss of WBCs and retention of MCF7 cells labeled with EpCAM-PE antibody is observed (FIGS. 6B, 6D). Following the run, 21,584 WBCs remained (removal of 99.8%), and 760 MCF7 cells remained (retention of 80%). Histograms from representative experiment, n=6.

In one representative experiment, six milliliters of blood containing about 19 million white blood cells was spiked with ~1,000 MCF-7 cells labeled with anti-EpCAM-PE antibody. After lysing the red blood cells using RBC lysis buffer, the remaining cells were resuspended in PBS and passed through a spiral enrichment structure. Following the run, about 21,584 white blood cells remained representing removal of about 99.8% of white blood cells (FIG. 6). Following the run about 760 MCF-7 cells remained representing retention of about 80% (FIG. 6). This process removed 99.8% of the white blood cells while retaining 70-100% of the spiked MCF-7 cancer cells in six separate experiments. Some variability in the recovery can be due to the high variability of counting cells at the beginning and end of each experiment.

Example 2: Fluidic-Dynamic Assisted Antibody Binding to CTCs

A design was tested in which antibodies were added to cancer cells and the mixture was injected through a mixing structure to enable fast and efficient cell labeling. Several commercially available antibodies were tested against EpCAM (an epithelial marker for CTCs). The results indicate that samples can potentially be labeled via a mixing structure disposable chip in 1-2 minutes (compared to 20-60 min.). This approach is possible in an OncoSorter system due to the disposable nature of the chip used for a microfluidic detector system. Initial testing showed excellent labeling efficiency. In some embodiments a microfluidic detector system is automated and is suitable for clinical settings where highly trained scientists in cell handling and flow cytometry are not available.

Figure 7:
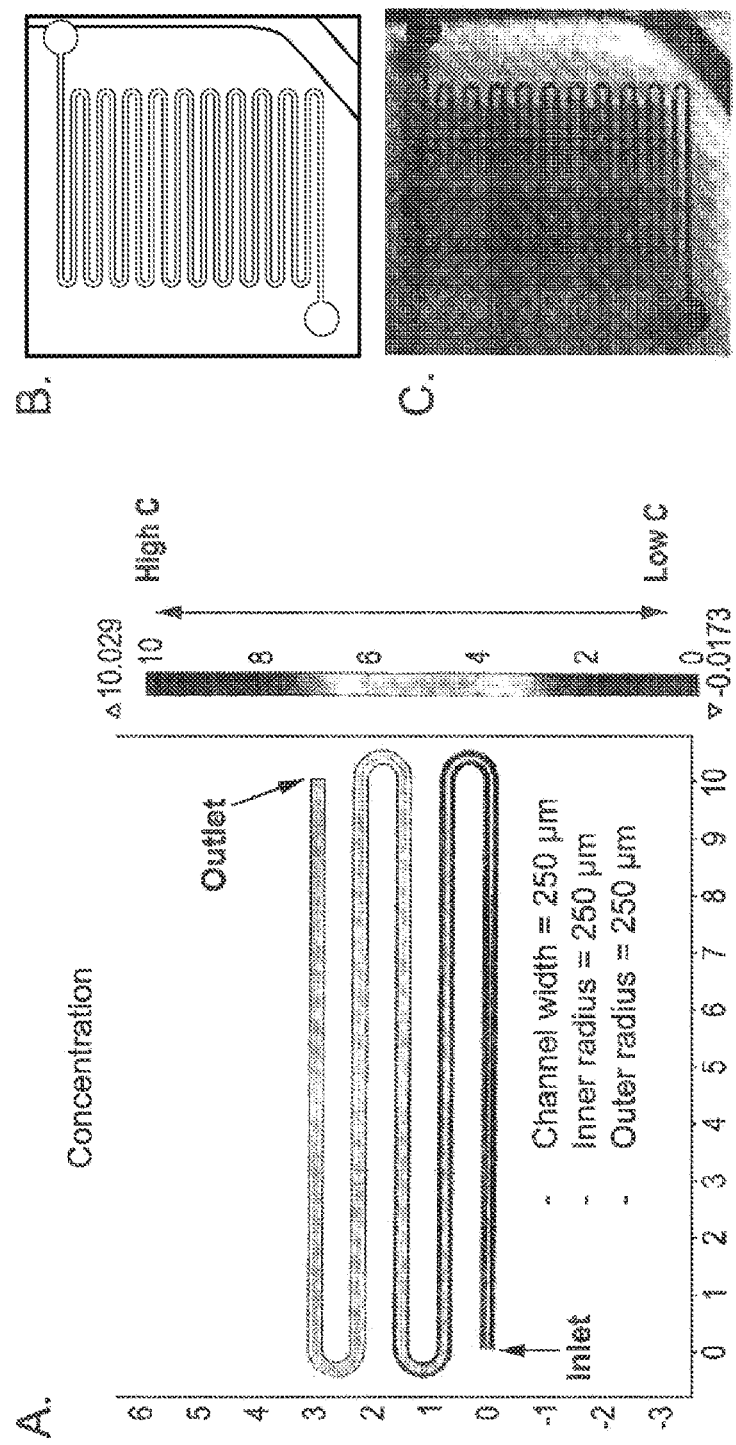
FIG. 7A shows a fluidic dynamic simulation with a serpentine mixing structure with 4 turns along with channel dimensions, and also illustrating a concentration gradient (from "High C" to a "Low C"), according to an embodiment. Two solutions with high concentration ("High C") and low concentration ("Low C") are injected. Inside the serpentine structure, the two solutions are mixed efficiently and at the outlet, wa mixed solution with 'medium' concentration is observed, indicating increased mixing.
FIG. 7B illustrates a serpentine microfluidic mixing structure with 20 turns, according to an embodiment.
FIG. 7C shows a manufactured prototype of the serpentine microfluidic mixing structure of FIG. 7B using PDMS.

Fluidic dynamic simulation software was used to design and analyze mixing structures to enhance the binding efficiency of antibodies to CTCs on a chip. Automatic mixing on a microfluidic chip using a closed on-chip design can reduce sample handling and provide for efficient antibody labeling of cells. A passive type mixing structure was developed and can be integrated with first and second stage enrichment and/or sorting structures. Several design iterations were produced and analyzed using fluidic dynamic simulation software (COMSOL). One effective design consisted of a "serpentine" mixing structure (FIG. 7). During simulations, complete mixing of two samples was observed after only 4 turns. To ensure sufficient mixing and binding opportunities, a mixing structure chip was designed and fabricated with 20 turns using PDMS (as in Example 1) and (in some embodiments) is used for detector systems described herein.

Evaluation and Testing

One advantage of the CTC label and capture platform described herein is the flexibility to use any fluorescent marker to label CTCs. In this example, EpCAM (a proven and effective marker) was used. For initial testing of antibody-labeling, two commercial antibodies, PerCP-e710 Human CD326 (clone 1B7, eBioscience) and PE-conjugated EpCAM (VU1D9, Cell Signaling Technologies (CST)) were tested. Both antibodies worked well, yet sufficient separation from unlabeled cells was not observed using eBioscience's EpCAM antibody. PE conjugated VU1D9 demonstrated improved separation from unlabeled cells using volume ratios of 1:100 (antibody to cell sample) and near complete separation using a mix ratio of 1:25 (FIG. 8). This antibody was tested on two epithelial derived cancer cell lines, HeLa and MCF-7 and both gave similar results. Excellent labeling was also observed with an MFC-7 cell line that is GFP positive that was used in some spiked experiments. Experimental results showed that GFP positive cancer cells can be gated properly for GFP and GFP/EpCAM positive cells (FIG. 8C-D). In summary, PE conjugated VU1D9 worked very well and was used in all EpCAM labeling experiments using the mixing structure.

Figure 9:
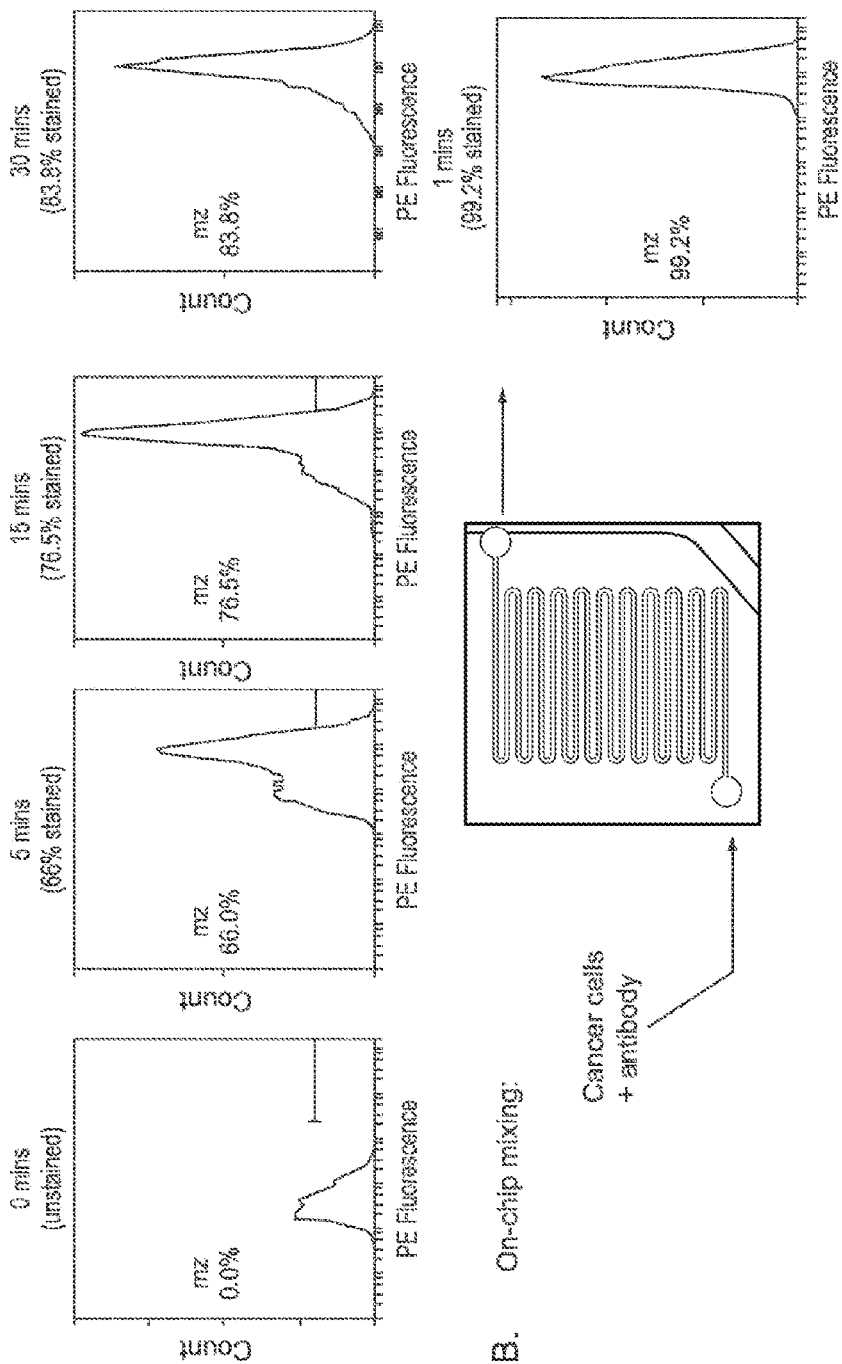
FIGS. 9A, 9B illustrate antibody binding facilitated by an on-chip mixing structure.

To evaluate and compare the mixing and labeling properties of the mixing structure chip, two methods were used; (1) conventional off-chip antibody mixing in an Eppendorf tube and (2) Antibody-labeling using a mixing structure designed herein (FIGS. 9A-9B). Using the micro-mixer, within 1 min, more than 99% of live MCF-7 cells were stained with PE antibodies whereas off-chip labeling took more than 30 minutes to reach 83% labeling of cancer cells. The fluorescence and labeling was also well above some detection limits when analyzed using a detector system. Excess antibody created some background during analysis if not washed. A simple washing step following the mixing structure run can remove non-bound antibodies and lower the background fluorescence noise but creates an extra step. This issue can be addressed with software during analysis to ignore (e.g., gate) very small, yet bright, signals and will be implemented in the next phase of development. A flow rate of 250 µl/min can be used and does not cause any cell death during the antibody mixing within the chip. Therefore, the mixing structure can be used as an intermediate step between the first spiral enrichment device and the microfluidic detector. An integrated sample preparation system will make the whole process easier and reduce sample inconsistency or contamination.

Example 3: Benchtop Microfluidic Detector for CTC Isolation

A microfluidic detector was developed to complete enumeration and isolation the CTCs. In some cases, an in-house designed microfluidic fluorescence-activated cell sorter (microfluidic detector) was modified for CTC isolation and analysis. One design modification of an alpha prototype maximized collection efficiency to assure nearly all CTCs are sorted. An AutoCAD design was generated and used to fabricate a microfluidic detector using PDMS in Nano3 and the Lo lab in UCSD (FIGS. 10A-B). The main channel was designed at a 200 µm width and split into three 50 µm sample collection channels with a height of 80 µm. A chip holder was also designed that allows chip exchange after each use or if there is a clog (FIG. 10C). The holder guarantees precise alignment of the microfluidic channel to the optical axis by using alignment markers already implemented into the device, thus eliminating any potential fluctuation of detection signals for different devices. The position of the holder (i.e., the position of the detection area) can be easily and precisely controlled by the optical xyz-stage (FIG. 10C, left). The device has three inlets and outlets that use Teflon tubing. One sample and two sheath flow inlets are located at the top and the three tubes located at the bottom are sample/waste collection channels. In some cases, the PZT actuator disc was permanently bonded to each microfluidic detector. In some cases, the PZT actuator disc was permanently bonded to an LOC.

A previous alpha prototype detector system used on-chip optical waveguides and a unique design of space-time coding architecture for fluorescence and scattering detection. Following the optical interrogation, the device used an integrated piezoelectric disk actuator to sort single cells by displacing a finite volume (100 picoliter to 1 nanoliter) of fluid. It also incorporated on-chip laser illumination using Teflon AF-coated optofluidic waveguide. This detection design and approach has some limitations for commercialization such as expense, a complicated fabrication process and the introduction of scattering light noise due to the quality of Teflon-AF layer coated on PDMS wall. A modified prototype in this objective was designed to have the laser excitation external to the chip, thus avoiding those critical problems. A 488 nm laser was focused by off-chip optical components that illuminates the detection area of the microfluidic channel with a diameter of 400 µm (this can be adjusted), thus simplifying the fabrication process. The optics components have been assembled on a compact breadboard. The fiber-coupled 488 laser (25 mW) is focused by off-chip optical components including a 50× long working distance microscope objective lens that illuminates the detection area with a diameter of about 400 µm. An initial electronics control system was completed and interfaced with the PMT (Detection) and the PZT (Sorting). An improved algorithm for estimating the bead's travel speed can continue to provide higher performance with sorting speeds and accuracy.

Evaluation and Testing

Detection systems using only one PMT (detector) to detect and analyze three or more fluorescent markers employ a unique Color-Space-Time (COST) algorithm. For improved detection, a new filter array was designed and tested that is placed at the image plane so that a pulse signal out of the PMT can be modulated with specific frequency, allowing further sophisticated digital signal processing such as velocity estimation, signal-to-noise ratio enhancement by applying a FIR match filter algorithm. Using this configuration, the detection system was sensitive enough to detect the fifth peak from rainbow calibration beads. This sensitivity range is more than sufficient to detect GFP-positive cells and MCF-7 cells labeled with EpCAM antibody (see FIG. 12A). The electronics system registers output signals from the PMT and sends out a sawtooth output waveform in order to trigger the PZT actuator mounted on a microfluidic detector. Output voltage for sorting is 100 V and the ramping up time is 1 millisecond, but this can be shorter in order to achieve higher sorting throughput in the future. FIG. 12B below shows images illustrating how sorting events occur in response to the pressure pulse applied by the PZT actuator. The sample flow (containing rhodamine dye for visualization) is deflected to the left channel by the pressure applied by the PZT and comes back to the original position when the PZT is turned off. An algorithm for the discrimination of multiple colors (e.g., COST) and the speed estimation of beads or cells is then used to capture only CTCs from a mixed sample. Electronics can be upgraded to use a faster real-time control electronics system. The electronics control system can be optimized in order to achieve higher sorting efficiency and sample purity.

The sorting capabilities of a microfluidic detector were tested and validated by sorting microbeads and GFP positive MCF7. Each detected sample that was positive for a microbead or CTC triggers a sorting event. To verify sorting, a downstream sorting verification system was used. First, an MCF7 cell is detected and generates a three-lobe peak signal (111-modulated). The FPGA based control system then calculates a delay time and triggers the on-chip piezoelectric actuator (PZT disc) by applying 10 (V) for 1 msec. The MCF7 cell is deflected to one of the downstream sorting channels and another spatially coded signal (1011-modulated) verifies a successful sorting event in real time. The table below shows that microfluidic detector prototype analyzed here can achieve about 70% sorting purity (i.e., recovery rate) when sorting beads or spiked cancer cells. In these experiments, a known number of microbeads or MCF-7 cells were introduced and the microfluidic detector was used for detection and sorting. On average, nearly 68% of about 109 CTCs were recovered after sorting (Table 1).

TABLE 1

Sorter testing and validation:

| | Number Detected (Avg) | Number Sorted (Avg) | Recovery Rate |
|---|---|---|---|
| FITC microbeads | 223 | 173.5 | 77.80% (+/−2.5 SD) |
| MCF-7 Cells | 109.5 | 74 | 67.58% (+/−6.72 SD) |

Cell viability differentiates systems described herein compared to current CTC detection systems that rely on fixing cells and are unfit for further downstream applications.

Cell viability was verified at two major steps in a microfluidic detector using propidium iodide (PI) or trypan blue. In the pre-enrichment spiral enrichment structure, the viability of mock MCF-7 cells (untreated, i.e., no spiral) and cells that were processed through a spiral enrichment structure were compared. No significant cell death of processed cells compared to mock cells was detected (see FIG. 13). In a final sorting stage, MCF-7 cells collected after sorting were visualized by microscopy and appeared to be in good shape. Sensitive cardiomyocyte cells were used to compare a current state of the art FACS systems (BD Aria II) to the microfluidic detector described herein. The commercial Aria II system resulted in 71% cell viability whereas the microfluidic detector demonstrated 98% cell viability. The increased cell viability of the microfluidic detector can be attributed, in part, to less shear stress in the microfluidic system.

In a final experiment, all three stages of the system were integrated to determine how well the integrated system can detect and collect cells: from pre-enrichment, to labeling and finally detection/collection with the microfluidic detector. MCF7 spiked cells were introduced into 7.5 mls of blood at a high range (2,000 live cells) and a low range (~10 live cells). Three full experiments were conducted for each range and the final collected cells were validated using a commercial flow cytometer (BD Accuri C6). Preliminary results showed impressive detection, collection efficiency and consistency at both low and high range of mock CTCs (Table 2). On average, 566 CTCs (or 28%) for the high range and 3.3 cells (or 31.2%) of the low range were collected. The collected samples were validated with a commercial flow cytometer (BD Accuri C6) and the same number of cells was detected. Selection and collection efficiency can be improved when each step is integrated into a single system with a start-to-finish fluidics and pump system, with an improved digital signal processing algorithm, and when forward and side scatter are included.

TABLE 2

Final testing of integrated system with 2000 and 10 live spiked "CTCs" in 7.5 ml of blood:

| Cells Spiked | Total collected Average | Std Dev | Total collected % | Std Dev |
|---|---|---|---|---|
| 2000 | 566.00 (477-615) | 77.21 | 28.30% | 3.86% |
| 10.67 (8-16) | 3.33 (3-4) | 0.58 | 31.25% | 5.41% |

SUMMARY

CTCs found in peripheral blood provide an opportunity for a less invasive "liquid biopsy" to determine the malignancy of a primary tumor and the presence of cells that can form metastases. Systems tested here demonstrated the ability to pre-enrich initial CTC populations by well over 100 fold (average of 429 fold enrichment), rapidly label CTCs with EpCAM antibodies using a microfluidic mixer, and finally sorting close to 70% of all cells detected. System described here can improve detection and also downstream molecular analysis and sequencing of single cancer cells, as well as personalized diagnosis and treatment. Also, systems described here can implement two dimensional flow confinement, improved electronics and detection speeds all embedded on disposable and manufacturable chips (e.g., thermal plastic chips).

Example 3: On-Chip Reagent Miring

An unmet need in flow cytometry is sample preparation and labeling prior to loading onto a flow cytometer for analysis and sorting. Typically, cells must be labeled by manually pipetting individual labeled antibodies (or dyes) into the cell samples. This procedure can result in large variations in data due to, for example, differences in antibody handling, pipetting inaccuracies, storage inconsistencies, variability in antibody lots, and/or the like. This is particularly a problem for clinical and point of care applications where less experienced technicians must perform the assay.

Having on chip reagents pre-loaded on the chip can make the process "turn-key" without having to worry about what antibody, how much antibody, or pipetting errors. The reagent can be pre-loaded and mixed with the sample prior analysis or after analysis depending on the assay or application.

Figure 67:
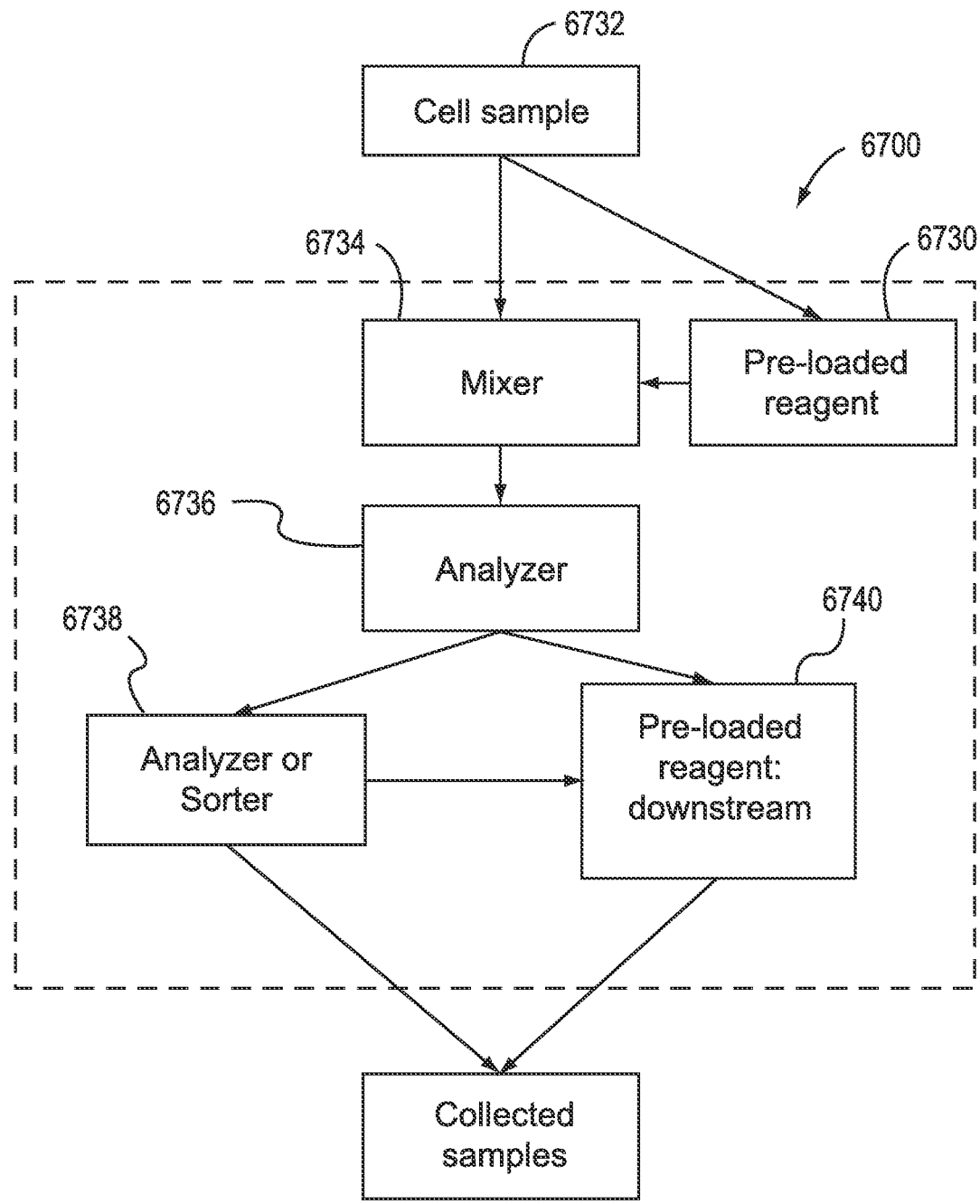
FIG. 67 is an illustration of a particle sorter including provisions for on-chip reagents, according to an embodiment.

Accordingly, in some embodiments described herein, a system/device of the disclosure (e.g., a particle sorter) can include one or more regions formed thereon for enabling storage and mixing of reagents with the particles under analysis. FIG. 67 illustrates a block diagram of a particle sorter 6700, according to some embodiments. The particle sorter includes a region 6730 for pre-loading one or more reagents. A mixer/mixing region 6734 is also formed that permits mixing of the pre-loaded reagents with a cell sample received at a cell sample port 6732 (e.g., similar to the port 5002). The one or more pre-loaded reagents can be any suitable for cell analysis and can include, but are not limited to, immuno-labeling antibodies, DNA/RNA labels (e.g., Propidium Iodide), cell state markers (e.g., for apoptosis, DNA cycle(s), and/or the like), nanoparticles (magnetic, fluorescent etc.), and/or the like. The particle-reagent mixture can be analyzed and/or sorted as also illustrated in FIG. 67, via the analyzer 6736 and/or the analyzer/sorter 6738. In some embodiments, and as also shown in FIG. 67, analyzed and/or sorted particles can be further treated with an additional pre-loaded reagent also formed on the particle sorter at a region 6740. The additional reagent can be any suitable for cell analysis and can include, but are not limited to, cell lysis buffer for downstream molecular analysis (e.g., for DNA/RNA/protein analysis), sample fixing (ex: para-formaldehyde) solution for cell preservation, immuno-labeling antibodies for downstream applications like imaging, growth media (growth factors, cytokines, amino acids, and/or the like), and/or the like.

Having on chip reagents pre-loaded on the chip makes the process "turn-key" without having to worry about, for example, what antibody, how much antibody, pipetting errors, and/or the like. The reagent can be pre-loaded and mixed with the sample prior analysis or after analysis depending on the assay or application.

Figure 68:
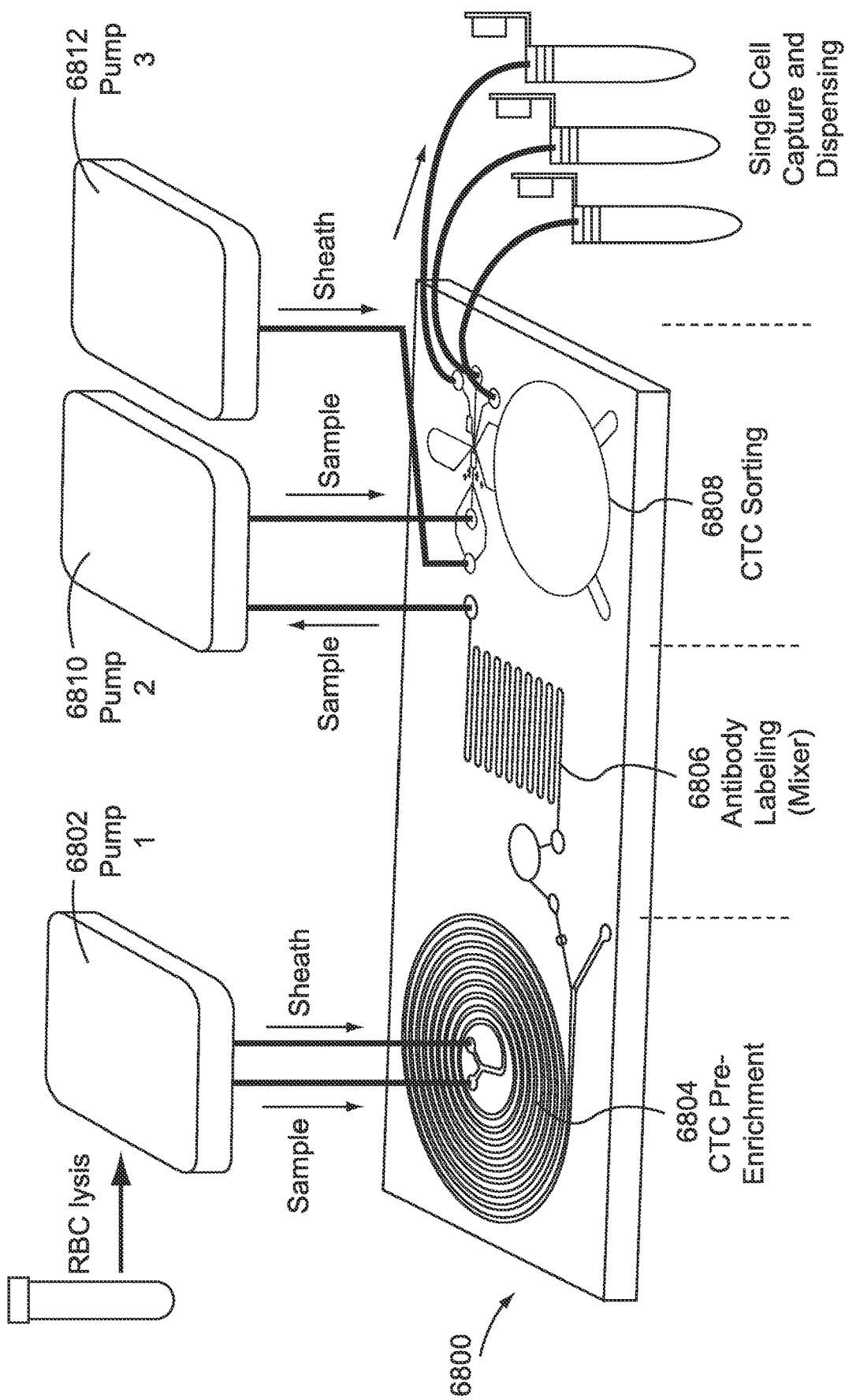
FIG. 68 is an illustration of an exemplary particle sorter including provisions for on-chip reagents, according to an embodiment.

FIG. 68 illustrates an exemplary particle sorting system employing an on-chip mixer to perform cell labeling and isolation of cells from blood (e.g., circulating tumor cells), starting with several milliliters (e.g., 6 mL) of blood (e.g., patient blood sample, and/or CTC spiked blood control sample). After lysis of red blood cells, the sample, consisting of a mixture of CTCs and WBCs, can be loaded to syringe pump 6802 in the integrated microfluidic chip 6800 as shown in FIG. 68. The sample goes through a pre-enrichment microfluidic system 6804, the antibody mixing chamber 6806, and the on-chip cell sorter 6808, in series. During operation, when pump 6802 injects the sample to the spiral device (or any suitable enrichment design) to separate CTCs from WBCs, the CTCs from the outlet of the enrichment device enter the chamber on the chip preloaded with antibodies before travelling through the serpentine path of the mixer. Flow balance can be achieved by coordinating the injection rate of pump 6802 and withdraw rate of pump 6810. After the CTC-antibody binding, pump 6802 can be stopped and pump 6810 can inject the sample into the microFACS section, while pump 6812 provides the sheath flow. In this stage every antibody labeled CTC can be detected fluorescently and sorted.

Example 4: Color Compensation for the Color-Space-Time (Cost) Cytometer System

Color Compensation for the Color-Space-Time (Cost) Cytometer System

Color compensation is desirable for flow cytometer systems to achieve accurate detection and representation of objects that are fluorescently labeled by two or more types of fluorophores. It is also one of the most challenging tasks that require significant user experience and knowledge about the nature of the sample in order to perform color compensation correctly. In a simple example of color compensation involving two fluorescent colors, one can represent the detected signals from two PMTs after their respective color filters $$S_1 = T_{11}I_1 + T_{12}I_2 \tag{2-a}$$

$$S_2 = T_{21}I_1 + T_{22}I_2 \tag{2-b}$$

where $S_1$ and $S_2$ are the measured signals from PMT1 and PMT2. $I_1$ and $I_2$ are the true intensities we like to detect from fluorophore 1 and fluorophore 2. The elements for the 2×2 T-matrix represent the transmission of light emitted from each fluorophore to two PMTs behind the color filters (or dichroic mirrors). In the ideal case that the emission spectra of two fluorophores do not overlap, the off-diagonal elements $T_{12}$ and $T_{21}$ should both be zero. However, due to the relatively broad emission spectrum of the fluorophores, a substantial amount of light from one fluorophore can reach the PMT in the neighboring spectrum, yielding non-zero values for $T_{12}$ and $T_{21}$.

Color compensation is the process of finding the true intensities I's from the measured signals S's in Eq. (1). Solving eq. (2), we obtain $$I_1 = \frac{T_{22}}{D}\left(S_1 - \frac{T_{12}}{T_{22}}S_2\right) \tag{3-a}$$

$$I_2 = \frac{T_{11}}{D}\left(S_2 - \frac{T_{21}}{T_{11}}S_1\right) \tag{3-b}$$

Where D is the determinant of the T-matrix and is equal to $T_{11}T_{22} - T_{12}T_{21}$. In reality, due to the noise corruption, it can be difficult to recover the true signals from Equation (3). This is especially true when one signal has a significantly greater magnitude than the other, which can yield large errors in the final color-compensated results.

Figure 69:
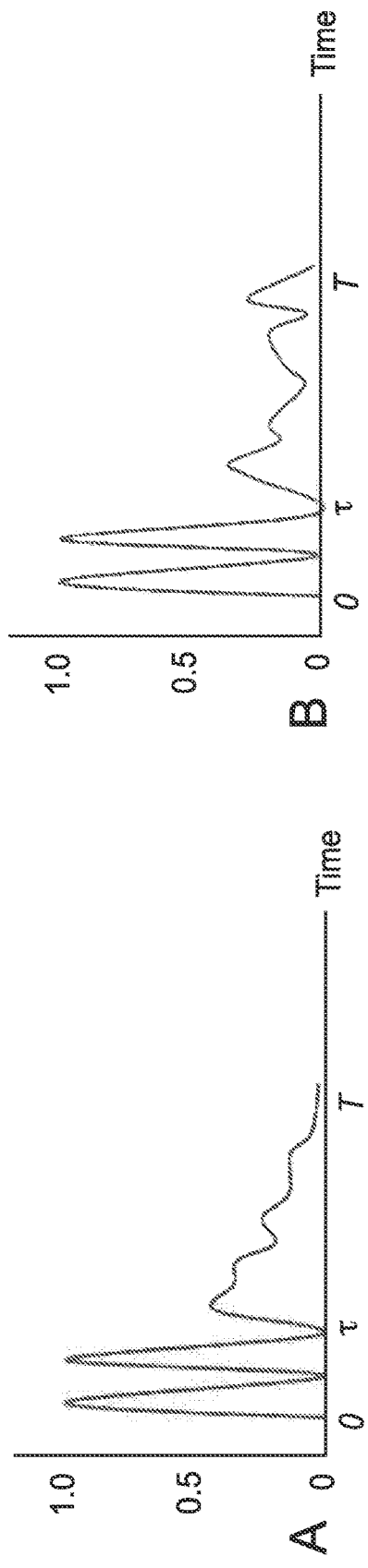
FIGS. 69A-69C is an illustration of color compensated results from a Color-Space-Time encoded system.

The COST algorithm deals with the color compensation problem in a fundamentally different manner than conventional flow cytometers. We make use of the signal waveform produced by each fluorophore to perform color compensation. FIG. 69A-69C shows the waveforms as signatures of two different fluorophores from a color filter designed according to the principle of COST algorithm. The first 2 peaks (see FIGS. 69A-69B) in the signal result from the transmission through the all-pass (white) windows in the COST filter, giving information about the total light intensity, and the remaining features following these two peaks correspond to the light transmission through the COST filter.

The measured signal from a single PMT, S(t), can be represented by $$S(t) = I_1 f_1(t) + I_2 f_2(t) \tag{4}$$

where $I_1$ and $I_2$ are the intensities of light emitted by fluorophore 1 and fluorophore 2, being the values we try to find out after the color compensation process. $f_1(t)$ and $f_2(t)$ are the normalized "signature waveforms" of each fluorophore, as illustrated in FIGS. 69A-69B. $f_1(t)$ and $f_2(t)$ are "normalized" in the sense that the height of the first two peaks is assumed to be unity, representing 100% light transmission over the all-pass (white) window. Two peaks are used here to help estimate the amount of intensity noise, besides offering information about the cell speed to aid downstream cell sorting.

The measured waveform S(t) will show two peaks in the waveform and the height of the peaks in S(t) can be written as $$S_p = I_1 + I_2 \qquad (5)$$

From Eqs. (4,5), we can find the intensity of individual fluorophore:

$$I_1 = \frac{1}{f_2(t) - f_1(t)} \{f_2(t) S_p - S(t)\} \quad \tau < t < T \qquad (6\text{-}a)$$

$$I_2 = \frac{1}{f_2(t) - f_1(t)} \{S(t) - f_1(t) S_p\} \quad \tau < t < T \qquad (6\text{-}b)$$

Here there is interest in the duration between $\tau<t<T$, which is the time interval between the end of the two leading peaks and the end of the COST signal. The values of $\tau$ and $T$ depend on the flow speed of the cell.

Note that the color compensation process for conventional flow cytometers and the COST system yields different mathematical expressions (i.e. Eq. 3 and Eq. 6). There exists a fundamental and significant difference between the two color compensation schemes. The results in Eq. (2) for conventional flow cytometers show that we obtain two numerical numbers $I_1$, $I_2$. We do not have an objective method to measure the quality or accuracy of the color compensation results, which can cause significant concerns when the noise is high. The method also requires separate calibration experiment and user judgment to decide whether the results of color compensation are reasonable.

The results from the COST system, as indicated in Eq. (6), have different characteristics than those from conventional flow cytometers. Note that the right-hand-side of the equation in Eq. (6) is time-dependent since both the 'waveform signatures" $f_1$ and $f_2$ of fluorophores and the measured signal $S(t)$ are time dependent. On the other hand, the left-hand-side of Eq. (6) is supposed to be time independent in an ideal case since $I_1$ and $I_2$ represent the magnitude of light emission through the transparent window (all-pass filter) by fluorophore 1 and fluorophore, respectively. In reality, due to the effects of noise, the actual values of $I_1$ and $I_2$ may show some variations with time, as illustrated in FIG. 69C. Now the extent of the variations over time, defined as $\Delta I / \bar{I}$ where $\Delta I$ and $\bar{I}$ are the variation and mean value of $I$ in Eq. (6), produces a quantitative, objective measure of the color-compensated results. Furthermore, one may make use of various mathematical algorithms to generate the most reliable values of I's for the fluorophore by minimizing the effects of noise and avoiding any singularities. For example, due to the characteristics of fluorophores, results from certain durations in Eq. (5) may show stronger variations than results from other durations. It can be beneficial that we ignore the fluctuating I values in those durations and only use the values when the fluctuations are within certain range.

To summarize, the COST algorithm can not only minimize the number of PMTs and critical optic components to detect multiple fluorescent colors, but also enhance the accuracy and reliability of the results of color compensation. Instead of producing fixed values for the intensities of the fluorophores as in conventional flow cytometers, the COST system generates intensity values of fluorophores that show fluctuations over a time interval. The extent of fluctuations produces quantitative measures of the quality and reliability of the results, and one can employ digital signal processing algorithms to reduce the variations for a more accurate result or develop criteria to accept or reject certain results, thus improving the overall system performance.

Methods to Increase the Dynamic Range

Because the COST algorithm uses a minimum number of photomultiplier tubes (PMTs) to detect multiple fluorescent colors, the technique has to deal with the dynamic range issue in different ways than conventional flow cytometers.

In conventional flow cytometers, each fluorescent color is directed to a specific PMT and the amplification factor of the PMT is set according to the intensity of the emitted light at the specific wavelength. In conventional flow cytometers, the problem of dynamic range occurs in situations where the spill-over intensity of the neighboring fluorophores in one cell is much greater than the emission intensity of the targeted fluorophores of another cell. The strong spillover effect can limit the maximum gain setting of the PMT and prevents the system from achieving the best signal-to-noise ratio for cells of weak fluorescence intensity.

For the COST system, a single PMT is used to detect multiple fluorophores. If the sample contains cells that give strong fluorescent intensity and cells that produce weak fluorescent intensity, the setting of the amplification factor of the PMT will be limited by the cells producing the strong fluorescent emission to prevent the PMT from entering saturation. As a result, the signal quality of cells with weak emission intensity will be compromised.

Figure 70:
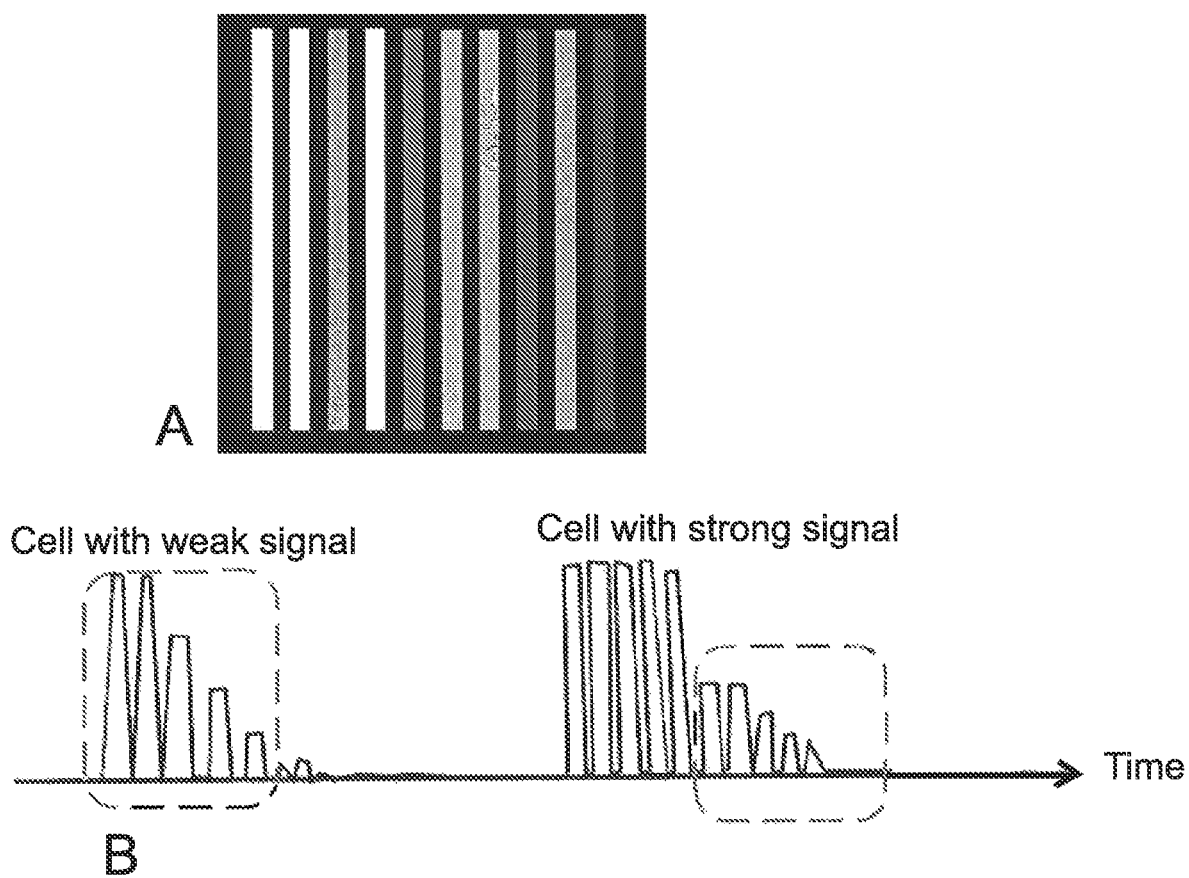
FIG. 70A is an illustrative design of a tandem filter. Each set of filter consists of multiple slits with different spectral characteristics. The second filter set has a lower overall transmission coefficient than the first set of the filter.
FIG. 70B is an illustration of exemplary cell signals received through the filter of FIG. 70A. The first cell has low fluorescent intensity so the output from the second filter set is hardly detectable. The second cell has strong fluorescent intensity and the output from the first filter set saturates the PMT detector. However, the fluorescent characteristics of both cells can be properly detected from the part of the signal with proper intensities as highlighted.

An effective method to overcome the dynamic range limitation is to create a tandem COST filter with different transmission coefficients. As shown in FIG. 70A, the tandem COST filter consists of two sets of optical filters. The first set of filter can have 5 slits, with (for example) two all-pass filters followed by three broadband color filters with their transmission peaks at green, yellow, and red wavelengths, respectively. Right next to the first set of 5-slit filter is the second 5-slit filter, arranged in the same sequence as the first set of filter except that the absolute transmission coefficient of the second filter set is lower (e.g. by 30 times) than the first filter set. The fluorescent emission from a travelling cell in the microfluidic channel is projected onto the slit filters in tandem before reaching the PMT detector, producing a 10-peak COST signal with the first half of the signal much stronger than the second half of the signal due to the attenuation of the second filter set (see FIG. 70B). The PMT amplification is set at a high value to accommodate the weakest signals among the cell populations under test. For cells having strong emission intensity, the first half of the PMT signal can become saturated and contain no useful information. However, the second half of the PMT signal contains all the needed information for the COST algorithm to detect the fluorescent color and intensity of the cell. On the other hand, for cells having weak emission intensity, the second half of the signal is of poor quality because of the optical attenuation but the first half of the signal has high quality with the proper level of PMT amplification. Benefiting from the tandem filter architecture, the system can always produce high quality signal with a single PMT detector regardless the signal strengths of the cells.

For PMTs connected to a post amplifier and a 16-bit A/D converter, it is easy to distinguish signals that are $\frac{1}{40}$ of the full output scale (i.e. 125 mV from a full output range of 5V). By attenuating the optical transmission by 30 times in the second filter set, one can achieve a dynamic range of over 1000. Such concept can be extended further if a dynamic range higher than 1000 is needed for certain applications. To change the dynamic range, one only needs to replace the COST filter without other adjustments of the system.

One tradeoff of such tandem filter set is the increasing time duration of the signal, which may limit the throughput of the system. This limitation can be alleviated with improved filter fabrication process such as micro fabrication or 3D printing processes that can produce fine slits and compact filter sets. For the tandem COST filter with 10 slits in total, microfabrication process can be applied to produce 100 µm wide slits with 50 µm spacing between slits, yielding a total filter length of about 1.5 mm. For an optical system with 50× magnification factor, the actual travel distance for the cell in the microfluidic channel to produce the full signal is 30 µm (i.e. 1.5 mm divided by 50). For a typical cell speed of 1 m/s in flow cytometers, the system can obtain a throughput greater than 30,000 cells/s, a sufficient throughput for most applications.

Embodiments of COST Filters with Increasing Dynamic Range

In the following we describe how the tandem COST filter can be implemented using microfabrication technologies. There exist, of course, other methods such as 3D printing and laser machining to produce similar devices.

Figure 71:
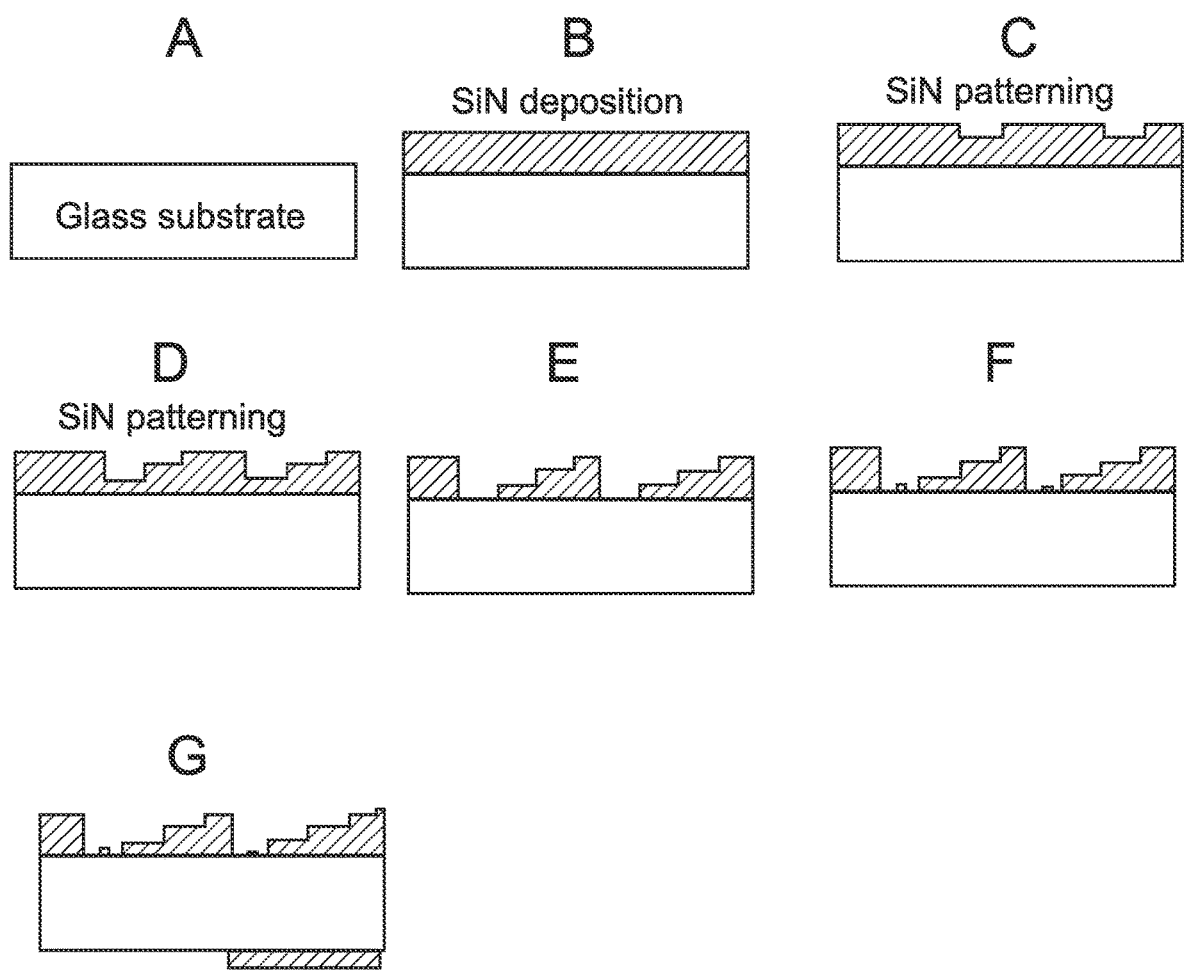
FIGS. 71A-G provide an illustration of process flow for microfabricating a tandem filter.

FIGS. 71A-71G illustrates the process flow of microfabricated tandem filters. On the glass substrate (FIG. 71A) with a refractive index between 1.41 and 1.46 over the spectral range of interest, a layer of silicon nitride ($Si_3N_4$) is deposited (FIG. 71B). Since silicon nitride has a refractive index between 1.9 and 2.1 over the same spectral range, the silicon nitride layer on glass behaves as an optical interferometer. The interferometer has its maximum transmission coefficient at the wavelength $\lambda_T$ where the following equation is satisfied:

$$\lambda_T = \frac{2n_{sin}d}{M};$$

M=1, 2 . . . . Similarly, the interferometer has the minimum transmission (or maximum reflection) at $\lambda_R$ that satisfies the relation $$\lambda_R = \frac{2n_{sin}d}{N+1/2};$$

N=0, 1, 2 . . . . The values of $\lambda_T$ and $\lambda_R$ define the spectral characteristics of a unit of the COST filter and can be controlled by the thickness of the silicon nitride layer.

Using the standard photolithography process, one can selectively remove part of the silicon nitride layer (i.e. changing the nitride thickness, d) to define a new set of wavelengths for maximum and minimum transmission coefficients (FIG. 71C). After repeating the photolithography and silicon nitride etching process a few times, an array of interferometers having different transmission characteristics can be obtained (FIG. 71D). To make all-pass filters, the silicon nitride layer is completely removed so the light transmits through only the glass substrate (FIG. 71E).

Following the fabrication of the array filters with the desired spectral characteristics, another photolithography step is performed to create the slits defined by metal thin films. The space between filters is covered by aluminum metal film, which, if needed, can be anodized to minimize light reflection FIG. 71F. As the final step, the optical attenuation layer is added to the backside of the glass substrate over the areas of the second set of filter (FIG. 71G). The simplest method is to form absorption type attenuator since the application is at very low power and heating is not a concern. Alternatively, diffraction type or reflection type of attenuator can be used. Due to the relatively large size of the attenuator area covering half size of the COST tandem filter, a shadow mask for deposition can be used. For example, a thin (e.g. 30 nm) layer of sputtered refractive metal film such as Cr or Ni can provide the needed attenuation easily. After the microfabrication process is completed, each tandem COST filter is diced into individual pieces for use in the flow cytometers. A 6" glass wafer can produce more than 300 COST tandem filters to support low cost production. For microfabrication process that gives 5% variations across the 6" wafer, the devices are expected to have good uniformity and high run-to-run repeatability.

Example 5: Post-Sort Valve(s)

Microfluidic sorting systems typically have continuous flow of sheath fluid exiting sorting channels, even if a cell is not being actively sorted. This presents a challenge when sorting very rare cell populations. For example, if a 1 ml sample contains 10 or even 100 sorted cells, it yields a diluted sample and would not be amendable for multiple downstream applications such as, for example, plating into 96-well plates. Examples for rare cell applications include isolation of circulating tumor cells or circulating fetal or circulating placental cells, among others.

Current methods to address this problem consists of placing the sorted volume in a centrifuge tube, centrifuging the sample, pipetting out the supernatant, and resuspending in a desired volume. This takes additional time, and increases the possibility of losing rare cells during the process, potentially resulting in a low unacceptable yield for downstream applications.

Accordingly, aspects of the disclosure can include one or more post-sort valve formed in a sorting channel to divert continuous sheath fluid during periods of no cell sorting events, to reduce the dilution of sorted cells due to continuous sheath fluidic exiting the sorting channels.

FIGS. 72A, 72B illustrate how a post-sort valve 7220 can employed with aspects of the particle sorter(s) described herein. FIG. 72A illustrates the problem being addressed, of a sorted particle (e.g., a cell) 7028 in a sorting channel 7210C (e.g. similar to the sorting channel 5010C of FIG. 50). The sorted particle 7210 can generate an impedance signal upon detection by a sensor 7214C, as disclosed in the embodiment of FIG. 50 as element 5014C, for example. Due to continuous sheath fluid collection from the sorting channel 7210C, the particle 7228 can be undetectable in a relatively large collection volume. FIG. 70B illustrates the post-sort valve 7220 formed in the sorting channel 7210C. The post-sort valve 7220 can be operable to receive a particle detection event signal (e.g. associated with an impedance detection signal from sensor 7214C, or a sorting signal from a sorting mechanism such as the piezoelectric actuator 5006). When no particle detection signal is received (i.e., no particle is detected in the sorting channel 7210C), the post-sort valve 7220 can simply remove the sheath fluid via a first outlet 7220A. When a particle detection signal is received, the post-sort valve 7220 can, remove the sorted particle 7228 via a second outlet 7220B. In this manner, a sorted volume associated with the sorted particle 7228 is reduced. In some embodiments, a particle sorter including such a post-sort valve is operable to estimate flow speed of a sorted particle, and operate the post-sort valve to open the second outlet 7220B (and to close the first outlet 7220A) when the sorted particle expected to reach the post-sort valve. In some embodiments, the estimation of particle speed can compensate/allow for variable volume displacement upstream and downstream of the estimated particle position (ex: +/−2 µL) to ensure it is captured.

The post-sort valve can be any type of valve (on-chip, off chip, mechanical, piezoelectric, and/or the like). In some embodiments, when particle detection events can be rare, the post-sort valve does not need to be operable for rapid switching.

Example 6: Alignment Using on-Chip Markers

In several embodiments described herein, sensitive detection and high-purity sorting desire accurate and repeatable alignment between the optical components (e.g. the optical components illustrated in FIG. 34, FIG. 52A, and/or FIG. 73) and the interrogation area (e.g., one or more channels of the particle sorter 5000) of the microfluidics system. In some embodiments, aspects disclosed herein achieve alignment with a semi-automated alignment system based on custom alignment software, an imaging system (e.g. a microscope), and a motorized XYZ-stage. Picomotors associated with the motorized XYZ-stage and driven via a piezoelectric actuator, can yield high accuracy (<5 µm), and within one minute.

Figure 73:
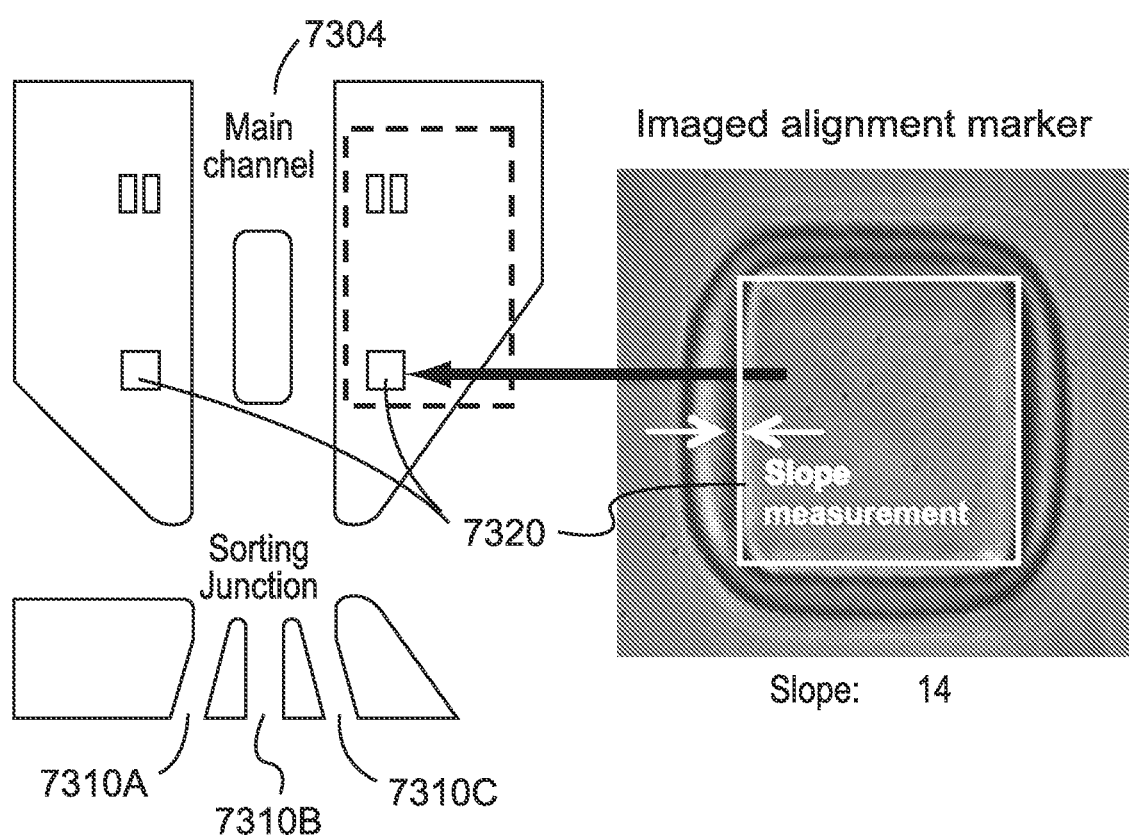
FIG. 73 is an illustration of the use of an alignment marker with a particle sorter, according to an embodiment.

As best illustrated in FIG. 73, one or more alignment markers 7320 can be formed on a particle sorter (e.g. the particle sorter of FIGS. 14-16). Any suitable size/form (e.g., 50 µm side squares), optical characteristics (e.g., reflective, fluorescent, scattering, and/or the like) of the alignment markers 7320 can be employed.

It is understood that various combinations of embodiments disclosed herein are within the scope of this disclosure. Such combinations can include, but are not limited to:

The use of one or more post-sort valves (e.g., FIG. 72B) in any sorting channel of any particle sorters disclosed herein (e.g. the particles sorters of FIGS. 14, 15, 16A-16C, 50, and/or the like);

The application of the color compensation approach (e.g., FIGS. 69-71) to any of the particle sorters disclosed herein (e.g. the particles sorters of FIGS. 14, 15, 16A-16C, 50, and/or the like);

The application of the methods for verification of sorting particles (e.g., FIGS. 57, 61, 64) to any of the particle sorters disclosed herein (e.g. the particle sorters of FIGS. 14, 15, 16A-16C, 50, and/or the like);

The use of on-chip reagents and mixers (FIGS. 67, 68) with any of the particle sorters disclosed herein (e.g. the particles sorters of FIGS. 14, 15, 16A-16C, 50, and/or the like), including pre-sorting mixers (as illustrated in FIGS. 67, 68) and post sorting mixers (as illustrated in FIG. 67).

In some embodiments described herein, a computer storage product with a non-transitory computer-readable medium (also referred to as a non-transitory processor-readable medium) has instructions or computer code thereon for performing various computer-implemented operations. The computer-readable medium (or processor-readable medium) is non-transitory in the sense that it does not include transitory propagating signals (e.g., a propagating electromagnetic wave carrying information on a transmission medium such as space or a cable). The media and computer code (also referred to herein as code) may be those designed and constructed for the specific purpose or purposes. Examples of non-transitory computer-readable media include, but are not limited to: magnetic storage media such as hard disks, optical storage media such as Compact Disc/Digital Video Discs (CD/DVDs), Compact Disc-Read Only Memories (CD-ROMs), magneto-optical storage media such as optical disks, carrier wave signal processing modules, and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages and/or other development tools.

The various embodiments described herein should not to be construed as limiting this disclosure in scope or spirit. It is to be understood that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of verification of sorting of particles, comprising:
   receiving a first detection signal, the first detection signal associated with optical characteristics of a first particle in a first channel;
   determining based on the first detection signal a sorting channel of a plurality of second channels into which the first particle is to be sorted;
   transmitting a first sorting signal to a sorting element comprising a piezoelectric actuator for sorting the first particle from the first channel into the sorting channel;
   receiving a second detection signal, the second detection signal associated with a presence of the first particle in the sorting channel;
   verifying the sorting of the first particle from the first channel into the sorting channel based on the second detection signal, wherein the second detection signal is associated with impedance detection;
   generating a second sorting signal based on the first sorting signal, the second detection signal, and a third detection signal associated with optical characteristics of a second particle in the first channel, wherein the second sorting signal is configured to change an operation parameter of the piezoelectric actuator;
   transmitting the second sorting signal for sorting the second particle from the first channel into the sorting channel.

2. The method of claim 1, wherein the first detection signal is associated with a plurality of optical signals.

3. The method of claim 2, wherein the plurality of optical signals includes one or more reference signals and one or more fluorescence signals.

4. The method of claim 1, wherein the optical characteristics include one or more fluorescence properties of the first particle.

5. The method of claim 4, wherein determining the sorting channel is based on the one or more fluorescence properties of the first particle.

6. The method of claim 1 further comprising generating the first sorting signal based on a required deformation of the piezoelectric actuator to sort the first particle into the sorting channel.

7. The method of claim 1, wherein the presence of the first particle in the sorting channel changes a detected impedance in the sorting channel.

8. The method of claim 1, further comprising:
receiving a fourth detection signal, the fourth detection signal associated with optical characteristics of a third particle in the first channel, wherein the optical characteristics of the third particle are different from the optical characteristics of the first particle;
determining based on the third detection signal a second sorting channel of the plurality of second channels into which the third particle is to be sorted, wherein the second sorting channel is different from the sorting channel;
transmitting a third sorting signal for sorting the third particle from the first channel into the second sorting channel;
receiving a fifth detection signal, the fifth detection signal associated with a presence of the third particle in the second sorting channel; and
verifying the sorting of the third particle from the first channel into the second sorting channel based on the fifth detection signal.

9. The method of claim 1, wherein the first particle is selected from inorganic particles, organic particles, and cells.

10. A non-transitory computer-executable storage media comprising instructions for executing the method of claim 1.

11. The method of claim 1, wherein the operation parameter of the piezoelectric actuator includes at least one of a voltage waveform applied to the piezoelectric actuator, a triggering timing and an alignment of the piezoelectric actuator.

12. The method of claim 1, further comprising:
receiving a fourth detection signal associated with a presence of the second particle in the sorting channel;
in response to the third detection signal not matching the first detection signal, generating a third sorting signal based on at least the second sorting signal, the third detection signal, and the fourth detection signal; and
transmitting the third sorting signal for sorting a third particle from the first channel into the sorting channel.

13. The method of claim 1, wherein the voltage waveform applied to the piezoelectric actuator includes a voltage waveform width applied to the piezoelectric actuator.

14. The method of claim 11, wherein the voltage waveform applied to the piezoelectric actuator includes an intensity of a signal applied to the piezoelectric actuator.

15. The method of claim 1, wherein the second sorting signal is configured to change the operation parameter of the piezoelectric actuator in real time.

* * * * *